(12) United States Patent
Byun et al.

(10) Patent No.: US 10,392,359 B2
(45) Date of Patent: Aug. 27, 2019

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Yun-Sun Byun, Daegu (KR); Jung Cheol Park, Suwon-si (KR); Jinho Yun, Cheonan-si (KR); Seung-Won Choi, Yongin-si (KR); Hyojin Kim, Cheonan-si (KR); Yeon Hee Choi, Cheonan-si (KR); Gyumin Lee, Cheonan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

(21) Appl. No.: 15/558,805

(22) PCT Filed: Mar. 8, 2016

(86) PCT No.: PCT/KR2016/002300
§ 371 (c)(1),
(2) Date: Sep. 15, 2017

(87) PCT Pub. No.: WO2016/148425
PCT Pub. Date: Sep. 22, 2016

(65) Prior Publication Data
US 2018/0072695 A1    Mar. 15, 2018

(30) Foreign Application Priority Data

Mar. 16, 2015 (KR) .......................... 10-2015-0036231

(51) Int. Cl.
| | | |
|---|---|---|
| *C07D 307/91* | (2006.01) | |
| *C07D 333/76* | (2006.01) | |
| *H01L 51/00* | (2006.01) | |
| *C09K 11/06* | (2006.01) | |
| *C07D 407/12* | (2006.01) | |
| *C07D 407/14* | (2006.01) | |
| *C07D 409/12* | (2006.01) | |
| *C07D 409/14* | (2006.01) | |
| *H01L 51/50* | (2006.01) | |
| *H05B 33/14* | (2006.01) | |

(52) U.S. Cl.
CPC ......... *C07D 307/91* (2013.01); *C07D 333/76* (2013.01); *C07D 407/12* (2013.01); *C07D 407/14* (2013.01); *C07D 409/12* (2013.01); *C07D 409/14* (2013.01); *C09K 11/06* (2013.01); *H01L 51/006* (2013.01); *H01L 51/0052* (2013.01); *H01L 51/0059* (2013.01); *H01L 51/0061* (2013.01); *H01L 51/0072* (2013.01); *H01L 51/0073* (2013.01); *H01L 51/0074* (2013.01); *H01L 51/5012* (2013.01); *H05B 33/14* (2013.01); *C09K 2211/1088* (2013.01); *C09K 2211/1092* (2013.01); *H01L 51/5056* (2013.01); *H01L 51/5064* (2013.01); *Y02E 10/549* (2013.01)

(58) Field of Classification Search
CPC ........................... C07D 307/91; C07D 333/76
See application file for complete search history.

(56) References Cited

FOREIGN PATENT DOCUMENTS

| | | | |
|---|---|---|---|
| KR | 10-2011-0117549 A | | 10/2011 |
| KR | 10-2012-0033945 A | | 4/2012 |
| KR | 10-2014-0035737 A | | 3/2014 |
| KR | 10-2014-0139306 A | | 12/2014 |
| KR | 10-2014-0145428 A | | 12/2014 |
| KR | 10-2015-0016896 A | | 2/2015 |
| KR | 10-2015-0033082 A | | 4/2015 |
| KR | 10-2015-0072768 A | | 6/2015 |
| KR | 10-2016-0053561 A | | 5/2016 |
| KR | 10-2016-0054870 A | | 5/2016 |
| WO | WO2014042420 | * | 3/2014 |
| WO | WO2016013867 | * | 1/2016 |
| WO | WO2016072691 | * | 5/2016 |

OTHER PUBLICATIONS

Lee et al, Machine translation of WO2016072691, p. 1-46. (Year: 2016).*
Lee et al, Machine translation of Korean Application No. 2014-0152779, p. 1-91 (Year: 2014).*

* cited by examiner

*Primary Examiner* — Karen Cheng
(74) *Attorney, Agent, or Firm* — Vorys, Sater, Seymour & Pease LLP; Mih Suhn Koh

(57) ABSTRACT

Provided are a compound represented by Formula 1, and an organic electric element comprising a first electrode, a second electrode, and an organic material layer formed between the first electrode and the second electrode, wherein the organic material layer comprised the compound represented by Formula 1, and the driving voltage of an organic electronic device can be lowered, and the luminous efficiency, color purity and life time of an organic electronic device can be improved by comprising the compound represented by Formula 1 in the organic material layer.

10 Claims, 1 Drawing Sheet

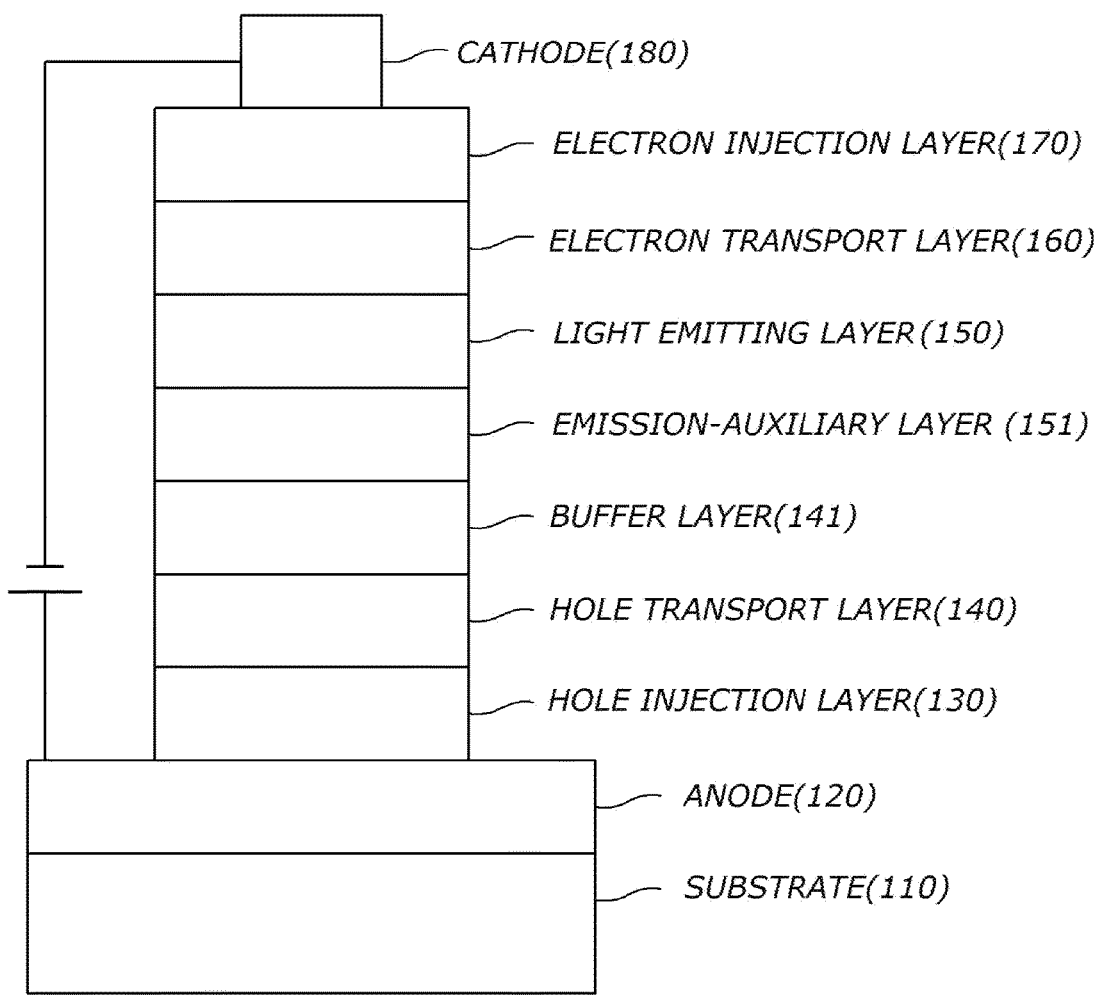

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0036231, filed on Mar. 16, 2015, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, recently, in order to solve the emission problem in a hole transport layer and driving voltage of an organic electric element, it is needed to form an emission-auxiliary layer (multilayered hole transport layer) between the hole transport layer and a light emitting layer, and it is time to develop different emission-auxiliary layers according to respective light emitting layers.

In general, an electron which is transferred from an electron transport layer to a light emitting layer and a hole which is transferred from a hole transport layer to the light emitting layer are recombined to form an exciton in a light emitting layer. However, when a material having a high hole mobility is used to lower a driving voltage, a positive polaron is accumulated at the interface between the light emitting layer and the hole transporting layer, thereby causing interface deterioration, as a result the lifetime and efficiency are reduced, and charge is out of balance, so that a surplus polaron in the light emitting layer attacks the weak bonding of the light emitting material to deform the light emitting material, thereby exhibiting a phenomenon such as a reduction in the lifetime, efficiency and color purity.

Therefore, the an emission-auxiliary layer should be present between a hole transport layer and the light-emitting layer and be a material having an appropriate HOMO value between the light-emitting layer and the hole transport layer in order to prevent the positive polaron from being accumulated on the interface of the light-emitting layer, and be a material having hole mobility within proper driving voltage (within the ble device driving voltage range of the full device) in order to increase charge balance in the light-emitting layer.

However, this cannot be achieved simply by the structural properties of the core of an emission-auxiliary layer material. High efficiency and long lifespan of device can be achieved when the characteristics of the core and the sub-substituent and the proper combination of the emission-auxiliary layer and the hole transport layer and of the emission-auxiliary layer and the light-emitting layer are met.

That is, it should be preceded that the materials consisting an organic material layer of the element, for example, a hole injection material, a hole transport material, a light emitting material, an electron transport material, an electron injection material, or the like, are supported by a stable and efficient material. Particularly, it is strongly required to develop materials of the emission-auxiliary layer and the hole transport layer.

SUMMARY

In order to solve one or more of the above-mentioned problems in prior art, an aspect of the present invention is to provide a compound having efficient electron blocking ability and hole transport ability and allowing to improve luminous efficiency, to lower a driving voltage, to have a high heat-resistance, and to improve color purity and lifetime of the element, an organic electric element comprising the same, and an electronic device thereof.

In accordance with an aspect of the present invention, the compound represented by the following formula is provided. The following formula represents a compound of which a core (dibenzofuran or dibenzothiophene) and two amine groups are bonded via a linking group. At least one of $R^1$ to $R^3$ in the following formula 1 is represented by the following formula 2.

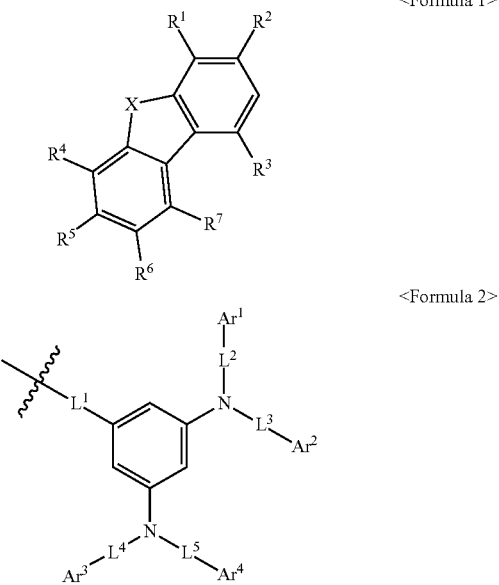

<Formula 1>

<Formula 2>

In another aspect of the present invention, organic electric elements comprising the compound represented by the formula 1 above and electronic devices including the organic electric element are provided.

According to the embodiments of the present invention, by using a specific compound as a material of the organic electric device, wherein the compounds have a specific types of linking group bonded to the core and an amine group bonded to the linking group, and the limited bonding position and number of amine groups, luminous efficiency, heat-resistance, color purity and lifetime of the organic electric elements can be improved and a driving voltage of the organic electric elements can be lowered due to HOMO energy level and the high T1 value which are easy to balance the charge in the light emitting layer.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

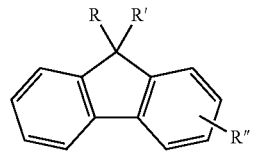

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

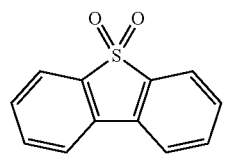 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of Spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a fluorenyl group, a $C_8$-$C_{20}$ arylalkenyl group, a silane group, a boron group, a germanium group, and a $C_5$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene, which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

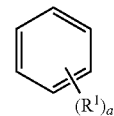

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

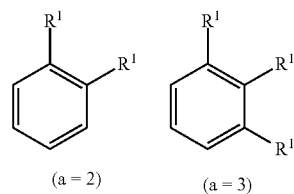

FIGURE illustrates an organic electric element according to an embodiment of the present invention.

Referring to FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may not be formed, the organic material layer may further include a hole blocking layer, an electron blocking layer, an emission-auxiliary layer 151, an electron transport auxiliary layer, a buffer layer 141, etc., the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, as a host material or a dopant material of a light emitting layer 150, or as a material a capping layer material. For example, the inventive compound may be used as material of the light emitting layer 150, the hole transport layer 140, and/or the emission-auxiliary layer 151, preferably, as the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B).

On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

According to the present invention, energy levels and T1 values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

And also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

A WOLED (White Organic Light Emitting Device) readily allows for the formation of ultra-high definition images, and is of excellent processability as well as enjoying the advantage of WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

[Formula 1]

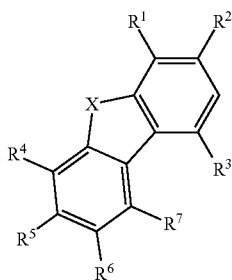

[Formula 2]

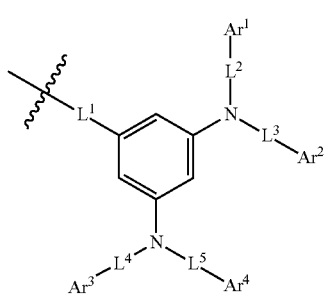

In formula 1 and 2 above, each of symbols may be defined as follows.

In Formula 1, X is O or S.

$R^1$ to $R^3$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and the above formula 2, with the proviso that at least one of $R^1$ to $R^3$ is the above formula 2.

When $R^1$ to $R^3$ are an aryl group, $R^1$ to $R^3$ may be preferably a $C_6$-$C_{30}$ aryl group, more preferably $C_6$-$C_{12}$ aryl group; when $R^1$ to $R^3$ are an alkyl group, $R^1$ to $R^3$ may be preferably $C_1$-$C_{10}$ alkyl group, more preferably $C_1$-$C_4$ alkyl group; and when $R^1$ to $R^3$ are an alkoxyl group, $R^1$ to $R^3$ may be preferably $C_1$-$C_{10}$ alkoxyl group, more preferably $C_1$-$C_4$ alkoxyl group. For example, $R^1$ to $R^3$ are each hydrogen, phenyl, phenylpyridine, methoxy, ethoxy, a cyano group, methyl, and the like.

$R^4$ to $R^7$ are each independently selected from the group consisting of hydrogen, deuterium, tritium, halogen, a cyano group, a nitro group, a $C_6$-$C_{60}$ aryl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and neighboring groups of $R^4$ to $R^7$ may be optionally linked each other to form a ring. However, dibenzofuryl group and dibenzothienyl group are excluded from $R^4$ to $R^7$.

When $R^4$ to $R^7$ are an aryl group, $R^4$ to $R^7$ may be preferably a $C_6$-$C_{30}$ aryl group, more preferably $C_6$-$C_{18}$ aryl group; when $R^4$ to $R^7$ are a heterocyclic group, $R^4$ to $R^7$ may be preferably a $C_2$-$C_{30}$ heterocyclic group, more preferably $C_2$-$C_9$ heterocyclic group; when $R^4$ to $R^7$ are an alkyl group, $R^1$ to $R^3$ may be preferably $C_1$-$C_{10}$ alkyl group, more preferably $C_1$-$C_4$ alkyl group; $R^4$ to $R^7$ are, for example, hydrogen, deuterium, tert-butyl, phenyl, naphthyl, terphenyl, phenanthrene, quinoline, isoquinoline and the like.

'Neighboring groups of $R^4$ to $R^7$ can be linked each other to form a ring' means that at least one pair of $R^4$ and $R^5$, $R^5$ and $R^6$, and $R^6$ and $R^7$ can be linked each other to form a ring together with the benzene ring to which they are attached. Here, at least one pair of neighboring groups can be independently linked each other to form a ring, for example, neighboring groups of $R^4$ and $R^5$ may be linked each other to form a ring while remaining groups of $R^5$ to $R^7$ may not form a ring.

The ring formed by linking between neighboring groups of $R^4$ and $R^5$, $R^5$ and $R^6$, or $R^6$ and $R^7$ may be usually 5- to 8-membered ring, preferably 5- or 6-membered ring, more preferably 6-membered ring. Here, the formed ring may be an aromatic ring or aliphatic ring, when it is an aromatic ring, it may be an aromatic hydrocarbon ring or an aromatic heterocyclic ring, preferably an aromatic hydrocarbon ring. Also, adjacent groups may be linked through alkylene or alkenylene to form an alicyclic ring, a monocyclic or polycyclic aromatic ring. Preferably, the rings formed by linking $R^4$ and $R^5$, $R^5$ and $R^6$, or $R^6$ and $R^7$ each other may be benzene rings, as a result, naphthalene, phenanthrene, and the like may be formed together with the benzene ring to which they are bonded.

In the Formula 2, $L^1$ to $L^5$ are each independently selected from the group consisting of a single bond, a $C_6$-$C_{60}$ arylene group, a $C_2$-$C_{60}$ heterocyclic group containing at least one heteroatom selected from O, N, S, Si, and P, a fluorenylene group, a fused ring group of a $C_3$-$C_{60}$ aliphatic ring and a $C_6$-$C_{60}$ aromatic ring, and an $C_1$-$C_{60}$ aliphatic hydrocarbon group, each of $L^1$ to $L^5$ (except a single bond) may be optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

When $L^1$ to $L^5$ are an arylene group, $L^1$ to $L^5$ may be preferably a $C_6$-$C_{30}$ arylene group, more preferably $C_6$-$C_{12}$ arylene group, for example, phenylene, naphthylene, biphenylene, and the like. When $L^1$ to $L^5$ are a heterocyclic group, $L^1$ to $L^5$ may be preferably a $C_2$-$C_{30}$ heterocyclic group, more preferably $C_2$-$C_{12}$ heterocyclic group, for example, pyridine, benzothiophene, benzofuran, dibenzothiophene, dibenzofurane and the like, and when $L^1$ to $L^5$ are fluorenylene groups, $L^1$ to $L^5$ may be 9,9-dimethyl-9H-fluorenylene.

$Ar^1$ to $Ar^4$ are each independently selected from the group consisting of a $C_6$-$C_{60}$ aryl group, a $C_2$-$C_{60}$ heterocyclic group containing at least one heteroatom selected from the group consisting of O, N, S, Si, and P, a fluorenyl group, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group. When $Ar^1$ to $Ar^4$ are an aryl group, $Ar^1$ to $Ar^4$ may be preferably a $C_6$-$C_{30}$ aryl group, more preferably $C_6$-$C_{18}$ aryl group, for example, phenyl, biphenyl, terphenyl, naphthyl, pyrenenyl, phenanthryl, triphenylene, and the like. When $Ar^1$ to $Ar^4$ are a fluorenyl group, $Ar^1$ to $Ar^4$ may be 9,9-dimethyl-9H-fluorenyl, 9,9-diphenyl-9H-fluorenyl, 9,9'-spirobifluorenyl, spirobenzofluorene-7,9'-fluorenyl, and the like. When $Ar^1$ to $Ar^4$ are a heterocyclic group, $Ar^1$ to $Ar^4$ may be preferably a $C_2$-$C_{30}$ heterocyclic group, more preferably $C_2$-$C_{12}$ heterocyclic group, for example, pyridine, isoquinoline, benzoquinoline, carb azole, benzocarbazole, benzothiophene, dibenzothiophene, benzonaphtothiophene, dibenzofurane, trimethylsilane, triphenylene and the like. When $Ar^1$ to $Ar^4$ are an alkyl group, $Ar^1$ to $Ar^4$ may be $C_1$-$C_{10}$ alkyl group, more preferably $C_1$-$C_1$ alkyl group, for example, methyl, and the like. When $Ar^1$ to $Ar^4$ are an alkenyl group, $Ar^1$ to $Ar^4$ may be $C_1$-$C_{10}$ alkenyl group, more preferably $C_1$-$C_1$ alkenyl group, for example, ethenyl, prophenyl, and the like. When $Ar^1$ to $Ar^4$ are an alkoxyl group, $Ar^1$ to $Ar^4$ may be $C_1$-$C_{10}$ alkoxyl group, more preferably $C_1$-$C_1$ alkoxyl group, for example, methoxyl, buthoxyl, tert-buthoxyl, and the like.

In formula 1 above, when the symbols are each the aryl group, fluorenyl group, heterocyclic group, fused ring group, alkyl group, alkenyl group, alkynyl group, alkoxyl group or aryloxy group, each of these may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and each of these substituents may be further substituted, for example, when an aryl group substituted with alkyl group, the substituent alkyl group may be further substituted with alkenylarylalkoxyl group

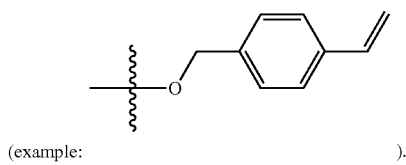 [SMILES: *OCc1ccc(C=C)cc1]

(example:                            ).

When at least one of $R^1$ to $R^3$ in the above formula 1 is a compound represented by the above formula 2, energy level (HOMO, LUMO), T1 value, thermal stability, and hole mobility are different depending on the core (benzofuran or benzothiophene) having hole properties and the kind of the amine group bonded to the linker, the bonding position and number of the amine group.

In the above Formula 1, the Formula 1 may be represented by any one of the following Formulas 3 to 5 when R', $R^2$ or $R^3$ is the formula 2.

[Formula 3]

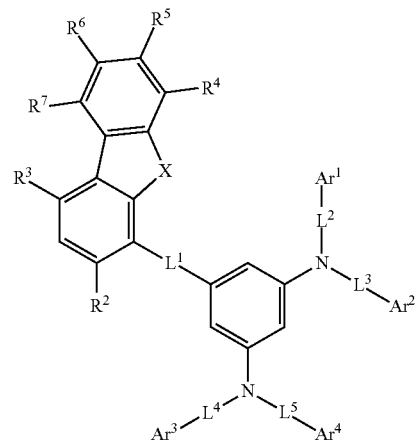

[Formula 4]

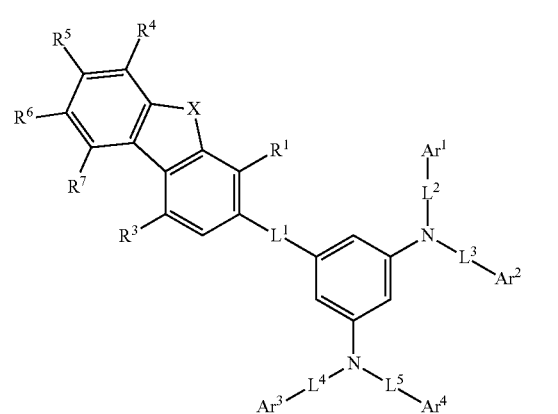

[Formula 5]

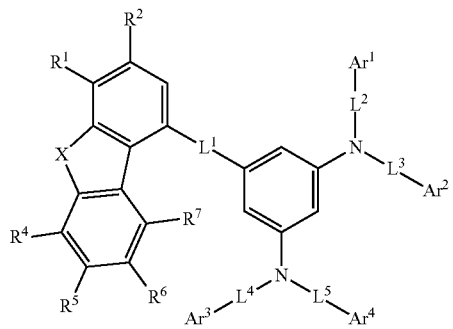

In the above Formulas 3 to 5, X, $R^1$ to $R^7$, $Ar^1$ to $Ar^4$, and $L^1$ to $L^5$ are the same as defined in Formulas 1 and 2.

In the Formula 1, neighboring groups of $R^4$ to R7 may be linked each other to form a ring, and Formula 1 may be represented by any one of the following Formulas 6 to 9 when at least one pair of neighboring groups are linked each other to form an aromatic ring, particularly, a benzene ring. Specifically, Formula 1 may be represented by the following formula 6 when neighboring $R^4$ and $R^5$ are bonded to each other, represented by the following formula 7 when neighboring $R^5$ and $R^6$ are bonded to each other, represented by the following formula 8 when neighboring $R^6$ and $R^7$ are bonded to each other, represented by the following formula 9 when neighboring $R^4$ and $R^5$, and neighboring $R^6$ and $R^7$ are each bonded to each other. Here, when a benzene ring is formed by bonding between neighboring groups, as a result, naphthalene or phenanthrene may be formed together with the benzene ring to which they are bonded.

[Formula 6]

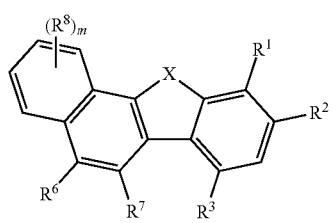

[Formula 7]

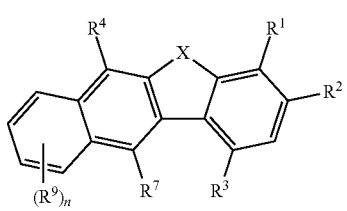

[Formula 8]

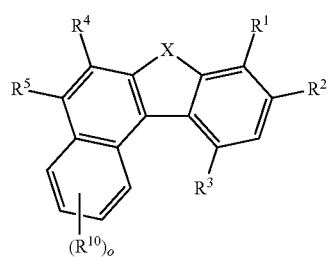

[Formula 9]

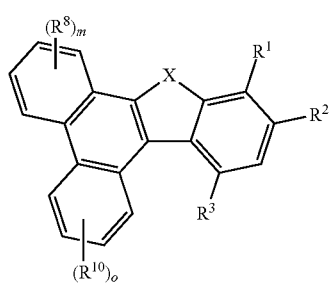

[Formula 10]

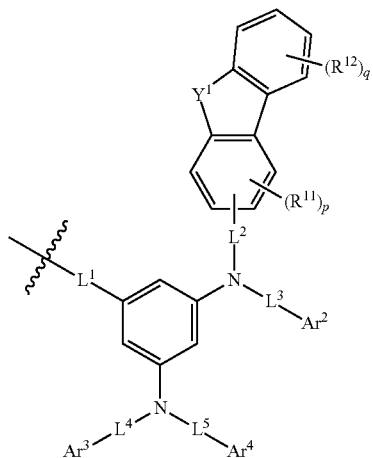

[Formula 11]

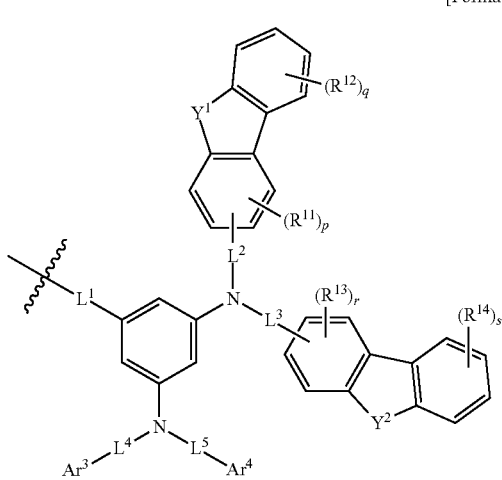

[Formula 12]

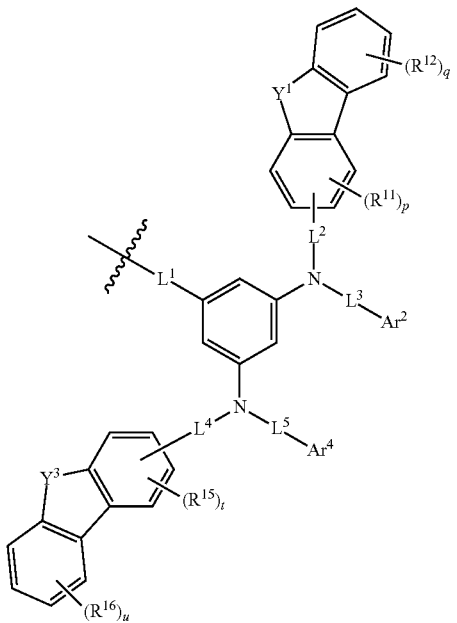

In the above Formulas 6 to 9, X, $R^1$ to $R^7$ are the same as defined in claim 1, and $R^8$ to $R^{10}$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group. Also, m, n and o are each an integer of 0 to 4, and $R^8$ to $R^{10}$ are each the same or different from each other when m, n and o are each an integer of 2 or more. For example, when m is an integer of 3, a plural $R^8$ are the same or different from each other.

Preferably, the above formula 2 may be represented by any one of the following formulas 10 to 14.

[Formula 13]

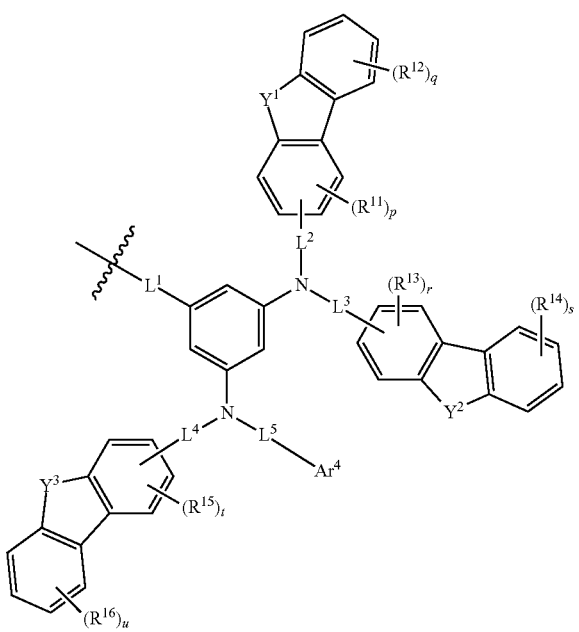

[Formula 14]

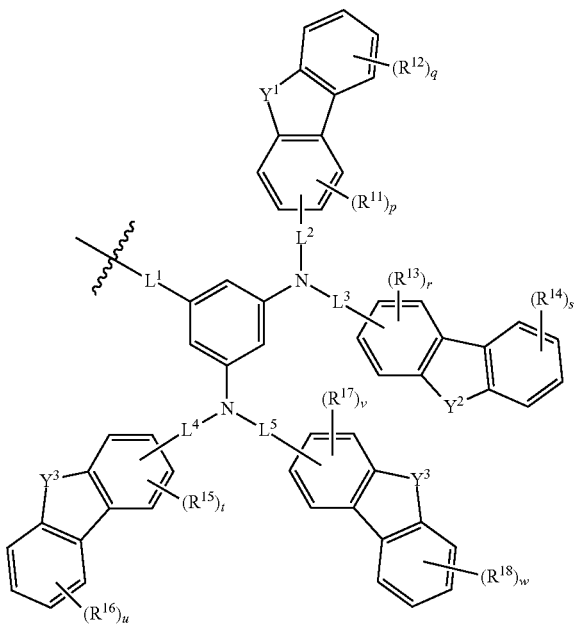

In the above Formulas 10 to 14, $Ar^2$ to $Ar^4$, and $L^1$ to $L^5$ are the same as defined in formula 2, and $Y^1$ to $Y^4$ are each independently S, O, $C(R^a)(R^b)$ or $N(R^c)$, wherein $R^a$ to $R^c$ may be each independently a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and $R^a$ and $R^b$ may be optionally linked each other to form a spiro compound together with C bonded to them, for example, 9,9'-spirobifluorene.

Also, in the above Formulas, $R^{11}$ to $R^{18}$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and the combination thereof. Or at least one pair of neighboring groups of $R^{11}$ to $R^{18}$, for example, at least one pair of neighboring groups of $R^{11}$, $R^{12}$, $R^{13}$, $R^{14}$, $R^{15}$, $R^{16}$, $R^{17}$ and $R^{18}$, may be linked each other to form at least one ring. For example, neighboring groups of $R^1$ and neighboring groups of $R^{12}$ may be linked each other to form, but $R^{13}$ to $R^{18}$ remaining may not form a ring even though neighboring groups are present.

The ring formed by linking between neighboring groups of $R^{13}$, $R^{14}$, $R^{15}$, $R^{16}$, $R^{17}$, or $R^{18}$ may be usually 5- to 8-membered ring, preferably 5- or 6-membered ring, more preferably 6-membered ring. Here, the formed ring may be an aromatic ring or aliphatic ring, when it is an aromatic ring, it may be an aromatic hydrocarbon ring or an aromatic heterocyclic ring, preferably an aromatic hydrocarbon ring. Also, adjacent groups may be linked through alkylene or alkenylene to form an alicyclic ring, a monocyclic or polycyclic aromatic ring. Preferably, the rings formed by bonding between $R^{13}$s, $R^{14}$s, $R^{15}$s, $R^{16}$s, $R^{17}$s, or $R^{18}$s to each other may be benzene rings, and as a result, naphthalene and the like may be formed together with the benzene ring to which they are bonded.

In the above Formulas, p, r, t and v are each independently an integer of 0 to 3, $R^{11}$s, $R^{13}$s, $R^{15}$s and $R^{17}$s are each the same or different from each other when p, r, t and v are each an integer of 2 or more, and q, s, u and w are each an integer of 0 to 4, $R^{12}$s, $R^{14}$s, $R^{16}$s and $R^{18}$s are each the same or different from each other when q, s, u and w each an integer of 2 or more.

Specifically, the compound represented by Formula 1 may be any one of the following compounds.

P-1

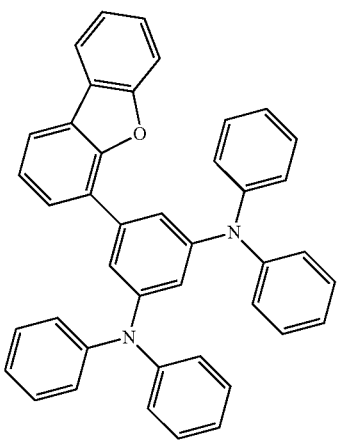

P-2
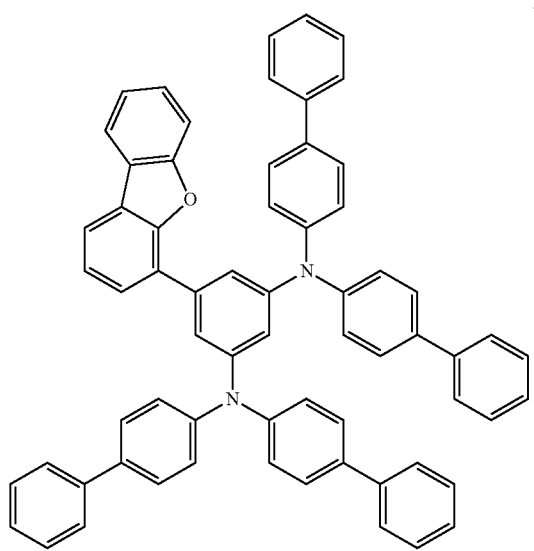
P-3
P-4
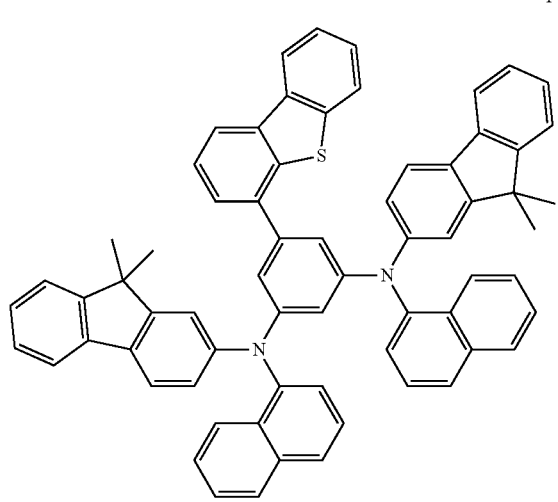
P-5
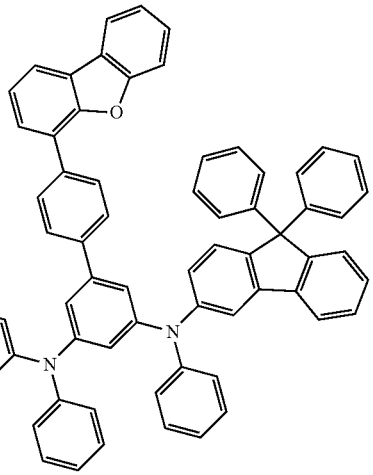
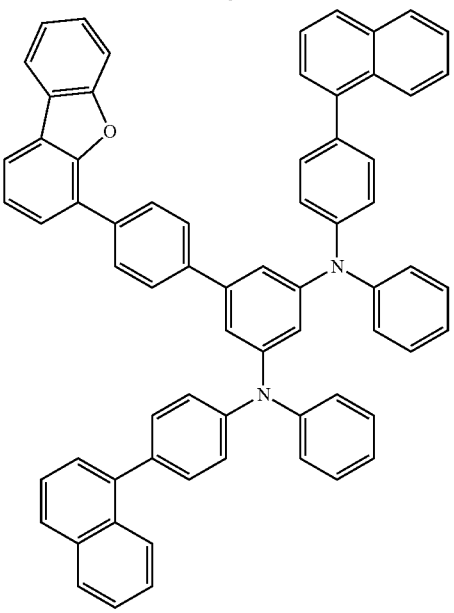
P-7
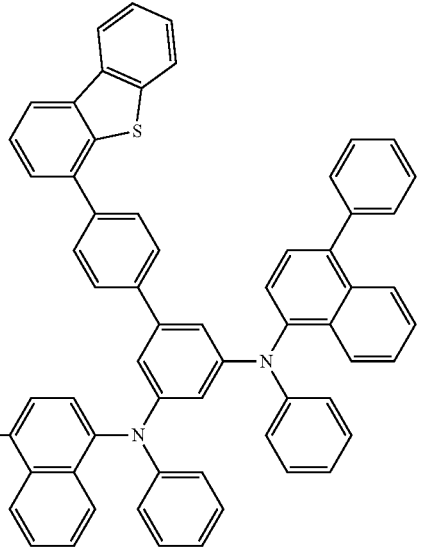

-continued
P-8
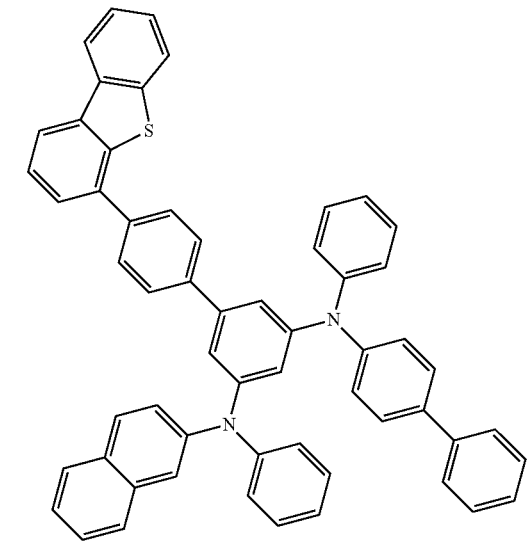
P-9
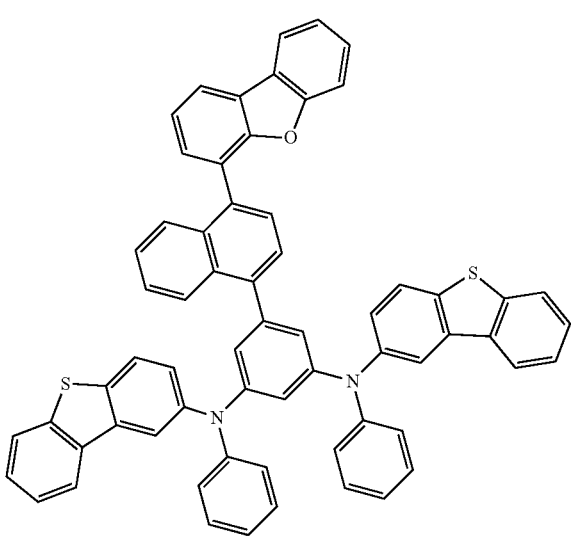
P-10
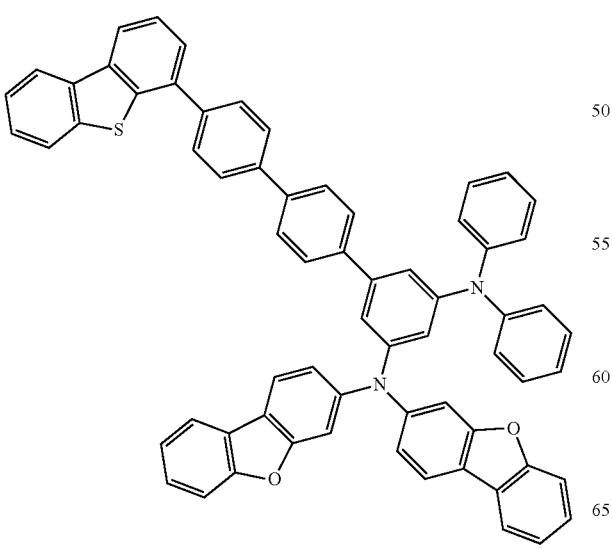
P-11
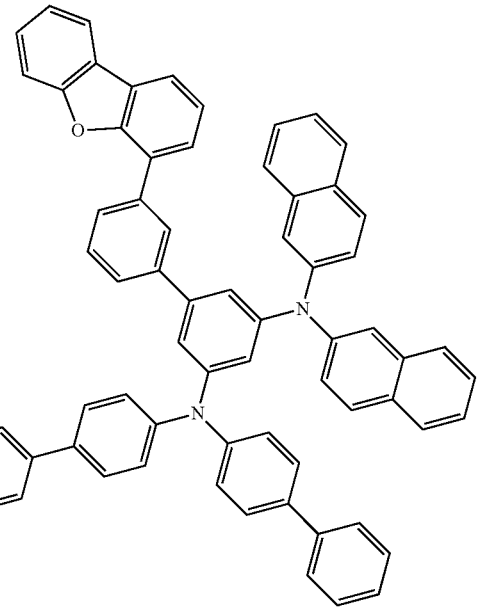
P-12
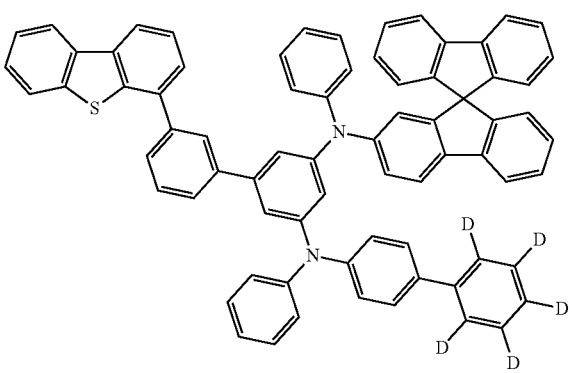
P-13
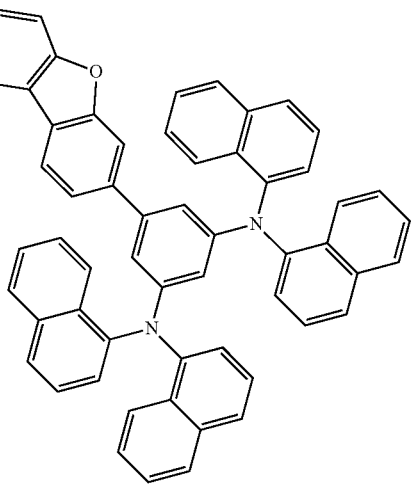

P-14
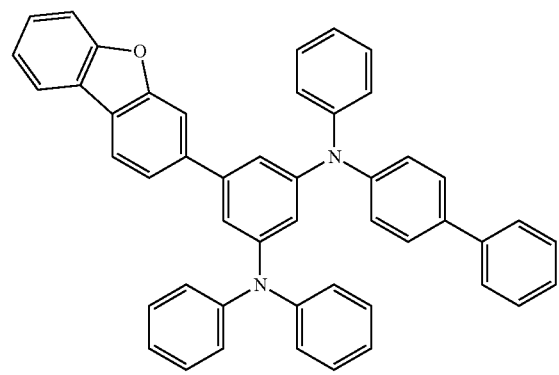
P-15
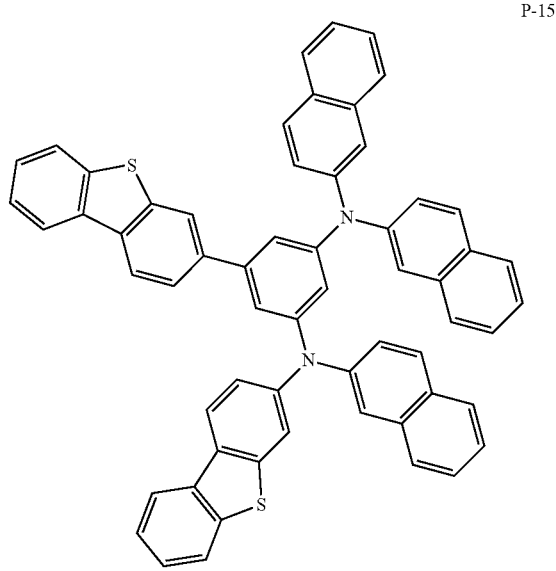
P-16
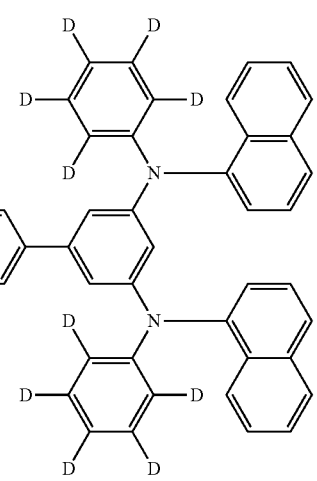
P-17
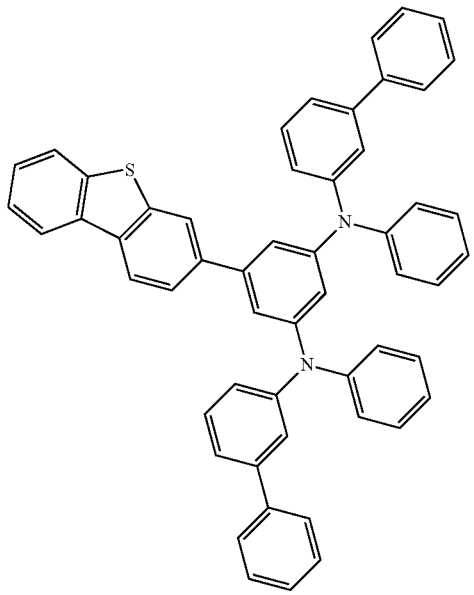
P-18
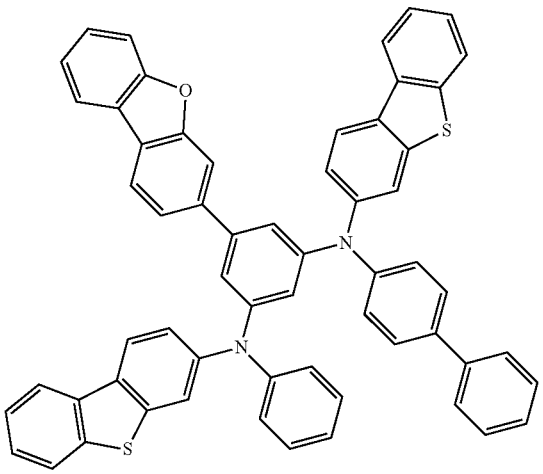
P-19
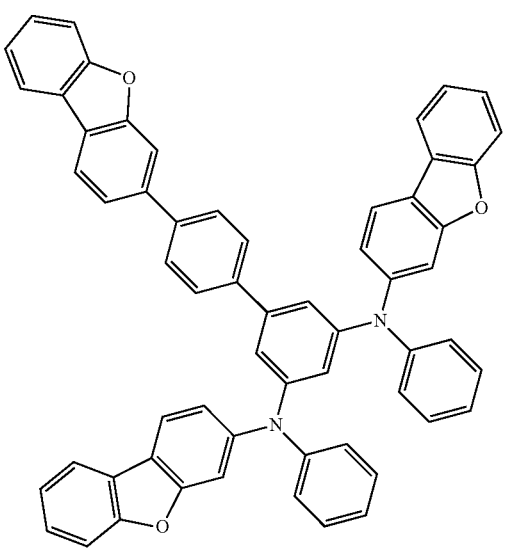

P-20
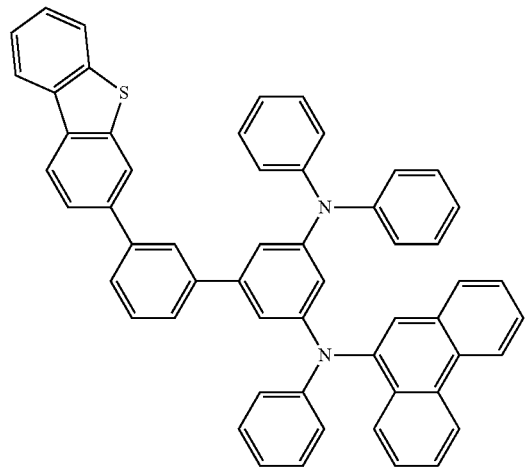
P-21
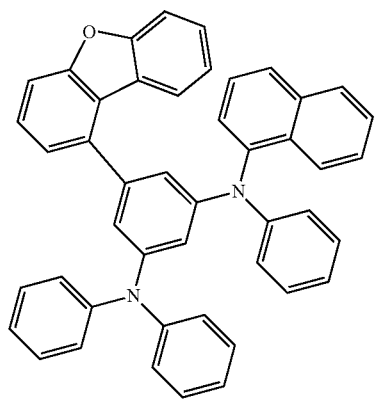
P-22
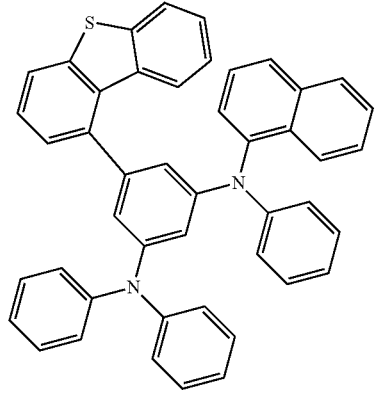
P-23
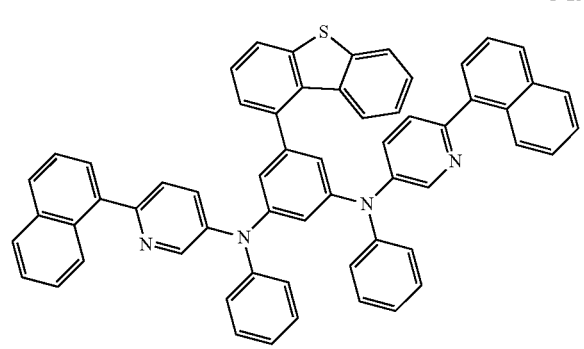
P-24
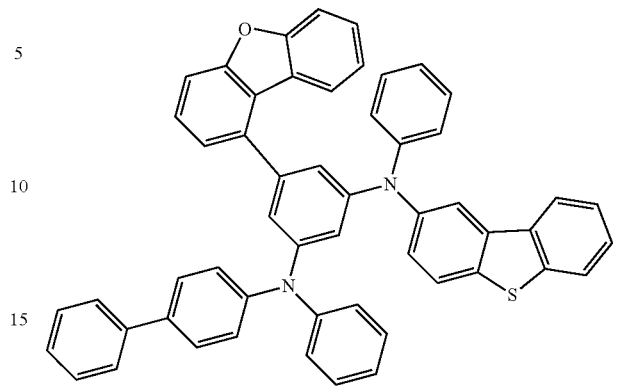
P-25
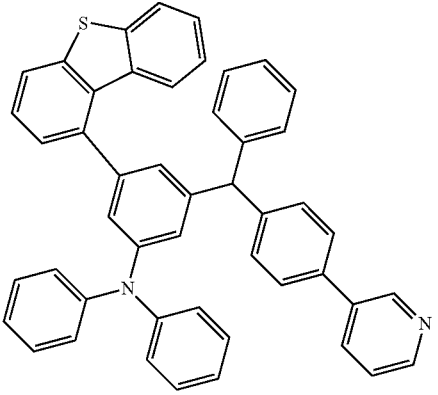
P-26
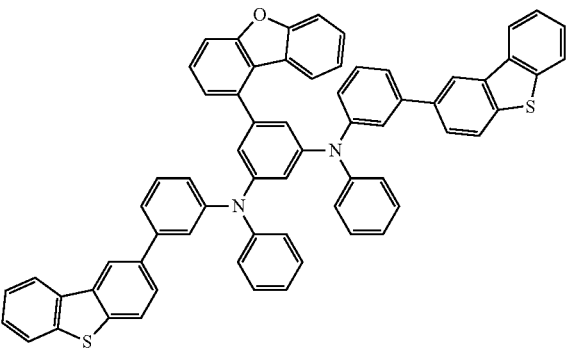

P-27
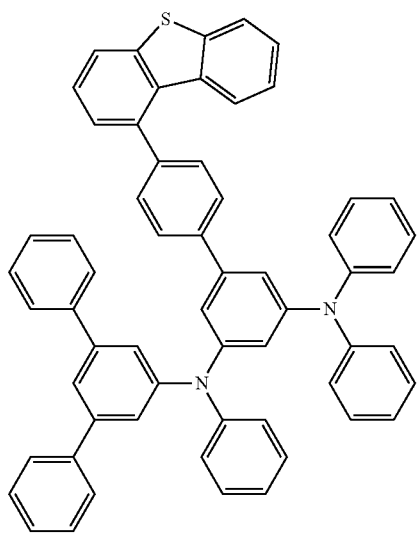
P-28
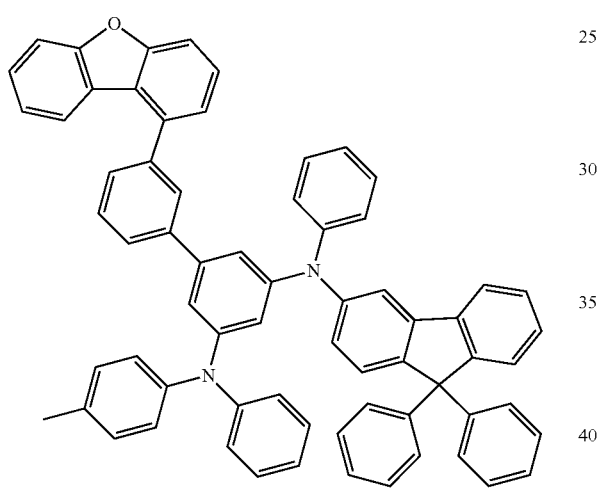
P-29
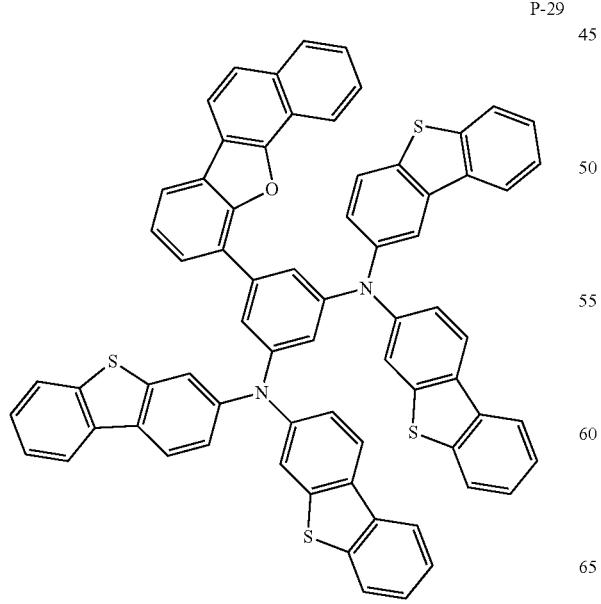
P-30
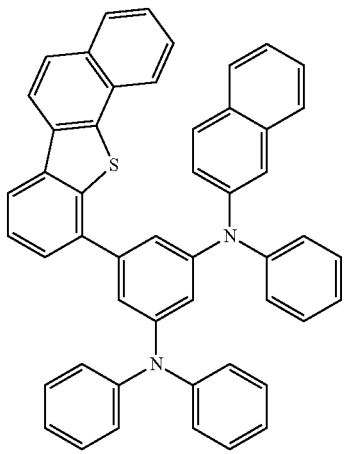
P-31
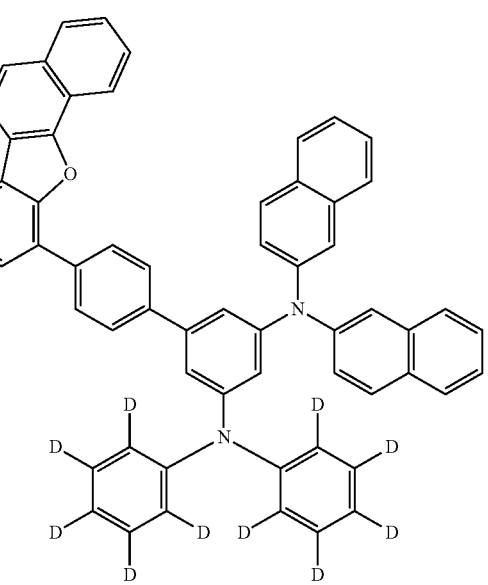

P-32
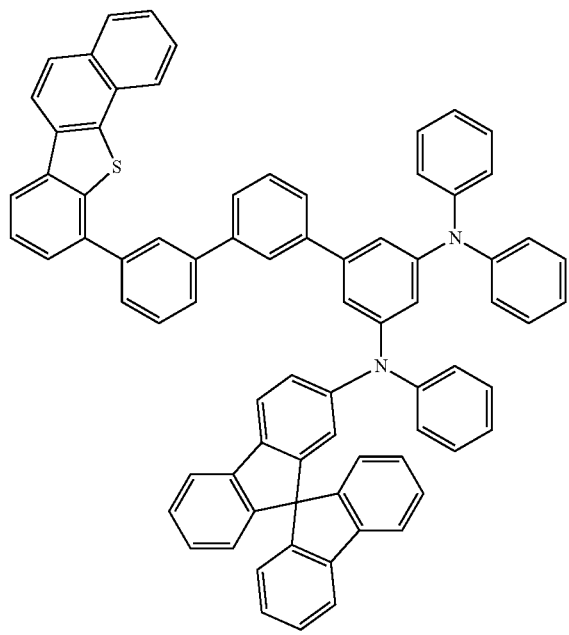
P-33
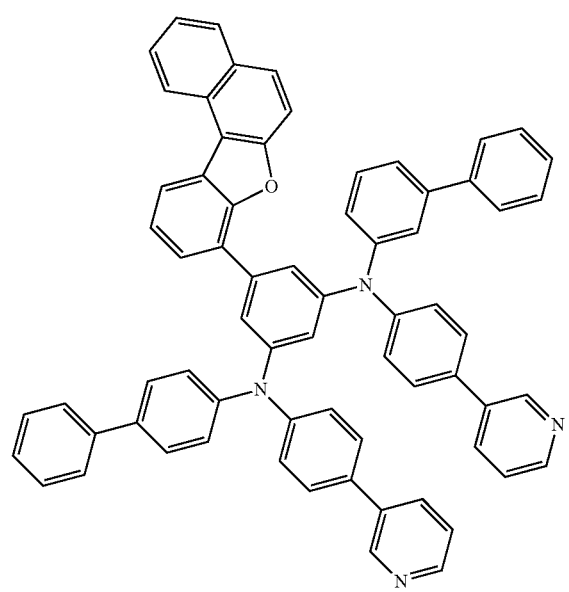
P-34
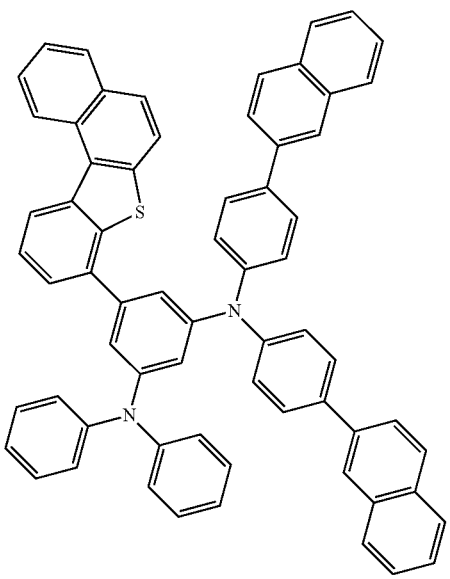
P-35
[structure shown mid-page right column]
P-36
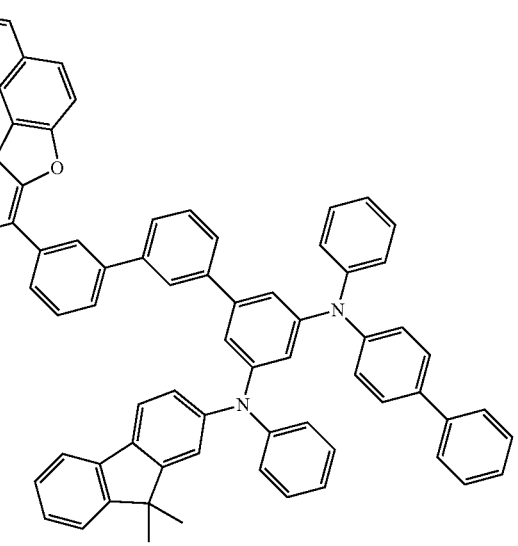

P-37
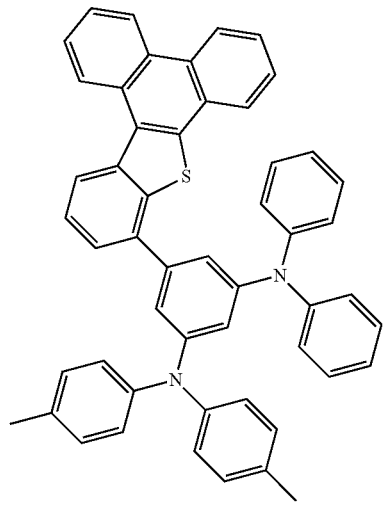
P-40
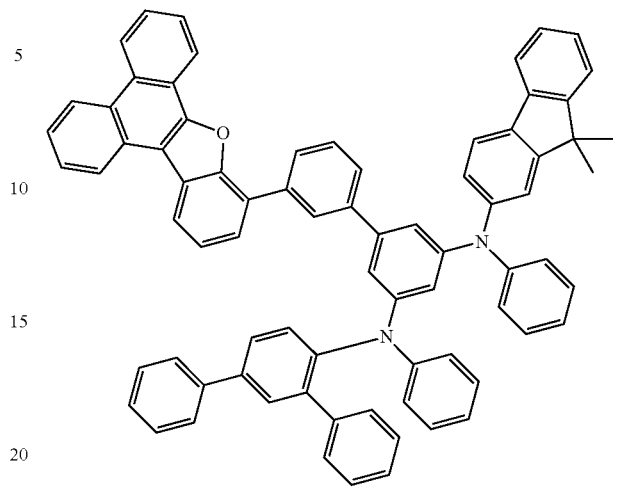
P-38
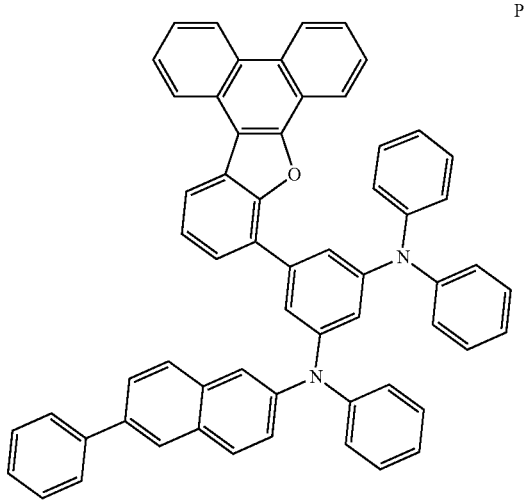
P-41
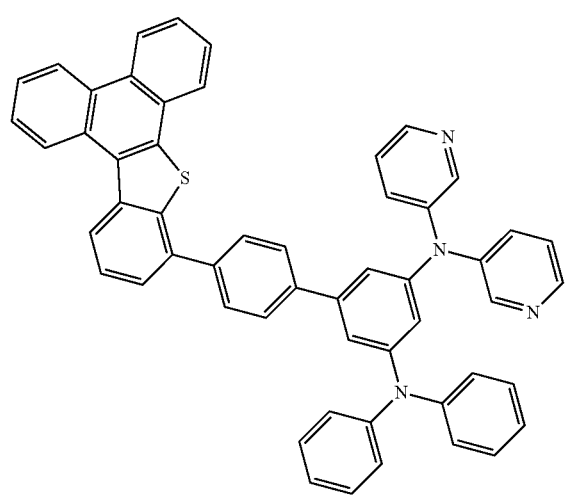
P-39
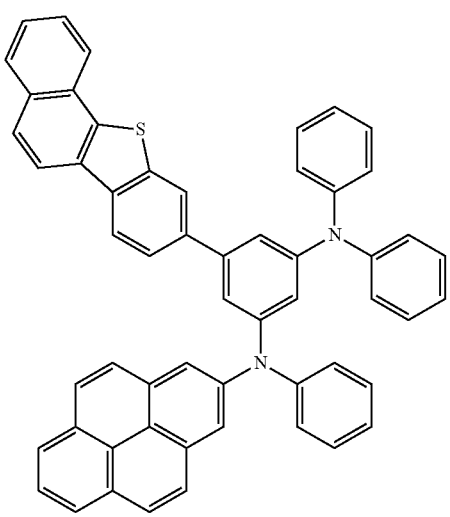
P-42

-continued
P-43
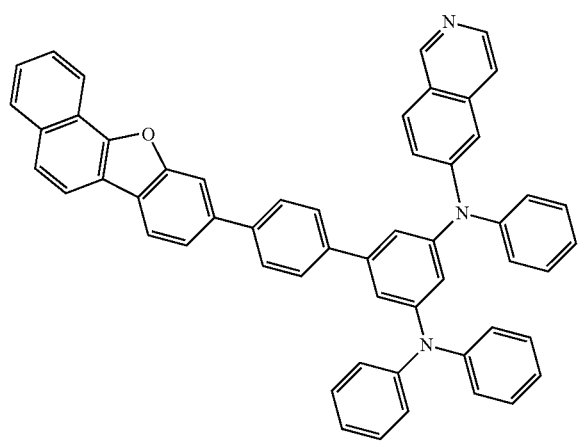
P-44
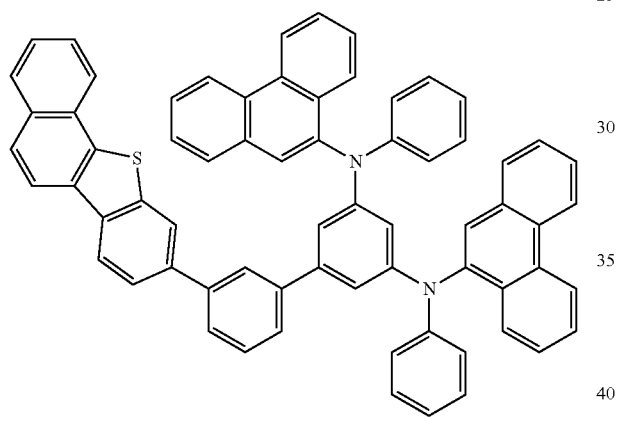
P-45
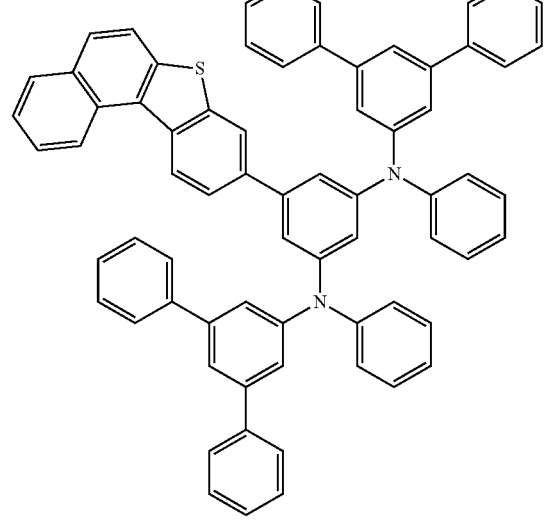
-continued
P-46
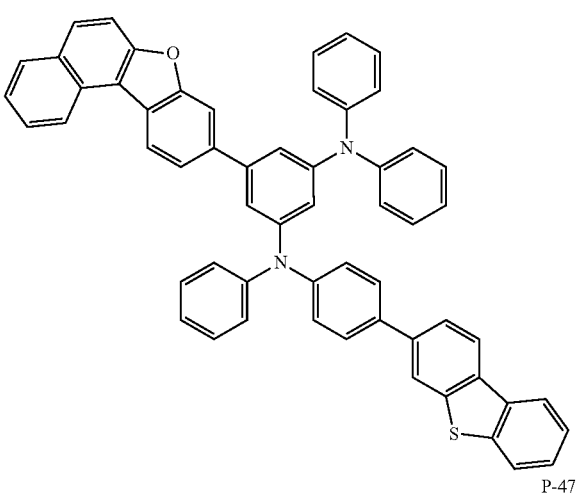
P-47
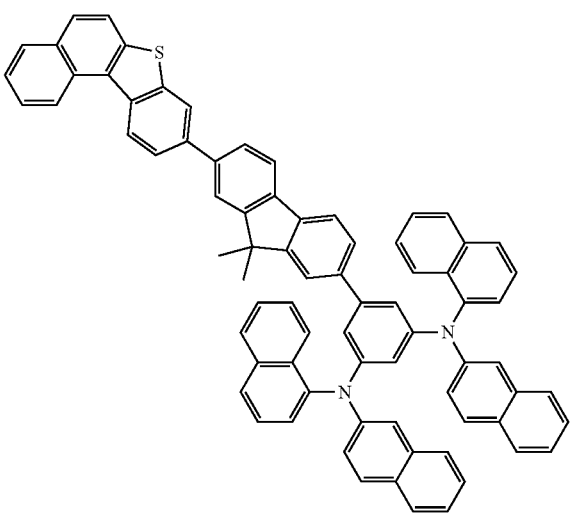
P-48
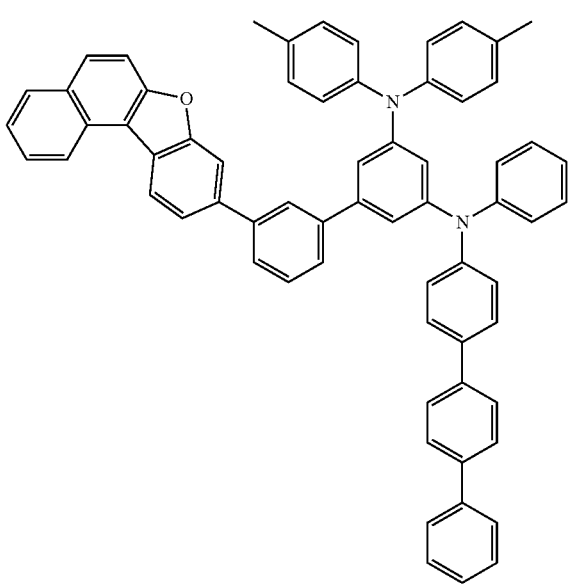

P-49
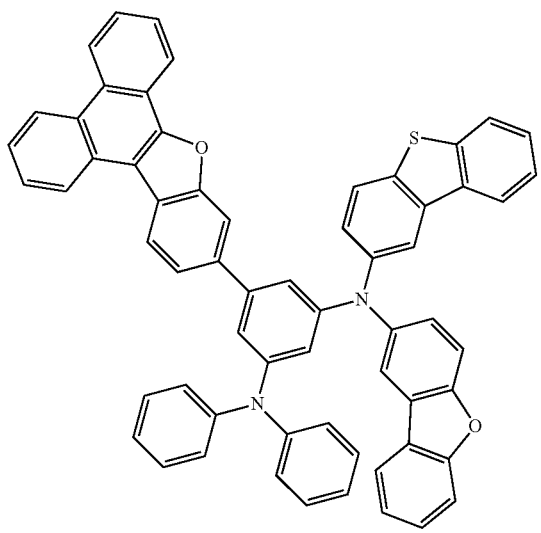
P-51
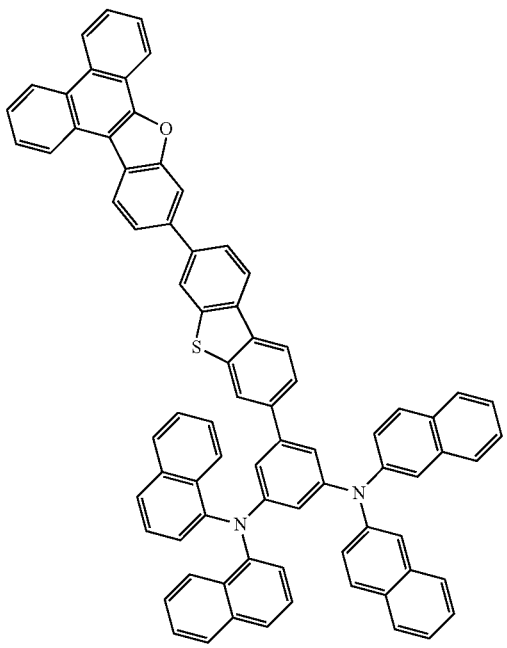
P-50
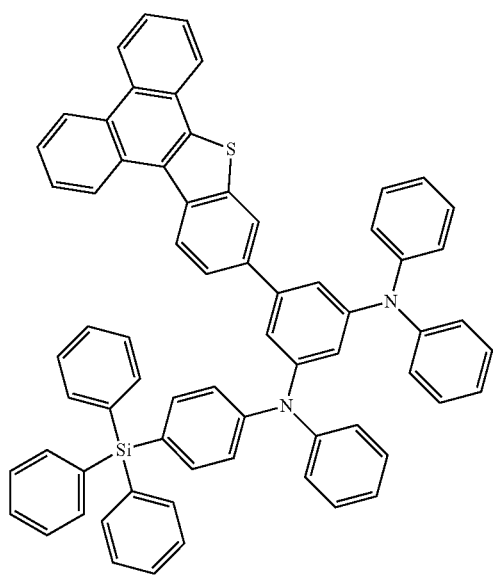
P-52
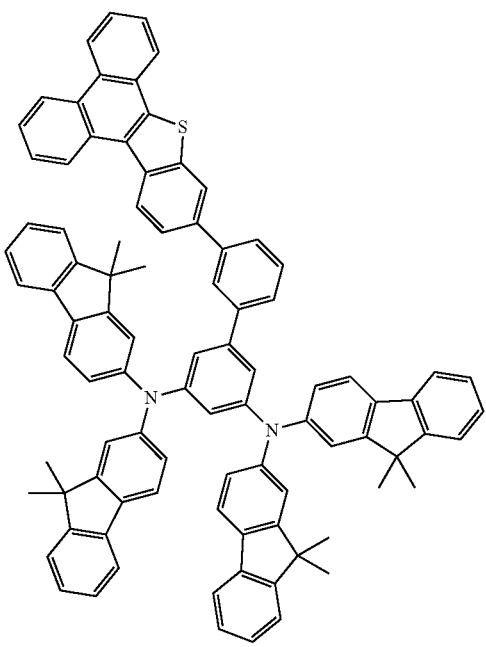

P-53
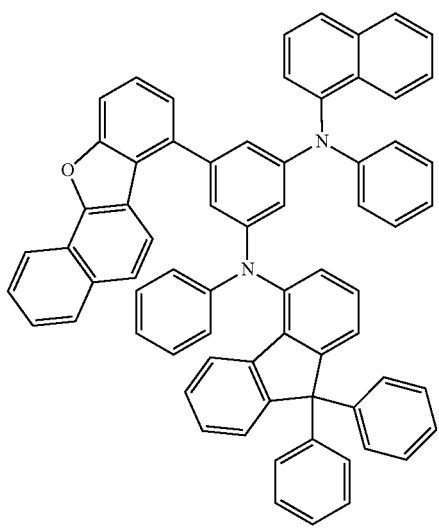
P-56
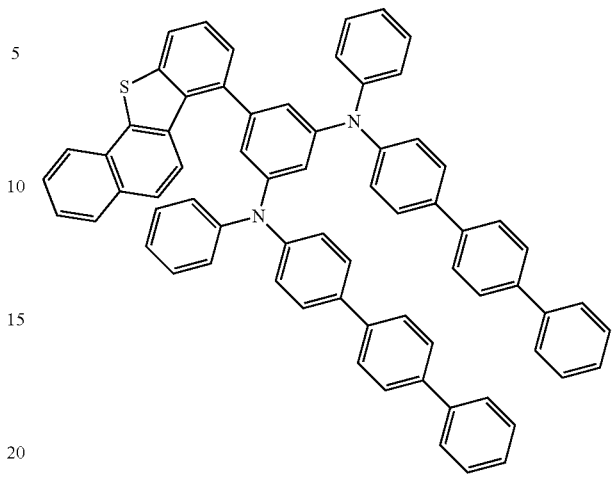
P-54
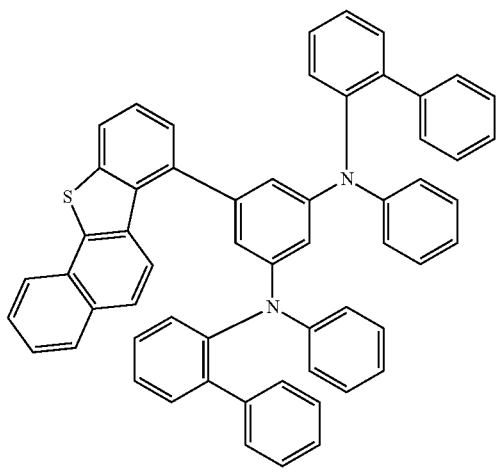
P-57
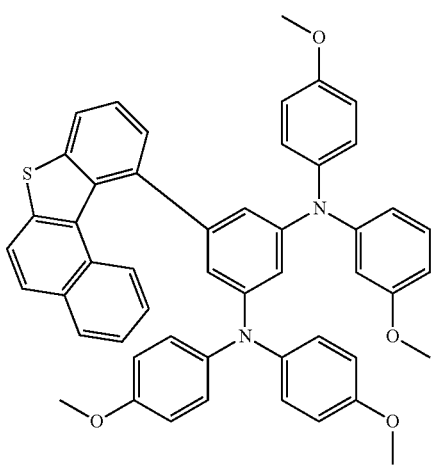
P-55
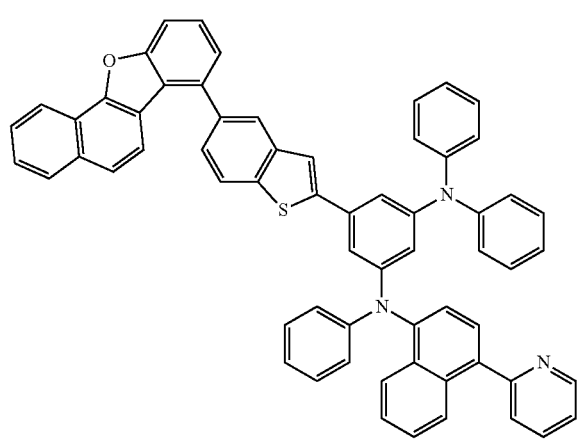
P-58
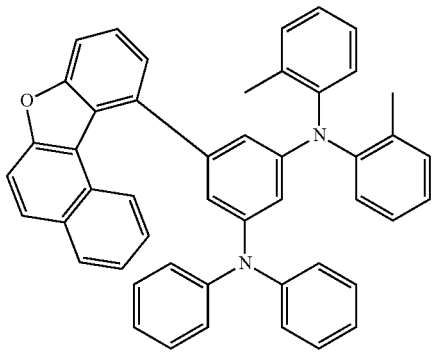

-continued
P-59
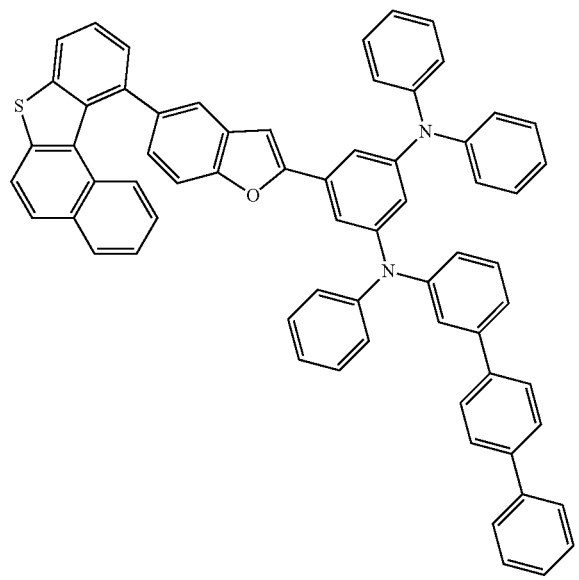
P-60
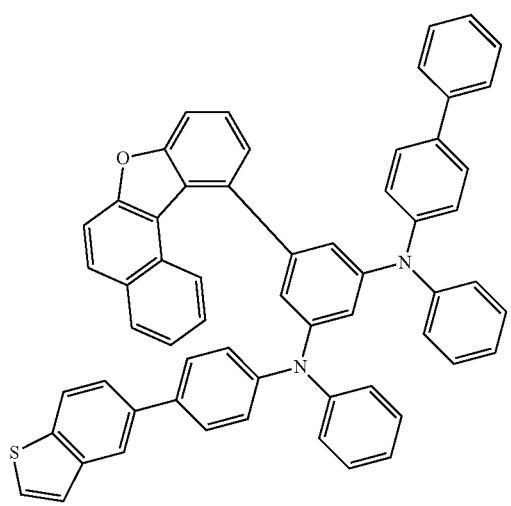
P-61
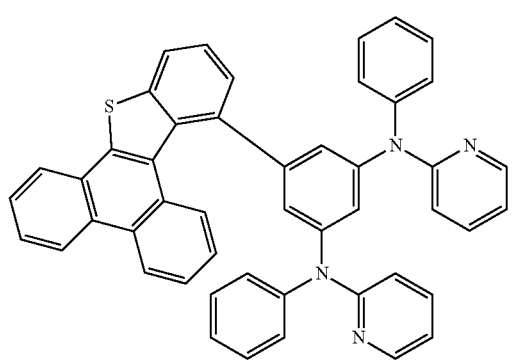
-continued
P-62
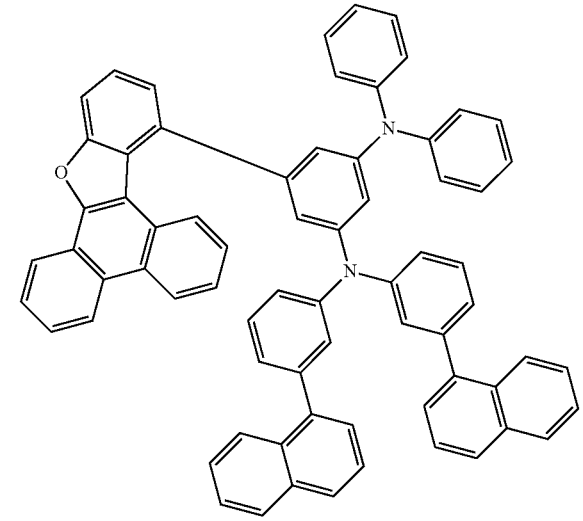
P-63
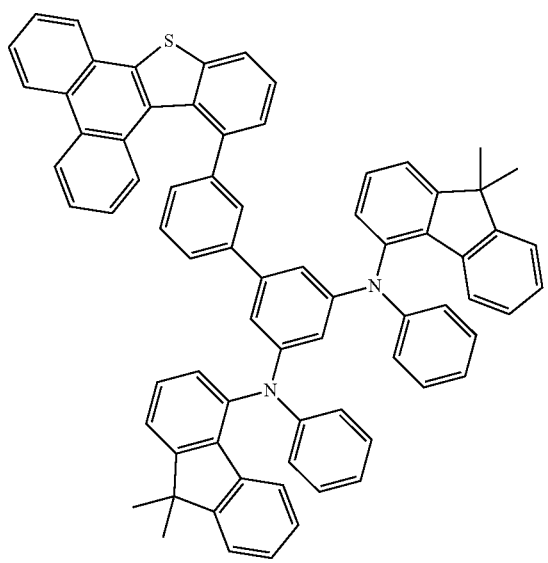
P-64
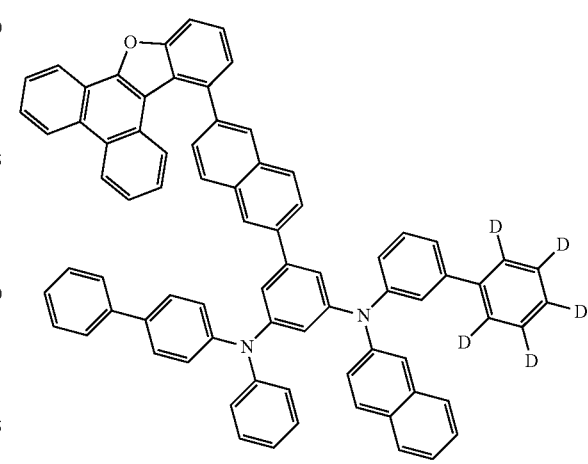

P-65
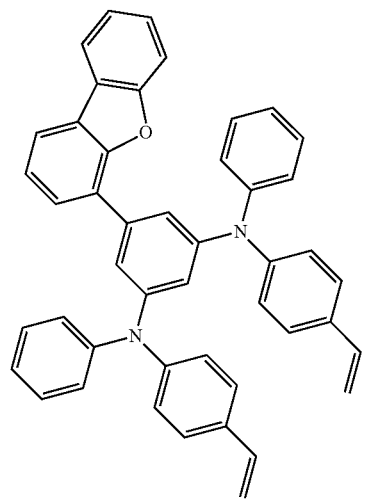
P-66
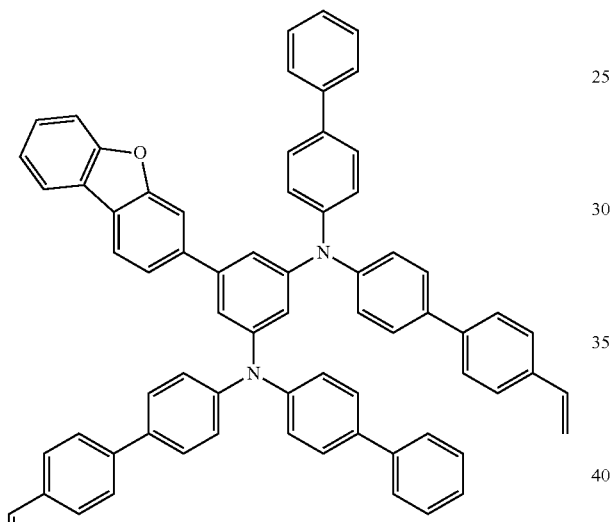
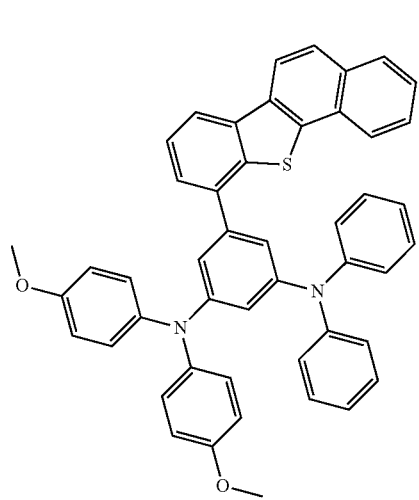
P-68
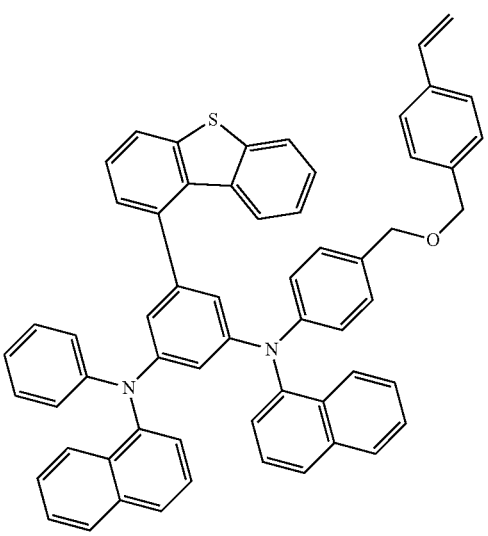
P-69
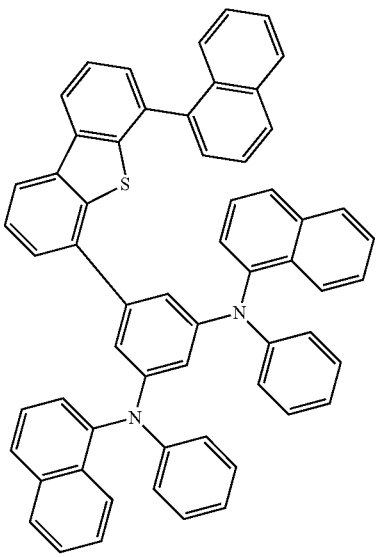
P-70
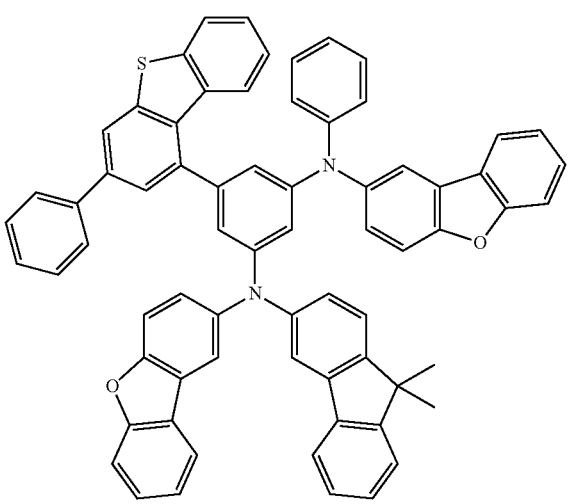

-continued
P-71
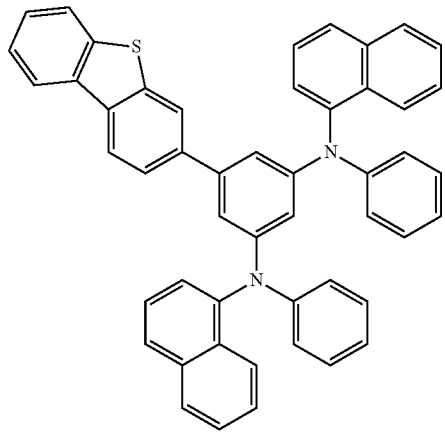
P-74
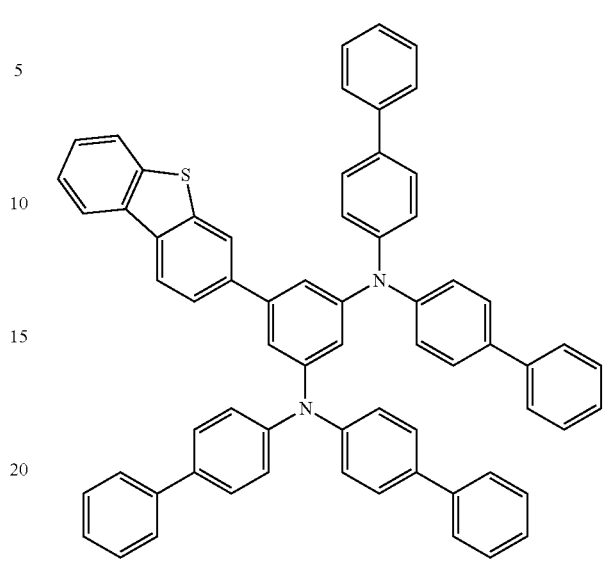
P-72
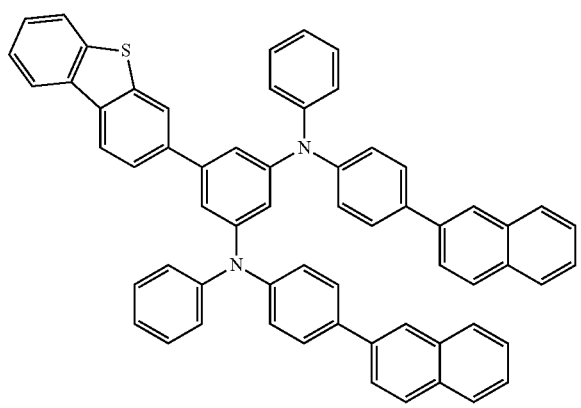
P-75
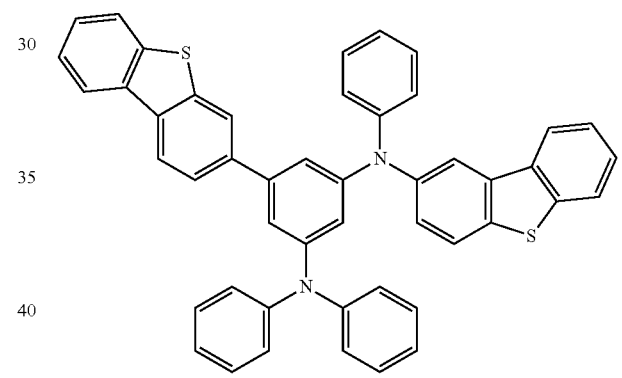
P-73
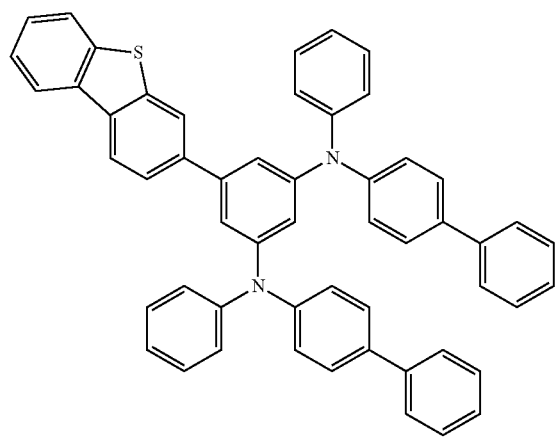
P-76
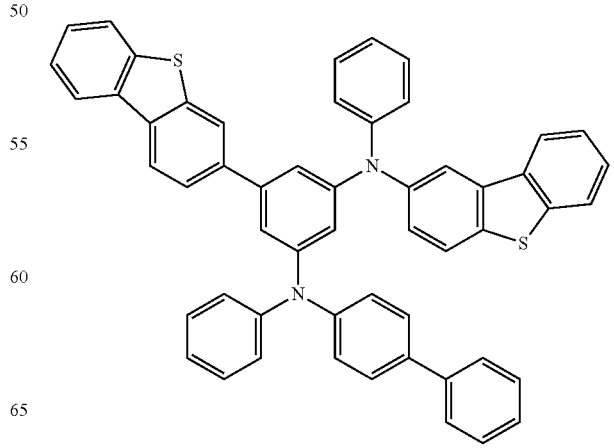

P-77
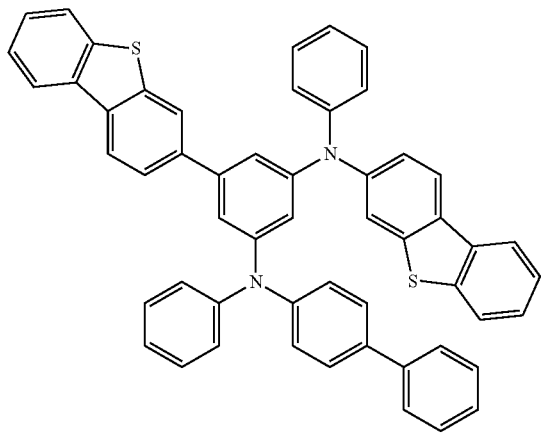
P-80
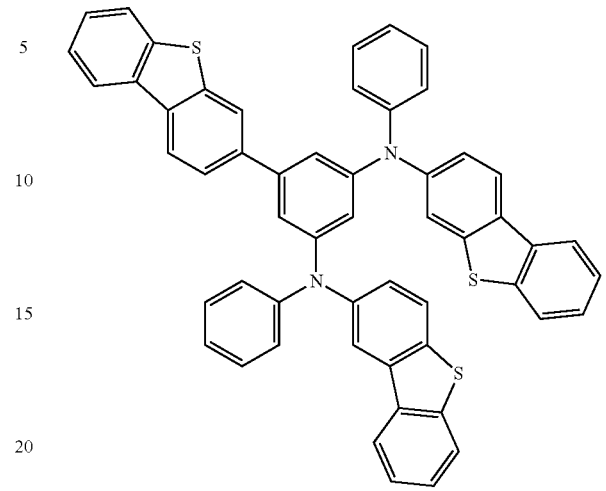
P-78
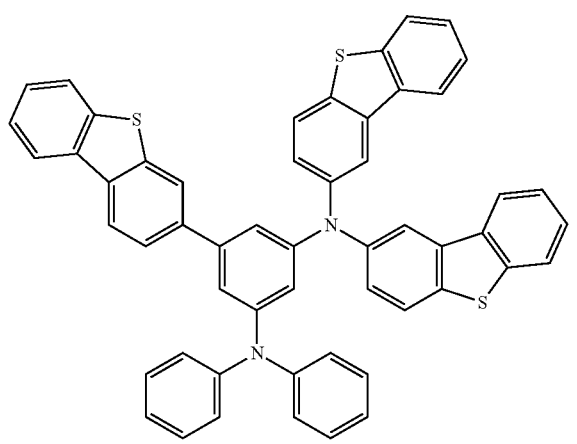
P-81
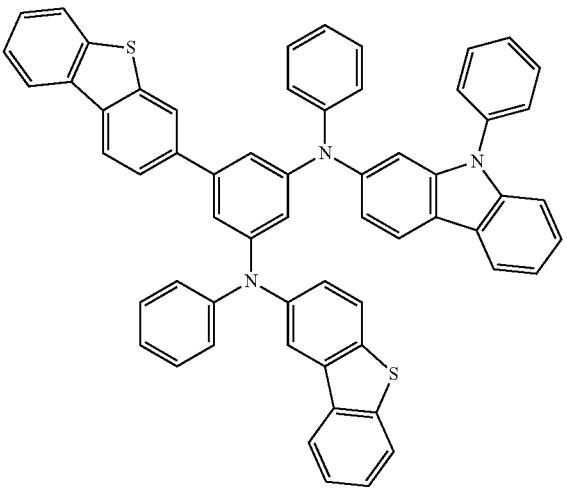
P-79
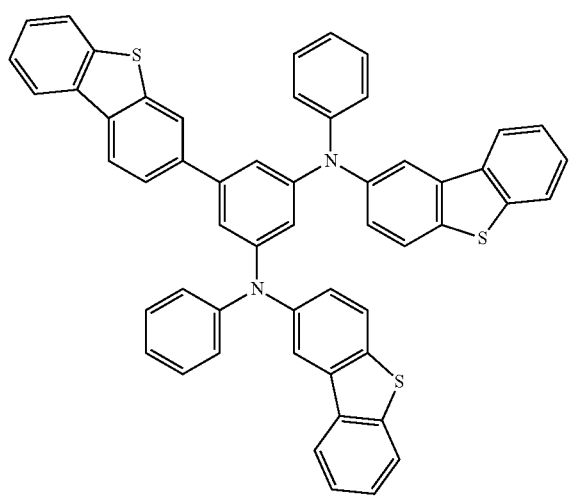
P-82
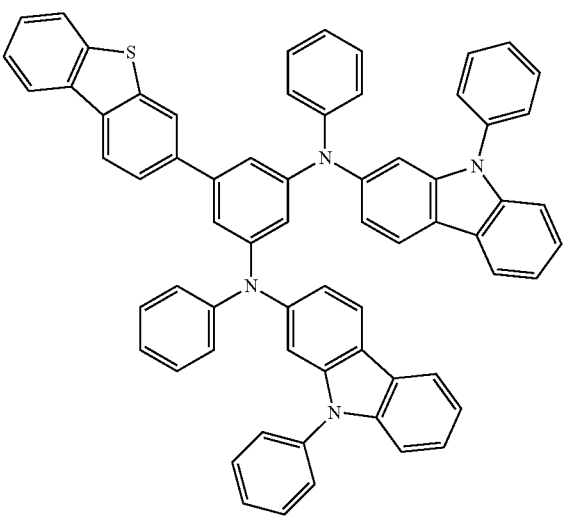

-continued
P-83
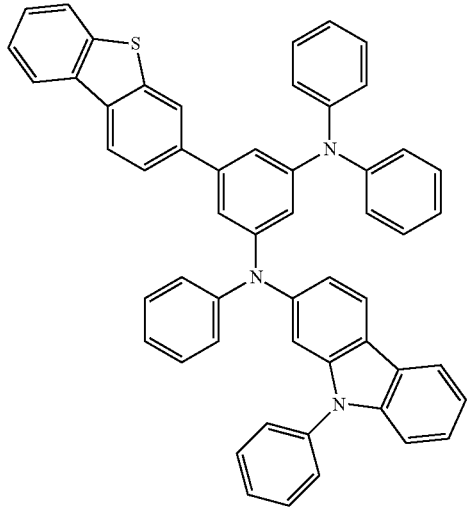
P-84
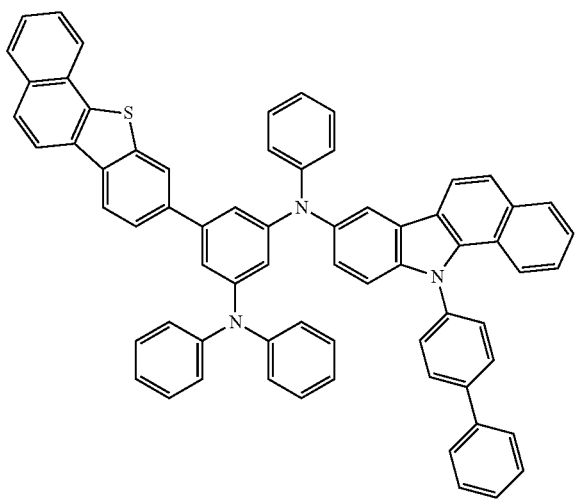
P-85
P-86
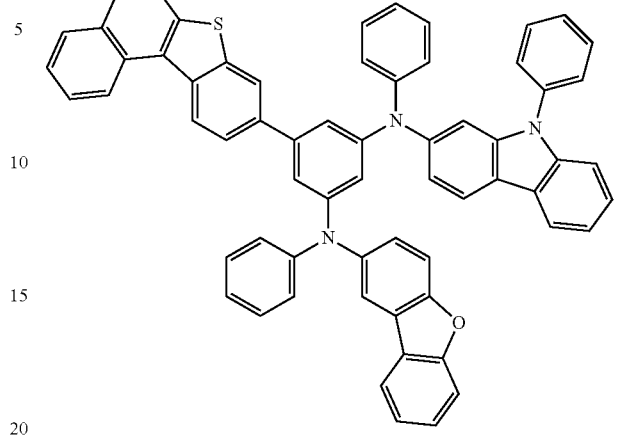
P-87
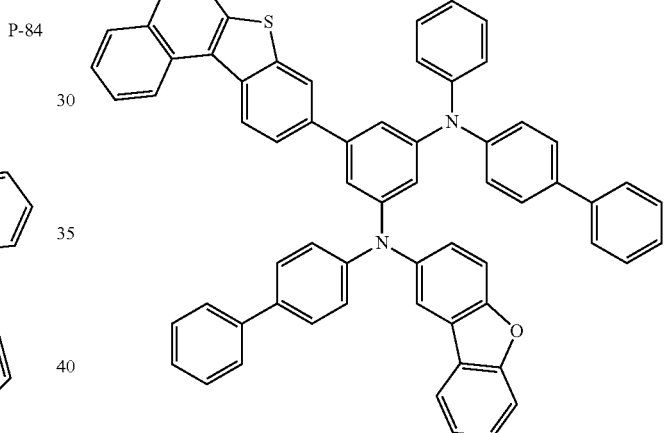
P-88
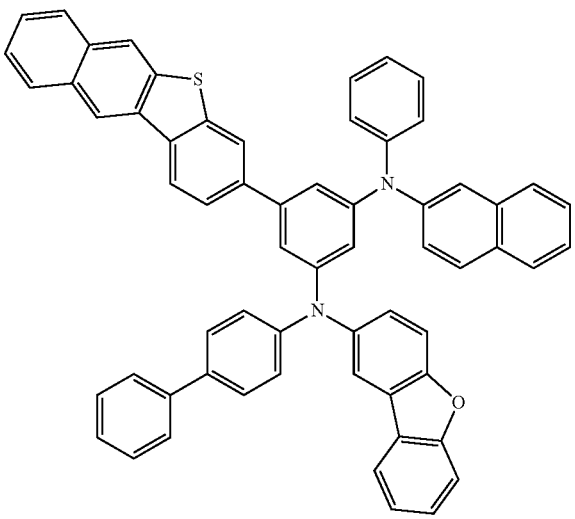

P-89
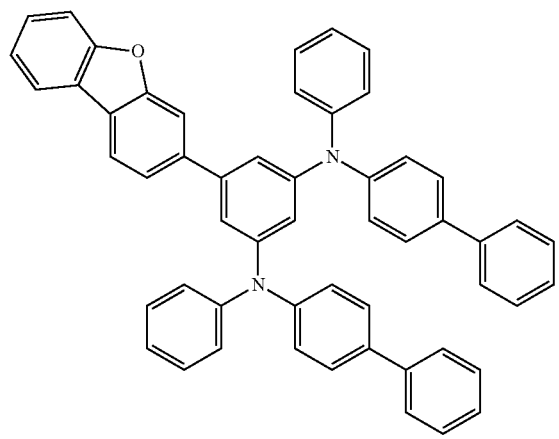
P-90
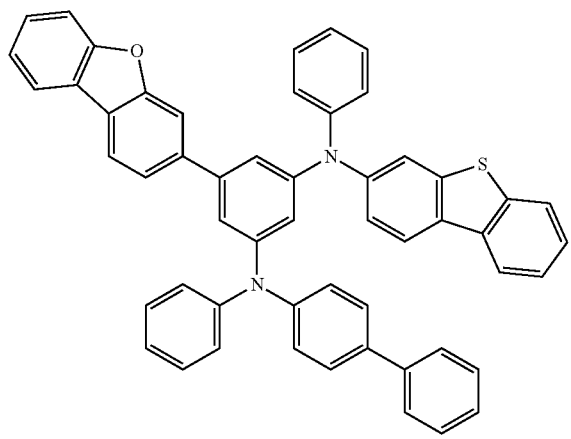
P-91
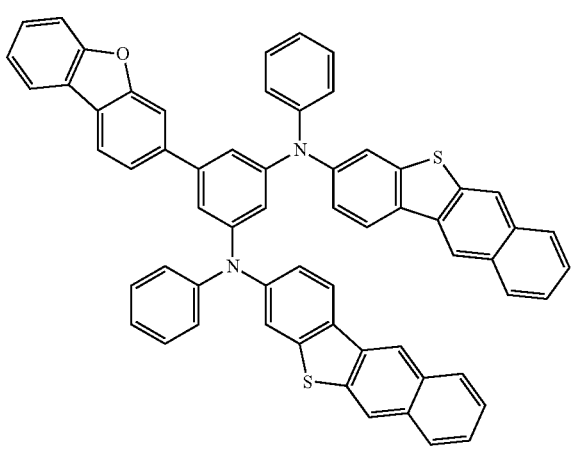
P-92
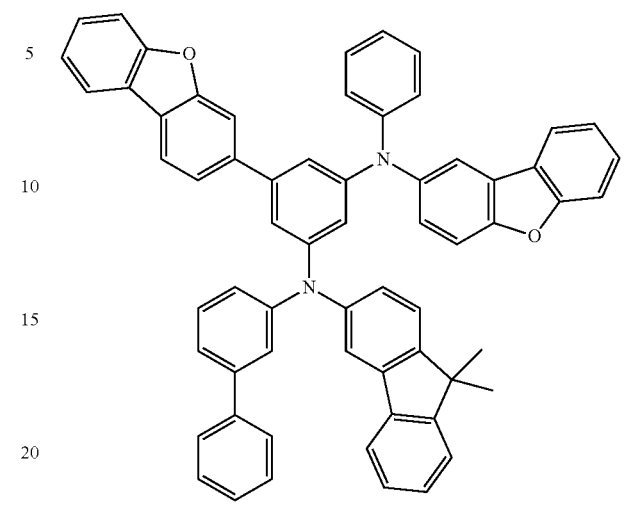
P-93
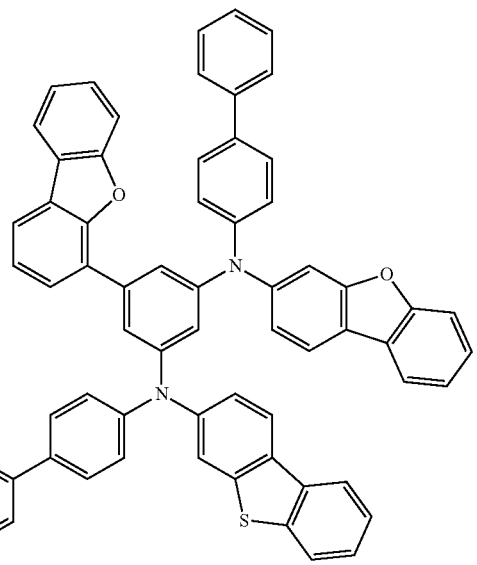
P-94
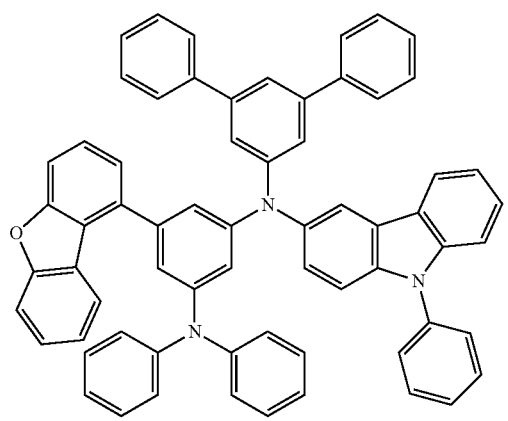

P-95
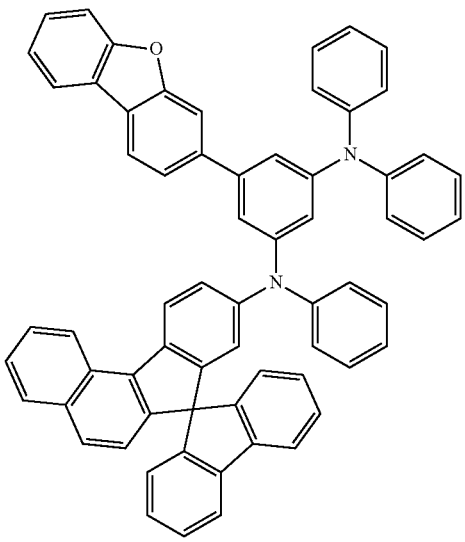
P-96
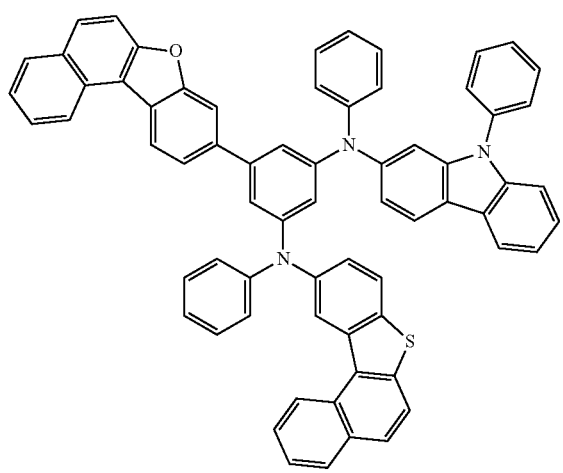
P-97
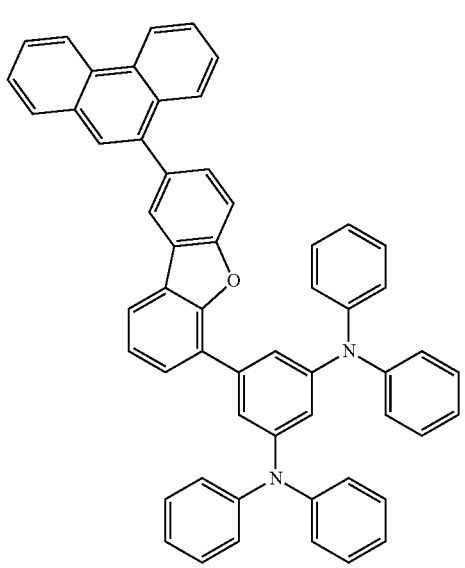
P-98
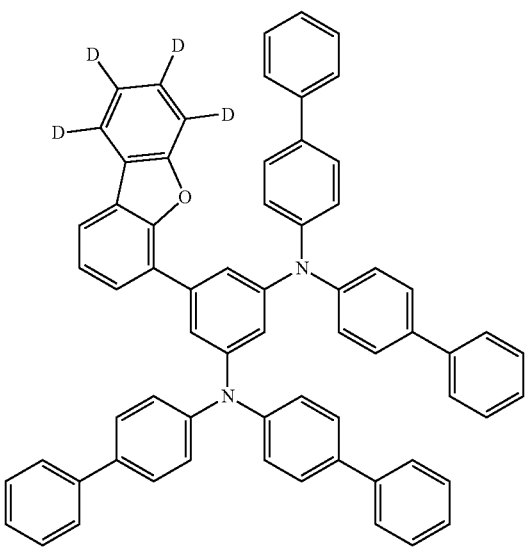
P-99
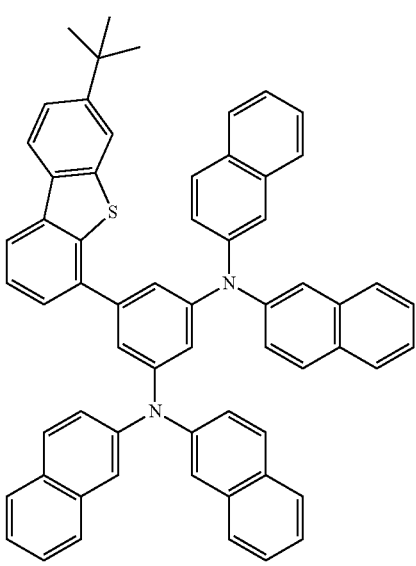

P-100
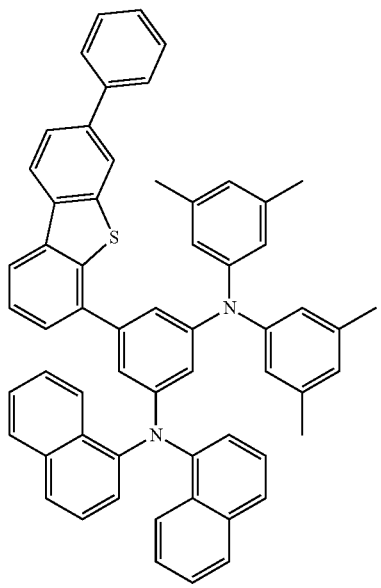
P-101
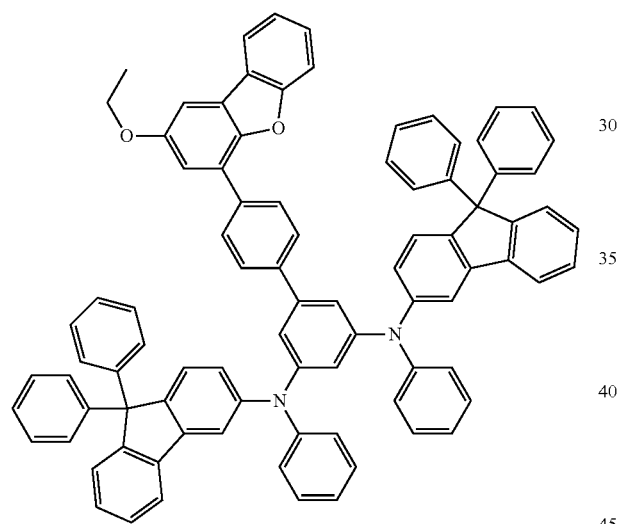
P-102
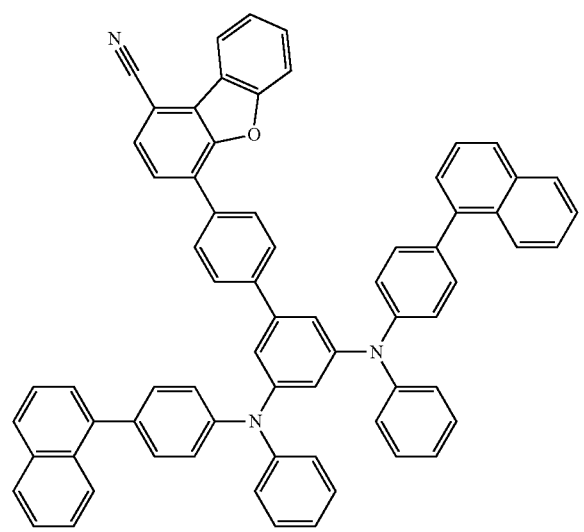
P-103
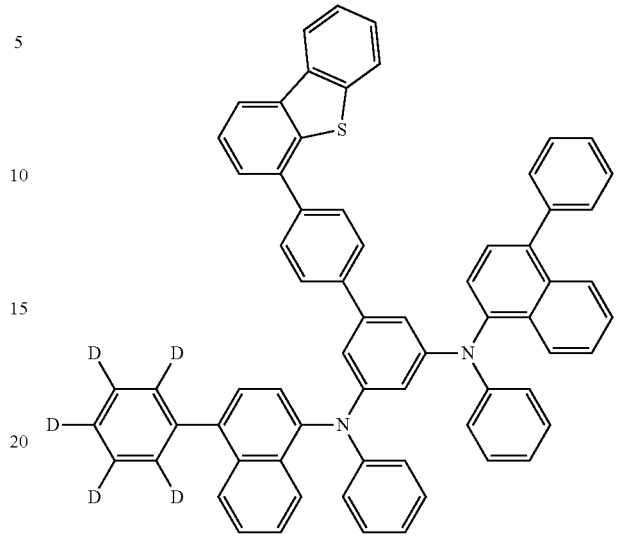
P-104
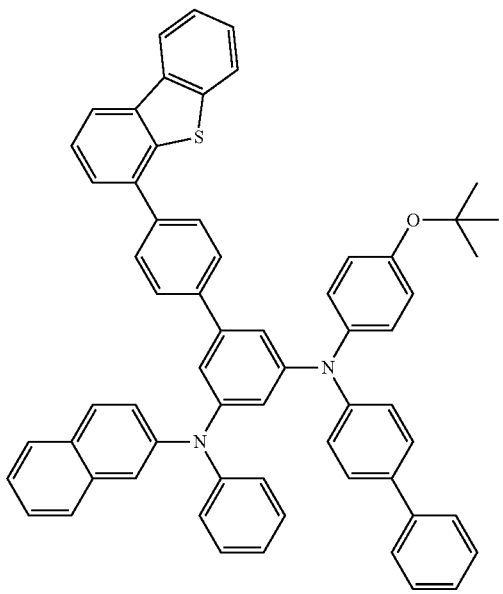
P-105
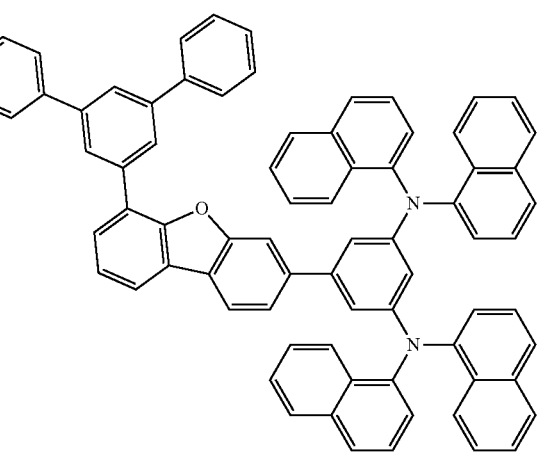

P-106
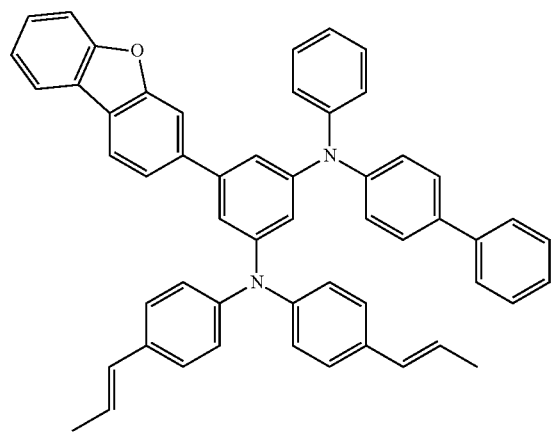
P-107
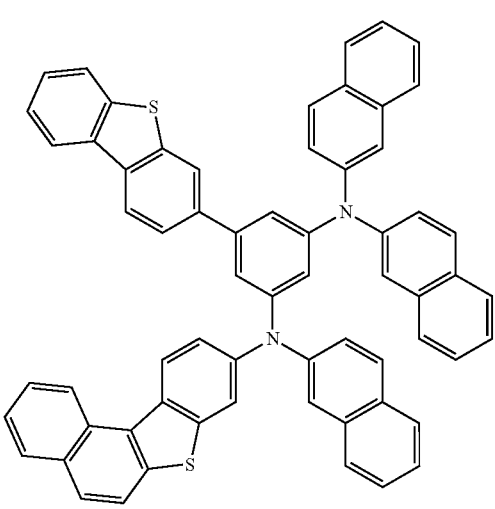
P-108
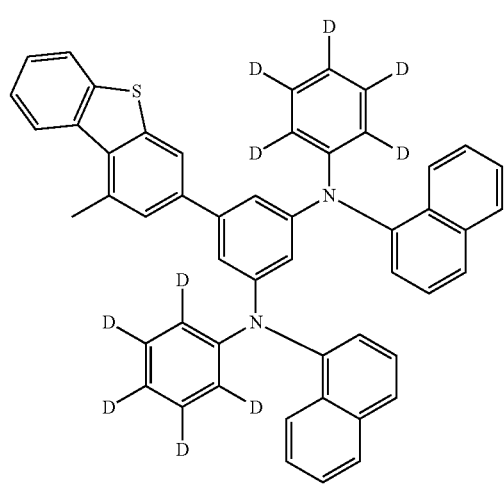
P-109
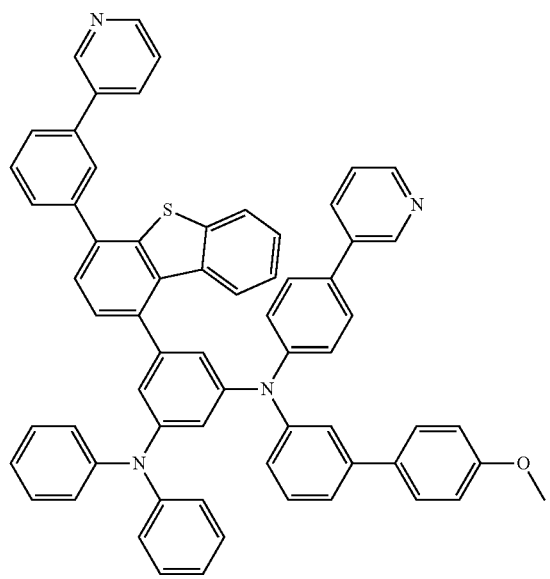
P-110
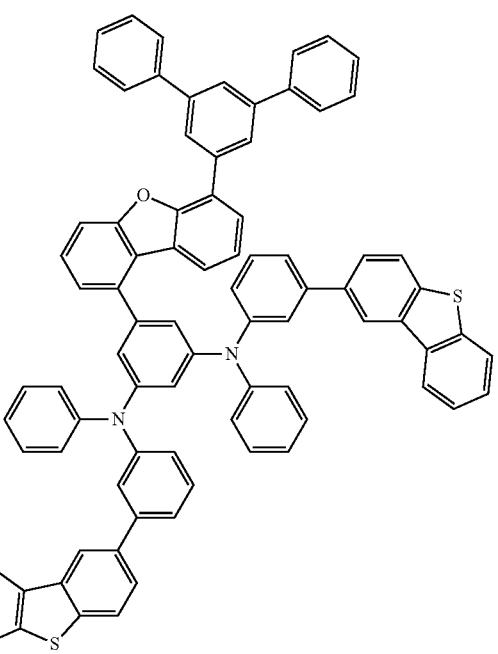

P-111
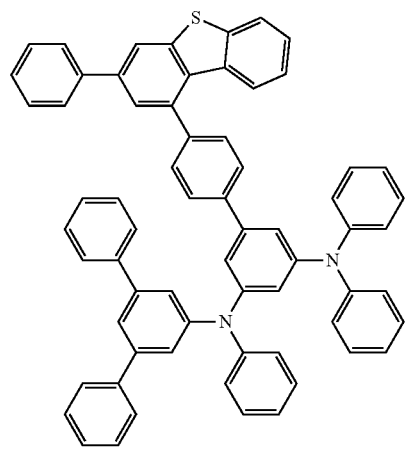
P-112
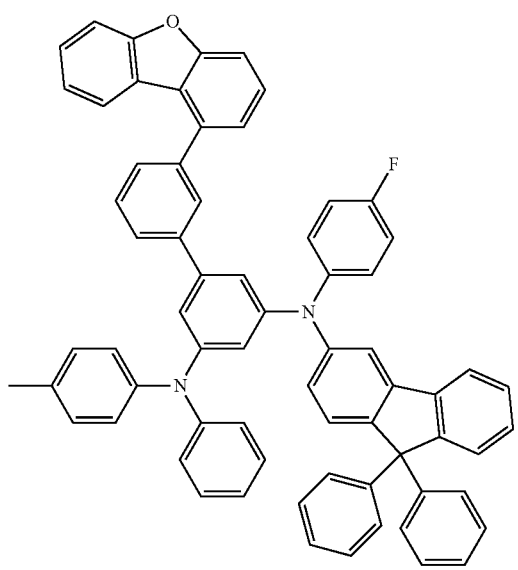
P-113
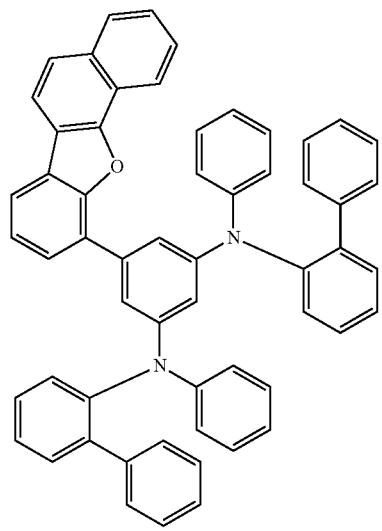
P-114
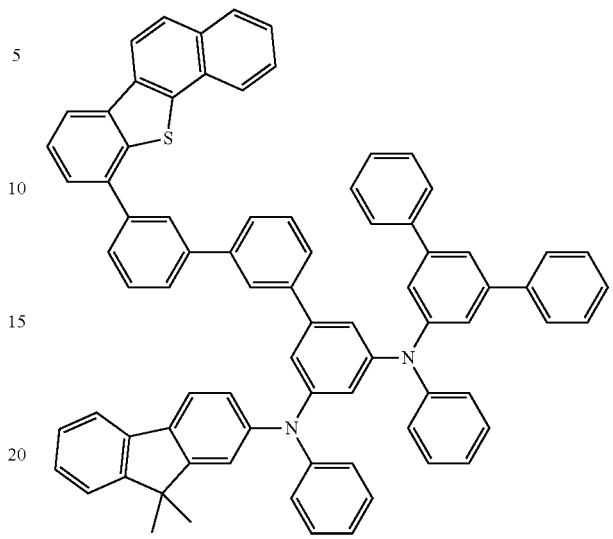
P-115
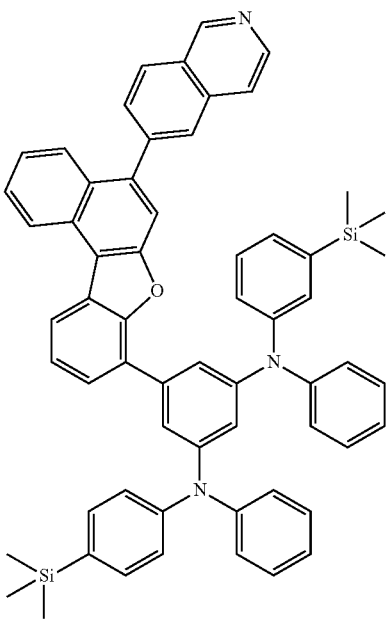

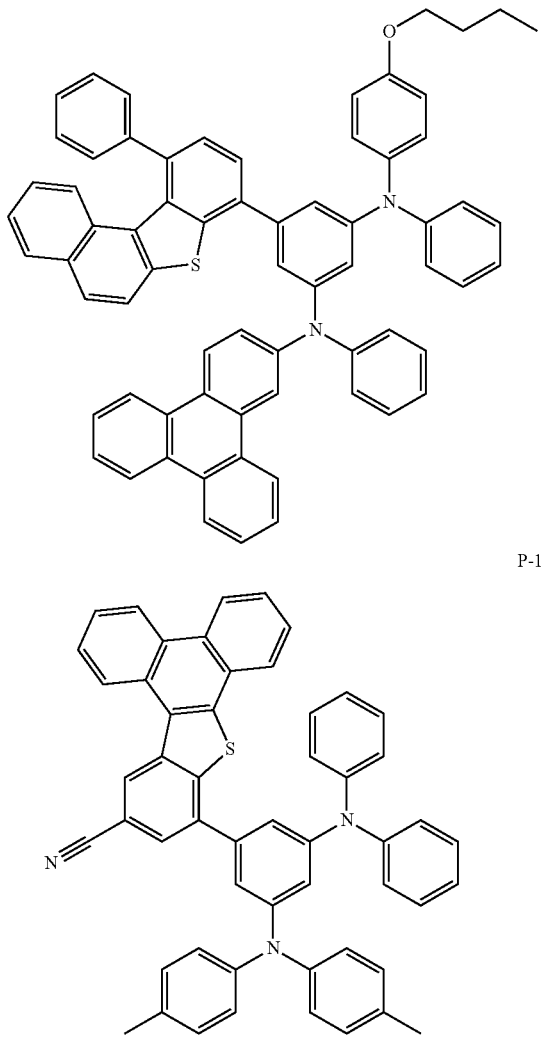
P-116
P-117
P-118
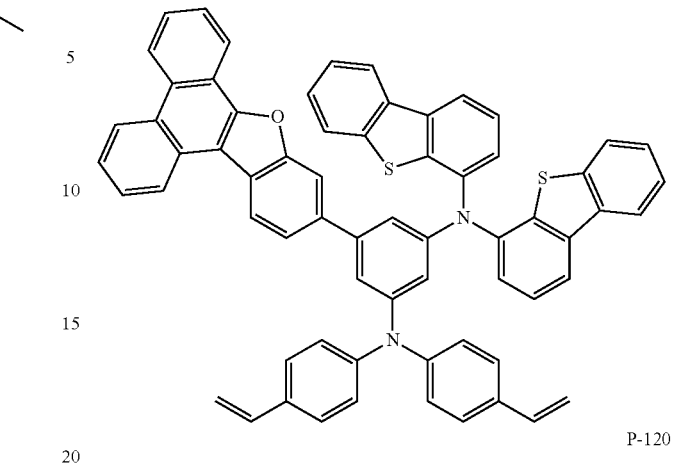
P-119
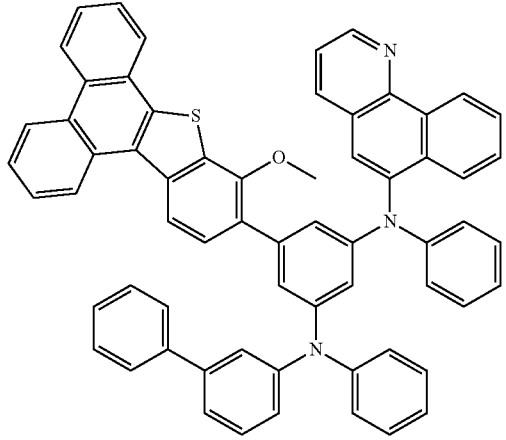
P-120
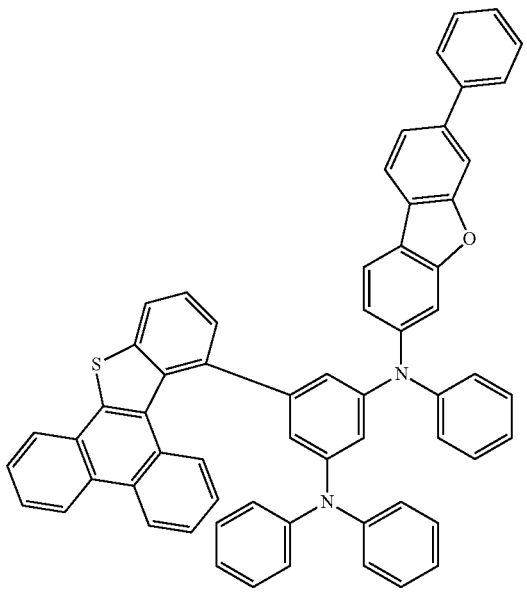
P-121

P-122

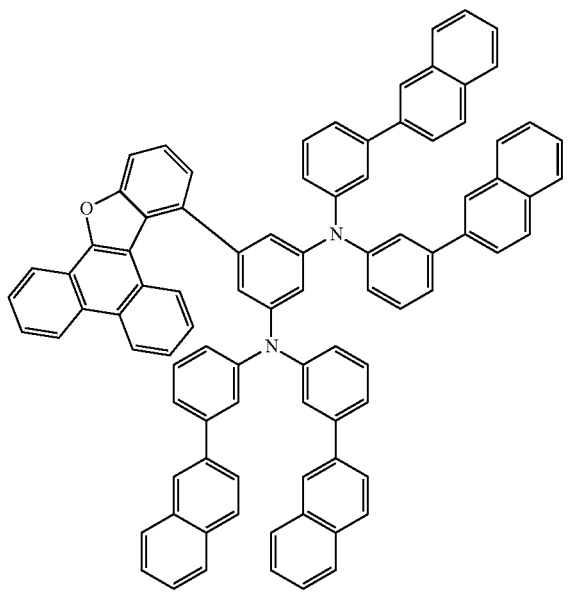

P-124

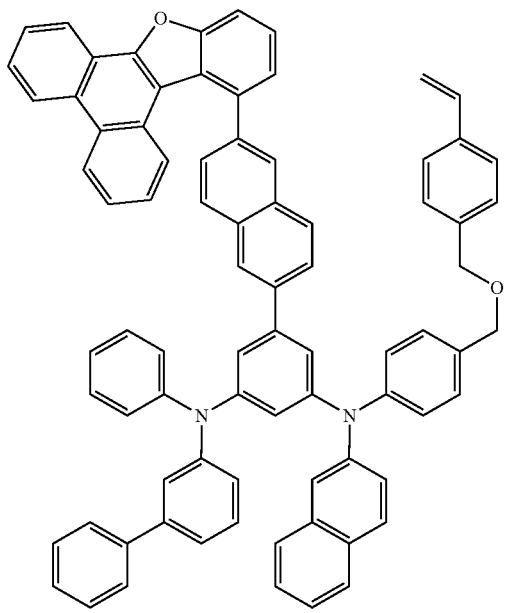

P-123

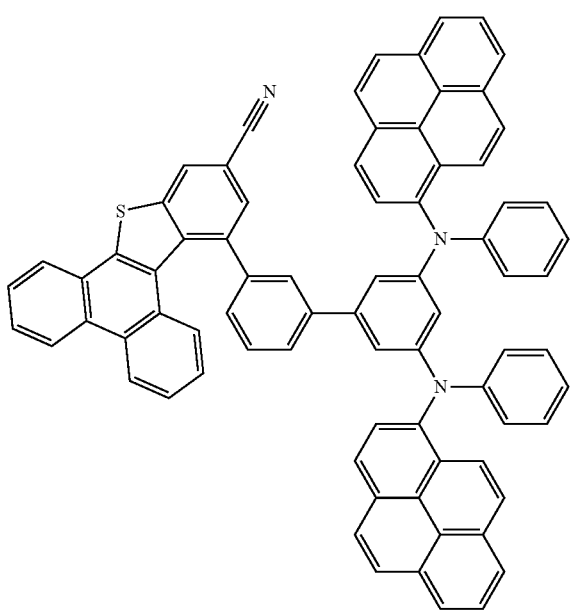

In another aspect of the present invention, the present invention provides an organic electric element comprising a first electrode, a second electrode, and an organic material layer formed between the first electrode and the second electrode. The organic material layer may comprise at least one layer of a hole injection layer, a hole transport layer, an emission-auxiliary layer, a light emitting layer, an electron transport-auxiliary layer, an electron transport layer and an electron injection layer, and at least one compound of the above compounds may be comprised in the organic material layer. That is, the organic material layer may be formed as a single compound or a mixture of two or more kinds represented by Formula 1.

Hereinafter, Synthesis method of the compound represented by Formula 1 according to one embodiment of the present invention and Preparation method of an organic electric element will be described in detail by way of examples. However, the present invention is not limited to the following examples.

Synthesis Example

The compound (final products) represented by Formula 1 according to the present invention are synthesized by reacting Sub 1 and Sub 2 as shown in Reaction Scheme 1, but are not limited thereto.

Reaction Scheme 1
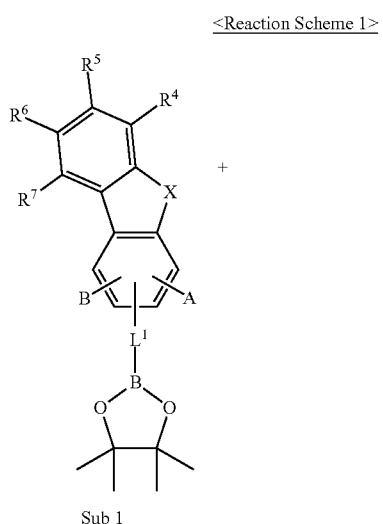
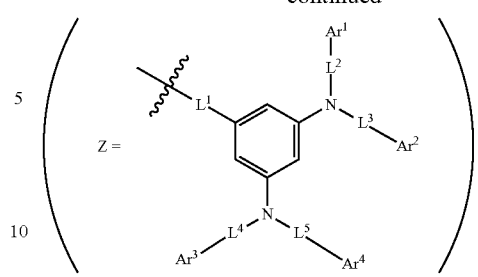
X, $R^1$ to $R^7$, $Ar^1$ to $Ar^4$, and $L^1$ to $L^5$ are the same as defined in the Formula 1 and the Formula 2. A, B, and Z are each independently selected from $R^1$ to $R^3$, they may be different each other.
I. Synthesis of Sub 1
Sub 1 of the Reaction Scheme 1 can be synthesized according to, but not limited to, the following Reaction Schemes 2 to 5.
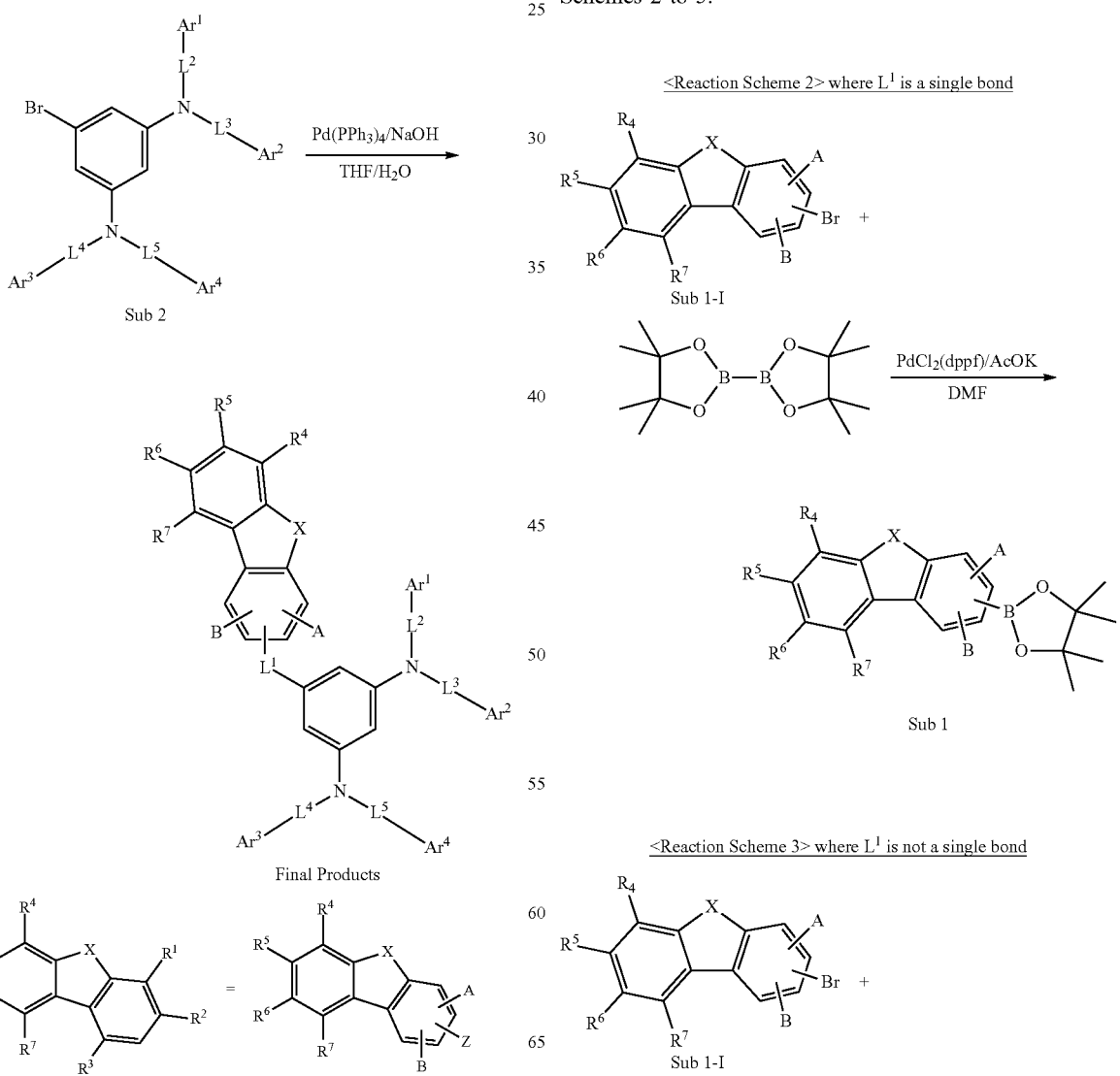

-continued

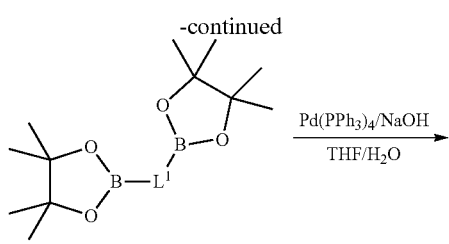

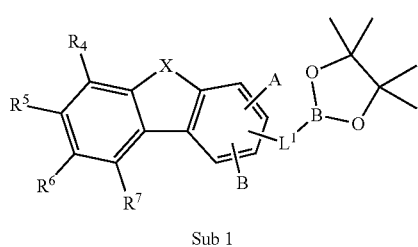

<Reaction Scheme 4> where X is S

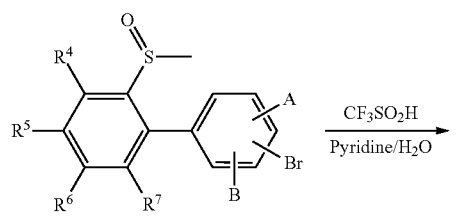

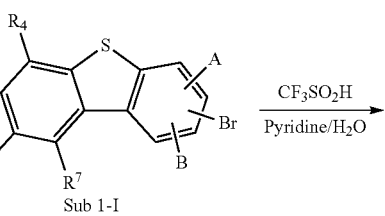

Sub 1-I

<Reaction Scheme 5> where X is O

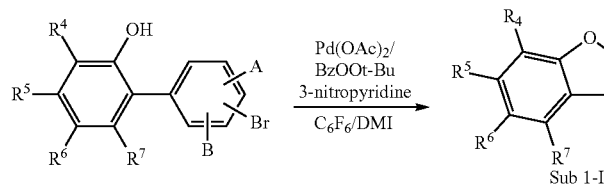

Synthesis Examples of compounds comprised in Sub 1 are as follows.

1. Synthesis Examples of Sub 1-1

<Reaction Scheme 6>

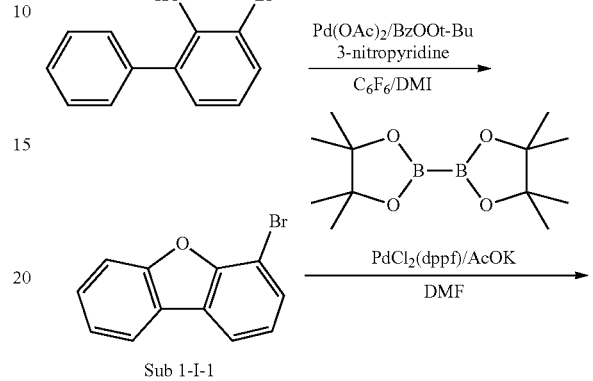

Sub 1-I-1

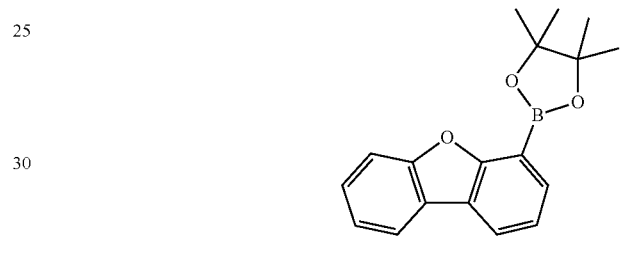

Sub 1-1

(1) Synthesis of Sub 14-1

3-bromo-[1,1'-biphenyl]-2-ol (32.42 g, 130.15 mmol) as a starting material, Pd(OAc)$_2$ (2.92 g, 13.01 mmol), and 3-nitropyridine (1.62 g, 13.01 mmol) were added into a round bottom flask, then, dissolved in C$_6$F$_6$ (195 ml), DMI (130 ml). After adding tert-butyl peroxybenzoate (50.56 g, 260.30 mmol), stirring at 90 □ was followed. When the reaction was completed, the reaction product was extracted with CH$_2$Cl$_2$ and water, and then, the organic layer was dried with MgSO$_4$ and concentrated. Then, the concentrate was passed through silica gel column, then recrystallized to obtain 15.76 g (yield: 49%) of the product.

(2) Synthesis of Sub 1-1

Sub 14-1 (15.76 g, 63.78 mmol) was added into a round bottom flask, then, dissolved in DMF (320 ml). After adding

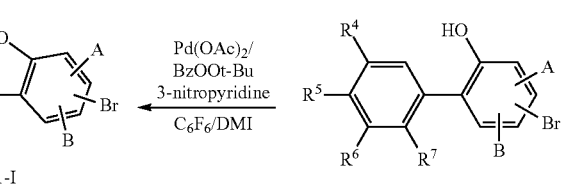

Bis(pinacolato)diboron (17.82 g, 70.16 mmol), Pd(dppf)Cl$_2$ (1.56 g, 1.91 mmol), KOAc (18.78 g, 191.35 mmol), stirring at 90 □ was followed. When the reaction was completed, DMF was removed by distillation, and then extracting with CH$_2$Cl$_2$ and water was followed. The organic layer was dried with MgSO$_4$ and concentrated. Then, the concentrate was passed through silica gel column, then recrystallized to obtain 15.38 g (yield: 82%) of the product.

2. Synthesis Examples of Sub 1-8

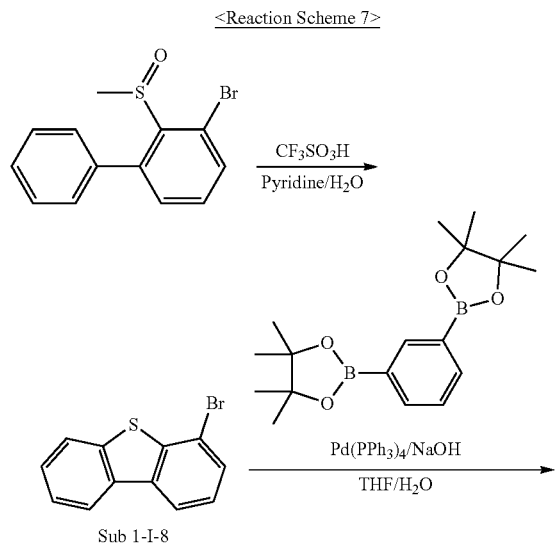

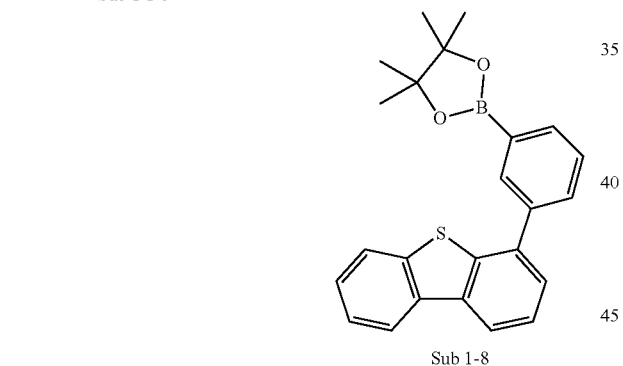

Sub 1-8

(1) Synthesis of Sub 1-I-8

3-bromo-2-(methylsulfinyl)-1,1'-biphenyl (20.03 g, 67.85 mmol) and triflic acid (90 ml, 1017.82 mmol) were added into a round bottom flask, then, stirred at room temperature for 24 hours. After adding pyridine aqueous solution (1190 ml, pyridine:H$_2$O=1:5), refluxing and stirring were followed for 30 minutes. When the reaction was completed, the reaction product was extracted with CH$_2$Cl$_2$ and water, and then, the organic layer was dried with MgSO$_4$ and concentrated. Then, the concentrate was passed through silica gel column, then recrystallized to obtain 14.46 g (yield: 81%) of the product.

(2) Synthesis of Sub 1-8

Sub 1-I-8 (14.46 g, 54.95 mmol) was dissolved in THF (190 ml) in a round bottom flask, and 1,3-bis(4,4,5,5-tetramethyl-1,3,2-dioxaborolan-2-yl)benzene (19.95 g, 60.44 mmol), Pd(PPh$_3$)$_4$ (2.10 g, 1.81 mmol), NaOH (7.25 g, 181.33 mmol), and water (95 ml) were added, then stirring at 80 □ was followed. When the reaction was completed, the reaction product was extracted with CH$_2$Cl$_2$ and water, and then, the organic layer was dried with MgSO$_4$ and concentrated. Then, the concentrate was passed through silica gel column, then recrystallized to obtain 13.37 g (yield: 63%) of the product.

3. Synthesis Examples of Sub 1-10

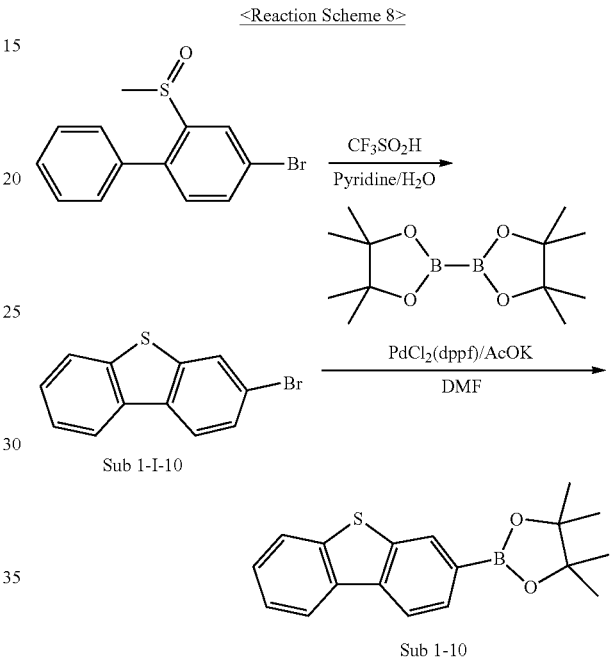

(1) Synthesis of Sub 14-10

35.87 g (yield: 87%) of the product was obtained by using 4-bromo-2-(methylsulfinyl)-1,1'-biphenyl (46.25 g, 156.68 mmol), triflic acid (208 ml, 2350.18 mmol), and pyridine aqueous solution (2745 ml, pyridine:H$_2$O=1:5) in the same manner as described above for the synthesis of Sub 1-I-8.

(2) Synthesis of Sub 1-10

15.94 g (yield: 85%) of the product was obtained by using Sub 14-10 (15.91 g, 60.46 mmol), Bis(pinacolato)diboron (16.89 g, 66.51 mmol), Pd(dppf)Cl$_2$ (1.48 g, 1.81 mmol), KOAc (17.80 g, 181.38 mmol), and DMF (300 ml) in the same manner as described above for the synthesis of Sub 1-1.

4. Synthesis Examples of Sub 1-12

<Reaction Scheme 9>

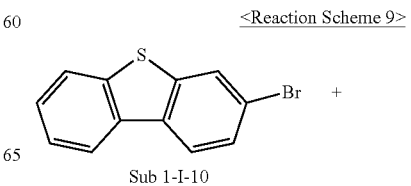

Sub 1-I-10

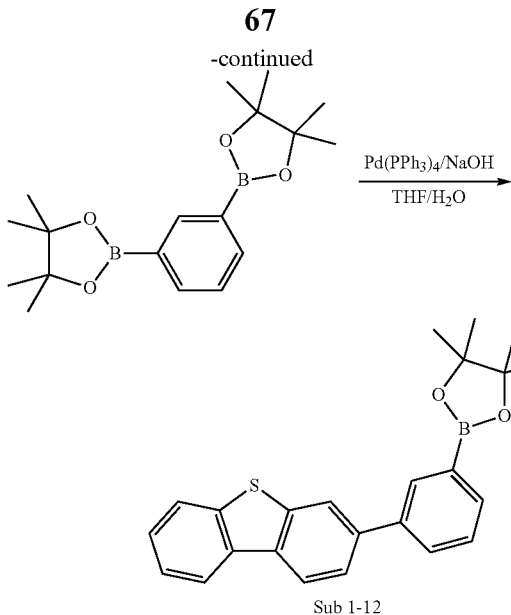

15.57 g (yield: 55%) of the product was obtained by using Sub 14-10 (19.28 g, 73.27 mmol), 1,3-bis(4,4,5,5-tetramethyl-1,3,2-dioxaborolan-2-yl)benzene (26.60 g, 80.59 mmol), Pd(PPh₃)₄ (2.79 g, 2.42 mmol), NaOH (9.67 g, 241.78 mmol), THF (260 ml), and water (130 ml) in the same manner as described above for the synthesis of Sub 1-8.

5. Synthesis Examples of Sub 1-13

<Reaction Scheme 10>

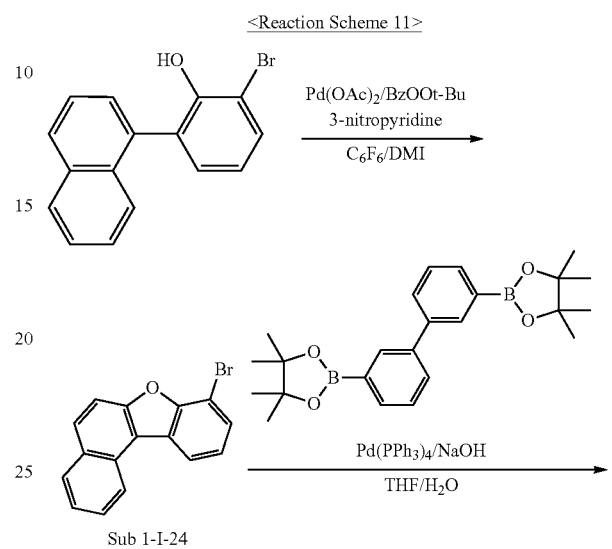

18.97 g (yield: 70%) of the product was obtained by using 1-bromodibenzo[b,d]furan (Sub 1-I-13, CAS No. 50548-45-3) (22.76 g, 92.11 mmol) bought from Tractus-Chemistry company, Bis(pinacolato)diboron (25.73 g, 101.32 mmol), Pd(dppf)Cl₂ (2.26 g, 2.76 mmol), KOAc (27.12 g, 276.34 mmol), and DMF (460 ml) in the same manner as described above for the synthesis of Sub 1-1.

6. Synthesis Examples of Sub 1-24

<Reaction Scheme 11>

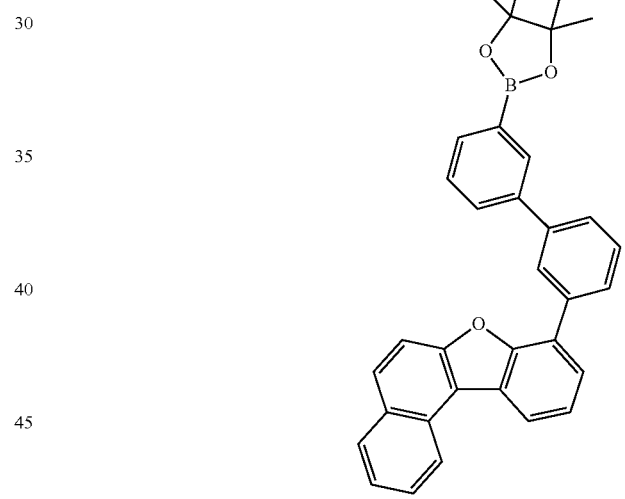

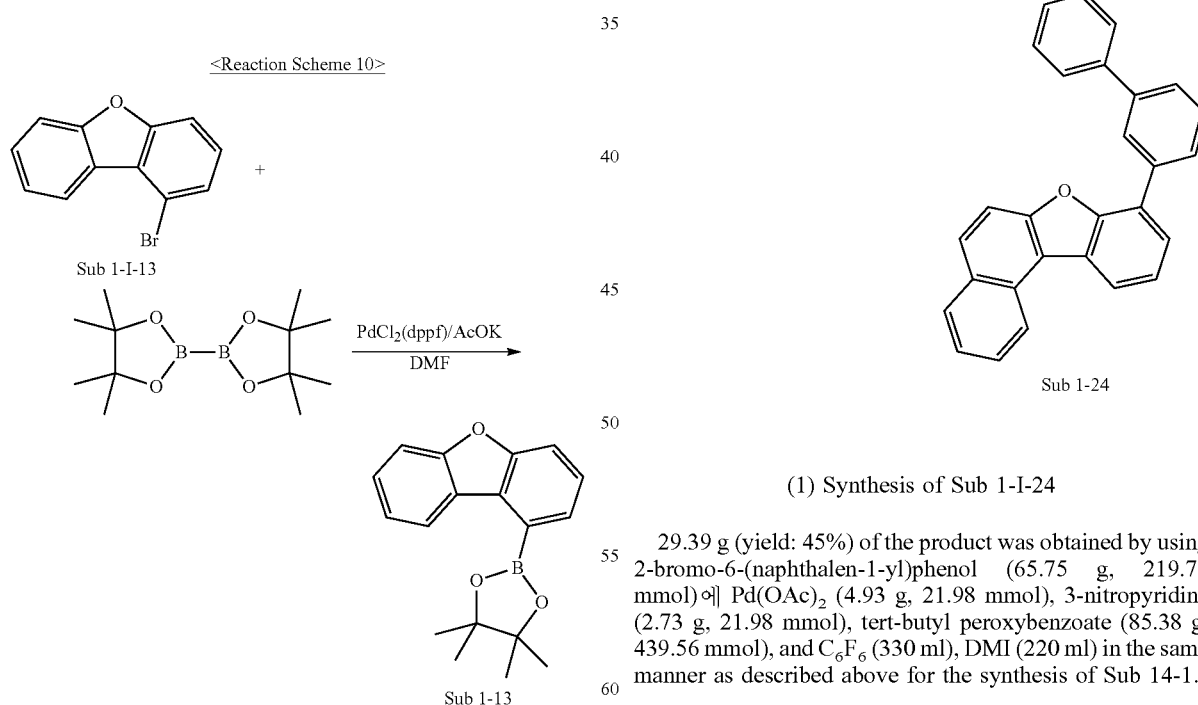

(1) Synthesis of Sub 1-I-24

29.39 g (yield: 45%) of the product was obtained by using 2-bromo-6-(naphthalen-1-yl)phenol (65.75 g, 219.78 mmol)에] Pd(OAc)₂ (4.93 g, 21.98 mmol), 3-nitropyridine (2.73 g, 21.98 mmol), tert-butyl peroxybenzoate (85.38 g, 439.56 mmol), and C₆F₆ (330 ml), DMI (220 ml) in the same manner as described above for the synthesis of Sub 14-1.

(2) Synthesis of Sub 1-24

24.55 g (yield: 50%) of the product was obtained by using Sub 1-I-24 (29.39 g, 98.91 mmol), 3,3'-bis(4,4,5,5-tetramethyl-1,3,2-dioxaborolan-2-yl)-1,1'-biphenyl (44.19 g, 108.80 mmol), Pd(PPh₃)₄ (3.77 g, 3.26 mmol), NaOH (13.06 g, 326.39 mmol), THF (340 ml), and water (170 ml) in the same manner as described above for the synthesis of Sub 1-8.

7. Synthesis Examples of Sub 1-35

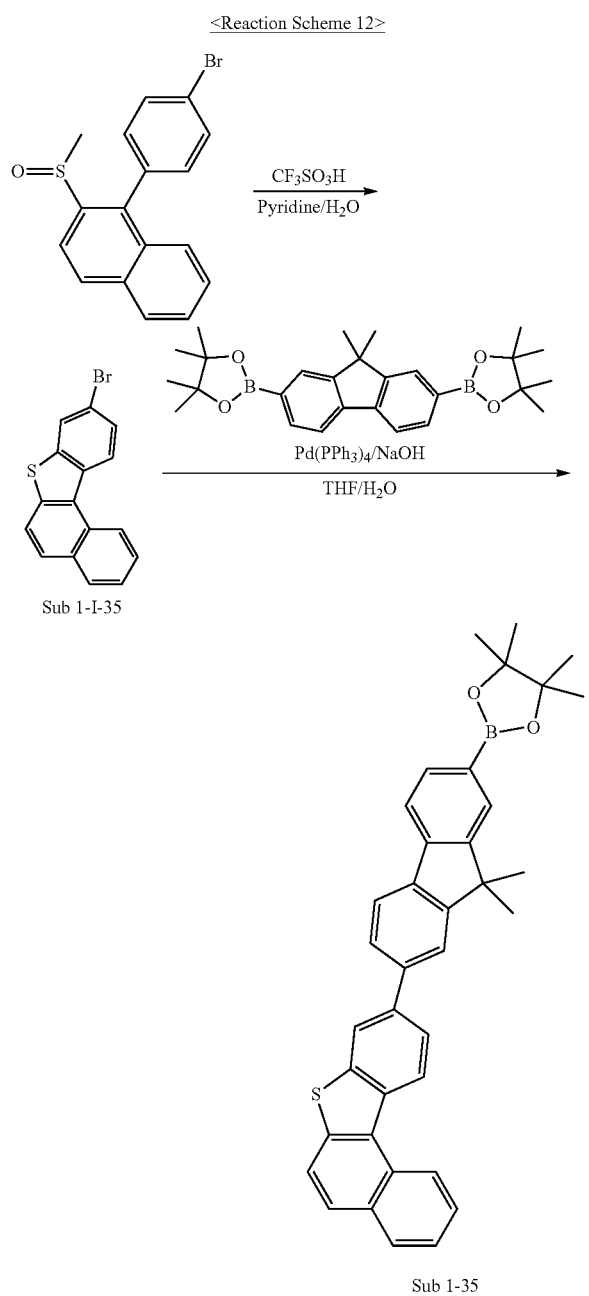

Sub 1-35

(1) Synthesis of Sub 1-I-35

26.67 g (yield: 85%) of the product was obtained by using 1-(4-bromophenyl)-2-(methylsulfinyl)naphthalene (34.59 g, 100.19 mmol), triflic acid (133 ml, 1502.82 mmol), and pyridine aqueous solution (1755 ml, pyridine:$H_2O$=1:5) in the same manner as described above for the synthesis of Sub 1-I-8.

(2) Synthesis of Sub 1-35

28.23 g (yield: 60%) of the product was obtained by using Sub 1-I-35 (26.67 g, 85.15 mmol), 2,2'-(9,9-dimethyl-9H-fluorene-2,7-diyl)bis(4,4,5,5-tetramethyl-1,3,2-dioxaborolane) (41.79 g, 93.67 mmol), Pd(PPh$_3$)$_4$ (3.25 g, 2.81 mmol), NaOH (11.24 g, 281.00 mmol), THF (300 ml), and water (150 ml) in the same manner as described above for the synthesis of Sub 1-8.

8. Synthesis Examples of Sub 1-39

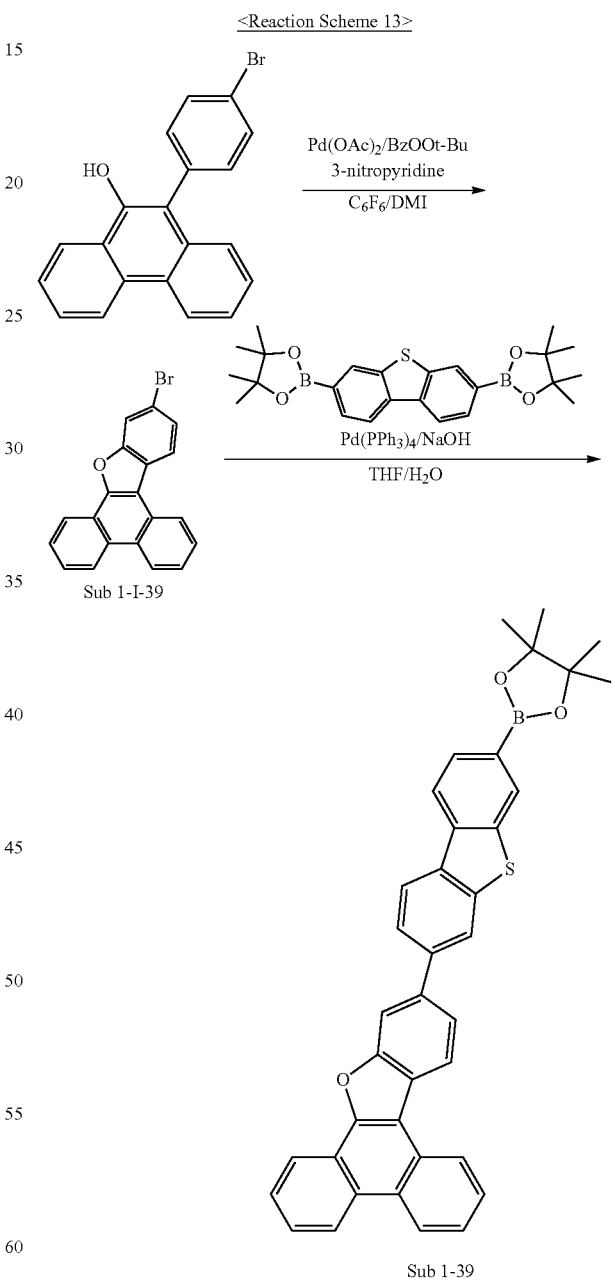

Sub 1-39

(1) Synthesis of Sub 1-I-39

26.28 g (yield: 42%) of the product was obtained by using 10-(4-bromophenyl)phenanthren-9-ol (62.94 g, 180.23 mmol), Pd(OAc)$_2$ (4.05 g, 18.02 mmol), 3-nitropyridine (2.24 g, 18.02 mmol), tert-butyl peroxybenzoate (70.01 g, 360.46 mmol), C$_6$F$_6$ (270 ml), and DMI (180 ml) in the same manner as described above for the synthesis of Sub 14-1.

(2) Synthesis of Sub 1-39

24.87 g (yield: 57%) of the product was obtained by using Sub 1-I-39 (26.28 g, 75.69 mmol), 3,7-bis(4,4,5,5-tetramethyl-1,3,2-dioxaborolan-2-yl)dibenzo[b, d]thiophene (36.32 g, 83.26 mmol), Pd(PPh$_3$)$_4$ (2.89 g, 2.50 mmol), NaOH (9.99 g, 249.78 mmol), THF (260 ml), and water (130 ml) in the same manner as described above for the synthesis of Sub 1-8.

9. Synthesis Examples of Sub 1-47

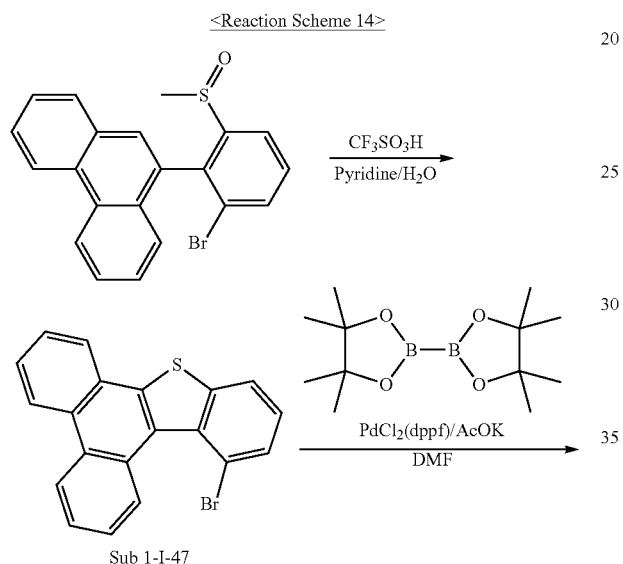

(1) Synthesis of Sub 1-I-47

54.42 g (yield: 68%) of the product was obtained by using 9-(2-bromo-6-(methylsulfinyl)phenyl)phenanthrene (87.09 g, 220.31 mmol), triflic acid (292 ml, 3304.62 mmol), and pyridine aqueous solution (3860 ml, pyridine:H$_2$O=1:5) in the same manner as described above for the synthesis of Sub 1-I-8.

(2) Synthesis of Sub 1-47

24.72 g (yield: 80%) of the product was obtained by using Sub 1-I-47 (27.36 g, 75.32 mmol), Bis(pinacolato)diboron (21.04 g, 82.85 mmol), Pd(dppf)Cl$_2$ (1.85 g, 2.26 mmol), KOAc (22.17 g, 225.95 mmol), and DMF (380 ml) in the same manner as described above for the synthesis of Sub 1-1.

10. Synthesis Examples of Sub 1-49

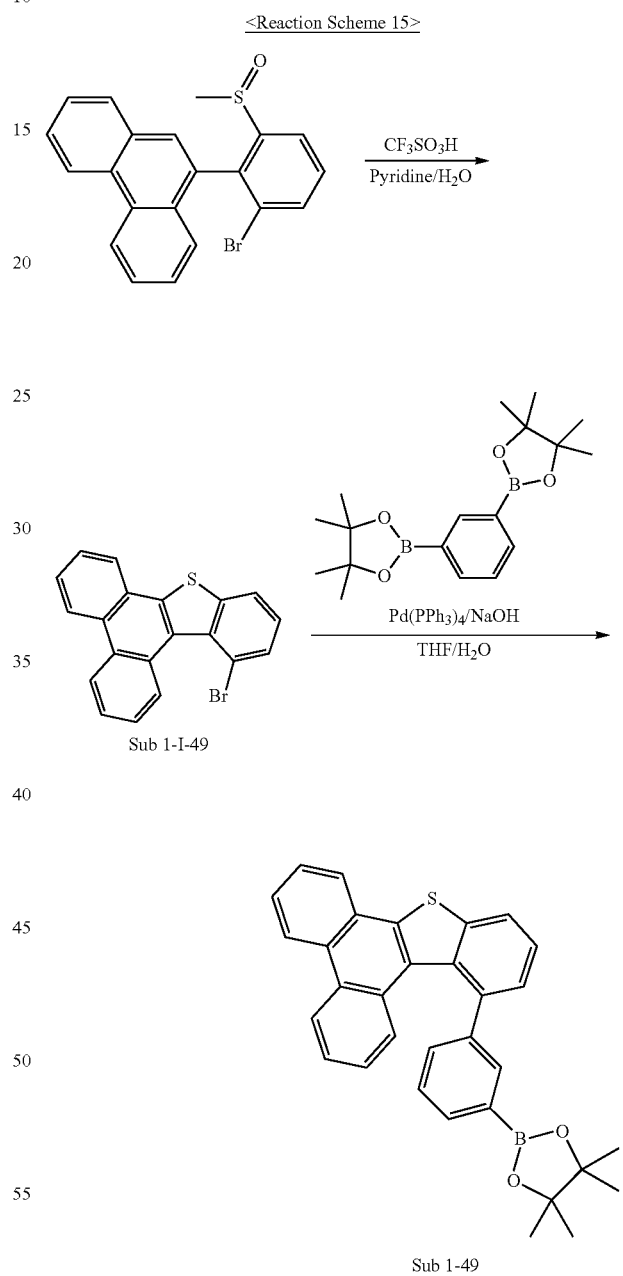

19.43 g (yield: 60%) of the product was obtained by using Sub 1-I-47 (24.19 g, 66.59 mmol), 1,3-bis(4,4,5,5-tetramethyl-1,3,2-dioxaborolan-2-yl)benzene (24.17 g, 73.25 mmol), Pd(PPh$_3$)$_4$ (2.54 g, 2.20 mmol), NaOH (8.79 g, 219.75 mmol), THF (230 ml), and water (115 ml) in the same manner as described above for the synthesis of Sub 1-8.

11. Synthesis Examples of Sub 1-52

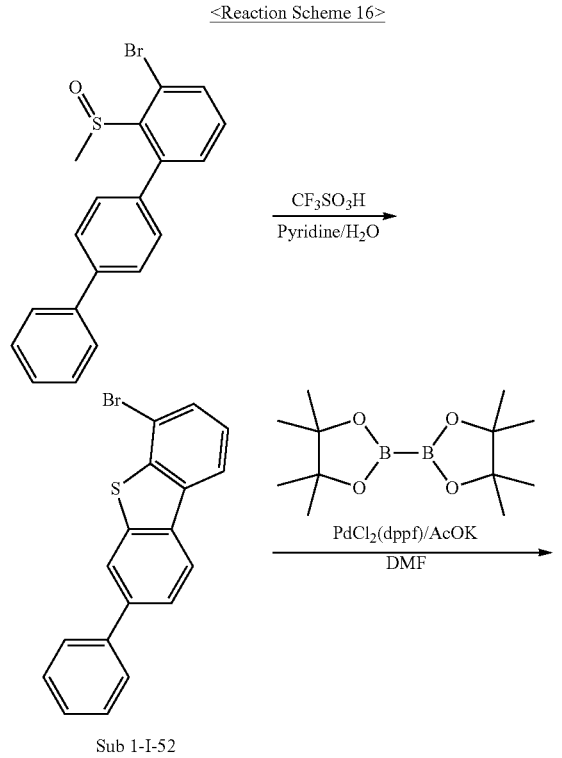

12. Synthesis Examples of Sub 1-58

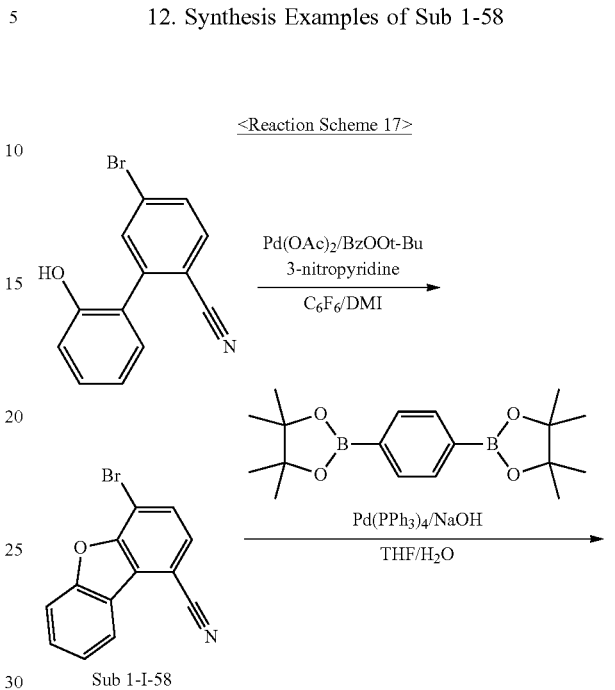

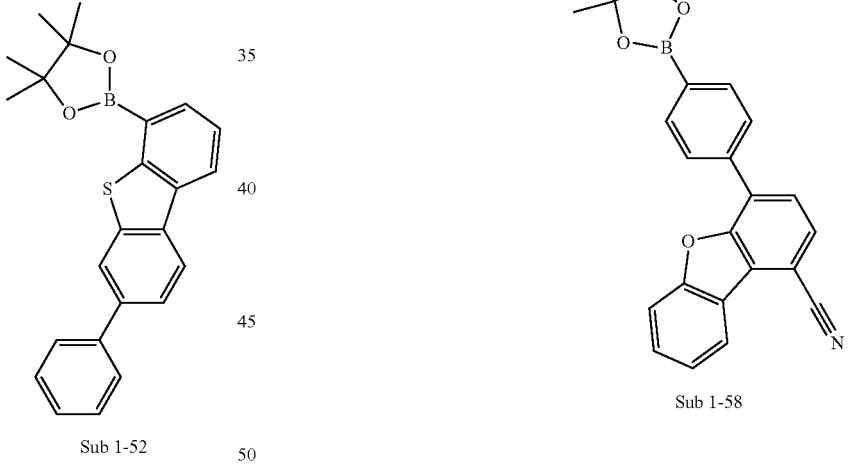

(1) Synthesis of Sub 1-I-52

12.34 g (yield: 54%) of the product was obtained by using 3-bromo-2-(methylsulfinyl)-1,1':4',1''-terphenyl (25.00 g, 67.33 mmol), triflic acid (89 ml, 1009.99 mmol), and pyridine aqueous solution (1180 ml, pyridine:H$_2$O=1:5) in the same manner as described above for the synthesis of Sub 1-I-8.

(2) Synthesis of Sub 1-52

11.94 g (yield: 85%) of the product was obtained by using Sub 1-I-52 (12.34 g, 36.37 mmol), Bis(pinacolato)diboron (10.16 g, 40.01 mmol), Pd(dppf)Cl$_2$ (0.89 g, 1.09 mmol), KOAc (10.71 g, 109.12 mmol), and DMF (180 ml) in the same manner as described above for the synthesis of Sub 1-1.

(1) Synthesis of Sub 1-I-58

19.07 g (yield: 39%) of the product was obtained by using 5-bromo-2'-hydroxy-[1,1'-biphenyl]-2-carbonitrile (49.25 g, 179.67 mmol), Pd(OAc)$_2$ (4.03 g, 17.97 mmol), 3-nitropyridine (2.23 g, 17.97 mmol), tert-butyl peroxybenzoate (69.80 g, 359.34 mmol), C$_6$F$_6$ (270 ml), DMI (180 ml) in the same manner as described above for the synthesis of Sub 14-1.

(2) Synthesis of Sub 1-58

14.96 g (yield: 54%) of the product was obtained by using Sub 1-I-58 (19.07 g, 70.08 mmol), 1,4-bis(4,4,5,5-tetramethyl-1,3,2-dioxaborolan-2-yl)benzene (25.44 g, 77.09 mmol), Pd(PPh$_3$)$_4$ (2.67 g, 2.31 mmol), NaOH (9.25 g, 231.28 mmol), THF (240 ml), and water (120 ml) in the same manner as described above for the synthesis of Sub 1-8.
The compound belonging to Sub 1 may be, but not limited to, the following compounds, and Table 1 shows FD-MS (Field Desorption-Mass Spectrometry) values of compounds belonging to Sub 1.
Sub 1-1
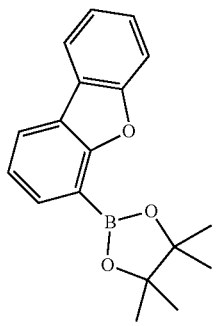
Sub 1-2
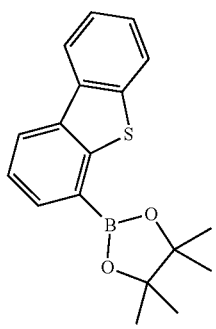
Sub 1-3
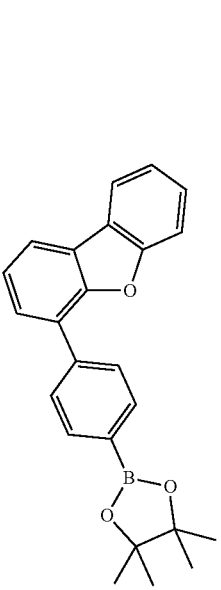
-continued
Sub 1-4
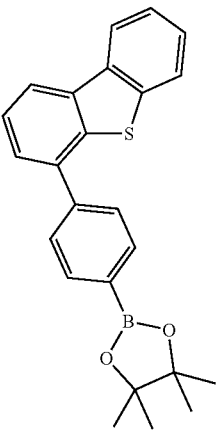
Sub 1-5
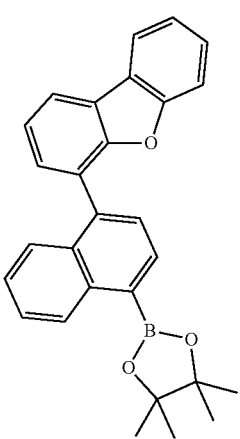
Sub 1-6
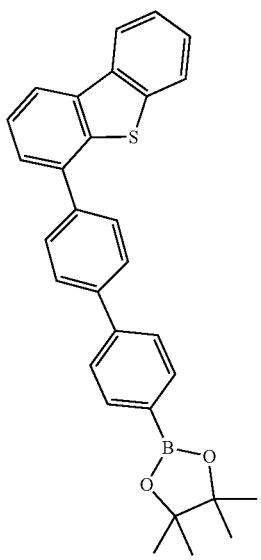

Sub 1-7
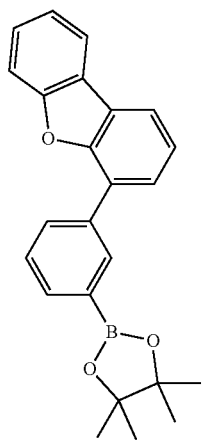
Sub 1-8
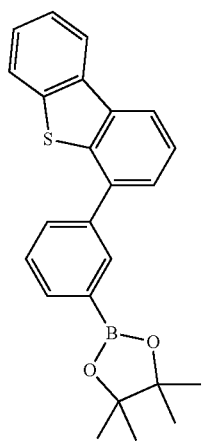
Sub 1-9
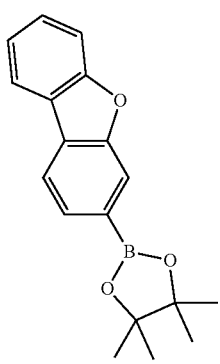
Sub 1-10
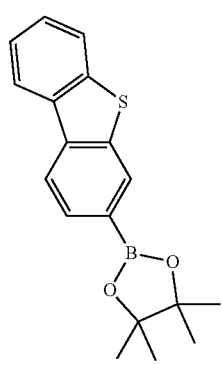
Sub 1-11
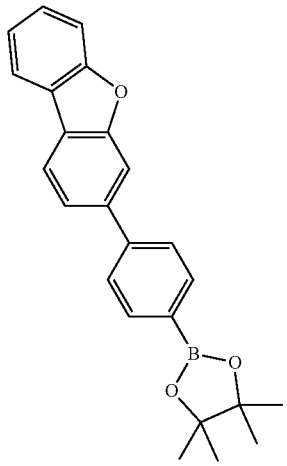
Sub 1-12
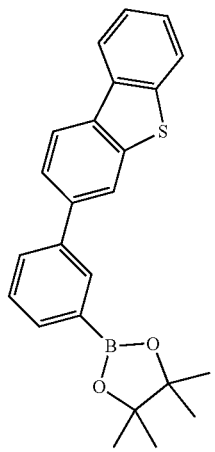
Sub 1-13
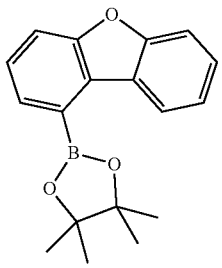
Sub 1-14
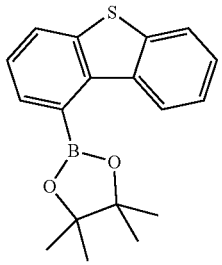

Sub 1-15
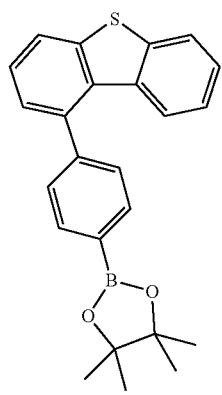
Sub 1-16
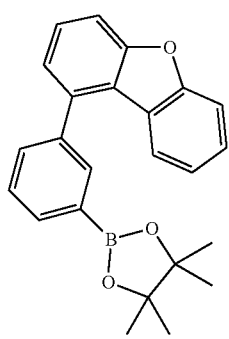
Sub 1-17
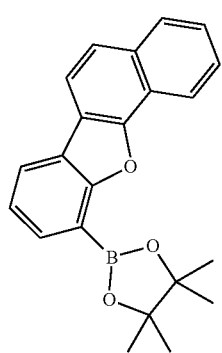
Sub 1-18
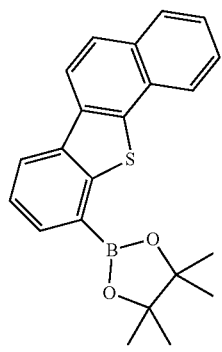
Sub 1-19
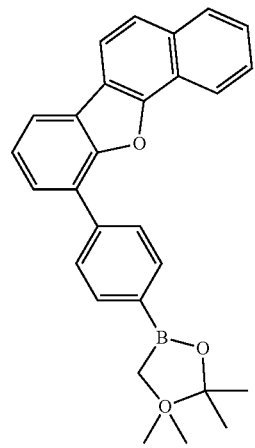
Sub 1-20
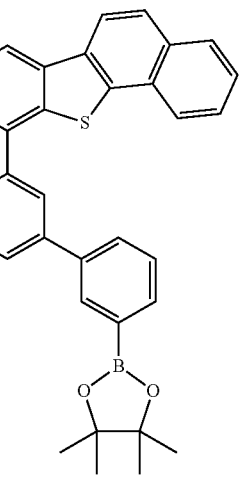
Sub 1-21
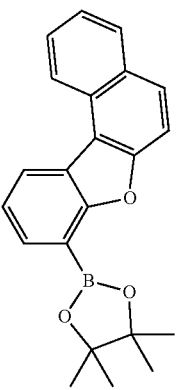

Sub 1-22
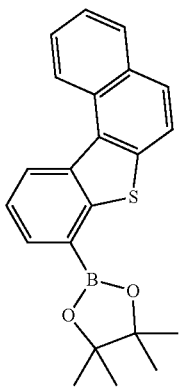
Sub 1-23
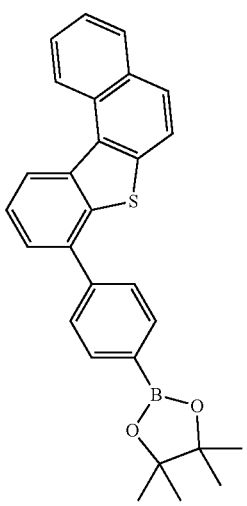
Sub 1-24
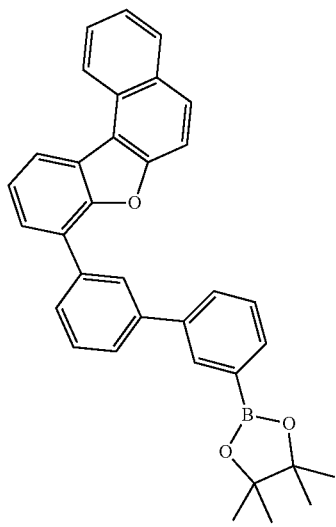
Sub 1-25
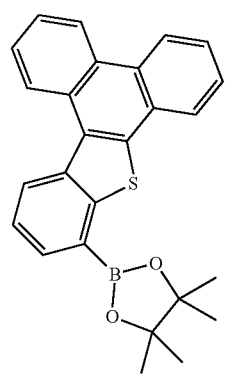
Sub 1-26
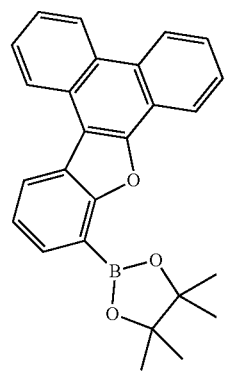
Sub 1-27
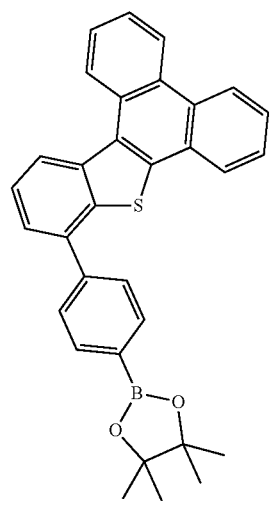

Sub 1-28
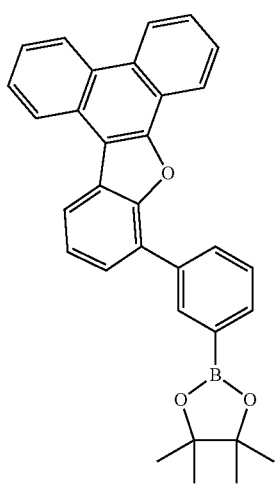
Sub 1-29
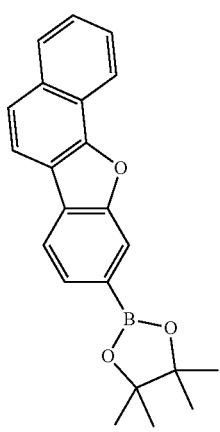
Sub 1-30
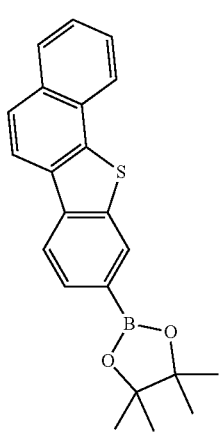
Sub 1-31
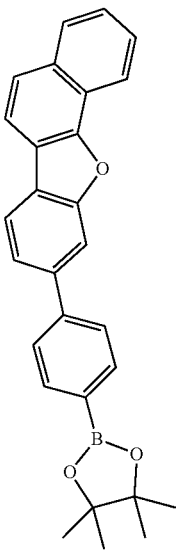
Sub 1-32
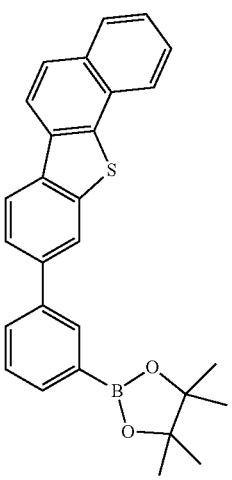
Sub 1-33
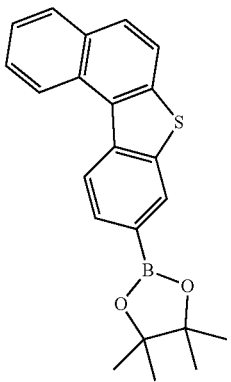

Sub 1-34
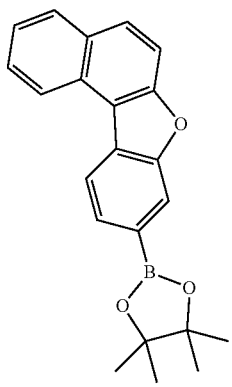
Sub 1-37
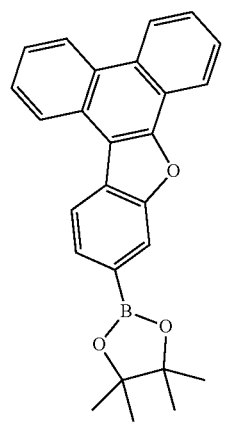
Sub 1-35
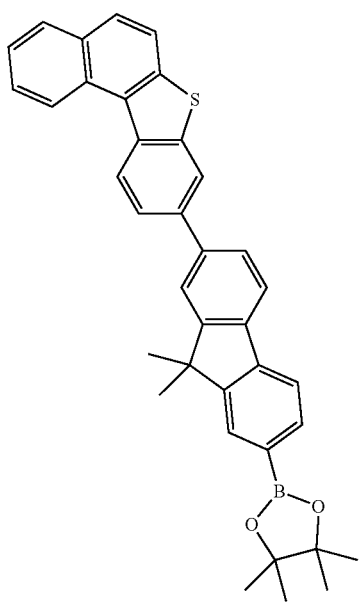
Sub 1-38
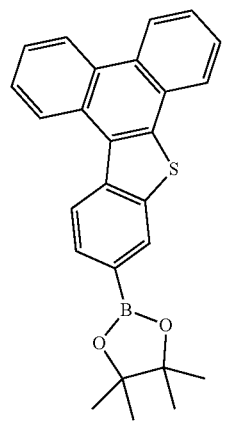
Sub 1-36
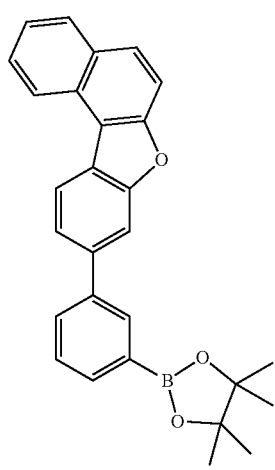
Sub 1-39
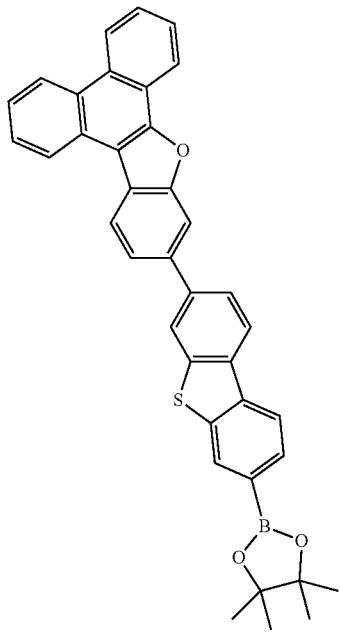

Sub 1-40
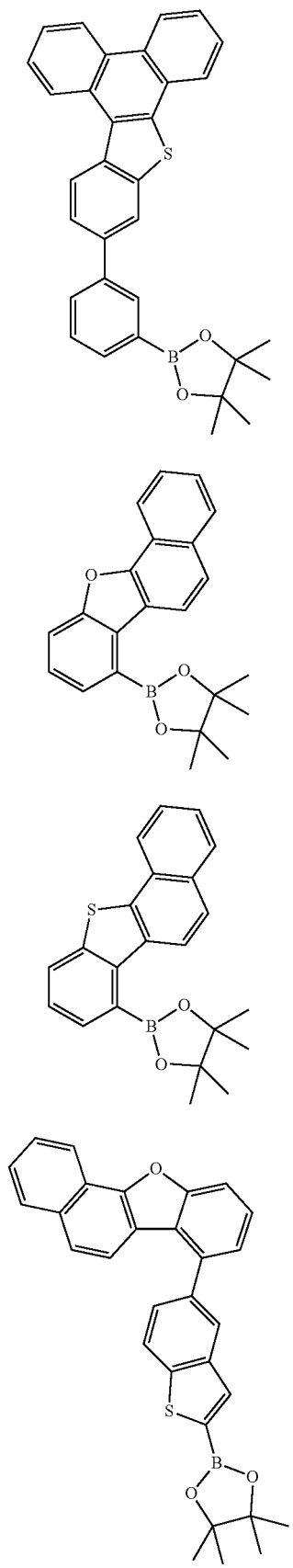
Sub 1-41
Sub 1-42
Sub 1-43
Sub 1-44
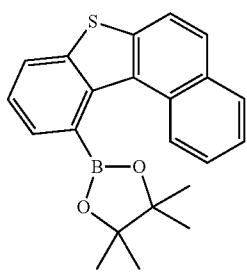
Sub 1-45
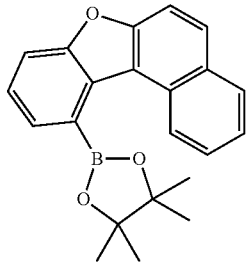
Sub 1-46
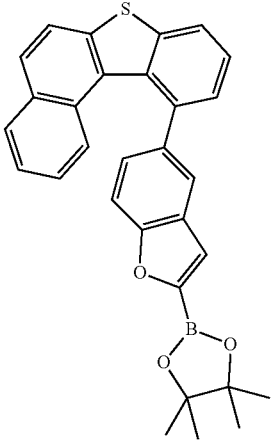
Sub 1-47
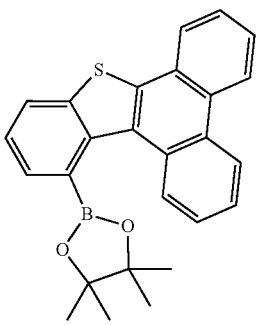
Sub 1-48
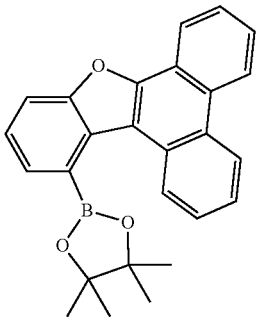

-continued
Sub 1-49
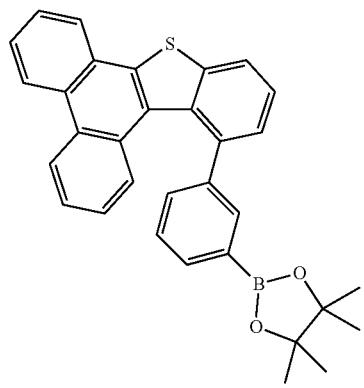
Sub 1-50
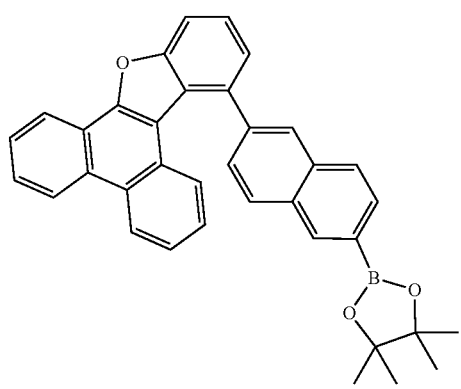
Sub 1-51
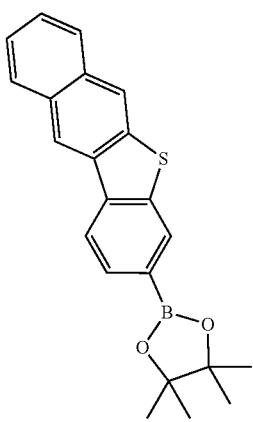
Sub 1-52
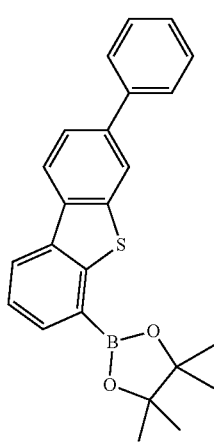
-continued
Sub 1-53
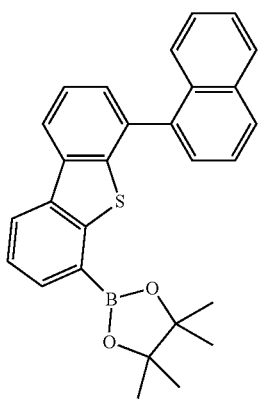
Sub 1-54
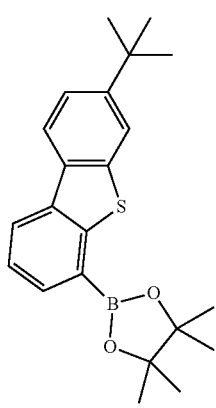
Sub 1-55
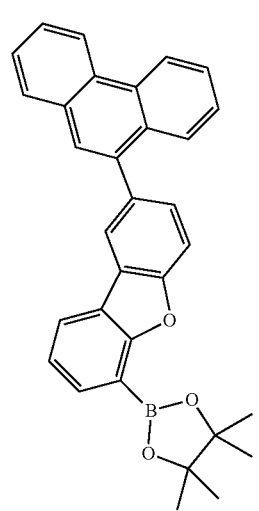

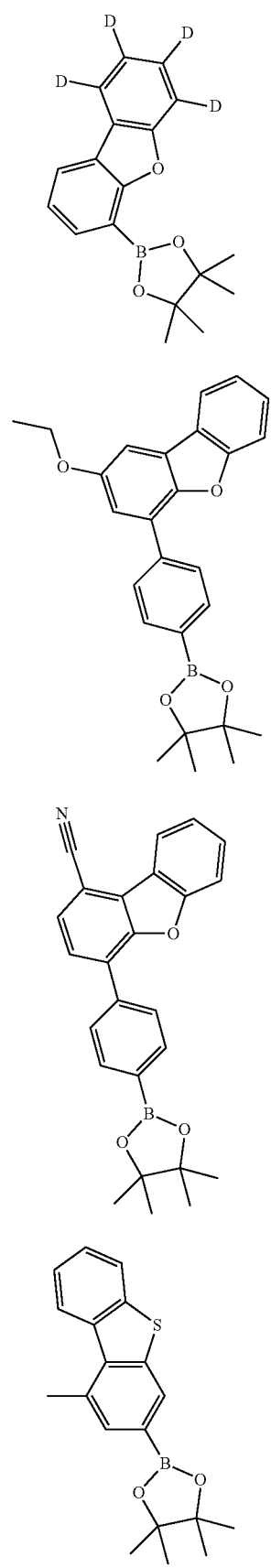
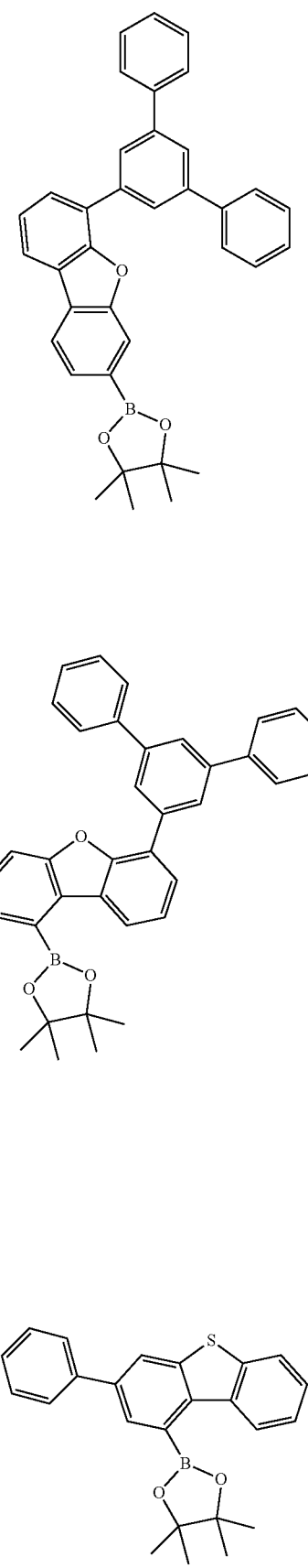
Sub 1-56
Sub 1-57
Sub 1-58
Sub 1-59
Sub 1-60
Sub 1-61
Sub 1-62

Sub 1-63
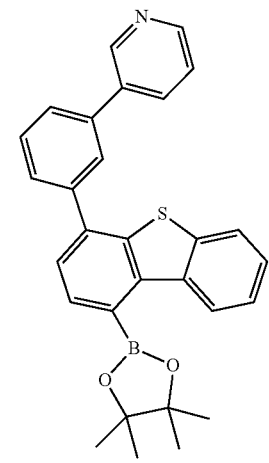
Sub 1-64
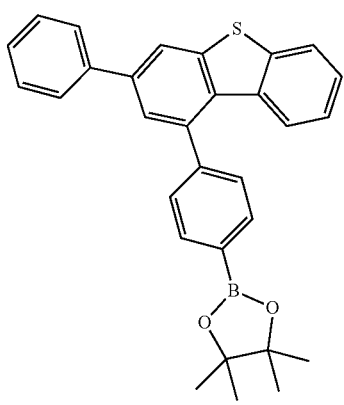
Sub 1-65
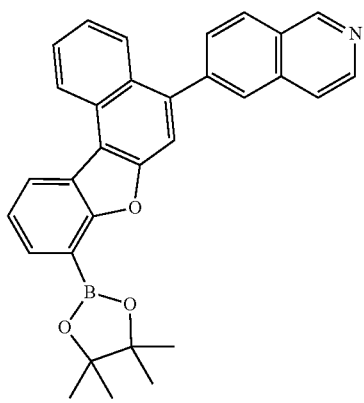
Sub 1-66
Sub 1-67
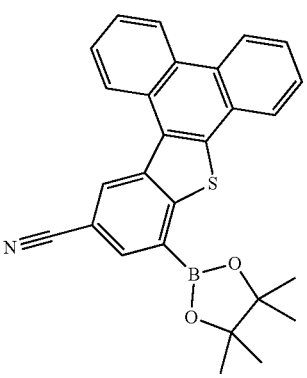
Sub 1-68
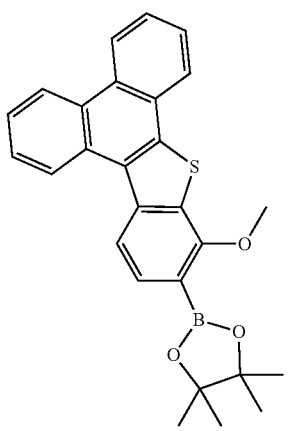
Sub 1-69
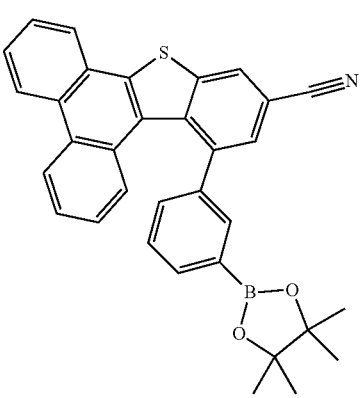

TABLE 1

| Compound | FD-MS | Compound | FD-MS |
|---|---|---|---|
| Sub 1-1 | m/z = 294.14($C_{18}H_{19}BO_3$ = 294.15) | Sub 1-2 | m/z = 310.12($C_{18}H_{19}BO_2S$ = 310.22) |
| Sub 1-3 | m/z = 370.17($C_{24}H_{23}BO_3$ = 370.25) | Sub 1-4 | m/z = 386.15($C_{24}H_{23}BO_2S$ = 386.31) |
| Sub 1-5 | m/z = 420.19($C_{28}H_{25}BO_3$ = 420.31) | Sub 1-6 | m/z = 462.18($C_{30}H_{27}BO_2S$ = 462.41) |
| Sub 1-7 | m/z = 370.17($C_{24}H_{23}BO_3$ = 370.25) | Sub 1-8 | m/z = 386.15($C_{24}H_{23}BO_2S$ = 386.31) |
| Sub 1-9 | m/z = 294.14($C_{18}H_{19}BO_3$ = 294.15) | Sub 1-10 | m/z = 310.12($C_{18}H_{19}BO_2S$ = 310.22) |
| Sub 1-11 | m/z = 370.17($C_{24}H_{23}BO_3$ = 370.25) | Sub 1-12 | m/z = 386.15($C_{24}H_{23}BO_2S$ = 386.31) |
| Sub 1-13 | m/z = 294.14($C_{18}H_{19}BO_3$ = 294.15) | Sub 1-14 | m/z = 310.12($C_{18}H_{19}BO_2S$ = 310.22) |
| Sub 1-15 | m/z = 386.15($C_{24}H_{23}BO_2S$ = 386.31) | Sub 1-16 | m/z = 370.17($C_{24}H_{23}BO_3$ = 370.25) |
| Sub 1-17 | m/z = 344.16($C_{22}H_{21}BO_3$ = 344.21) | Sub 1-18 | m/z = 360.14($C_{22}H_{21}BO_2S$ = 360.28) |
| Sub 1-19 | m/z = 420.19($C_{28}H_{25}BO_3$ = 420.31) | Sub 1-20 | m/z = 512.20($C_{34}H_{29}BO_2S$ = 512.47) |
| Sub 1-21 | m/z = 344.16($C_{22}H_{21}BO_3$ = 344.21) | Sub 1-22 | m/z = 360.14($C_{22}H_{21}BO_2S$ = 360.28) |
| Sub 1-23 | m/z = 436.17($C_{28}H_{25}BO_2S$ = 436.37) | Sub 1-24 | m/z = 496.22($C_{34}H_{29}BO_3$ = 496.40) |
| Sub 1-25 | m/z = 410.15($C_{26}H_{23}BO_2S$ = 410.34) | Sub 1-26 | m/z = 394.17($C_{28}H_{23}BO_3$ = 394.27) |
| Sub 1-27 | m/z = 486.18($C_{32}H_{27}BO_2S$ = 486.43) | Sub 1-28 | m/z = 470.21($C_{32}H_{27}BO_3$ = 470.37) |
| Sub 1-29 | m/z = 344.16($C_{22}H_{21}BO_3$ = 344.21) | Sub 1-30 | m/z = 360.14($C_{22}H_{21}BO_2S$ = 360.28) |
| Sub 1-31 | m/z = 420.19($C_{28}H_{25}BO_3$ = 420.31) | Sub 1-32 | m/z = 436.17($C_{28}H_{25}BO_2S$ = 436.37) |
| Sub 1-33 | m/z = 360.14($C_{22}H_{21}BO_2S$ = 360.28) | Sub 1-34 | m/z = 344.16($C_{22}H_{21}BO_3$ = 344.21) |
| Sub 1-35 | m/z = 552.23($C_{37}H_{33}BO_2S$ = 552.53) | Sub 1-36 | m/z = 420.19($C_{28}H_{25}BO_3$ = 420.31) |
| Sub 1-37 | m/z = 394.17($C_{26}H_{23}BO_3$ = 394.27) | Sub 1-38 | m/z = 410.15($C_{26}H_{23}BO_2S$ = 410.34) |
| Sub 1-39 | m/z = 576.19($C_{38}H_{29}BO_3S$ = 576.51) | Sub 1-40 | m/z = 486.18($C_{32}H_{27}BO_2S$ = 486.43) |
| Sub 1-41 | m/z = 344.16($C_{22}H_{21}BO_3$ = 344.21) | Sub 1-42 | m/z = 360.14($C_{22}H_{21}BO_2S$ = 360.28) |
| Sub 1-43 | m/z = 476.16($C_{30}H_{25}BO_3S$ = 476.39) | Sub 1-44 | m/z = 360.14($C_{22}H_{21}BO_2S$ = 360.28) |
| Sub 1-45 | m/z = 344.16($C_{22}H_{21}BO_3$ = 344.21) | Sub 1-46 | m/z = 475.16($C_{30}H_{25}BO_3S$ = 476.39) |
| Sub 1-47 | m/z = 410.15($C_{26}H_{23}BO_2S$ = 410.34) | Sub 1-48 | m/z = 394.17($C_{28}H_{23}BO_3$ = 394.27) |
| Sub 1-49 | m/z = 486.18($C_{32}H_{27}BO_2S$ = 486.43) | Sub 1-50 | m/z = 520.22($C_{35}H_{29}BO_3$ = 52.42) |
| Sub 1-51 | m/z = 360.14($C_{22}H_{21}BO_2S$ = 360.28) | Sub 1-52 | m/z = 386.15($C_{24}H_{23}BO_2S$ = 386.31) |
| Sub 1-53 | m/z = 436.17($C_{28}H_{25}BO_2S$ = 436.37) | Sub 1-54 | m/z = 366.18($C_{22}H_{27}BO_2S$ = 366.32) |
| Sub 1-55 | m/z = 470.21($C_{32}H_{27}BO_3$ = 470.37) | Sub 1-56 | m/z = 298.17($C_{18}H_{15}D_4BO_3$ = 298.18) |
| Sub 1-57 | m/z = 414.20($C_{26}H_{27}BO_4$ = 414.30) | Sub 1-58 | m/z = 395.17($C_{25}H_{22}BNO_3$ = 395.26) |
| Sub 1-59 | m/z = 324.14($C_{19}H_{21}BO_2S$ = 324.24) | Sub 1-60 | m/z = 522.24($C_{36}H_{31}BO_3$ = 522.44) |
| Sub 1-61 | m/z = 522.24($C_{36}H_{31}BO_3$ = 522.44) | Sub 1-62 | m/z = 386.15($C_{24}H_{23}BO_2S$ = 386.31) |
| Sub 1-63 | m/z = 463.18($C_{29}H_{26}BNO_2S$ = 463.40) | Sub 1-64 | m/z = 462.18($C_{30}H_{27}BO_2S$ = 462.41) |
| Sub 1-65 | m/z = 471.20($C_{31}H_{16}BNO_3$ = 471.35) | Sub 1-66 | m/z = 436.17($C_{28}H_{25}BO_2S$ = 436.37) |
| Sub 1-67 | m/z = 435.15($C_{27}H_{22}BNO_2S$ = 435.35) | Sub 1-68 | m/z = 440.16($C_{27}H_{25}BO_3S$ = 440.36) |
| Sub 1-69 | m/z = 511.18($C_{33}H_{26}BNO_2S$ = 511.44) | | |

II. Synthesis of Sub 2

Sub 2 of the above Reaction Scheme 1 may be synthesized by the reaction route of Reaction Scheme 15, but is not limited thereto.

<Reaction Scheme 18>

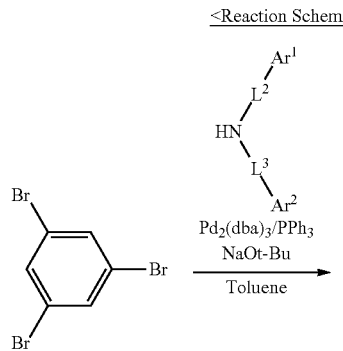

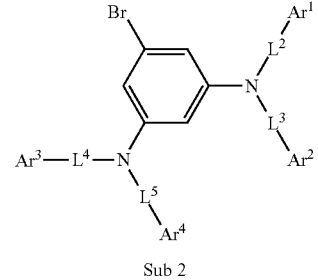

Sub 2

Synthesis Examples of compounds belonging to Sub 2 are as follows.

1. Synthesis Examples of Sub 2-1

<Reaction Scheme 19>

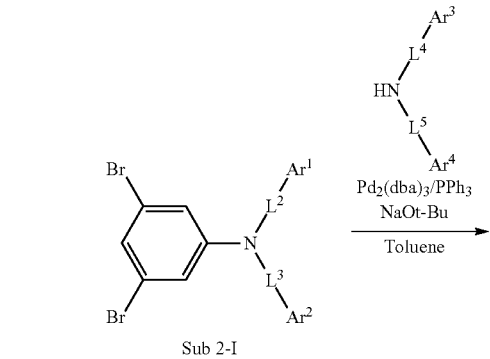

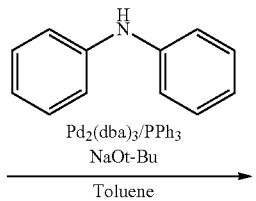

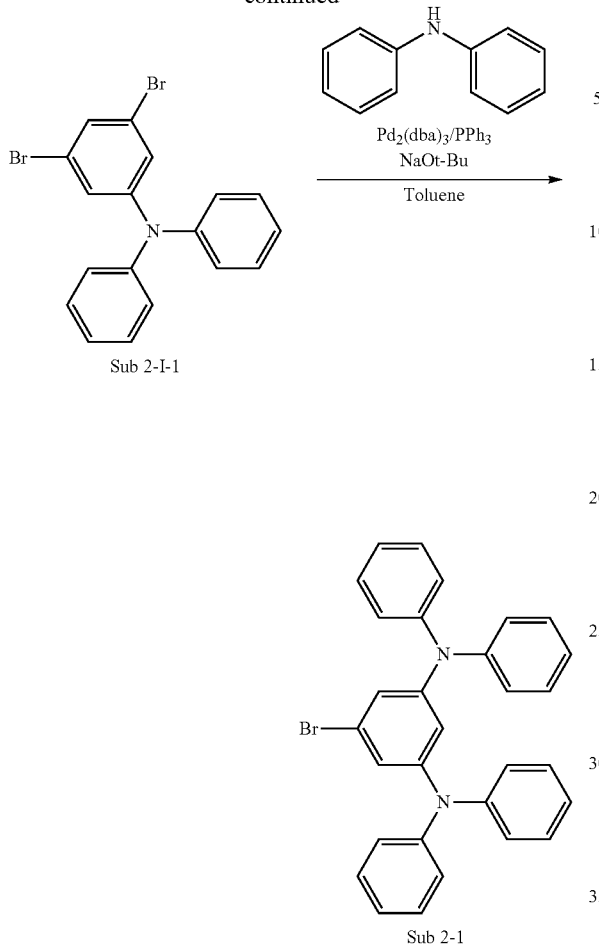

2. Synthesis Examples of Sub 2-6

<Reaction Scheme 20>

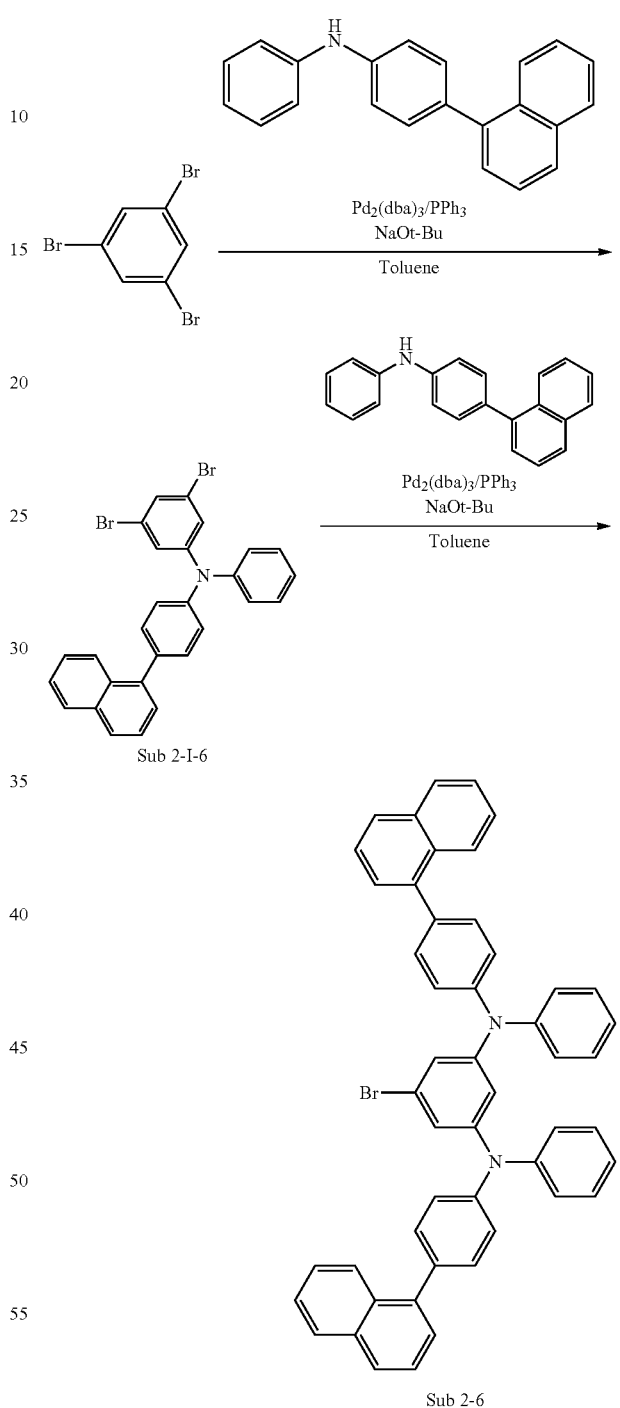

(1) Synthesis of Sub 2-I-1

Diphenylamine (25.74 g, 152.11 mmol) was dissolved in toluene (880 ml) in a round bottom flask, and 1,3,5-tribromobenzene (62.25 g, 197.74 mmol), $Pd_2(dba)_3$ (4.18 g, 4.56 mmol), $PPh_3$ (3.19 g, 12.17 mmol), and NaOt-Bu (58.48 g, 608.44 mmol) were added, then, stirring at 80 □ was followed. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 27.59 g (yield: 45%) of the product.

(2) Synthesis of Sub 2-1

Diphenylamine (8.91 g, 52.65 mmol) was dissolved in toluene (300 ml) in a round bottom flask, and Sub 2-I-1 (27.59 g, 68.45 mmol), $Pd_2(dba)_3$ (1.45 g, 1.58 mmol), $PPh_3$ (1.10 g, 4.21 mmol), and NaOt-Bu (20.24 g, 210.61 mmol) were added, then, stirring at 80 □ was followed. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 12.16 g (yield: 47%) of the product.

(1) Synthesis of Sub 2-I-6

34.92 g (yield: 55%) of the product was obtained by using 4-(naphthalen-1-yl)-N-phenylaniline (35.43 g, 119.95 mmol), 1,3,5-tribromobenzene (49.09 g, 155.93 mmol), $Pd_2(dba)_3$ (3.30 g, 3.60 mmol), $PPh_3$ (2.52 g, 9.60 mmol), NaOt-Bu (46.11 g, 479.79 mmol), and toluene (690 ml) in the same manner as described above for the synthesis of Sub 2-I-1.

(2) Synthesis of Sub 2-6

18.12 g (yield: 48%) of the product was obtained by using 4-(naphthalen-1-yl)-N-phenylaniline (14.99 g, 50.75 mmol), Sub 2-I-6 (34.92 g, 65.97 mmol), $Pd_2(dba)_3$ (1.39 g, 1.52 mmol), $PPh_3$ (1.06 g, 4.06 mmol), NaOt-Bu (19.51 g, 202.99 mmol), toluene (290 ml) in the same manner as described above for the synthesis of Sub 2-1.

3. Synthesis Examples of Sub 2-12

<Reaction Scheme 21>

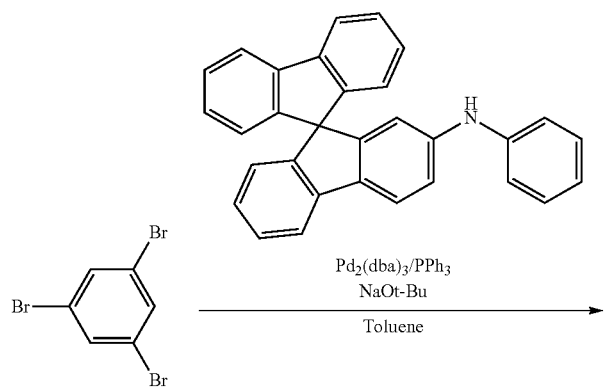

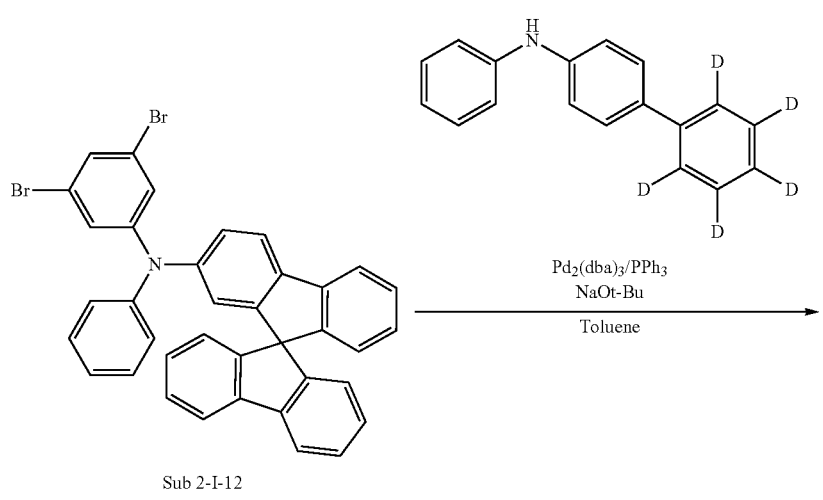

Sub 2-I-12

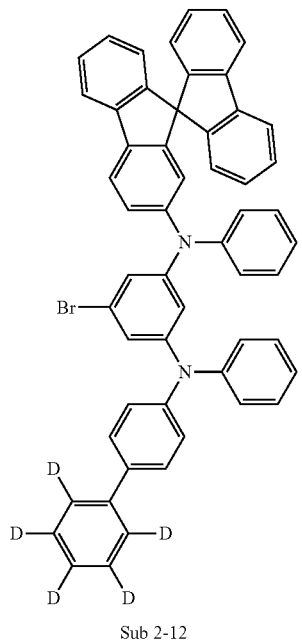

Sub 2-12

(1) Synthesis of Sub 2-I-12

29.14 g (yield: 48%) of the product was obtained by using N-phenyl-9,9'-spirobi[fluoren]-2-amine (38.57 g, 94.65 mmol), 1,3,5-tribromobenzene (38.73 g, 123.04 mmol), Pd$_2$(dba)$_3$ (2.60 g, 2.84 mmol), PPh$_3$ (1.99 g, 7.57 mmol), NaOt-Bu (36.39 g, 378.59 mmol), toluene (540 ml) in the same manner as described above for the synthesis of Sub 2-I-1.

(2) Synthesis of Sub 2-12

15.59 g (yield: 55%) of the product was obtained by using N-phenyl-[1,1'-biphenyl]-2',3',4',5',6'-d$_5$-4-amine (8.75 g, 34.95 mmol), Sub 2-I-12 (29.14 g, 45.44 mmol), Pd$_2$(dba)$_3$ (0.96 g, 1.05 mmol), PPh$_3$ (0.73 g, 2.80 mmol), NaOt-Bu (13.44 g, 139.80 mmol), toluene (200 ml) in the same manner as described above for the synthesis of Sub 2-1.

4. Synthesis Examples of Sub 2-20

<Reaction Scheme 22>

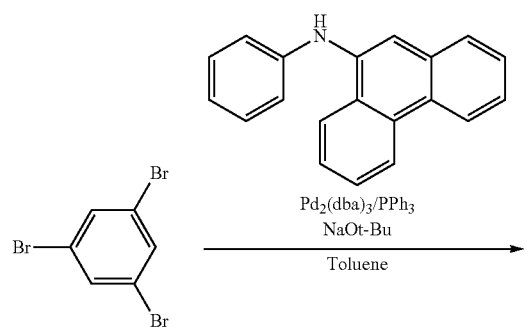

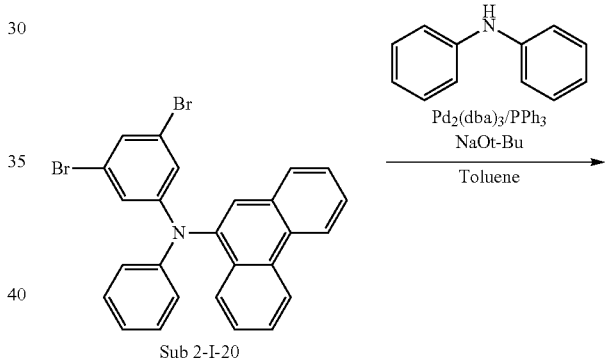

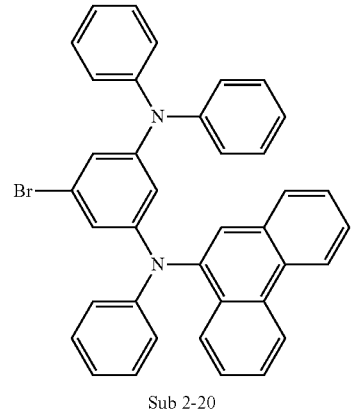

Sub 2-20

(1) Synthesis of Sub 2-I-20

28.69 g (yield: 47%) of the product was obtained by using N-phenylphenanthren-9-amine (32.67 g, 121.30 mmol), 1,3,5-tribromobenzene (49.64 g, 157.69 mmol), Pd$_2$(dba)$_3$ (3.33 g, 3.64 mmol), PPh$_3$ (2.55 g, 9.70 mmol), NaOt-Bu (46.63 g, 485.19 mmol), toluene (700 ml) in the same manner as described above for the synthesis of Sub 2-I-1.

(2) Synthesis of Sub 2-20

12.97 g (yield: 50%) of the product was obtained by using diphenylamine (7.42 g, 43.85 mmol), Sub 2-I-20 (28.69 g, 57.00 mmol), Pd$_2$(dba)$_3$ (1.20 g, 1.32 mmol), PPh$_3$ (0.92 g, 3.51 mmol), NaOt-Bu (16.86 g, 175.39 mmol), toluene (250 ml) in the same manner as described above for the synthesis of Sub 2-1.

5. Synthesis Examples of Sub 2-24

<Reaction Scheme 23>

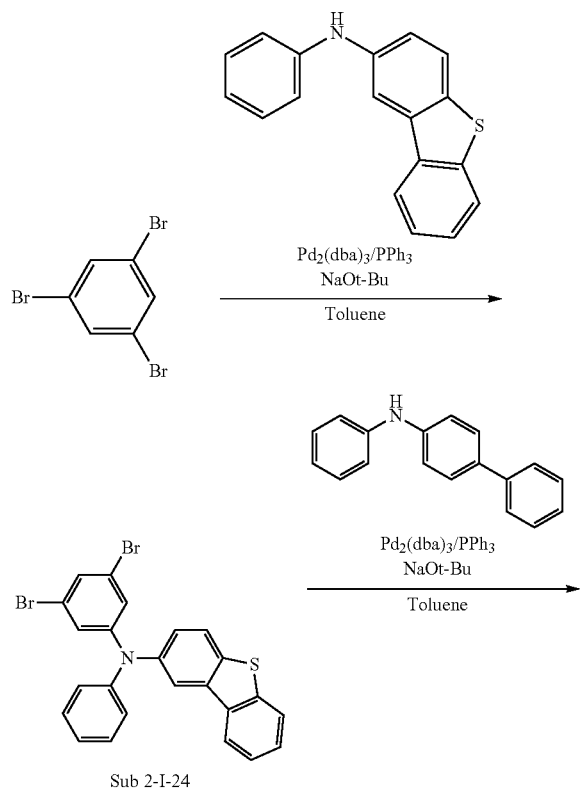

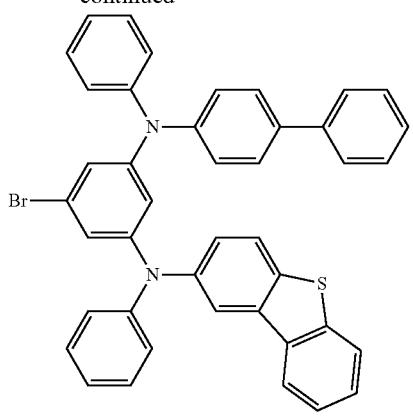

Sub 2-24

(1) Synthesis of Sub 2-I-24

61.56 g (yield: 50%) of the product was obtained by using N-phenyldibenzo[b,d]thiophen-2-amine (66.57 g, 241.75 mmol), 1,3,5-tribromobenzene (98.93 g, 314.27 mmol), Pd$_2$(dba)$_3$ (6.64 g, 7.25 mmol), PPh$_3$ (5.07 g, 19.34 mmol), NaOt-Bu (92.94 g, 966.99 mmol), toluene (1390 ml) in the same manner as described above for the synthesis of Sub 2-I-1.

(2) Synthesis of Sub 2-24

36.33 g (yield: 58%) of the product was obtained by using N-phenyl-[1,1'-biphenyl]-4-amine (22.81 g, 92.98 mmol), Sub 2-I-24 (61.56 g, 120.87 mmol), Pd$_2$(dba)$_3$ (2.55 g, 2.79 mmol), PPh$_3$ (1.95 g, 7.44 mmol), NaOt-Bu (35.75 g, 371.92 mmol), toluene (540 ml) in the same manner as described above for the synthesis of Sub 2-1.

6. Synthesis Examples of Sub 2-36

<Reaction Scheme 24>

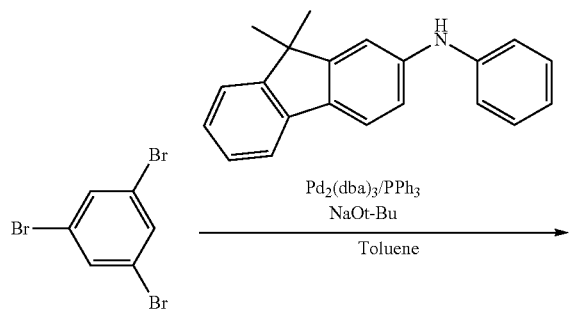

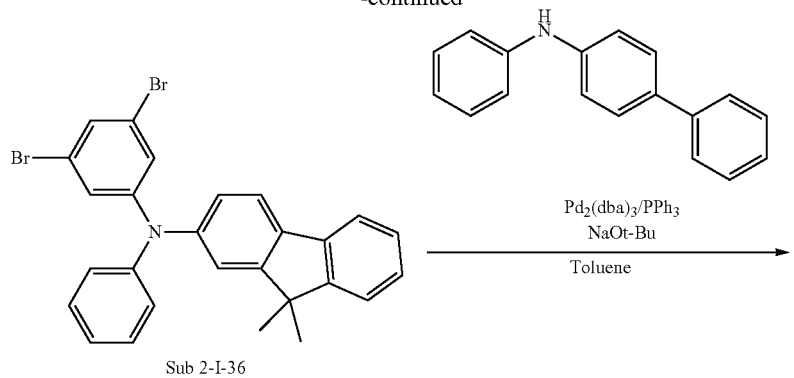

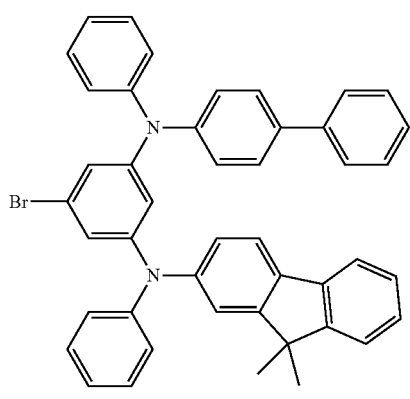

(1) Synthesis of Sub 2-I-36

39.29 g (yield: 49%) of the product was obtained by using 9,9-dimethyl-N-phenyl-9H-fluoren-2-amine (44.07 g, 154.43 mmol), 1,3,5-tribromobenzene (63.20 g, 200.75 mmol), $Pd_2(dba)_3$ (4.24 g, 4.63 mmol), $PPh_3$ (3.24 g, 12.35 mmol), NaOt-Bu (59.37 g, 617.70 mmol), toluene (890 ml) in the same manner as described above for the synthesis of Sub 2-I-1.

(2) Synthesis of Sub 2-36

21.09 g (yield: 53%) of the product was obtained by using N-phenyl-[1,1'-biphenyl]-4-amine (14.28 g, 58.21 mmol), Sub 2-I-36 (39.29 g, 75.67 mmol), $Pd_2(dba)_3$ (1.60 g, 1.75 mmol), $PPh_3$ (1.22 g, 4.66 mmol), NaOt-Bu (22.38 g, 232.84 mmol), toluene (340 ml) in the same manner as described above for the synthesis of Sub 2-1.

7. Synthesis Examples of Sub 2-47

<Reaction Scheme 25>

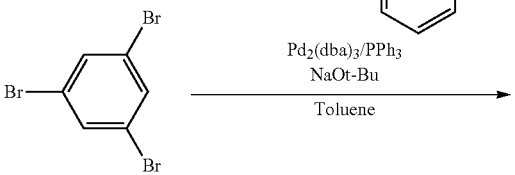

107
-continued

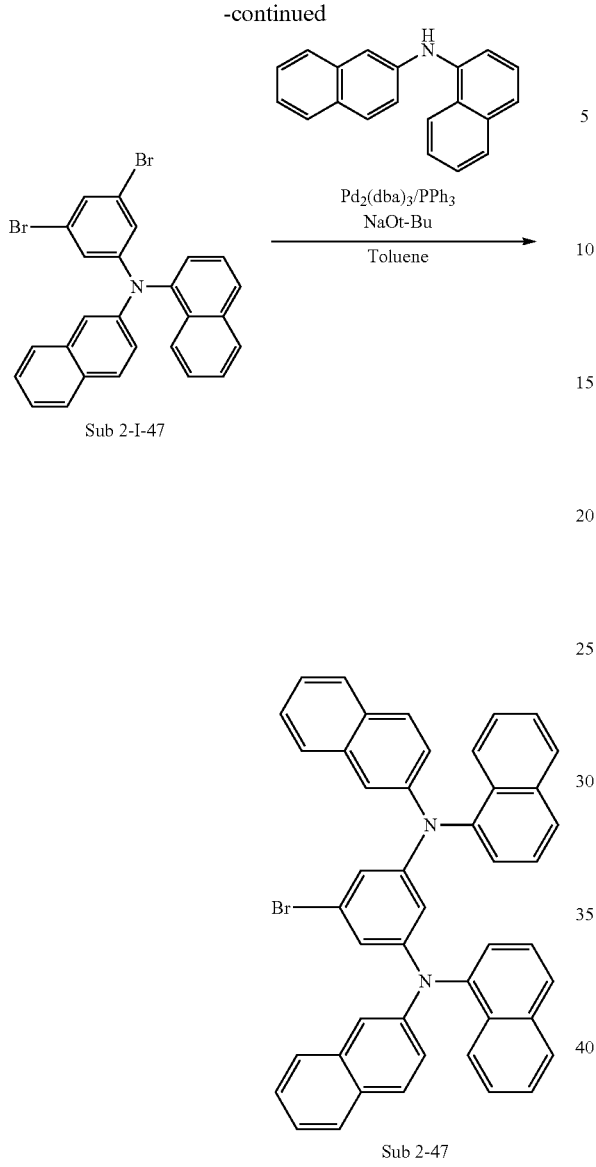

108
8. Synthesis Examples of Sub 2-51

<Reaction Scheme 26>

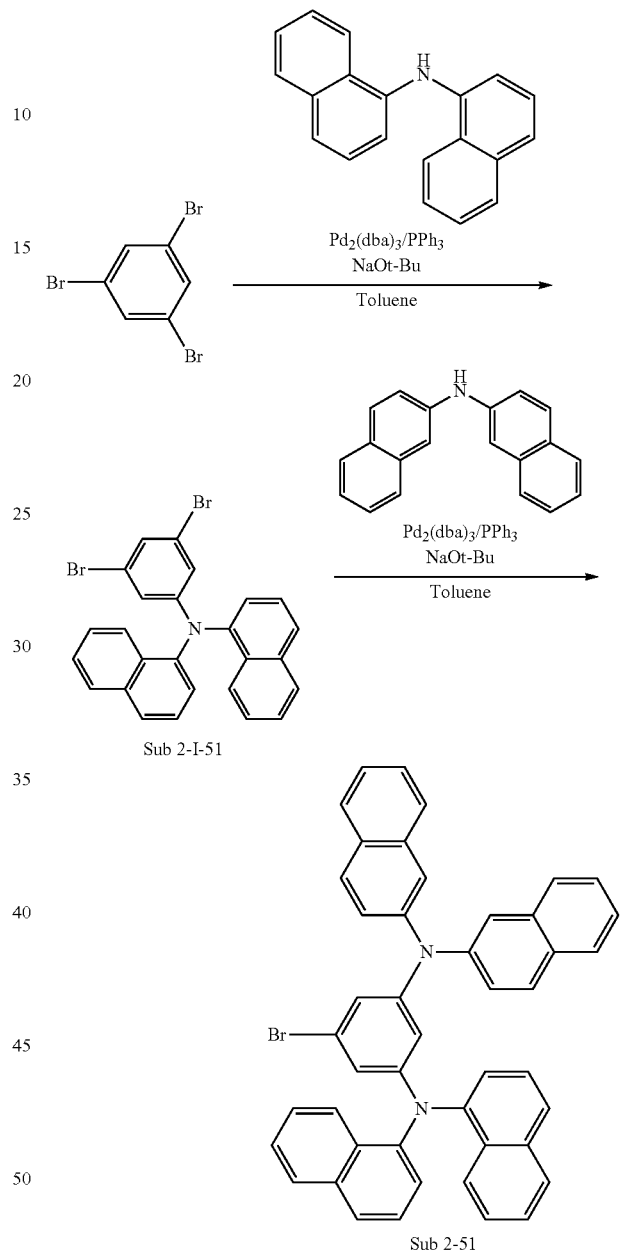

(1) Synthesis of Sub 2-I-47

37.11 g (yield: 48%) of the product was obtained by using N-(naphthalen-2-yl)naphthalen-1-amine (41.38 g, 153.63 mmol), 1,3,5-tribromobenzene (62.87 g, 199.73 mmol), Pd$_2$(dba)$_3$ (4.22 g, 4.61 mmol), PPh$_3$ (3.22 g, 12.29 mmol), NaOt-Bu (59.06 g, 614.54 mmol), toluene (880 ml) in the same manner as described above for the synthesis of Sub 2-I-1.

(2) Synthesis of Sub 2-47

20.01 g (yield: 51%) of the product was obtained by using N-(naphthalen-2-yl)naphthalen-1-amine (15.28 g, 56.73 mmol), Sub 2-I-47 (37.11 g, 73.75 mmol), Pd$_2$(dba)$_3$ (1.56 g, 1.70 mmol), PPh$_3$ (1.19 g, 4.54 mmol), NaOt-Bu (21.81 g, 226.93 mmol), toluene (330 ml) in the same manner as described above for the synthesis of Sub 2-1.

(1) Synthesis of Sub 2-I-51

36.65 g (yield: 49%) of the product was obtained by using di(naphthalen-1-yl)amine (40.03 g, 148.62 mmol), 1,3,5-tribromobenzene (60.82 g, 193.21 mmol), Pd$_2$(dba)$_3$ (4.08 g, 4.46 mmol), PPh$_3$ (3.12 g, 11.89 mmol), NaOt-Bu (57.14 g, 594.49 mmol), toluene (860 ml) in the same manner as described above for the synthesis of Sub 2-I-1.

(2) Synthesis of Sub 2-51

20.54 g (yield: 53%) of the product was obtained by using di(naphthalen-2-yl)amine (15.09 g, 56.03 mmol), Sub 2-I-51

(36.65 g, 72.83 mmol), Pd₂(dba)₃ (1.54 g, 1.68 mmol), PPh₃ (1.18 g, 4.48 mmol), NaOt-Bu (21.54 g, 224.10 mmol), toluene (320 ml) in the same manner as described above for the synthesis of Sub 2-1.

9. Synthesis Examples of Sub 2-63

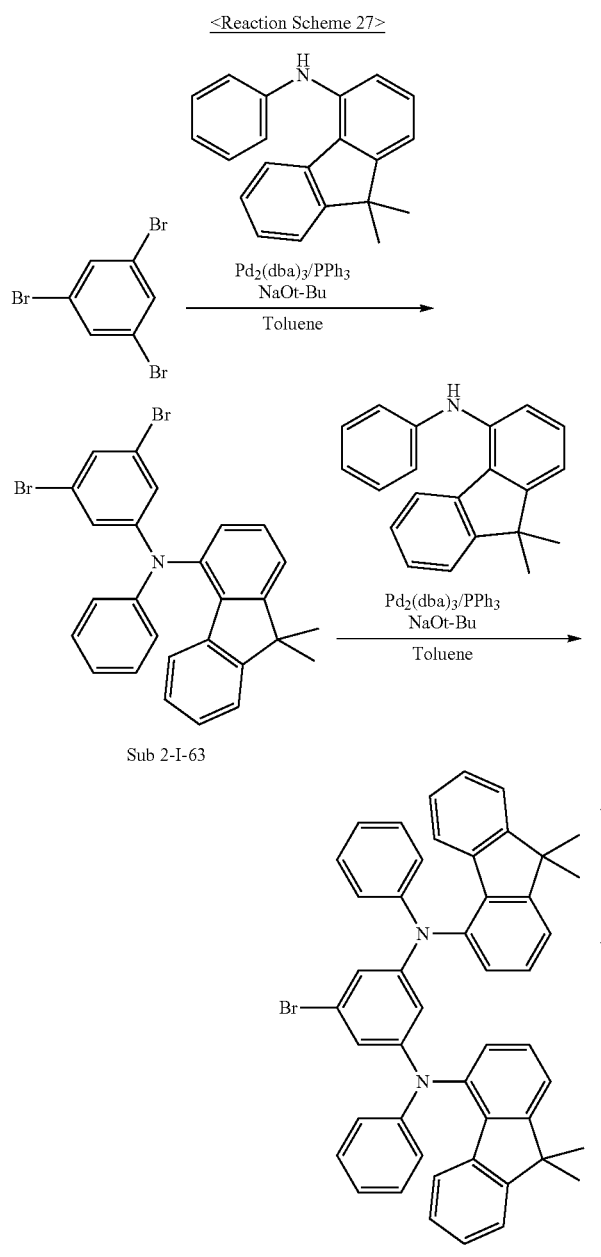

Sub 2-I-63

Sub 2-63

(1) Synthesis of Sub 2-I-63

35.98 g (yield: 46%) of the product was obtained by using 9,9-dimethyl-N-phenyl-9H-fluoren-4-amine (42.99 g, 150.64 mmol), 1,3,5-tribromobenzene (61.65 g, 195.83 mmol), Pd₂(dba)₃ (4.14 g, 4.52 mmol), PPh₃ (3.16 g, 12.05 mmol), NaOt-Bu (57.91 g, 602.57 mmol), toluene (870 ml) in the same manner as described above for the synthesis of Sub 2-I-1.

(2) Synthesis of Sub 2-63

18.52 g (yield: 48%) of the product was obtained by using 9,9-dimethyl-N-phenyl-9H-fluoren-4-amine (15.21 g, 53.30 mmol), Sub 2-I-63 (35.98 g, 69.29 mmol), Pd₂(dba)₃ (1.46 g, 1.60 mmol), PPh₃ (1.12 g, 4.26 mmol), NaOt-Bu (20.49 g, 213.19 mmol), toluene (310 ml) in the same manner as described above for the synthesis of Sub 2-1.

10. Synthesis Examples of Sub 2-77

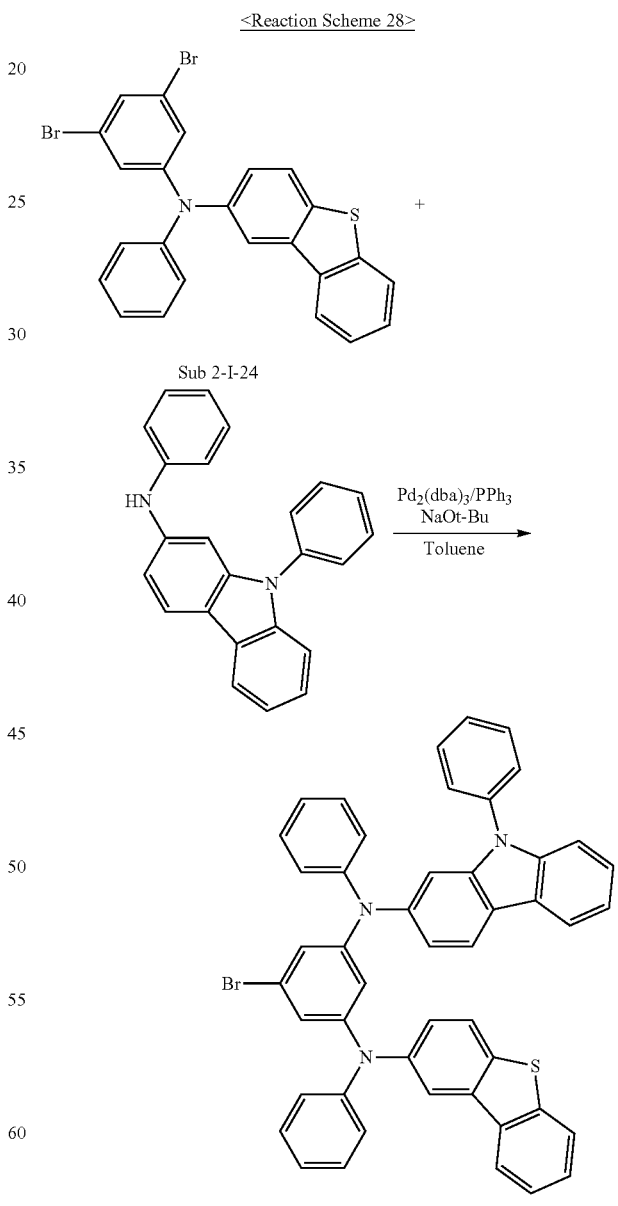

Sub 2-I-24

Sub 2-77

22.95 g (yield: 54%) of the product was obtained by using N,9-diphenyl-9H-carbazol-2-amine (18.63 g, 55.71 mmol), Sub 2-I-24 (36.88 g, 72.42 mmol), Pd$_2$(dba)$_3$ (1.53 g, 1.67 mmol), PPh$_3$ (1.17 g, 4.46 mmol), NaOt-Bu (21.42 g, 222.84 mmol), toluene (320 ml) in the same manner as described above for the synthesis of Sub 2-1.

11. Synthesis Examples of Sub 2-91

<Reaction Scheme 29>

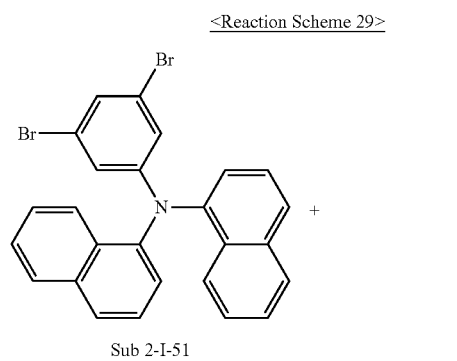

Sub 2-I-51

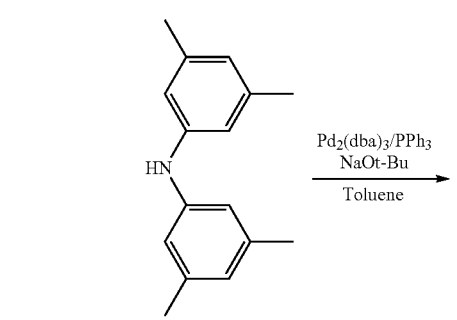

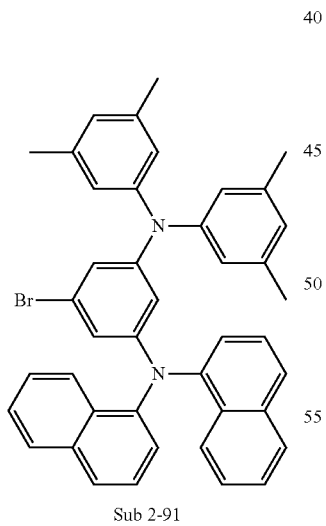

Sub 2-91

15.71 g (yield: 46%) of the product was obtained by using bis(3,5-dimethylphenyl)amine (11.88 g, 52.72 mmol), Sub 2-I-51 (34.49 g, 68.54 mmol), Pd$_2$(dba)$_3$ (1.45 g, 1.58 mmol), PPh$_3$ (1.11 g, 4.22 mmol), NaOt-Bu (20.27 g, 210.89 mmol), toluene (300 ml) in the same manner as described above for the synthesis of Sub 2-1.

12. Synthesis Examples of Sub 2-104

<Reaction Scheme 30>

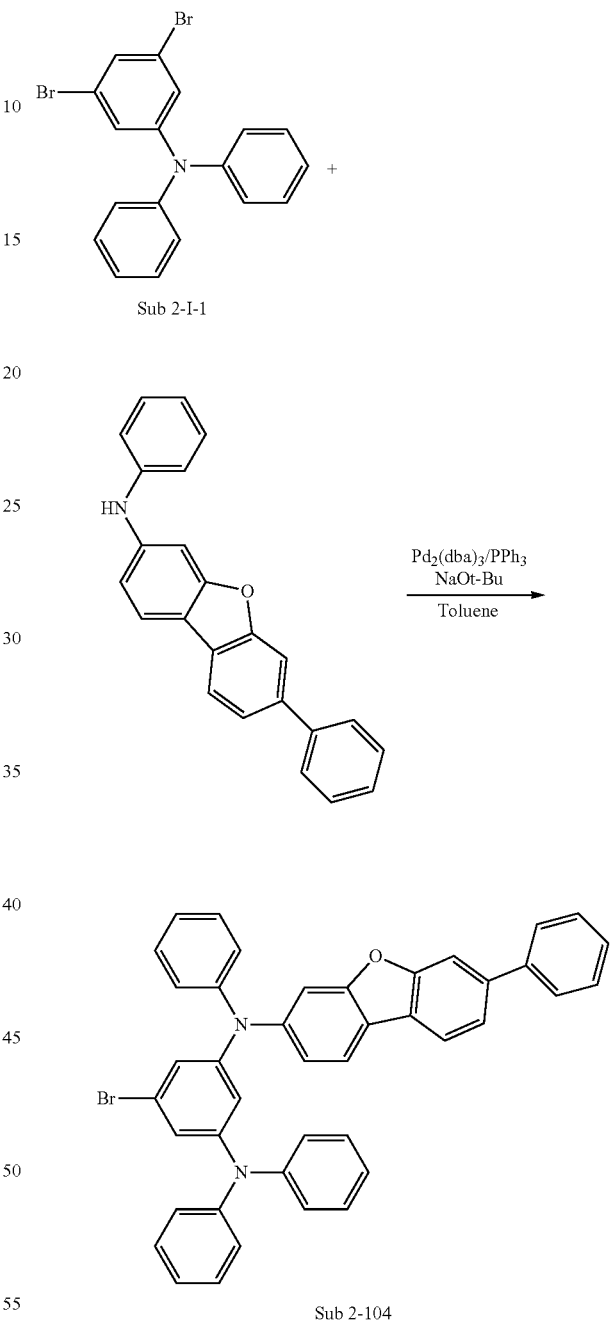

17.58 g (yield: 53%) of the product was obtained by using N,7-diphenyldibenzo[b,d]furan-3-amine (16.92 g, 50.45 mmol), Sub 2-I-1 (26.44 g, 65.58 mmol), Pd$_2$(dba)$_3$ (1.39 g, 1.51 mmol), PPh$_3$ (1.06 g, 4.04 mmol), NaOt-Bu (19.39 g, 201.79 mmol), toluene (290 ml) in the same manner as described above for the synthesis of Sub 2-1.

The compound belonging to Sub 2 may be, but not limited to, the following compounds, and Table 2 shows FD-MS values of compounds belonging to Sub 2.

Sub 2-1
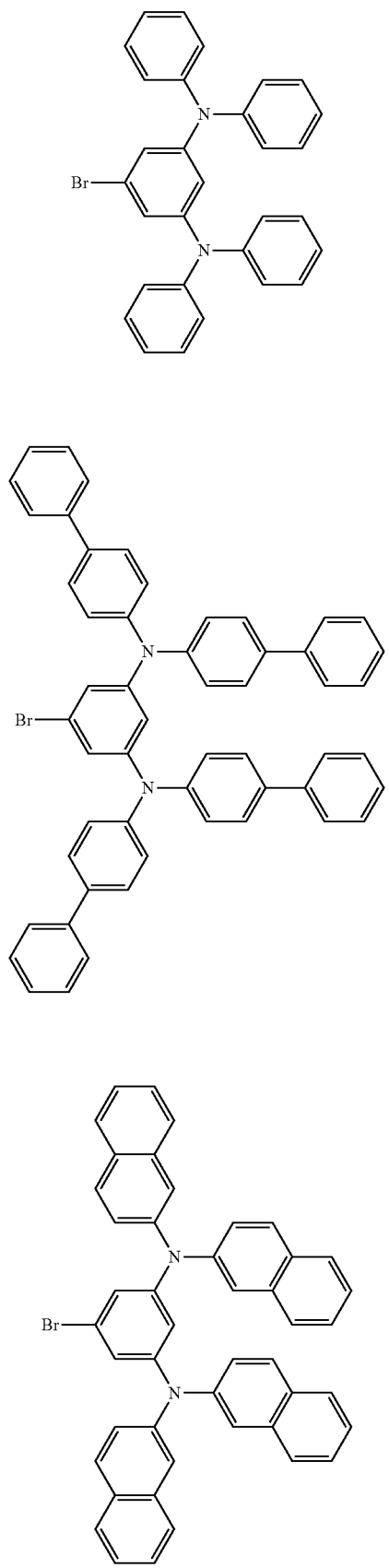
Sub 2-2
Sub 2-3
Sub 2-4
Sub 2-5

Sub 2-6
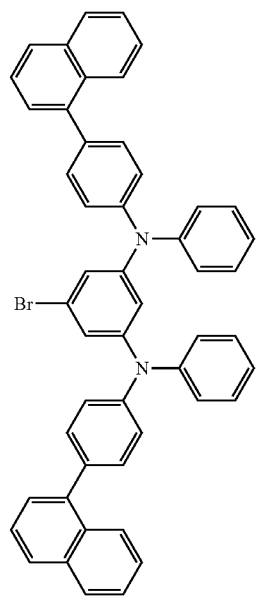
Sub 2-7
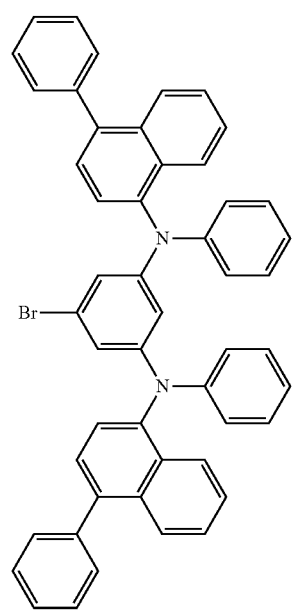
Sub 2-8
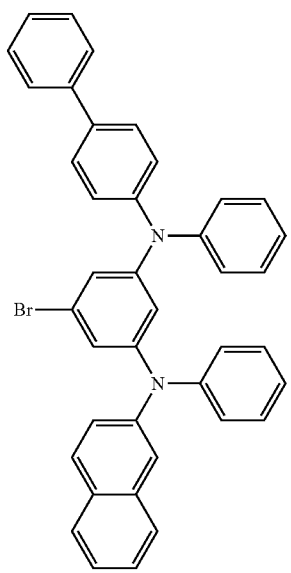
Sub 2-9
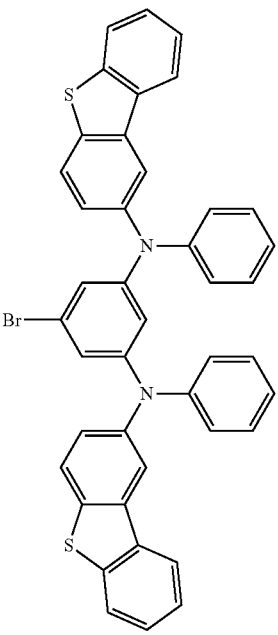

Sub 2-10
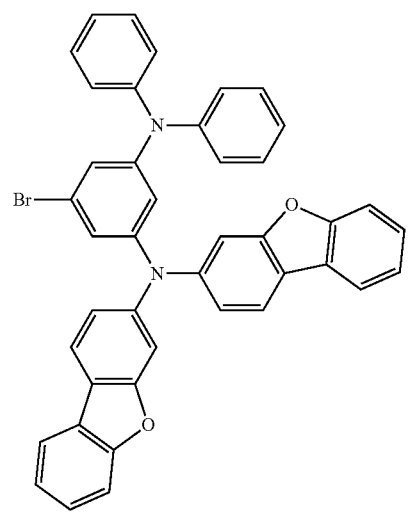
Sub 2-11
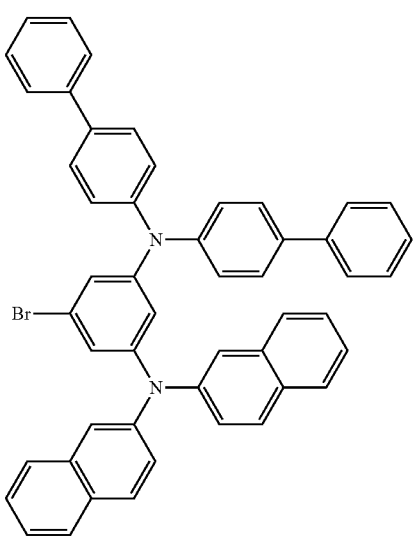
Sub 2-12
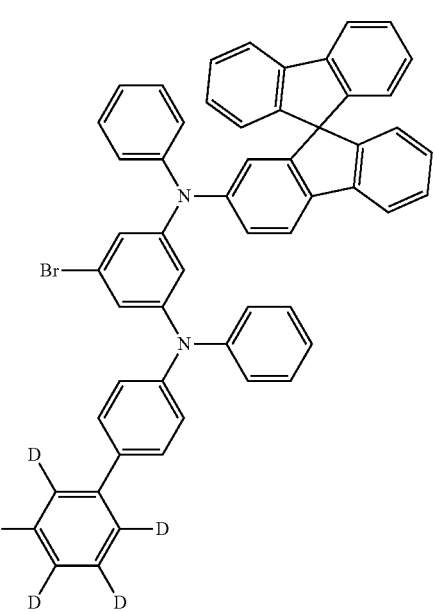
Sub 2-13
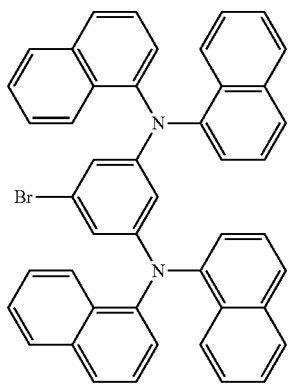
Sub 2-14
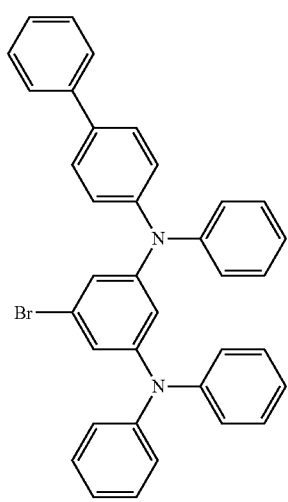
Sub 2-15
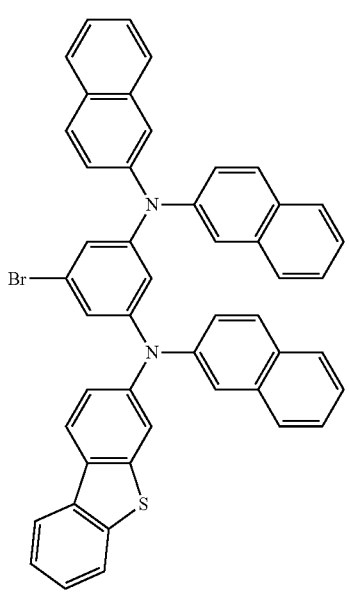

-continued
Sub 2-16
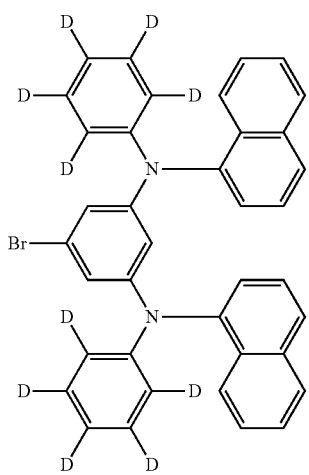
Sub 2-18
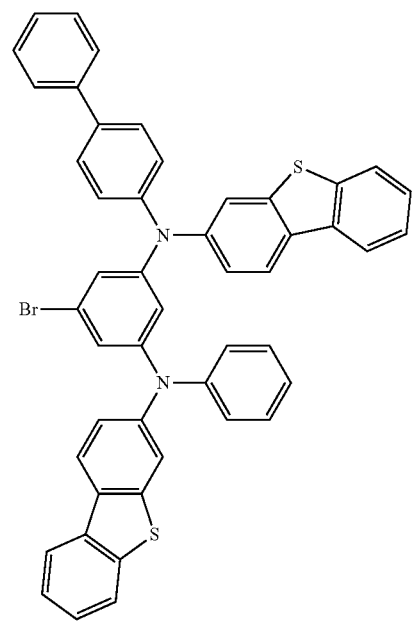
Sub 2-19
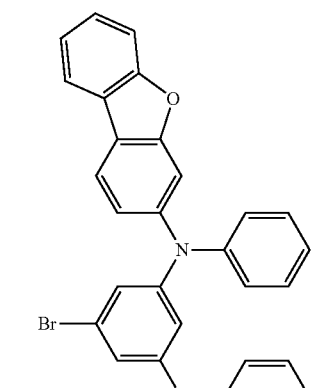
Sub 2-17
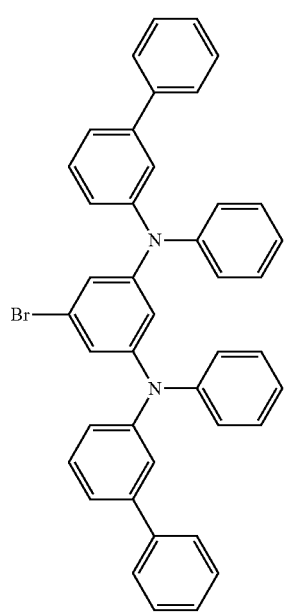
Sub 2-20
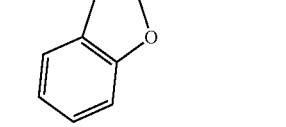

Sub 2-21
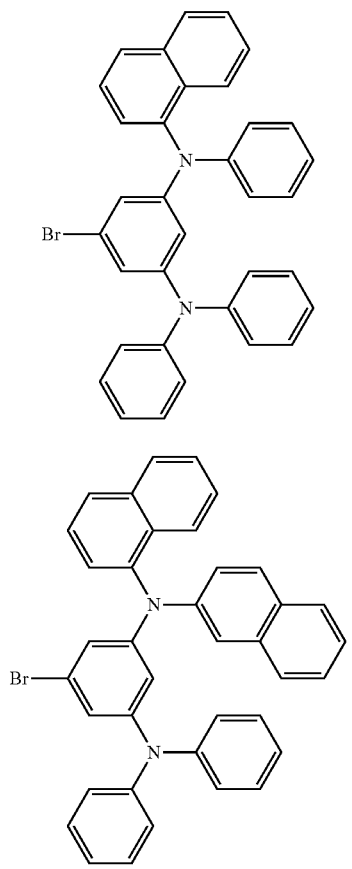
Sub 2-22
Sub 2-24
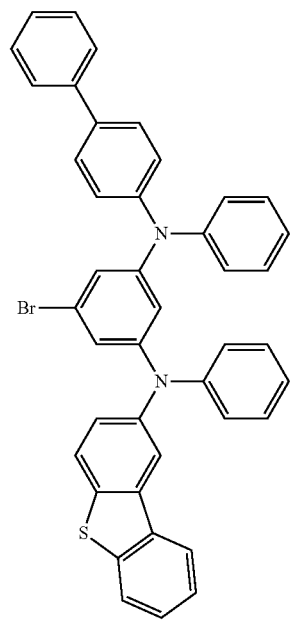
Sub 2-23
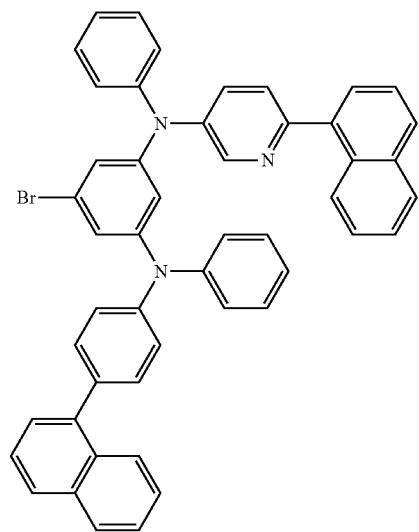
Sub 2-25
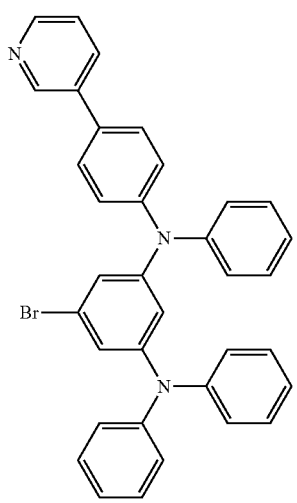

-continued
Sub 2-26
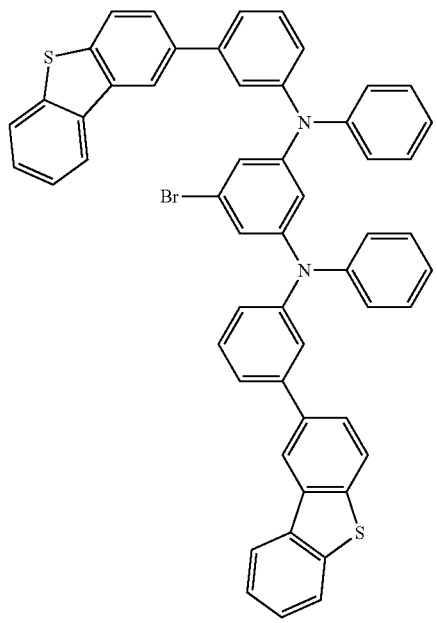
Sub 2-27
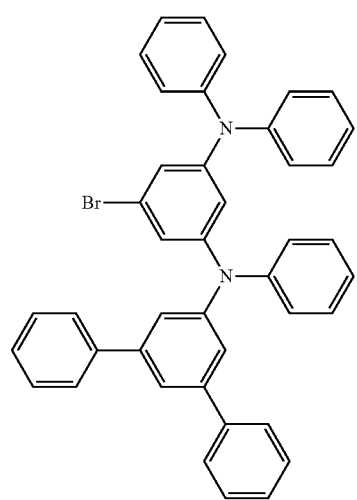
-continued
Sub 2-28
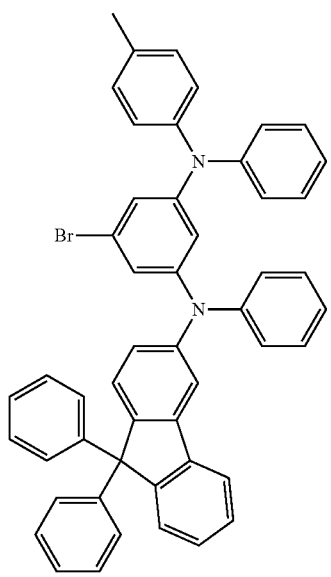
Sub 2-29
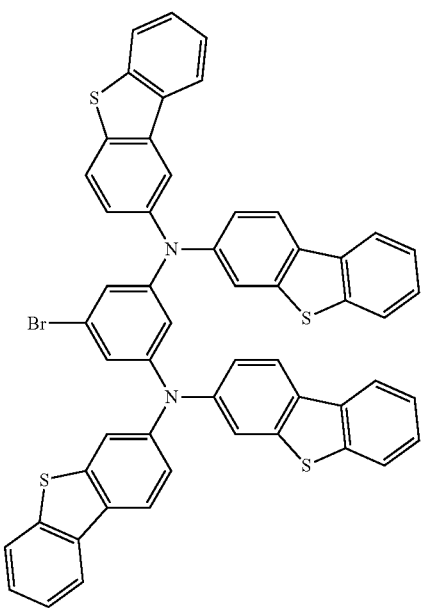
Sub 2-30
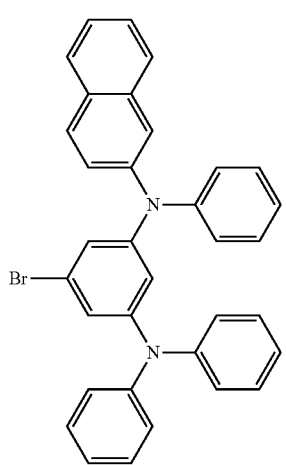

Sub 2-31
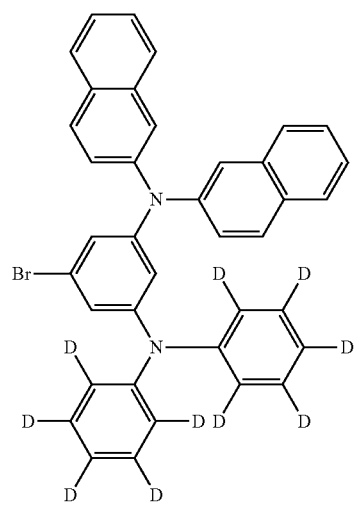
Sub 2-32
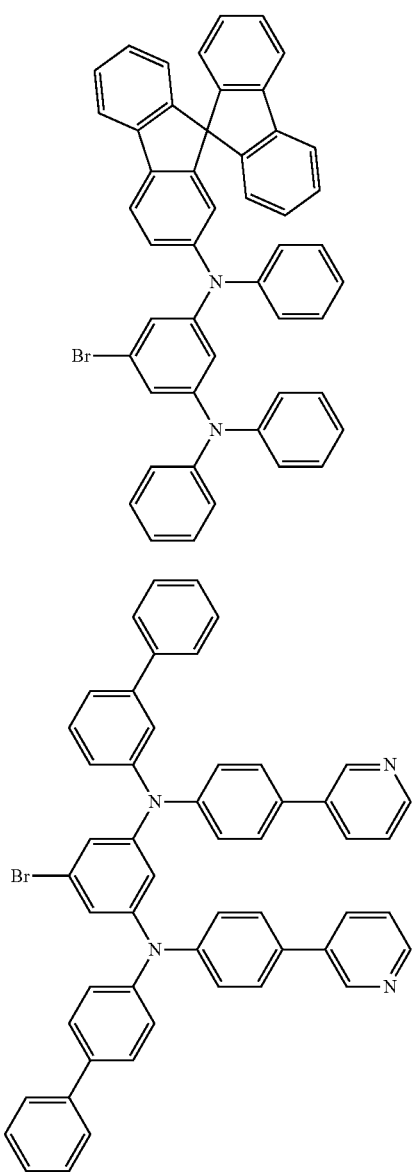
Sub 2-33
Sub 2-34
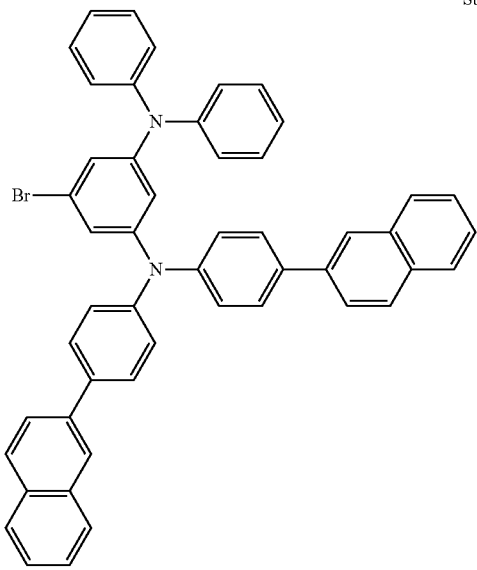
Sub 2-35
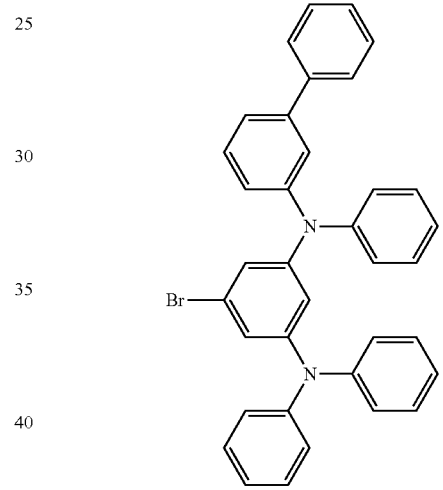
Sub 2-36
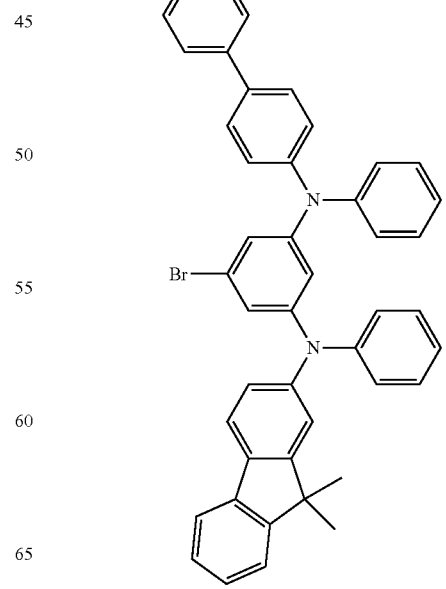

Sub 2-37
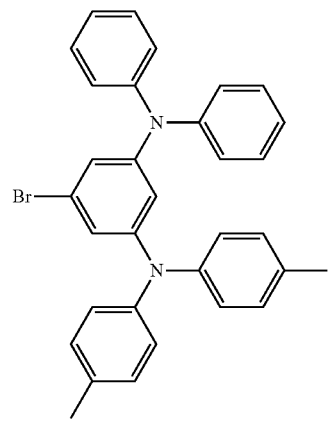
Sub 2-38
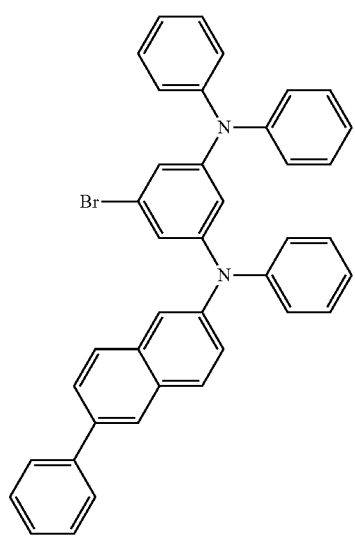
Sub 2-39
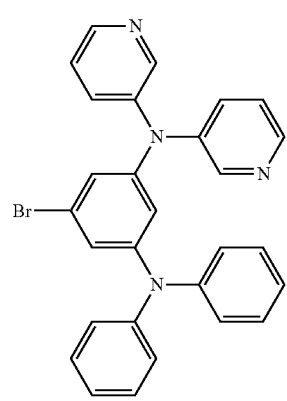
Sub 2-40
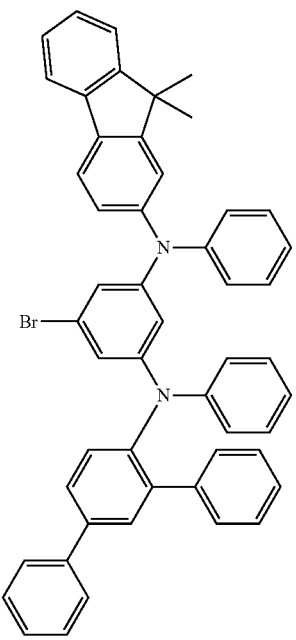
Sub 2-41
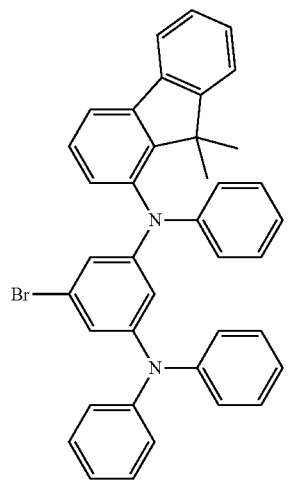
Sub 2-42
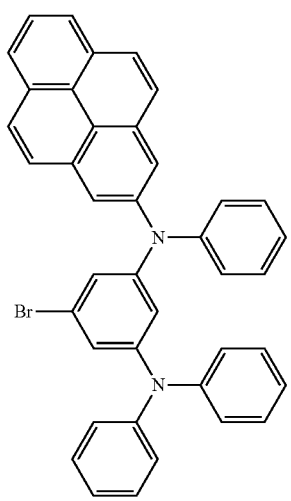

Sub 2-43
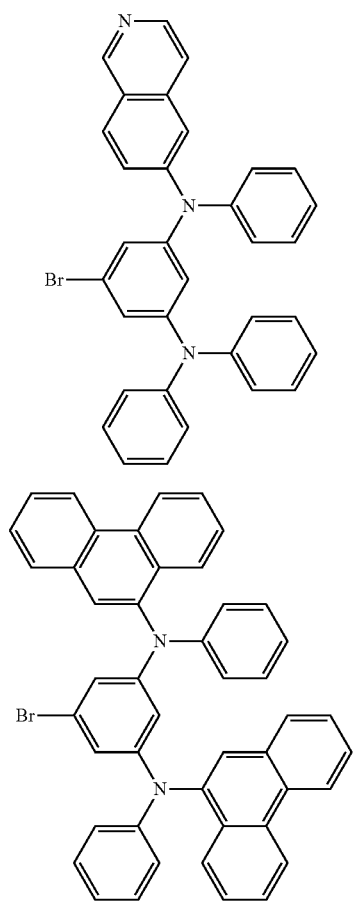
Sub 2-44
Sub 2-45
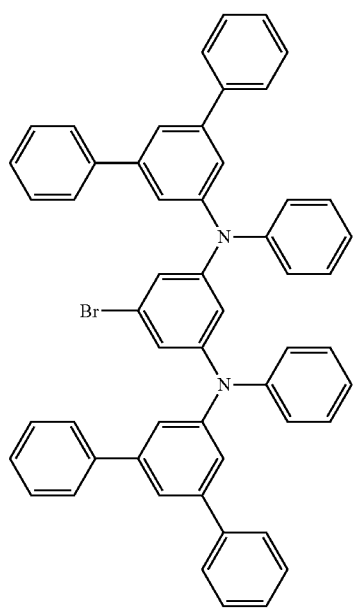
Sub 2-46
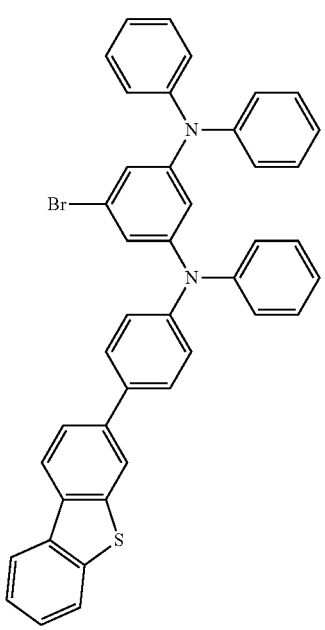
Sub 2-47
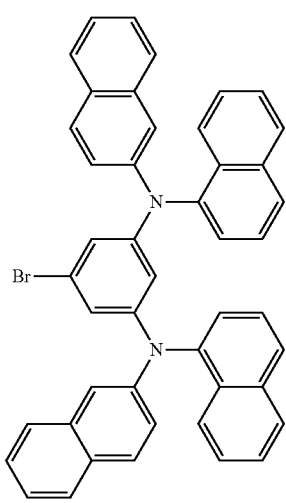

Sub 2-48
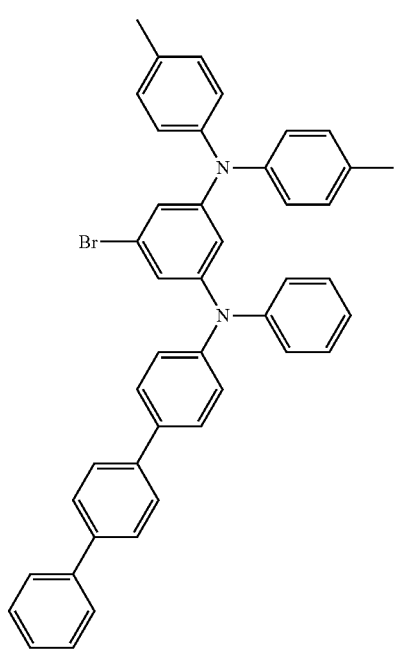
Sub 2-49
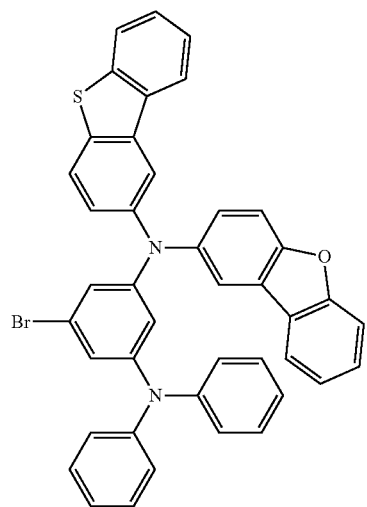
Sub 2-50
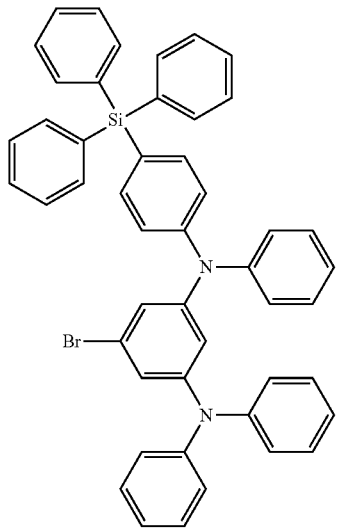
Sub 2-51
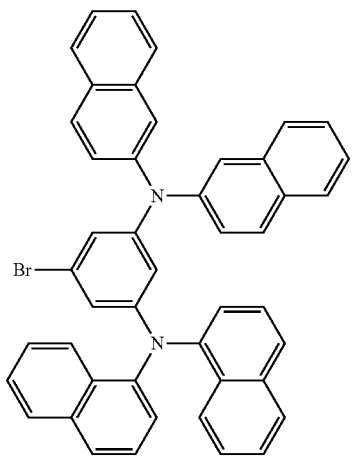
Sub 2-52
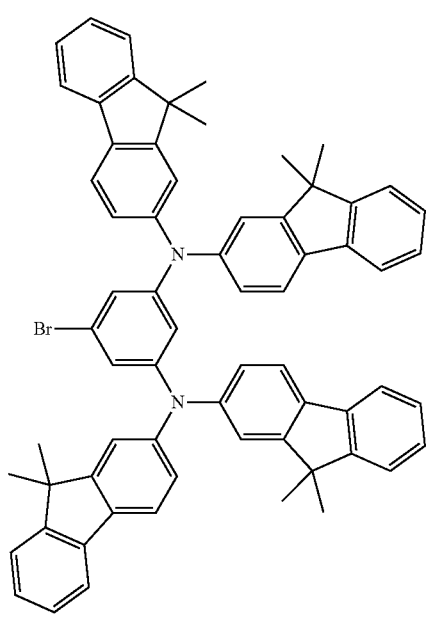
Sub 2-53
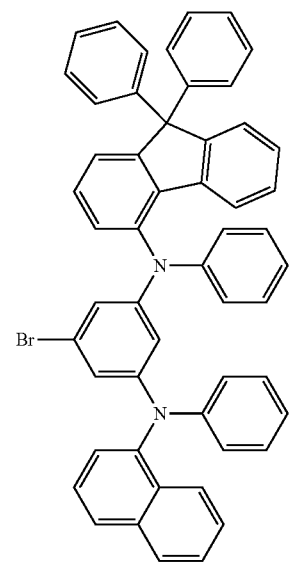

Sub 2-54
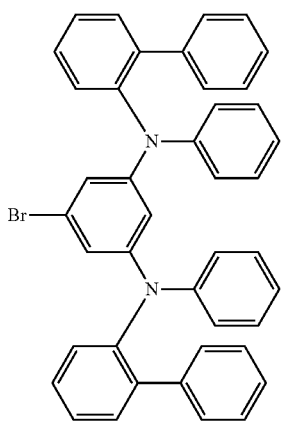
Sub 2-56
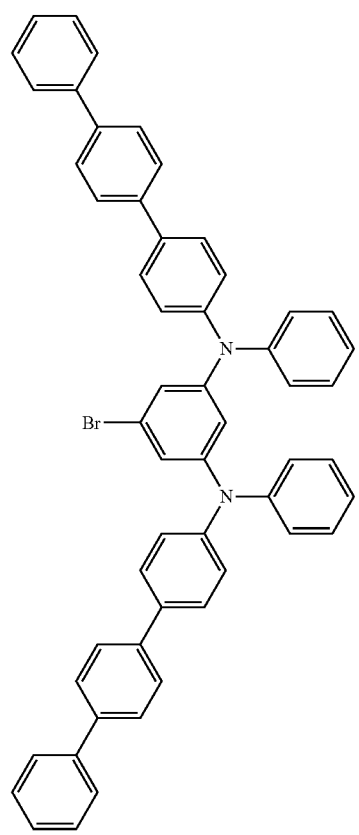
Sub 2-55
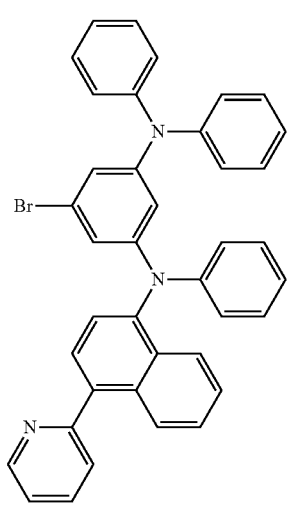
Sub 2-57
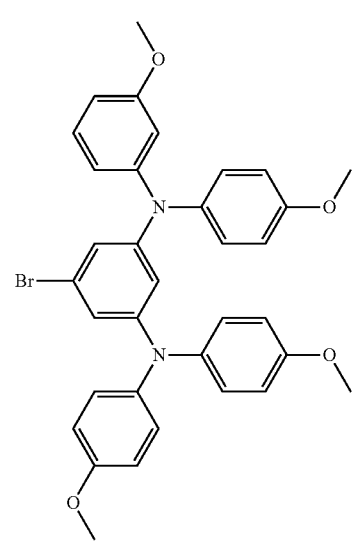

-continued
Sub 2-58
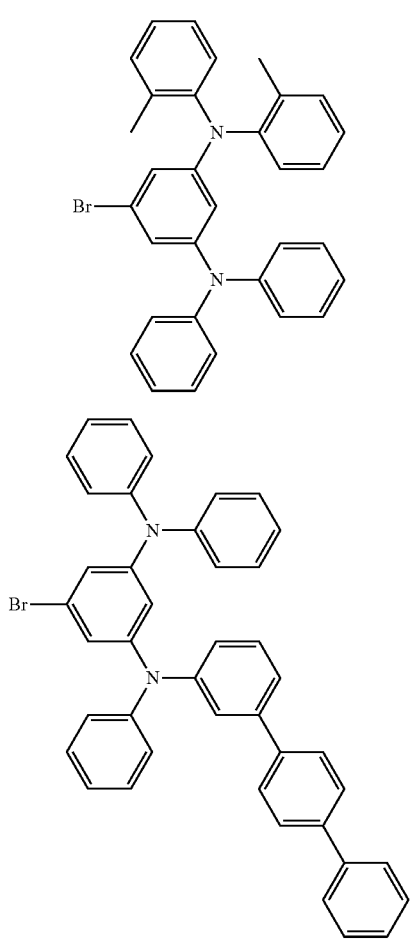
Sub 2-59
Sub 2-60
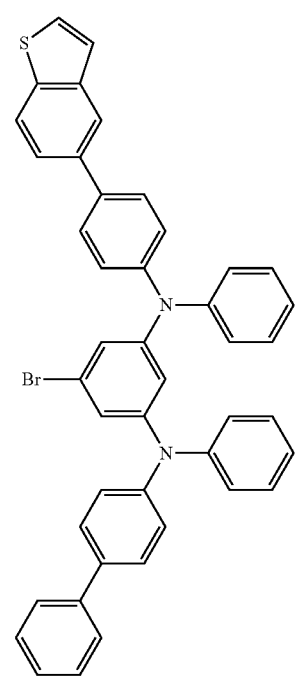
Sub 2-61
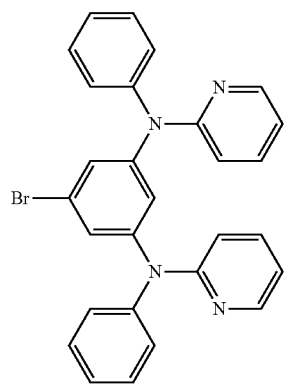
Sub 2-62
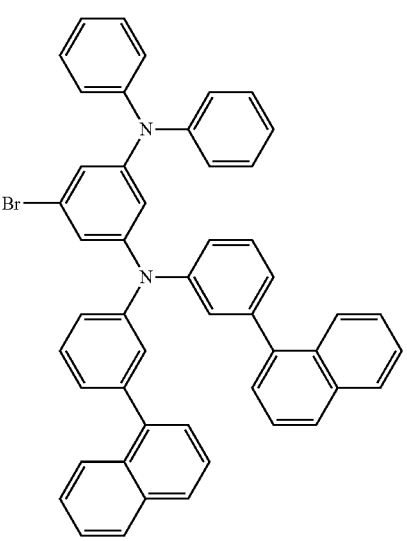
Sub 2-63
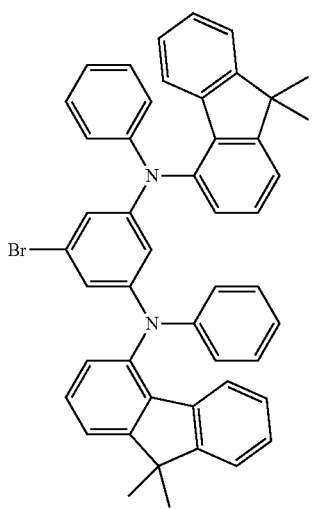

Sub 2-64
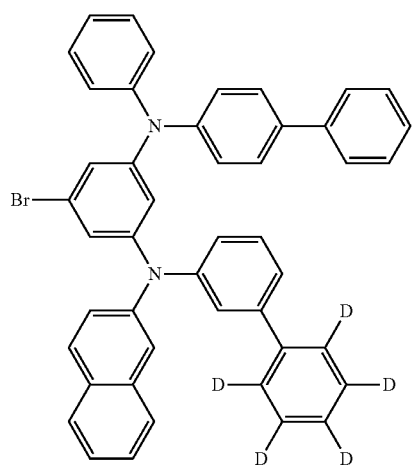
Sub 2-65
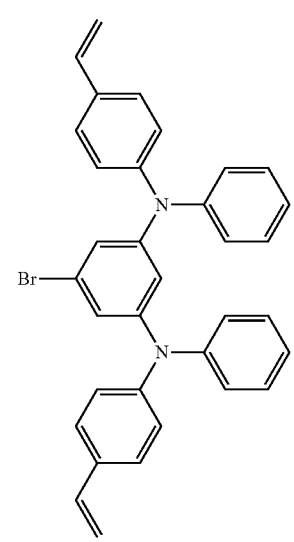
Sub 2-66
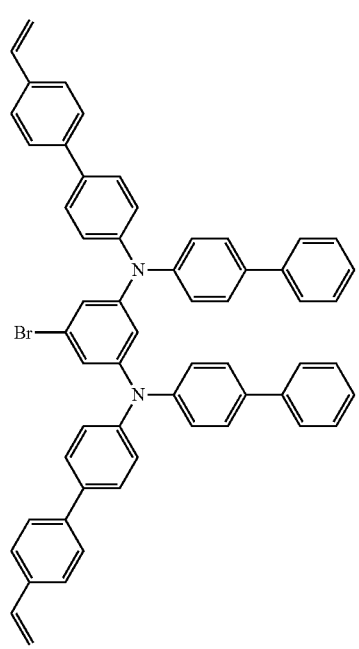
Sub 2-67
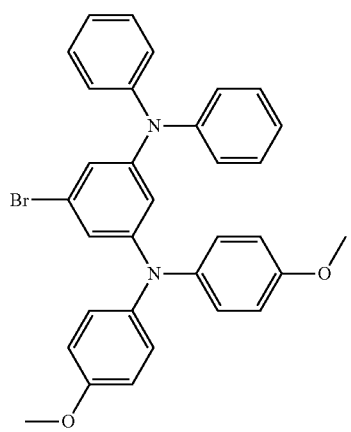
Sub 2-68
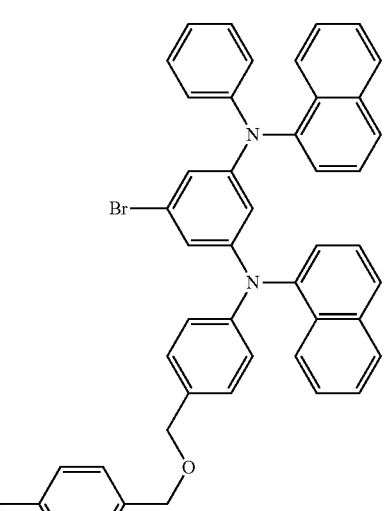
Sub 2-69
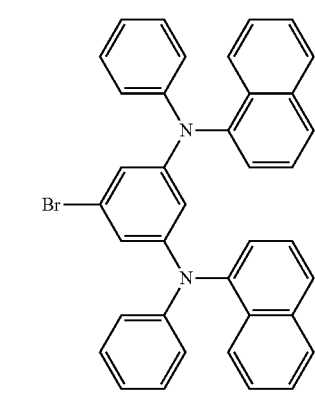

Sub 2-70
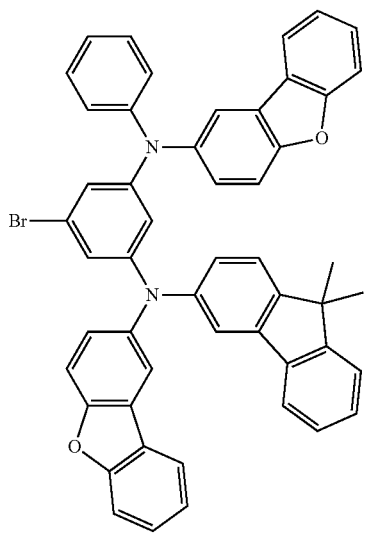
Sub 2-72
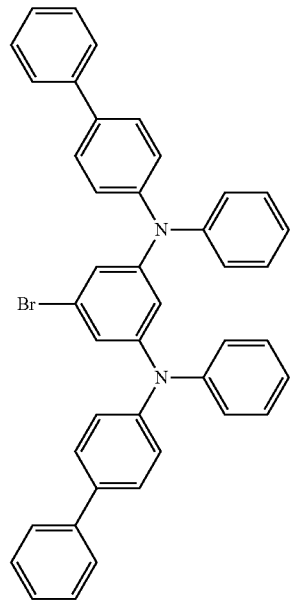
Sub 2-71
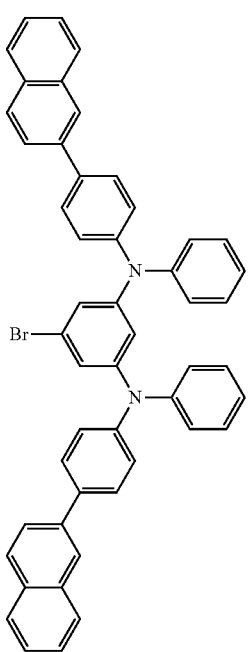
Sub 2-73
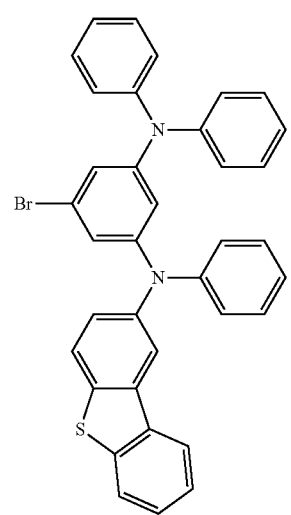

Sub 2-74
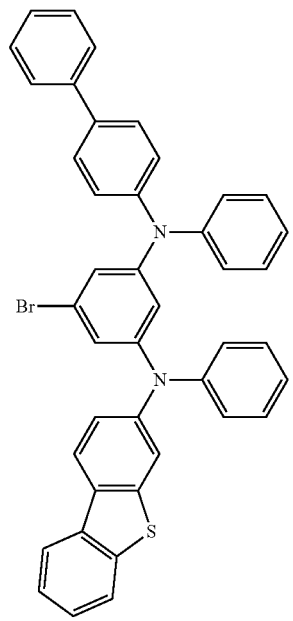
Sub 2-75
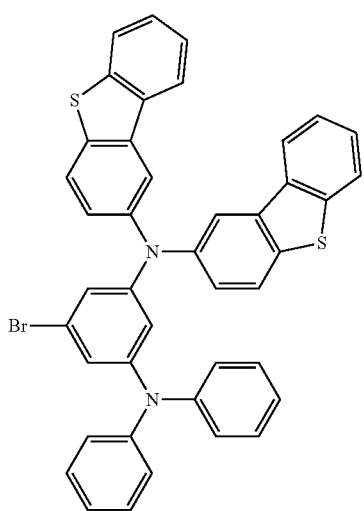
Sub 2-76
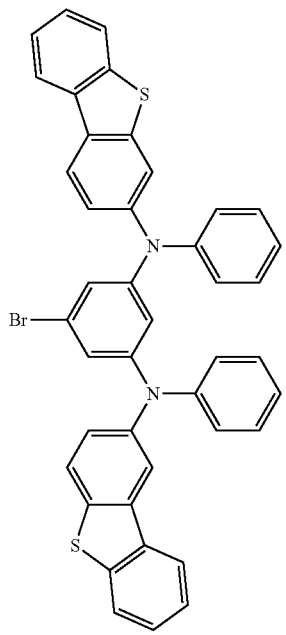
Sub 2-77
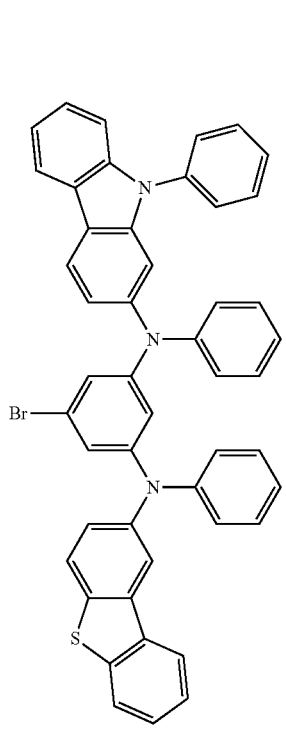

Sub 2-78
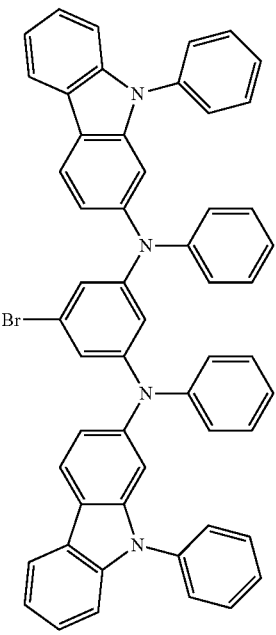
Sub 2-79
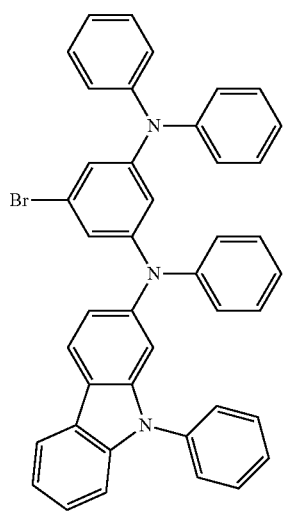
Sub 2-80
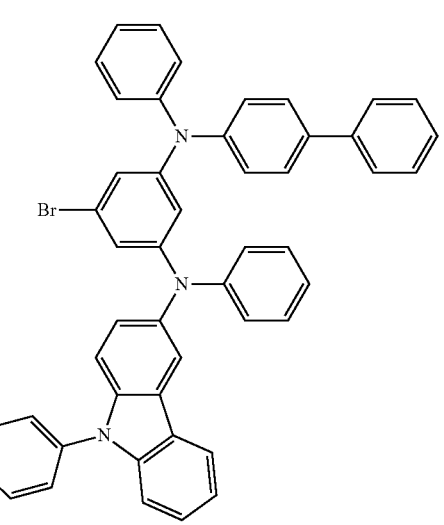
Sub 2-81
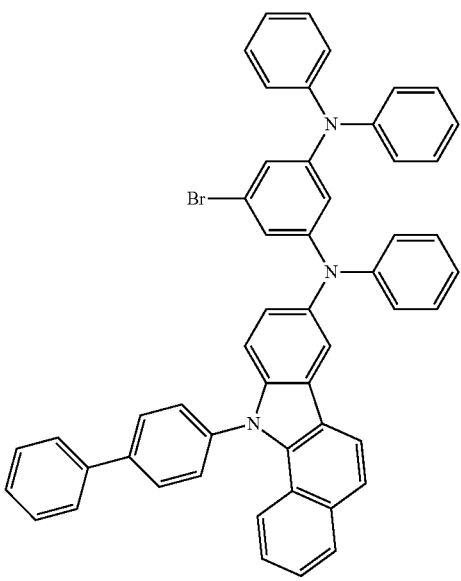
Sub 2-82
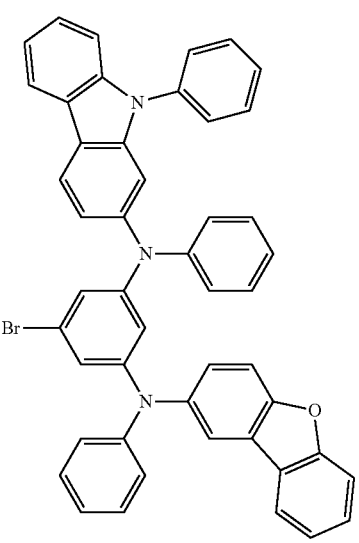
Sub 2-83
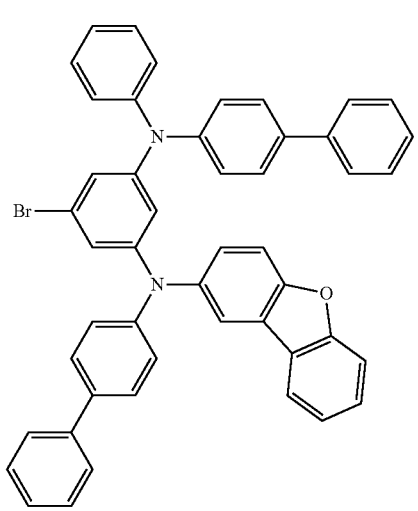

Sub 2-84
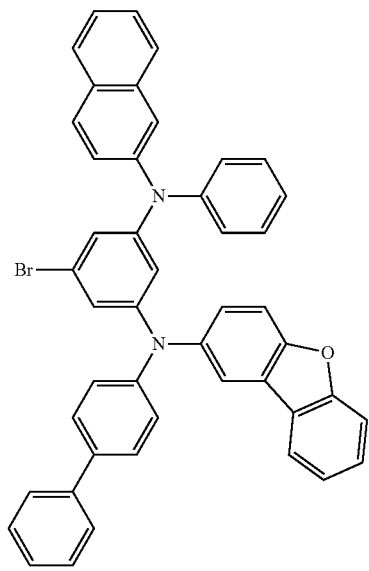
Sub 2-86
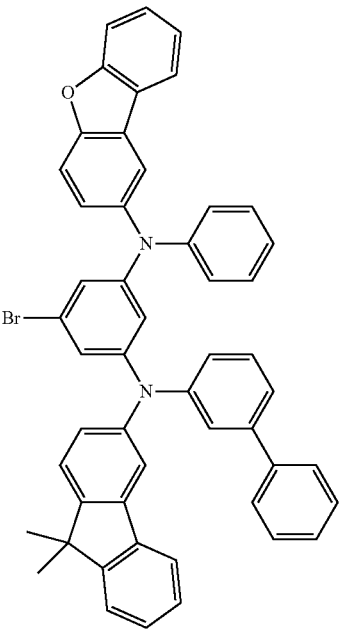
Sub 2-85
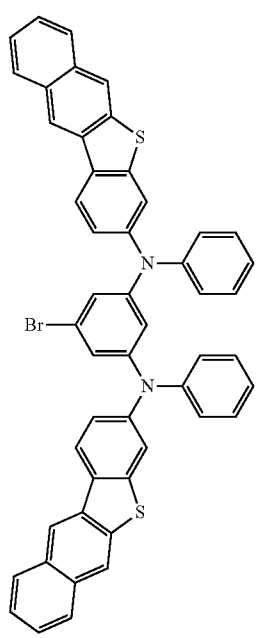
Sub 2-87
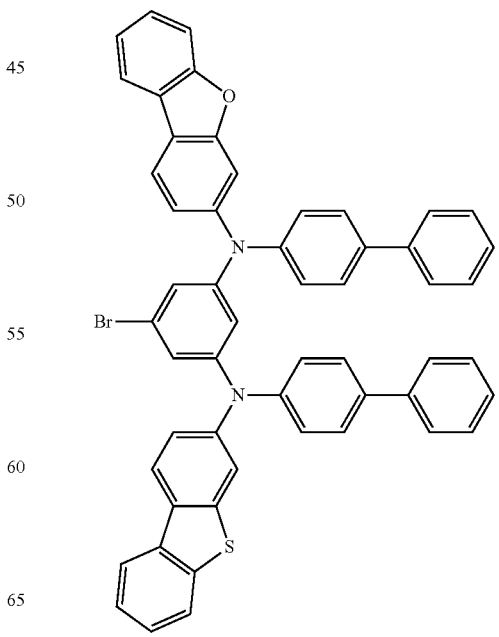

Sub 2-88
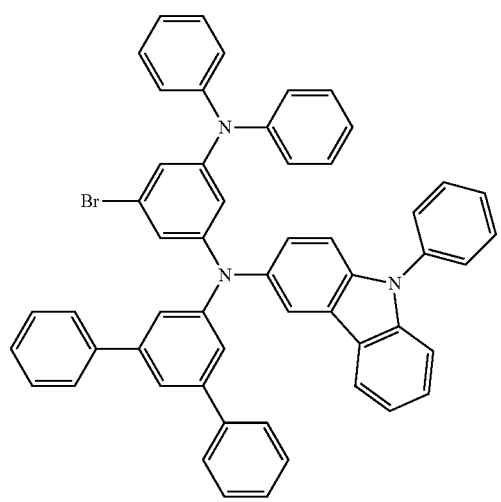
Sub 2-90
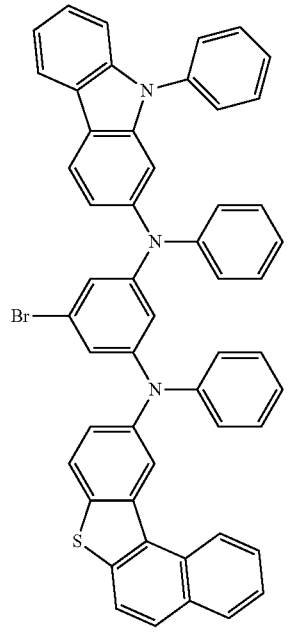
Sub 2-89
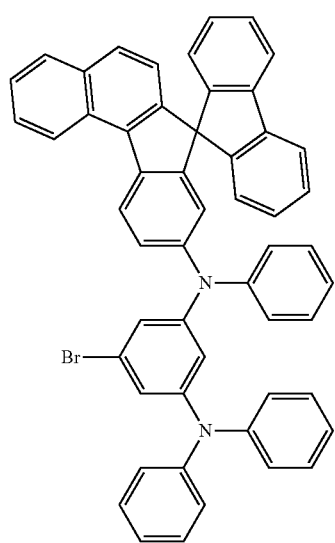
Sub 2-91
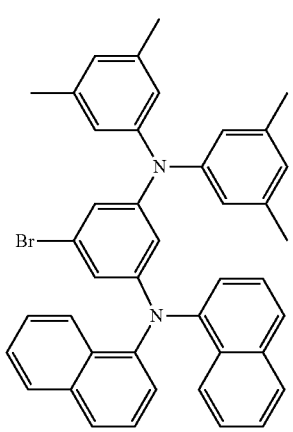

Sub 2-92
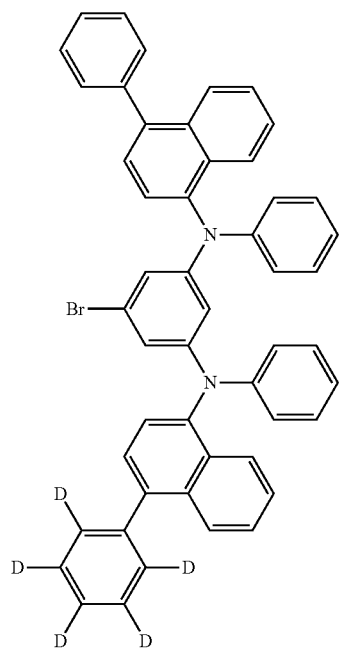
Sub 2-94
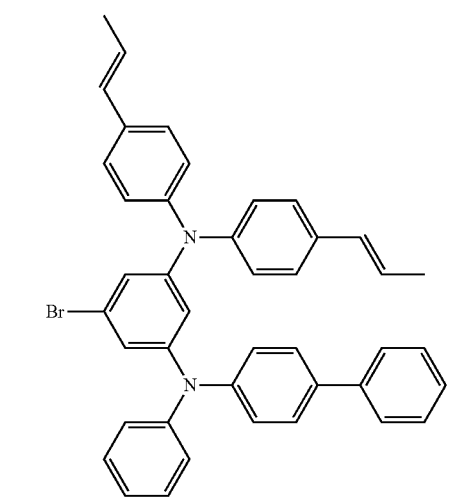
Sub 2-95
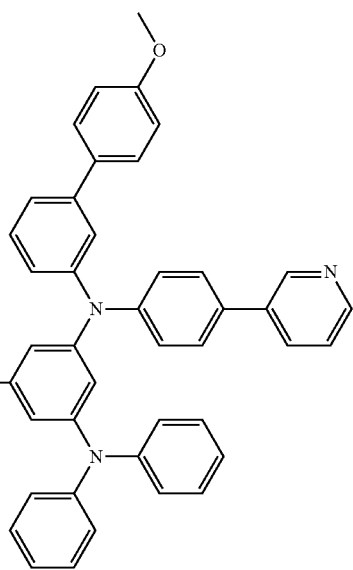
Sub 2-93
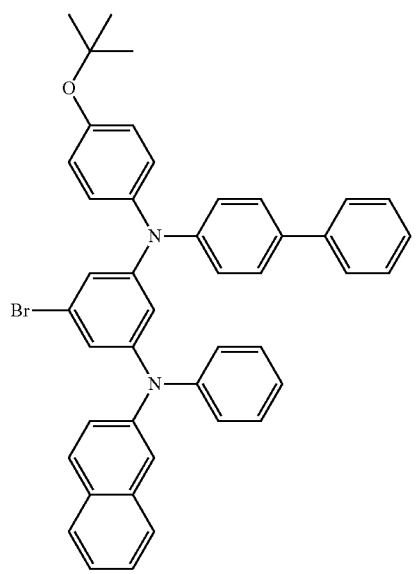
Sub 2-96

Sub 2-97
Sub 2-98
Sub 2-99
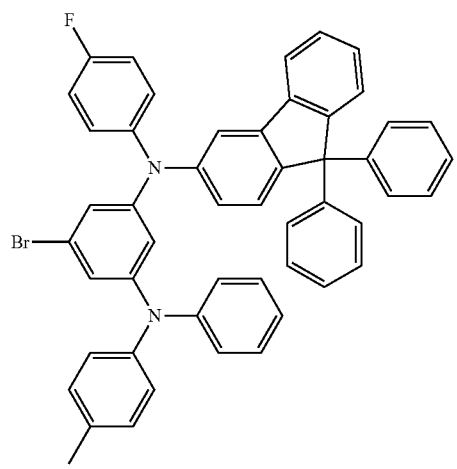
Sub 2-100
Sub 2-101
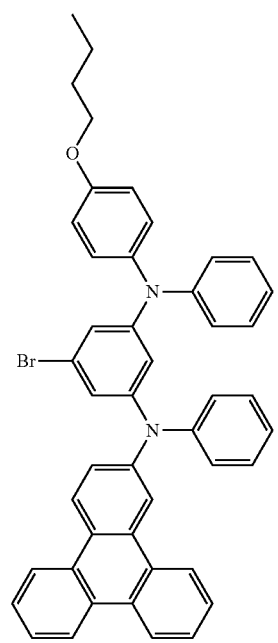

Sub 2-102
Sub 2-105
Sub 2-103
Sub 2-104
Sub 2-106
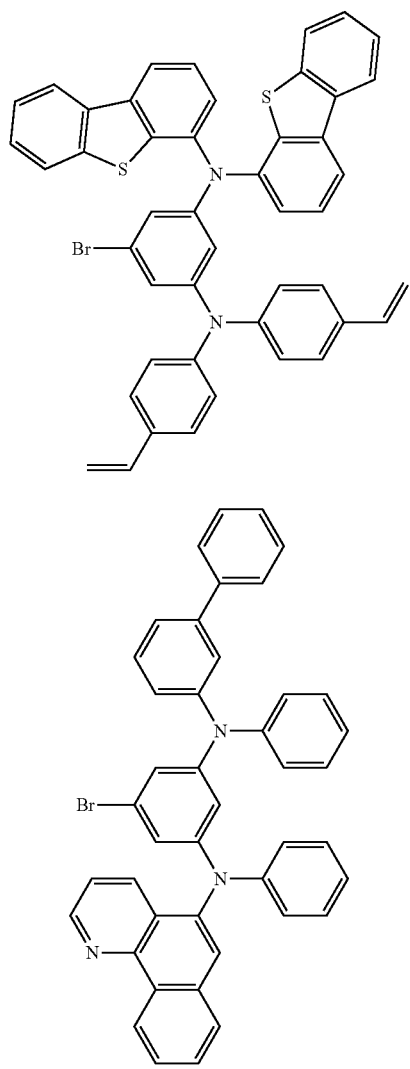
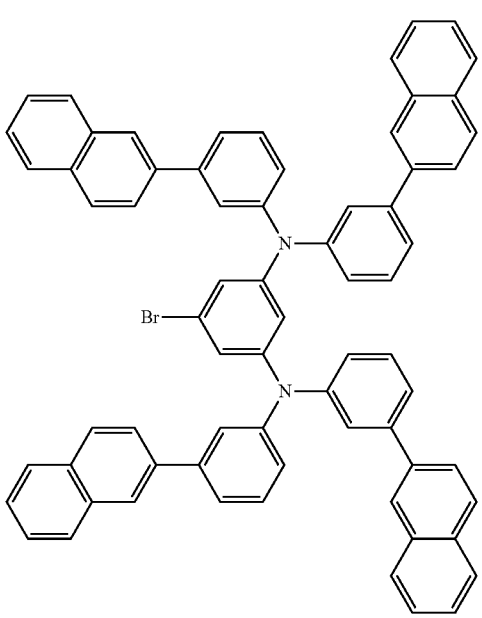
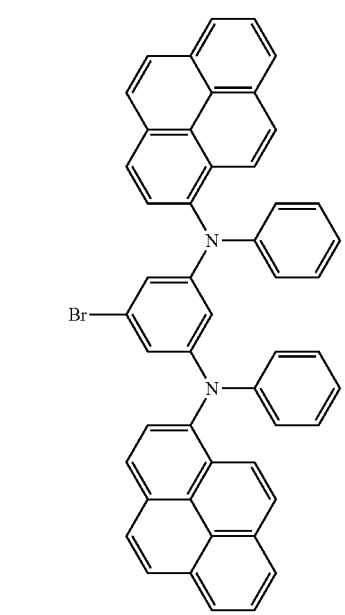

Sub 2-107

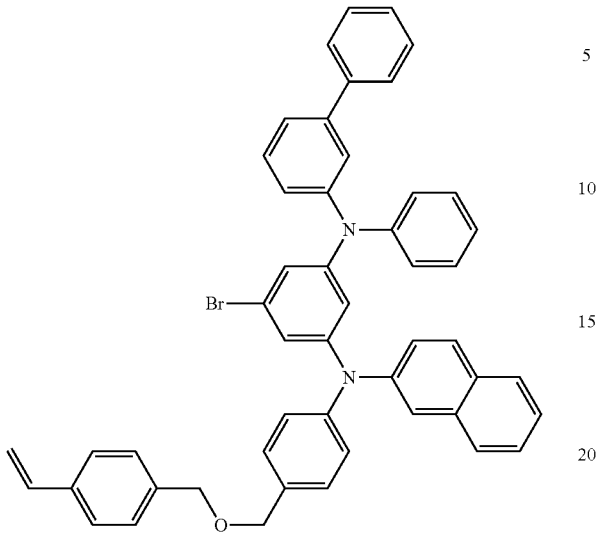

TABLE 2

| Compound | FD-MS | Compound | FD-MS |
|---|---|---|---|
| Sub 2-1 | m/z = 490.10($C_{30}H_{23}BrN_2$ = 491.42) | Sub 2-2 | m/z = 794.23($C_{54}H_{39}BrN_2$ = 795.80) |
| Sub 2-3 | m/z = 690.17($C_{46}H_{31}BrN_2$ = 691.66) | Sub 2-4 | m/z = 822.26($C_{56}H_{43}BrN_2$ = 823.86) |
| Sub 2-5 | m/z = 970.29($C_{68}H_{47}BrN_2$ = 972.02) | Sub 2-6 | m/z = 742.20($C_{50}H_{35}BrN_2$ = 743.73) |
| Sub 2-7 | m/z = 742.20($C_{50}H_{35}BrN_2$ = 743.73) | Sub 2-8 | m/z = 616.15($C_{40}H_{29}BrN_2$ = 617.58) |
| Sub 2-9 | m/z = 702.08($C_{42}H_{27}BrN_2S_2$ = 703.71) | Sub 2-10 | m/z = 670.13($C_{42}H_{27}BrN_2O_2$ = 671.58) |
| Sub 2-11 | m/z = 742.20($C_{50}H_{35}BrN_2$ = 743.73) | Sub 2-12 | m/z = 809.25($C_{55}H_{32}D_5BrN_2$ = 810.83) |
| Sub 2-13 | m/z = 690.17($C_{46}H_{31}BrN_2$ = 691.66) | Sub 2-14 | m/z = 566.14($C_{36}H_{27}BrN_2$ = 567.52) |
| Sub 2-15 | m/z = 746.14($C_{48}H_{31}BrN_2S$ = 747.74) | Sub 2-16 | m/z = 600.20($C_{33}H_{17}D_{10}BrN_2$ = 601.60) |
| Sub 2-17 | m/z = 642.17($C_{42}H_{31}BrN_2$ = 643.61) | Sub 2-18 | m/z = 778.11($C_{48}H_{31}BrN_2S_2$ = 779.81) |
| Sub 2-19 | m/z = 670.13($C_{42}H_{27}BrN_2O_2$ = 671.58) | Sub 2-20 | m/z = 590.14($C_{38}H_{27}BrN_2$ = 591.54) |
| Sub 2-21 | m/z = 540.12($C_{34}H_{25}BrN$ = 541.48) | Sub 2-22 | m/z = 590.14($C_{38}H_{27}BrN_2$ = 591.54) |
| Sub 2-23 | m/z = 744.19($C_{48}H_{33}BrN_4$ = 745.71) | Sub 2-24 | m/z = 672.12($C_{42}H_{29}BrN_2S$ = 673.66) |
| Sub 2-25 | m/z = 567.13($C_{35}H_{26}BrN_3$ = 568.51) | Sub 2-26 | m/z = 854.14($C_{54}H_{35}BrN_2S_2$ = 855.90) |
| Sub 2-27 | m/z = 642.17($C_{42}H_{31}BrN_2$ = 643.63) | Sub 2-28 | m/z = 744.21($C_{50}H_{37}BrN_2$ = 745.75) |
| Sub 2-29 | m/z = 914.06($C_{54}H_{31}BrN_2S_4$ = 916.00) | Sub 2-30 | m/z = 540.12($C_{34}H_{25}BrN_2$ = 541.48) |
| Sub 2-31 | m/z = 600.20($C_{38}H_{17}D_{10}BrN_2$ = 601.60) | Sub 2-32 | m/z = 728.18($C_{49}H_{33}BrN_2$ = 729.70) |
| Sub 2-33 | m/z = 796.22($C_{52}H_{37}BrN_4$ = 797.78) | Sub 2-34 | m/z = 742.20($C_{50}H_{35}BrN_2$ = 743.73) |
| Sub 2-35 | m/z = 566.14($C_{36}H_{27}BrN_3$ = 567.52) | Sub 2-36 | m/z = 682.20($C_{45}H_{31}BrN_2$ = 683.68) |
| Sub 2-37 | m/z = 518.14($C_{32}H_{27}BrN_2$ = 519.47) | Sub 2-38 | m/z = 616.15($C_{40}H_{29}BrN_2$ = 617.58) |
| Sub 2-39 | m/z = 492.09($C_{28}H_{21}BrN_4$ = 493.40) | Sub 2-40 | m/z = 758.23($C_{51}H_{39}BrN_2$ = 759.77) |
| Sub 2-41 | m/z = 606.17($C_{38}H_{31}BrN_2$ = 607.58) | Sub 2-42 | m/z = 614.14($C_{40}H_{27}BrN_2$ = 615.56) |
| Sub 2-43 | m/z = 541.12($C_{33}H_{24}BrN_3$ = 542.47) | Sub 2-44 | m/z = 690.17($C_{46}H_{31}BrN_2$ = 691.66) |
| Sub 2-45 | m/z = 794.23($C_{54}H_{39}BrN_2$ = 795.80) | Sub 2-46 | m/z = 672.12($C_{42}H_{29}BrN_2S$ = 673.66) |
| Sub 2-47 | m/z = 690.17($C_{46}H_{31}BrN_2$ = 691.66) | Sub 2-48 | m/z = 670.20($C_{44}H_{35}BrN_2$ = 671.67) |
| Sub 2-49 | m/z = 686.10($C_{42}H_{27}BrN_2OS$ = 687.65) | Sub 2-50 | m/z = 748.19($C_{48}H_{37}BrN_2Si$ = 749.81) |
| Sub 2-51 | m/z = 690.17($C_{46}H_{31}BrN_2$ = 691.66) | Sub 2-52 | m/z = 954.35($C_{66}H_{55}BrN_2$ = 956.06) |
| Sub 2-53 | m/z = 780.21 ($C_{53}H_{37}BrN_2$ = 781.78) | Sub 2-54 | m/z = 642.17($C_{42}H_{31}BrN_2$ = 643.61) |
| Sub 2-55 | m/z = 617.15($C_{39}H_{28}BrN_3$ = 618.56) | Sub 2-56 | m/z = 794.23($C_{54}H_{39}BrN_2$ = 795.80) |
| Sub 2-57 | m/z = 610.15($C_{34}H_{31}BrN_2O_4$ = 611.52) | Sub 2-58 | m/z = 518.14($C_{32}H_{27}BrN_2$ = 519.47) |
| Sub 2-59 | m/z = 642.17($C_{42}H_{31}BrN_2$ = 643.61) | Sub 2-60 | m/z = 698.14($C_{44}H_{31}BrN_2S$ = 699.70) |
| Sub 2-61 | m/z = 492.09($C_{28}H_{21}BrN_4$ = 493.40) | Sub 2-62 | m/z = 742.20($C_{50}H_{35}BrN_2$ = 743.73) |
| Sub 2-63 | m/z = 722.23($C_{48}H_{39}BrN_2$ = 723.74) | Sub 2-64 | m/z = 697.21($C_{46}H_{28}D_5BrN_2$ = 698.70) |
| Sub 2-65 | m/z = 542.14($C_{34}H_{27}BrN_2$ = 543.50) | Sub 2-66 | m/z = 846.26($C_{58}H_{43}BrN_2$ = 847.88) |
| Sub 2-67 | m/z = 550.13($C_{32}H_{27}BrN_2O_2$ = 551.47) | Sub 2-68 | m/z = 736.21($C_{48}H_{37}BrN_2O$ = 737.72) |
| Sub 2-69 | m/z = 590.14($C_{38}H_{27}BrN_2$ = 591.54) | Sub 2-70 | m/z = 786.19($C_{51}H_{35}BrN_2O_2$ = 787.74) |
| Sub 2-71 | m/z = 742.20($C_{50}H_{35}BrN_2$ = 743.73) | Sub 2-72 | m/z = 642.17($C_{42}H_{31}BrN_2$ = 643.61) |
| Sub 2-73 | m/z = 596.09($C_{36}H_{25}BrN_2S$ = 597.57) | Sub 2-74 | m/z = 672.12($C_{42}H_{29}BrN_2S$ = 673.66) |
| Sub 2-75 | m/z = 702.08($C_{42}H_{27}BrN_2S_2$ = 703.71) | Sub 2-76 | m/z = 702.08($C_{42}H_{27}BrN_2S_2$ = 703.71) |
| Sub 2-77 | m/z = 761.15($C_{48}H_{32}BrN_3S$ = 762.76) | Sub 2-78 | m/z = 820.22($C_{54}H_{37}BrN_4$ = 821.80) |
| Sub 2-79 | m/z = 655.16($C_{42}H_{30}BrN_3$ = 656.61) | Sub 2-80 | m/z = 731.19($C_{48}H_{34}BrN_3$ = 732.71) |
| Sub 2-81 | m/z = 781.21($C_{52}H_{35}BrN_3$ = 782.77) | Sub 2-82 | m/z = 745.17($C_{48}H_{32}BrN_3O$ = 746.69) |
| Sub 2-83 | m/z = 732.18($C_{48}H_{33}BrN_2O$ = 733.69) | Sub 2-84 | m/z = 706.17($C_{46}H_{31}BrN_2O$ = 707.66) |
| Sub 2-85 | m/z = 802.11($C_{50}H_{31}BrN_2S_2$ = 803.83) | Sub 2-86 | m/z = 772.21($C_{51}H_{37}BrN_2O$ = 773.76) |
| Sub 2-87 | m/z = 838.17($C_{54}H_{35}BrN_2OS$ = 839.84) | Sub 2-88 | m/z = 807.22($C_{54}H_{38}BrN_3$ = 808.80) |
| Sub 2-89 | m/z = 778.20($C_{53}H_{35}BrN_2$ = 779.76) | Sub 2-90 | m/z = 811.17($C_{52}H_{34}BrN_3S$ = 812.82) |
| Sub 2-91 | m/z = 646.20($C_{42}H_{35}BrN_2$ = 647.64) | Sub 2-92 | m/z = 747.23($C_{50}H_{30}D_5BrN_2$ = 748.76) |
| Sub 2-93 | m/z = 688.21($C_{44}H_{37}BrN_2O$ = 689.68) | Sub 2-94 | m/z = 646.20($C_{42}H_{35}BrN_2$ = 647.64) |

TABLE 2-continued

| Compound | FD-MS | Compound | FD-MS |
|---|---|---|---|
| Sub 2-95 | m/z = 796.15($C_{52}H_{33}BrN_2S$ = 797.80) | Sub 2-96 | m/z = 673.17($C_{42}H_{32}BrN_3O$ = 674.63) |
| Sub 2-97 | m/z = 762.20($C_{50}H_{35}BrFN_2$ = 763.74) | Sub 2-98 | m/z = 758.23($C_{51}H_{39}BrN_2$ = 759.77) |
| Sub 2-99 | m/z = 788.24($C_{46}H_{45}BrN_4Si_2$ = 789.95) | Sub 2-100 | m/z = 712.21($C_{46}H_{37}BrN_2O$ = 713.70) |
| Sub 2-101 | m/z = 742.20($C_{50}H_{35}BrN_2$ = 743.73) | Sub 2-102 | m/z = 754.11($C_{46}H_{31}BrN_2S_2$ = 755.79) |
| Sub 2-103 | m/z = 667.16($C_{43}H_{30}BrN_3$ = 668.62) | Sub 2-104 | m/z = 656.15($C_{42}H_{29}BrN_2O$ = 657.60) |
| Sub 2-105 | m/z = 994.29($C_{70}H_{47}BrN_2$ = 996.04) | Sub 2-106 | m/z = 738.17($C_{50}H_{31}BrN_2$ = 739.70) |
| Sub 2-107 | m/z = 762.22($C_{50}H_{39}BrN_2O$ = 763.76) | | |

III. Synthesis of Product

Sub 1 (1 eq.) was dissolved in THF in a round bottom flask, and Sub 2 (1 eq.), Pd(PPh$_3$)$_4$ (0.03 eq.), NaOH (3 eq.) and H$_2$O were added, then, stirring at 80□ was followed. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain final product.

1. Synthesis Examples of P-1

<Reaction Scheme 31>

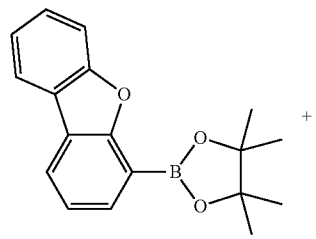

Sub-1-1

+

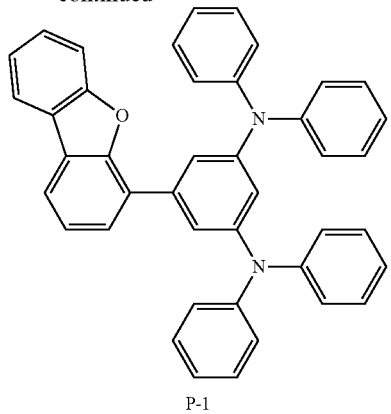

P-1

Sub 1-1 (6.83 g, 23.23 mmol) was dissolved in THF (80 ml) in a round bottom flask, and Sub 2-1 (11.42 g, 23.23 mmol), Pd(PPh$_3$)$_4$ (0.81 g, 0.70 mmol), NaOH (2.79 g, 69.69 mmol) and (40 ml) were added, then, stirring at 80 □ was followed. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain 10.08 g (yield: 75%) of product.

2. Synthesis Examples of P-12

<Reaction Scheme 32>

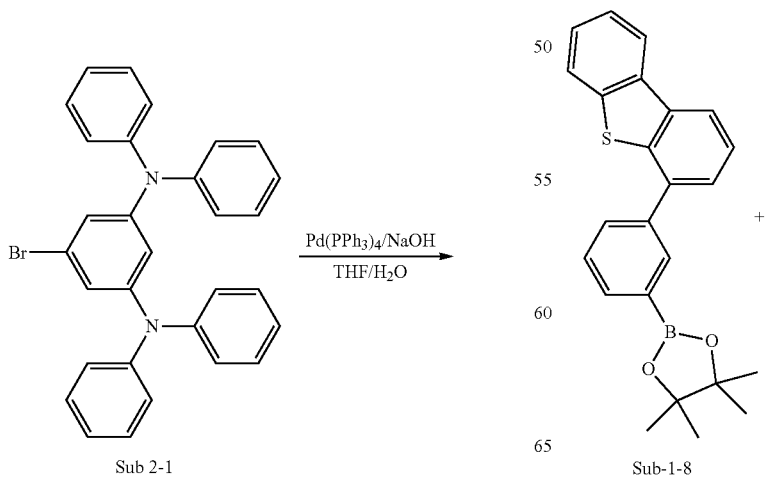

Sub 2-1    Pd(PPh$_3$)$_4$/NaOH / THF/H$_2$O →    Sub-1-8

+

3. Synthesis Examples of P-20

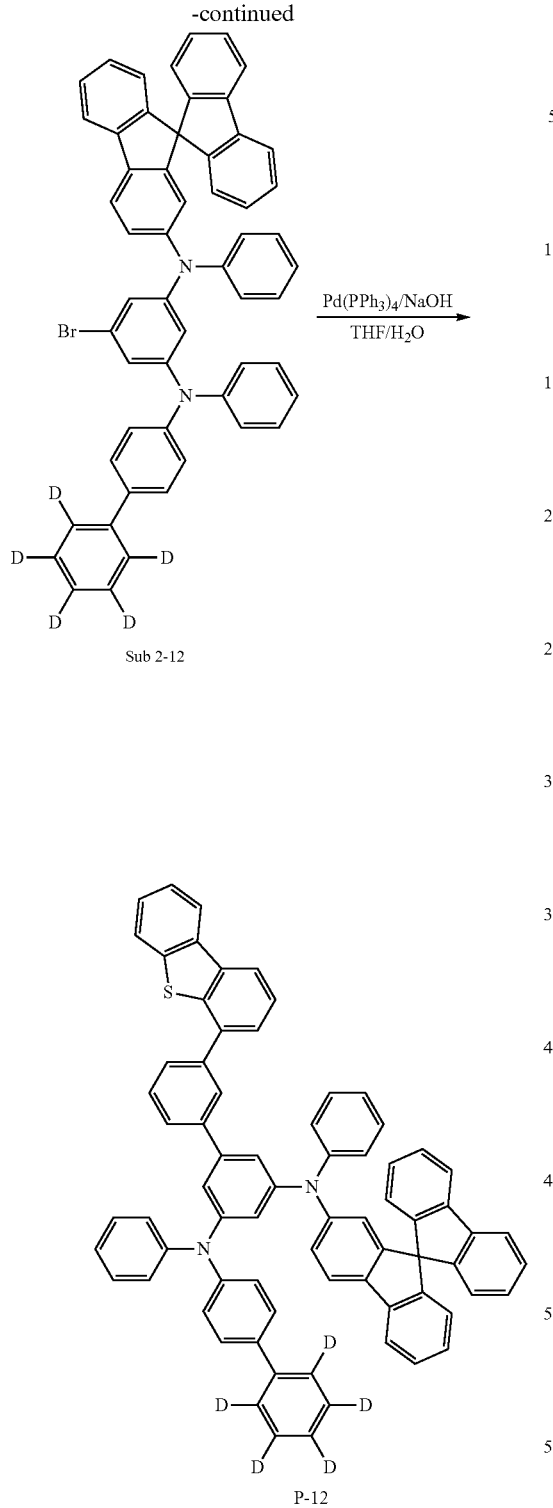

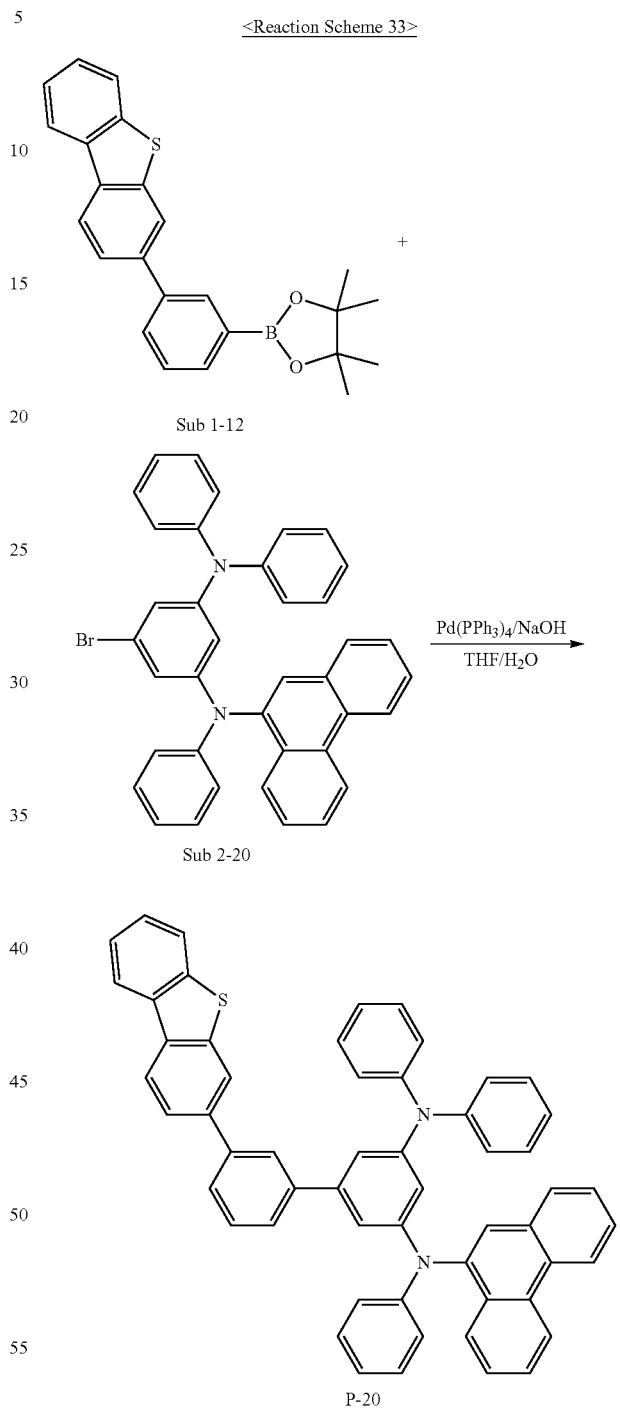

<Reaction Scheme 33>

Sub 2-12 (13.43 g, 16.56 mmol), Pd(PPh$_3$)$_4$ (0.57 g, 0.50 mmol), NaOH (1.99 g, 46.69 mmol), THF (60 ml) and water (30 ml) were added to Sub 1-8 (6.40 g, 16.56 mmol). Then, 10.66 g (yield: 65%) of the product was obtained by using the same manner as described above for the synthesis of compound P-1.

Sub 2-20 (10.85 g, 18.34 mmol), Pd(PPh$_3$)$_4$ (0.64 g, 0.55 mmol), NaOH (2.20 g, 55.03 mmol), THF (60 ml) and water (30 ml) were added to Sub 1-12 (7.09 g, 18.34 mmol). Then, 11.32 g (yield: 80%) of the product was obtained by using the same manner as described above for the synthesis of compound P-1.

4. Synthesis Examples of P-24
<Reaction Scheme 34>
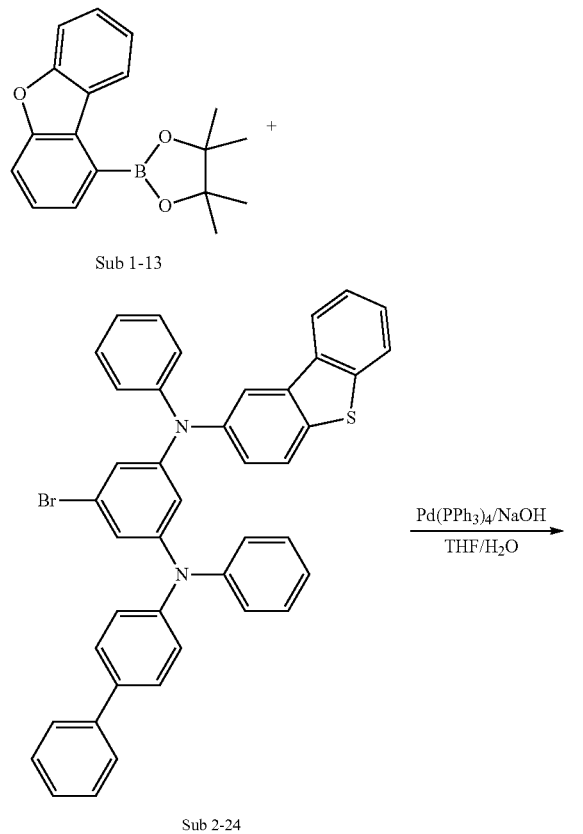
Sub 2-24 (19.78 g, 29.36 mmol), Pd(PPh$_3$)$_4$ (1.02 g, 0.88 mmol), NaOH (3.52 g, 88.08 mmol), THF (100 ml) and water (50 ml) were added to Sub 1-13 (8.64 g, 29.36 mmol). Then, 14.08 g (yield: 63%) of the product was obtained by using the same manner as described above for the synthesis of compound P-1.
5. Synthesis Examples of P-36
<Reaction Scheme 35>
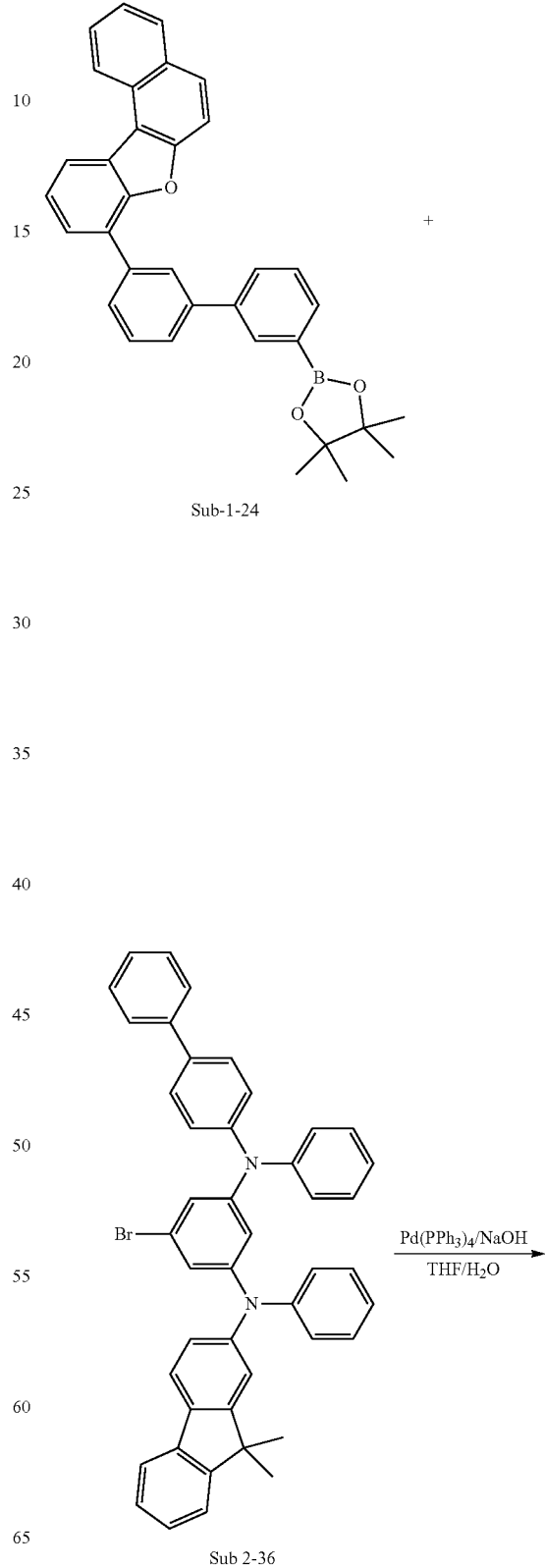

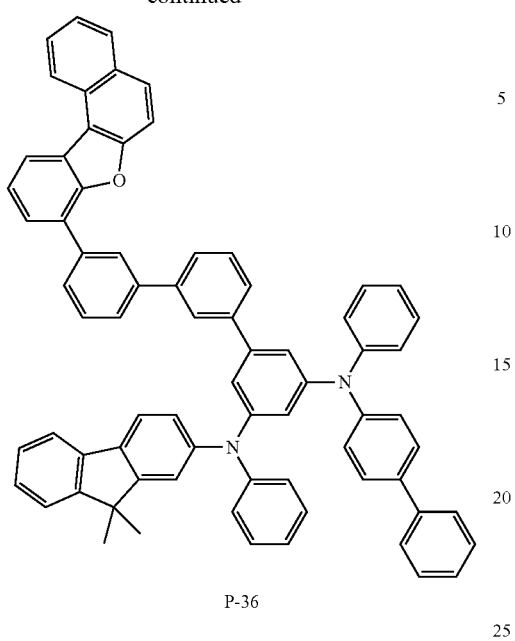

P-36

Sub 2-36 (17.10 g, 25.02 mmol), Pd(PPh₃)₄ (0.87 g, 0.75 mmol), NaOH (3.00 g, 75.05 mmol), THF (80 ml) and water (40 ml) were added to Sub 1-24 (12.42 g, 25.02 mmol). Then, 12.17 g (yield: 50%) of the product was obtained by using the same manner as described above for the synthesis of compound P-1.

6. Synthesis Examples of P-47

<Reaction Scheme 36>

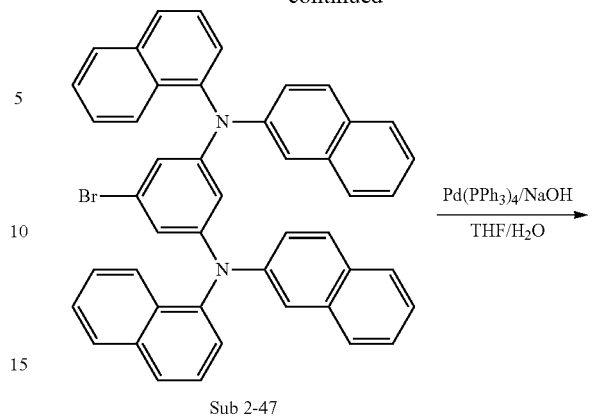

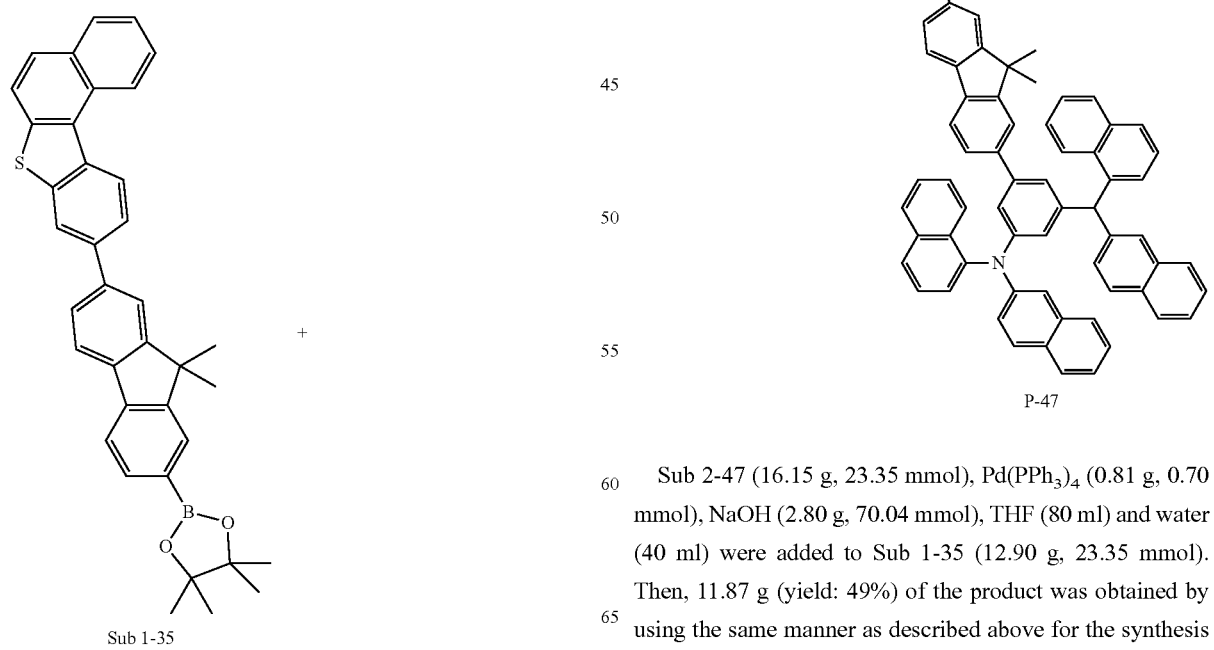

Sub 2-47 (16.15 g, 23.35 mmol), Pd(PPh₃)₄ (0.81 g, 0.70 mmol), NaOH (2.80 g, 70.04 mmol), THF (80 ml) and water (40 ml) were added to Sub 1-35 (12.90 g, 23.35 mmol). Then, 11.87 g (yield: 49%) of the product was obtained by using the same manner as described above for the synthesis of compound P-1.

7. Synthesis Examples of P-51
<Reaction Scheme 37>
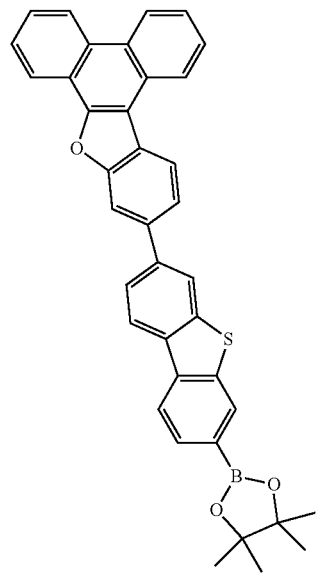
Sub-1-39
+
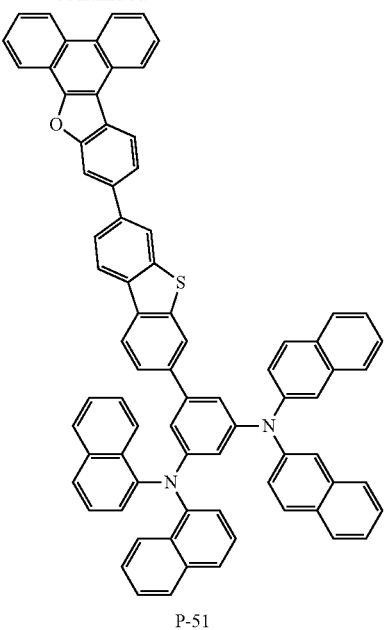
P-51
Sub 2-51 (14.12 g, 20.41 mmol), Pd(PPh$_3$)$_4$ (0.71 g, 0.61 mmol), NaOH (2.45 g, 61.25 mmol), THF (70 ml) and water (35 ml) were added to Sub 1-39 (11.77 g, 20.41 mmol). Then, 9.75 g (yield: 45%) of the product was obtained by using the same manner as described above for the synthesis of compound P-1.
8. Synthesis Examples of P-63
<Reaction Scheme 38>
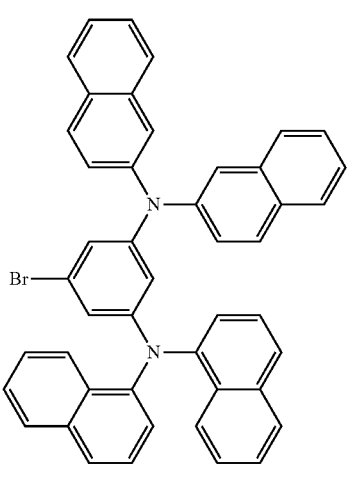
Sub 2-51
$\xrightarrow{\text{Pd(PPh}_3)_4/\text{NaOH}}_{\text{THF/H}_2\text{O}}$
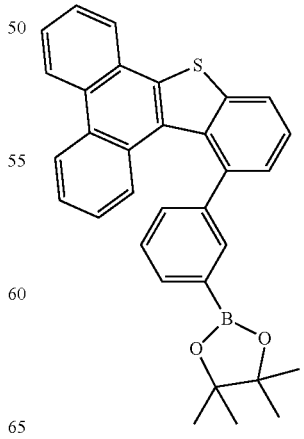
Sub 1-49
+

9. Synthesis Examples of P-76
<Reaction Scheme 39>
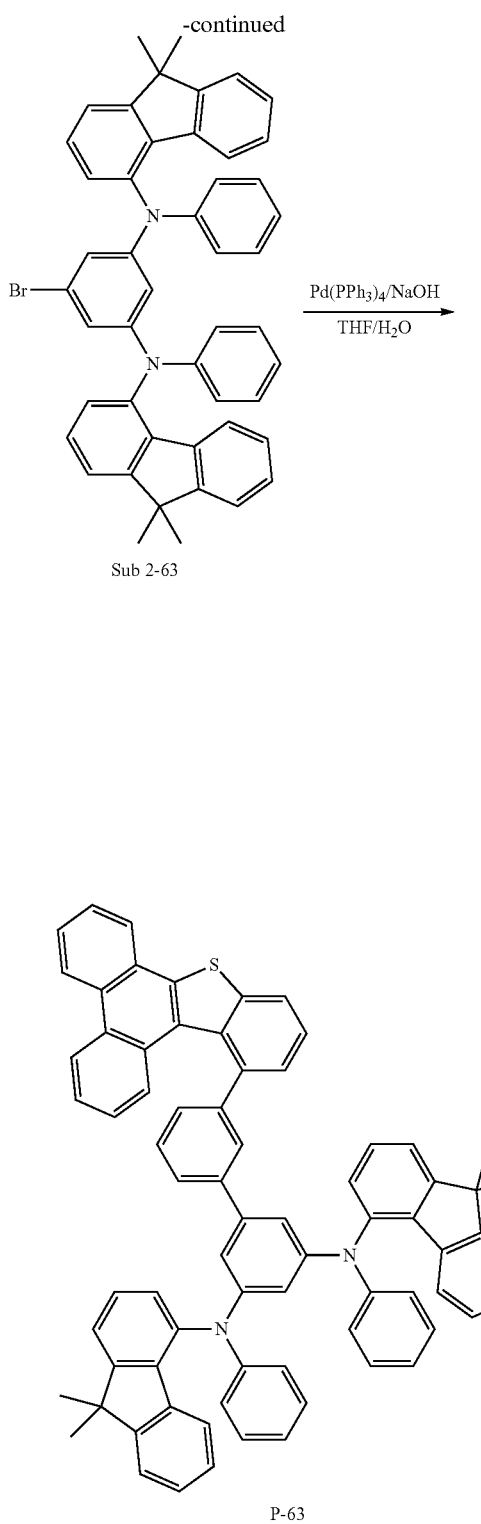
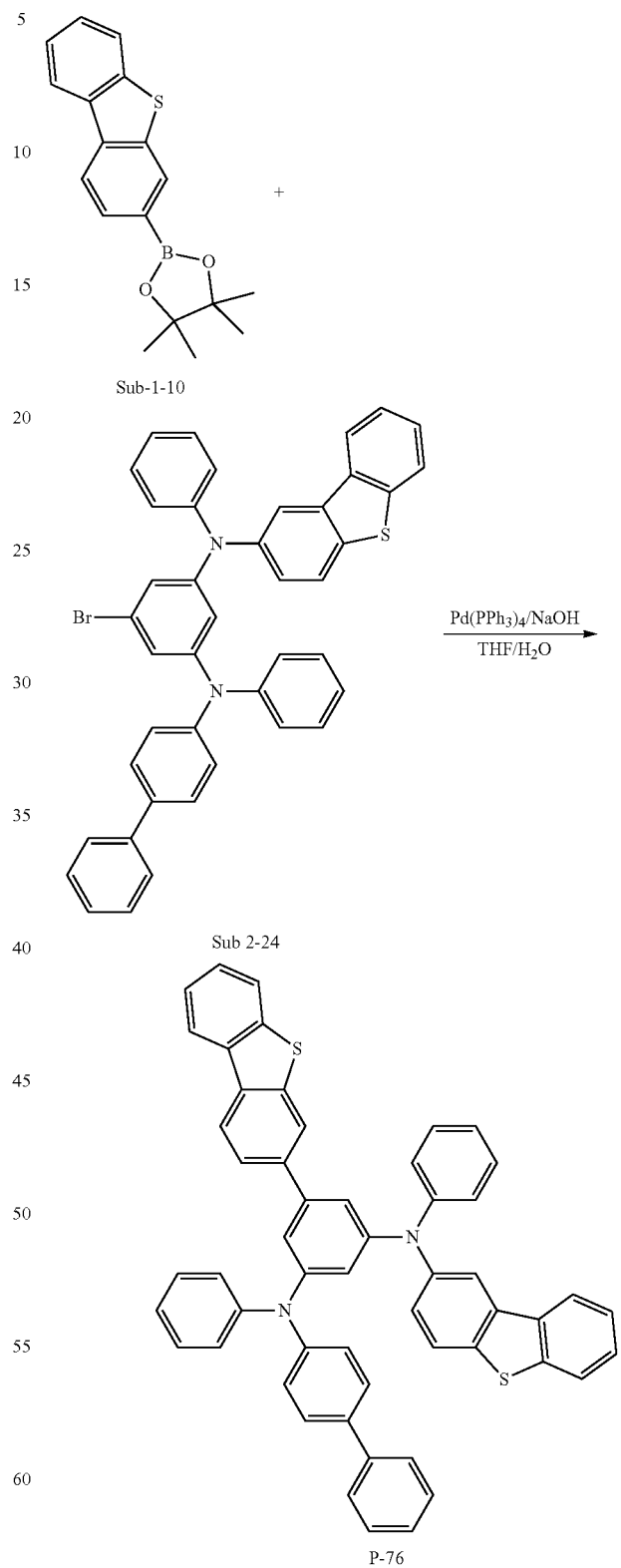
Sub 2-63 (13.88 g, 19.18 mmol), Pd(PPh₃)₄ (0.66 g, 0.58 mmol), NaOH (2.30 g, 57.54 mmol), THF (60 ml) and water (30 ml) were added to Sub 1-49 (9.33 g, 19.18 mmol). Then, 13.09 g (yield: 68%) of the product was obtained by using the same manner as described above for the synthesis of compound P-1.
Sub 2-24 (15.31 g, 22.73 mmol), Pd(PPh₃)₄ (0.79 g, 0.68 mmol), NaOH (2.73 g, 68.18 mmol), THF (80 ml) and water (40 ml) were added to Sub 1-10 (7.05 g, 22.73 mmol). Then, 12.71 g (yield: 72%) of the product was obtained by using the same manner as described above for the synthesis of compound P-1.

10. Synthesis Examples of P-81

<Reaction Scheme 40>

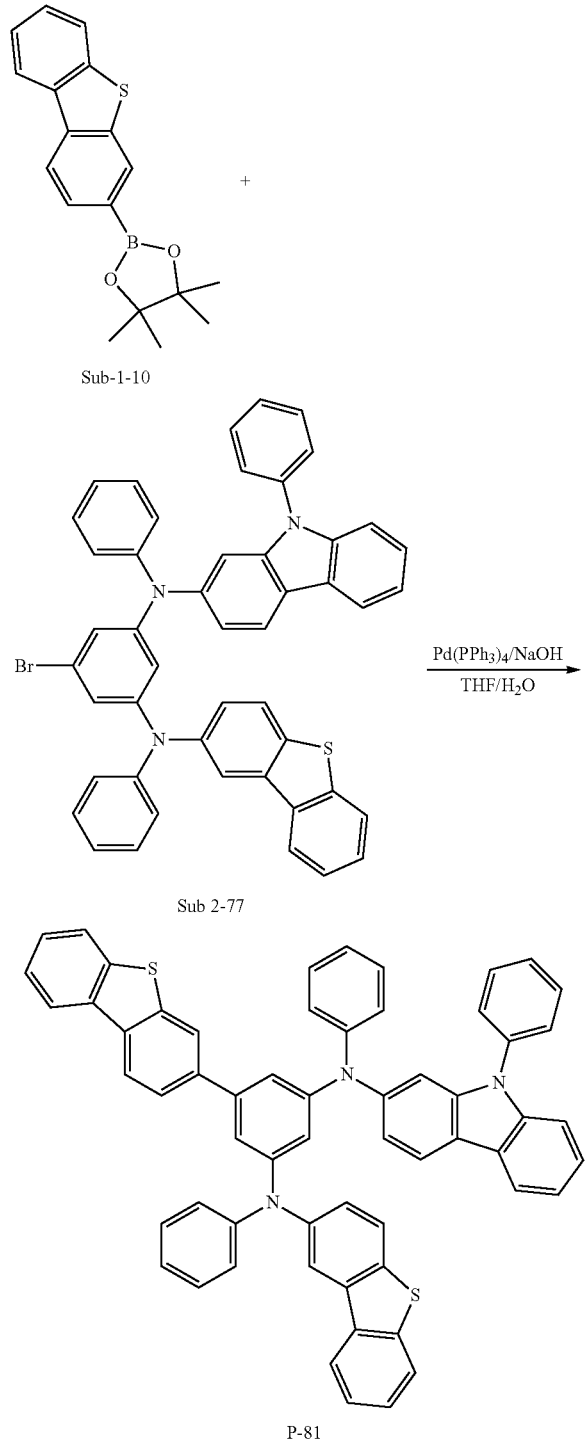

Sub 2-77 (20.65 g, 27.08 mmol), Pd(PPh$_3$)$_4$ (0.94 g, 0.81 mmol), NaOH (3.25 g, 81.23 mmol), THF (90 ml) and water (45 ml) were added to Sub 1-10 (8.40 g, 27.08 mmol). Then, 16.42 g (yield: 70%) of the product was obtained by using the same manner as described above for the synthesis of compound P-1.

11. Synthesis Examples of P-100

<Reaction Scheme 41>

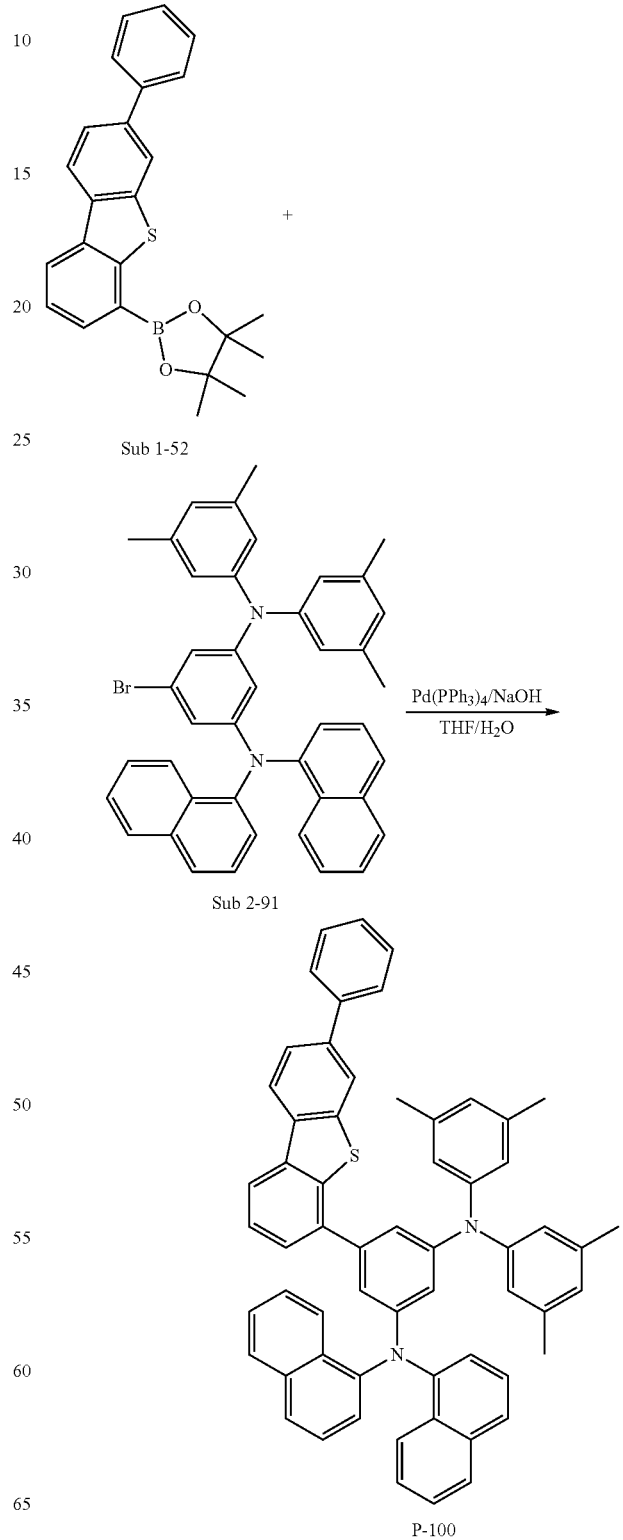

Sub 2-91 (13.71 g, 21.17 mmol), Pd(PPh$_3$)$_4$ (0.73 g, 0.64 mmol), NaOH (2.54 g, 63.52 mmol), THF (70 ml) and water (35 ml) were added to Sub 1-52 (8.18 g, 21.17 mmol). Then, 11.38 g (yield: 65%) of the product was obtained by using the same manner as described above for the synthesis of compound P-1.

12. Synthesis Examples of P-102

<Reaction Scheme 42>

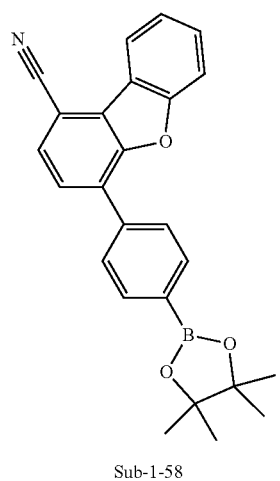

Sub-1-58

+

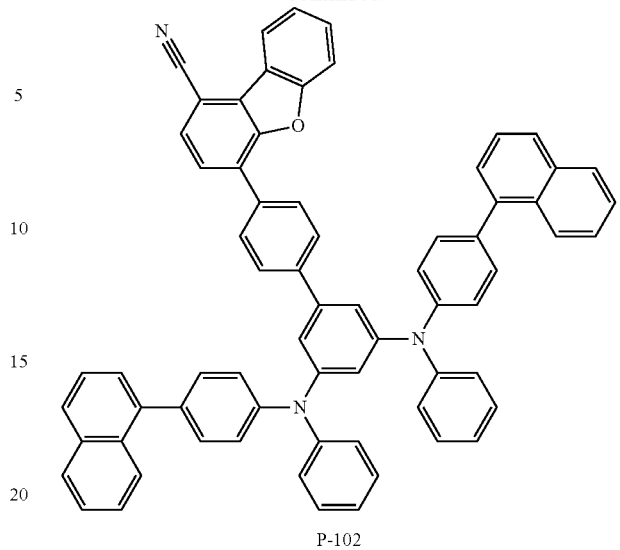

P-102

Sub 2-6 (15.99 g, 21.50 mmol), Pd(PPh$_3$)$_4$ (0.75 g, 0.65 mmol), NaOH (2.58 g, 64.51 mmol), THF (70 ml) and water (35 ml) were added to Sub 1-58 (8.50 g, 21.50 mmol). Then, 11.63 g (yield: 58%) of the product was obtained by using the same manner as described above for the synthesis of compound P-1.

13. Synthesis Examples of P-121

<Reaction Scheme 43>

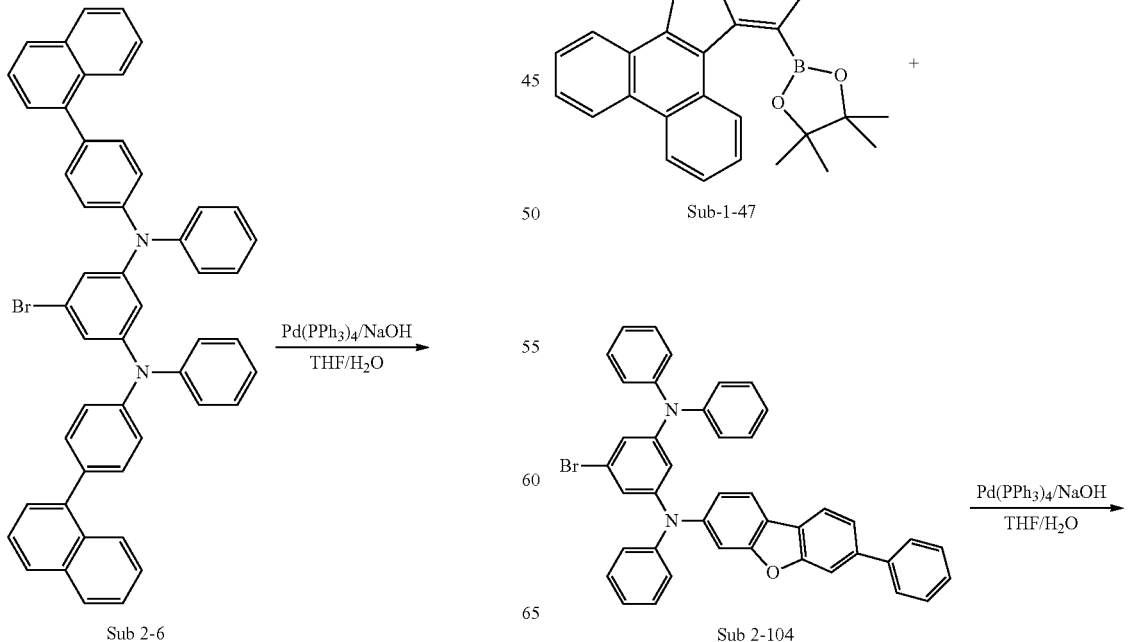

-continued

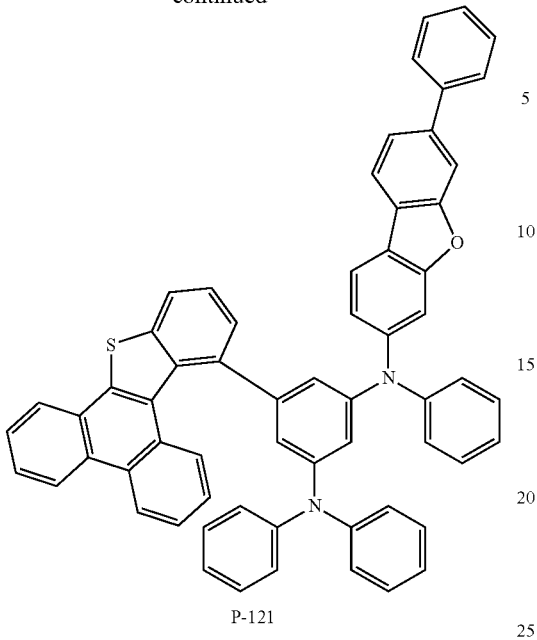

P-121

Sub 2-104 (16.03 g, 24.37 mmol), Pd(PPh$_3$)$_4$ (0.84 g, 0.73 mmol), NaOH (2.92 g, 73.11 mmol), THF (80 ml) and water (40 ml) were added to Sub 1-47 (10.00 g, 24.37 mmol). Then, 13.64 g (yield: 65%) of the product was obtained by using the same manner as described above for the synthesis of compound P-1.

The FD-MS values of some compounds of the present invention prepared according to the above synthesis examples are shown in Table 3 below.

TABLE 3

| Compound | FD-MS | Compound | FD-MS |
|---|---|---|---|
| P-1 | m/z = 578.24(C$_{42}$H$_{30}$N$_2$O = 578.70) | P-2 | m/z = 882.36(C$_{66}$H$_{46}$N$_2$O = 883.08) |
| P-3 | m/z = 794.28(C$_{58}$H$_{38}$N$_2$S = 795.00) | P-4 | m/z = 926.37(C$_{68}$H$_{50}$N$_2$S = 927.20) |
| P-5 | m/z = 1134.45(C$_{86}$H$_{58}$N$_2$O = 1135.39) | P-6 | m/z = 906.36(C$_{68}$H$_{46}$N$_2$O = 907.11) |
| P-7 | m/z = 922.34(C$_{68}$H$_{46}$N$_2$S = 923.17) | P-8 | m/z = 796.29(C$_{58}$H$_{40}$N$_2$S = 797.02) |
| P-9 | m/z = 916.26(C$_{64}$H$_{40}$N$_2$OS$_2$ = 917.15) | P-10 | m/z = 926.30(C$_{66}$H$_{42}$N$_2$O$_2$S = 927.12) |
| P-11 | m/z = 906.36(C$_{58}$H$_{46}$N$_2$O = 907.11) | P-12 | m/z = 989.39(C$_{73}$H$_{43}$D$_5$N$_2$S = 990.27) |
| P-13 | m/z = 778.30(C$_{58}$H$_{38}$N$_2$O = 778.94) | P-14 | m/z = 654.27(C$_{48}$H$_{34}$N$_2$O = 654.80) |
| P-15 | m/z = 850.25(C$_{50}$H$_{38}$N$_2$S$_2$ = 851.09) | P-16 | m/z = 704.31(C$_{50}$H$_{24}$D$_{10}$N$_2$S = 704.94) |
| P-17 | m/z = 746.28(C$_{54}$H$_{38}$N$_2$S = 746.96) | P-18 | m/z = 866.24(C$_{60}$H$_{38}$N$_2$OS$_2$ = 867.09) |
| P-19 | m/z = 834.29(C$_{60}$H$_{38}$N$_2$O$_3$ = 834.96) | P-20 | m/z = 770.28(C$_{55}$H$_{38}$N$_2$S = 770.98) |
| P-21 | m/z = 628.25(C$_{46}$H$_{32}$N$_2$O = 628.76) | P-22 | m/z = 694.24(C$_{50}$H$_{34}$N$_2$S = 694.88) |
| P-23 | m/z = 848.30(C$_{50}$H$_{40}$N$_4$S = 849.05) | P-24 | m/z = 760.25(C$_{54}$H$_{36}$N$_2$OS = 760.94) |
| P-25 | m/z = 671.24(C$_{47}$H$_{33}$N$_3$S = 671.85) | P-26 | m/z = 942.27(C$_{66}$H$_{42}$N$_2$OS$_2$ = 943.18) |
| P-27 | m/z = 822.31(C$_{60}$H$_{42}$N$_2$S = 823.05) | P-28 | m/z = 908.38(C$_{68}$H$_{48}$N$_2$O = 909.12) |
| P-29 | m/z = 1052.20(C$_{70}$H$_{40}$N$_2$OS$_4$ = 1053.34) | P-30 | m/z = 694.24(C$_{50}$H$_{34}$N$_2$S = 694.88) |
| P-31 | m/z = 814.38(C$_{50}$H$_{30}$D$_{10}$N$_2$O = 815.03) | P-32 | m/z = 1034.37(C$_{77}$H$_{50}$N$_2$S = 1035.30) |
| P-33 | m/z = 934.37(C$_{68}$H$_{46}$N$_4$O = 935.12) | P-34 | m/z = 896.32(C$_{66}$H$_{44}$N$_2$S = 897.13) |
| P-35 | m/z = 796.29(C$_{58}$H$_{40}$N$_2$S = 797.02) | P-36 | m/z = 972.41(C$_{73}$H$_{52}$N$_3$O = 973.21) |
| P-37 | m/z = 722.28(C$_{52}$H$_{38}$N$_2$S = 722.94) | P-38 | m/z = 804.31(C$_{60}$H$_{40}$N$_2$O = 804.97) |
| P-39 | m/z = 772.27(C$_{54}$H$_{36}$N$_4$S = 772.96) | P-40 | m/z = 1022.42(C$_{77}$H$_{54}$N$_2$O = 1023.27) |
| P-41 | m/z = 744.31(C$_{55}$H$_{43}$N$_2$O = 744.92) | P-42 | m/z = 768.26(C$_{56}$H$_{36}$N$_2$S = 768.96) |
| P-43 | m/z = 755.29(C$_{55}$H$_{37}$N$_3$O = 755.90) | p-44 | m/z = 920.32(C$_{68}$H$_{44}$N$_2$S = 921.16) |
| P-45 | m/z = 948.35(C$_{70}$H$_{48}$N$_2$S = 949.21) | P-46 | m/z = 810.27(C$_{58}$H$_{38}$N$_2$OS = 811.00) |
| P-47 | m/z = 1036.39(C$_{77}$H$_{52}$N$_2$S = 1037.32) | P-48 | m/z = 884.36(C$_{66}$H$_{48}$N$_2$O = 885.10) |
| P-49 | m/z = 874.27(C$_{62}$H$_{38}$N$_2$O$_2$S = 875.04) | P-50 | m/z = 952.33(C$_{68}$H$_{48}$N$_2$SSi = 953.27) |
| P-51 | m/z = 1060.35(C$_{78}$H$_{48}$N$_2$OS = 1061.29) | P-52 | m/z = 1234.53(C$_{92}$H$_{70}$N$_2$S = 1235.62) |
| P-53 | m/z = 918.36(C$_{69}$H$_{46}$N$_2$O = 919.12) | P-54 | m/z = 79629(C$_{58}$H$_{40}$N$_2$S = 797.02) |
| P-55 | m/z = 887.30(C$_{63}$H$_{41}$N$_3$OS = 888.08) | P-56 | m/z = 948.35(C$_{70}$H$_{48}$N$_2$S = 949.21 ) |
| P-57 | m/z = 764.27(C$_{50}$H$_{40}$N$_2$O$_4$S = 764.93) | P-58 | m/z = 656.28(C$_{48}$H$_{36}$N$_2$O = 656.81 ) |
| P-59 | m/z = 912.32(C$_{66}$H$_{44}$N$_2$OS = 913.13) | P-60 | m/z = 836.29(C$_{60}$H$_{40}$N$_2$OS = 837.04) |
| P-61 | m/z = 696.23(C$_{48}$H$_{32}$N$_4$S = 696.86) | P-62 | m/z = 930.36(C$_{70}$H$_{46}$N$_2$O = 931.13) |
| P-63 | m/z = 1002.40(C$_{74}$H$_{54}$N$_2$S = 1003.30) | P-64 | m/z = 1011.42(C$_{76}$H$_{45}$D$_5$N$_2$O = 1012.25) |
| P-65 | m/z = 630.27(C$_{46}$H$_{34}$N$_2$O = 630.77) | P-66 | m/z = 934.39(C$_{70}$H$_{50}$N$_2$O = 935.16) |
| P-67 | m/z = 704.25(C$_{48}$H$_{36}$N$_2$O$_2$S = 704.88) | P-68 | m/z = 840.32(C$_{60}$H$_{44}$N$_2$OS = 841.07) |

TABLE 3-continued

| Compound | FD-MS | Compound | FD-MS |
|---|---|---|---|
| P-69 | m/z = 820.29($C_{60}H_{40}N_2S$ = 821.04) | P-70 | m/z = 966.33($C_{69}H_{46}N_2O_2S$ = 967.18) |
| P-71 | m/z = 694.24($C_{50}H_{34}N_2S$ = 694.88) | P-72 | m/z = 846.31($C_{62}H_{42}N_2S$ = 847.08) |
| P-73 | m/z = 746.28($C_{54}H_{38}N_2S$ = 746.96) | P-74 | m/z = 898.34($C_{66}H_{46}N_2S$ = 899.15) |
| P-75 | m/z = 700.20($C_{48}H_{32}N_2S_2$ = 700.91) | P-76 | m/z = 776.23($C_{54}H_{36}N_2S_2$ = 777.01) |
| P-77 | m/z = 776.23($C_{54}H_{36}N_2S_2$ = 777.01) | P-78 | m/z = 806.19($C_{54}H_{34}N_2S_3$ = 807.06) |
| P-79 | m/z = 806.19($C_{54}H_{34}N_2S_3$ = 807.06) | P-80 | m/z = 806.19($C_{54}H_{34}N_2S_3$ = 807.06) |
| P-81 | m/z = 865.26($C_{50}H_{39}N_3S_2$ = 866.10) | P-82 | m/z = 924.33($C_{66}H_{44}N_4S$ = 925.15) |
| P-83 | m/z = 759.27($C_{54}H_{37}N_3S$ = 759.96) | P-84 | m/z = 835.30($C_{60}H_{41}N_3S$ = 836.05) |
| P-85 | m/z = 935.33($C_{68}H_{45}N_3S$ = 936.17) | P-86 | m/z = 899.30($C_{64}H_{41}N_3OS$ = 900.09) |
| P-87 | m/z = 886.30($C_{64}H_{42}N_2OS$ = 887.10) | P-88 | m/z = 860.29($C_{62}H_{40}N_2OS$ = 861.06) |
| P-89 | m/z = 730.30($C_{54}H_{38}N_2O$ = 730.89) | P-90 | m/z = 760.25($C_{54}H_{36}N_2OS$ = 760.94) |
| P-91 | m/z = 890.24($C_{62}H_{38}N_2OS_2$ = 891.11) | P-92 | m/z = 860.34($C_{63}H_{44}N_2O_2$ = 861.04) |
| P-93 | m/z = 926.30($C_{66}H_{42}N_2O_2S$ = 927.12) | P-94 | m/z = 895.36($C_{66}H_{45}N_3O$ = 896.08) |
| P-95 | m/z = 866.33($C_{65}H_{42}N_2O$ = 867.04) | P-96 | m/z = 949.31($C_{68}H_{43}N_3OS$ = 950.15) |
| P-97 | m/z = 754.30($C_{56}H_{38}N_2O$ = 754.91) | P-98 | m/z = 886.39($C_{66}H_{42}D_4N_2O$ = 887.11) |
| P-99 | m/z = 850.34($C_{62}H_{46}N_2S$ = 851.11) | P-100 | m/z = 826.34($C_{60}H_{46}N_2S$ = 827.09) |
| P-101 | m/z = 1178.48($C_{88}H_{62}N_2O_2$ = 1179.45) | P-102 | m/z = 931.36($C_{69}H_{45}N_3O$ = 932.12) |
| P-103 | m/z = 927.37($C_{68}H_{41}D_5N_2S$ = 928.20) | P-104 | m/z = 868.35($C_{62}H_{48}N_2OS$ = 869.12) |
| P-105 | m/z = 1006.39($C_{76}H_{50}N_2O$ = 1007.22) | P-106 | m/z = 734.33($C_{54}H_{42}N_2O$ = 734.92) |
| P-107 | m/z = 900.26($C_{64}H_{40}N_2S_2$ = 901.15) | P-108 | m/z = 718.32($C_{51}H_{26}D_{10}N_2S$ = 718.97) |
| P-109 | m/z = 930.34($C_{65}H_{46}N_4OS$ = 931.15) | P-110 | m/z = 1170.37($C_{84}H_{54}N_2OS_2$ = 1171.47) |
| P-111 | m/z = 898.34($C_{66}H_{46}N_2S$ = 899.15) | P-112 | m/z = 926.37($C_{68}H_{47}FN_2O$ = 927.11) |
| P-113 | m/z = 780.31($C_{58}H_{40}N_2O$ = 780.95) | P-114 | m/z = 1064.42($C_{79}H_{56}N_2S$ = 1065.37) |
| P-115 | m/z = 899.37($C_{61}H_{53}N_3OSi_2$ = 900.26) | P-116 | m/z = 942.36($C_{68}H_{50}N_2OS$ = 943.20) |
| P-117 | m/z = 747.27($C_{53}H_{37}N_3S$ = 747.95) | P-118 | m/z = 930.36($C_{70}H_{46}N_2O$ = 931.13) |
| P-119 | m/z = 942.27($C_{66}H_{42}N_2OS_2$ = 943.18) | P-120 | m/z = 901.31($C_{64}H_{43}N_3OS$ = 902.11) |
| P-121 | m/z = 860.29($C_{62}H_{40}N_2OS$ = 861.06) | P-122 | m/z = 1182.45($C_{90}H_{58}N_2O$ = 1183.44) |
| P-123 | m/z = 1043.33($C_{77}H_{45}N_3S$ = 1044.27) | P-124 | m/z = 1076.43($C_{80}H_{56}N_2O_2$ = 1077.31) |

In the above, even though an exemplary synthesis example of the present invention represented by the Formula 1 are described, all of them are based on Suzuki cross-coupling reaction, Miyaura boration reaction, Intramolecular acid-induced cyclization reaction (*J. mater. Chem.* 1999, 9, 2095.), Pd(II)-catalyzed oxidative cyclization reaction (*Org. Lett.* 2011, 13, 5504) and Buchwald-Hartwig cross coupling reaction. Therefore, it will be understood by those skilled in the art that the above reaction proceeds even when other substituents (substituents of X, $R^1$ to $R^7$, $Ar^1$ to $Ar^4$, $L^1$ to $L^5$ and the like) defined in Formula 1 are bonded, in addition to the substituents described in the specific synthesis example.

For example, the reaction of Sub 1 and Sub 2→Final Product in Reaction Scheme 1, and the reaction of Sub 1-I→Sub 1 in Reaction Scheme 3 are based on Suzuki cross-coupling reaction, the reaction of Sub 1-I→Sub 1 in Reaction Scheme 2 is based on Miyaura boration reaction, the reaction of starting materials→Sub 1-I is based on Intramolecular acid-induced cyclization reaction. The reaction of starting materials→Sub 1-I in Reaction Scheme 5 is based on Pd(II)-catalyzed oxidative cyclization reaction, the reaction of starting materials→Sub 2-I and the reaction of Sub 2-I→Sub 2 in Reaction Scheme 18 are based on Buchwald-Hartwig cross coupling reaction. The above reactions will proceed even if a substituent not specifically mentioned is attached.

Fabrication and Evaluation of Organic Electronic Element

[Example I-1] Green OLED (a Hole Transport Layer)

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, compound P-1 of the present invention was vacuum-deposited with a thickness of 60 nm on the hole injection layer to form a hole transport layer.

Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir (ppy)$_3$") as a dopant material in a weight ratio of 90:10.

Next, (((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example I-2] to [Example I-58] Green OLED (a Hole Transport Layer)

The OLEDs were fabricated in the same manner as described in Example I-1 except that the compounds P-2 to P-96 of the present invention described in Table 4 instead of the compound P-1 of the present invention were used as the hole transport layer material.

[Comparative Example I-1] to [Comparative Example I-5]

The OLEDs were fabricated in the same manner as described in Example 1 except that the following Comparative Compounds 1 to 5 described in Table 4 instead of the compound P-1 of the present invention were each used as the hole transport layer material.

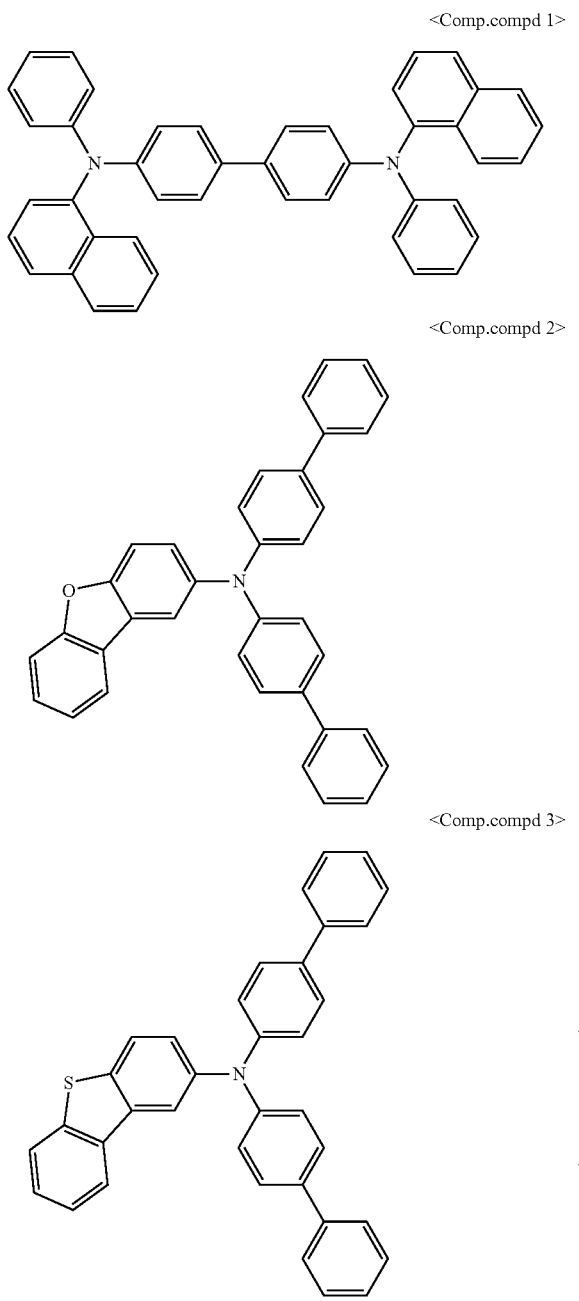

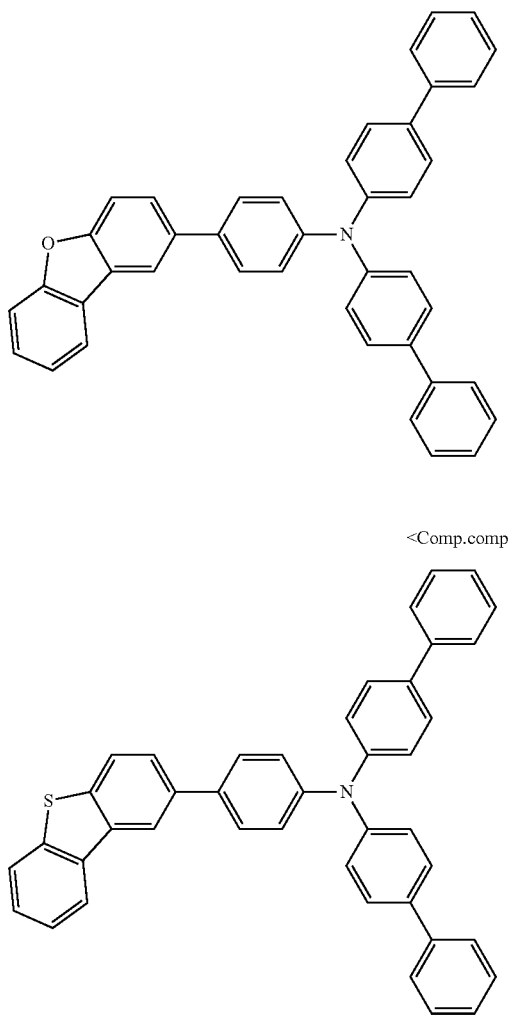

Electroluminescence (EL) characteristics were measured with a PR-650 (Photoresearch) by applying a forward bias DC voltage to the OLEDs prepared in Examples I-1 to I-58 of the present invention and Comparative Examples I-1 to I-5. And, the T95 life time was measured using a life time measuring apparatus manufactured by Macscience Inc. at reference brightness of 5000 cd/m². The measurement results are shown in Table 4 below.

TABLE 4

| | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex (I-1) | comp. Com 1 | 6.0 | 21.5 | 5000 | 23.3 | 57.2 | 0.32 | 0.61 |
| comp. Ex (I-2) | comp. Com 2 | 5.9 | 18.2 | 5000 | 27.5 | 74.5 | 0.32 | 0.62 |
| comp. Ex (I-3) | comp. Com 3 | 5.8 | 17.3 | 5000 | 29.0 | 78.6 | 0.33 | 0.61 |
| comp. Ex (I-4) | comp. Com 4 | 5.8 | 17.9 | 5000 | 27.9 | 76.5 | 0.33 | 0.62 |
| comp. Ex (I-5) | comp. Com 5 | 5.8 | 16.8 | 5000 | 29.8 | 79.2 | 0.33 | 0.61 |
| Ex. (I-1) | Com. (P-1) | 5.7 | 14.0 | 5000 | 35.8 | 130.2 | 0.33 | 0.61 |
| Ex. (I-2) | Com. (P-2) | 5.5 | 13.9 | 5000 | 36.1 | 130.5 | 0.33 | 0.61 |
| Ex. (I-3) | Com. (P-3) | 5.7 | 14.2 | 5000 | 35.1 | 124.0 | 0.33 | 0.61 |
| Ex. (I-4) | Com. (P-4) | 5.6 | 13.8 | 5000 | 36.3 | 125.9 | 0.33 | 0.62 |
| Ex. (I-5) | Com. (P-5) | 5.7 | 14.3 | 5000 | 35.0 | 131.1 | 0.33 | 0.62 |
| Ex. (I-6) | Com. (P-6) | 5.7 | 14.0 | 5000 | 35.8 | 130.5 | 0.33 | 0.61 |

TABLE 4-continued

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (I-7) | Com. (P-7) | 5.7 | 14.0 | 5000 | 35.6 | 131.2 | 0.33 | 0.61 |
| Ex. (I-8) | Com. (P-8) | 5.6 | 14.0 | 5000 | 35.6 | 130.6 | 0.33 | 0.61 |
| Ex. (I-9) | Com. (P-11) | 5.7 | 14.9 | 5000 | 33.6 | 120.8 | 0.33 | 0.62 |
| Ex. (I-10) | Com. (P-12) | 5.7 | 14.3 | 5000 | 34.9 | 112.6 | 0.33 | 0.61 |
| Ex. (I-11) | Com. (P-13) | 5.6 | 12.9 | 5000 | 38.7 | 142.8 | 0.33 | 0.62 |
| Ex. (I-12) | Com. (P-14) | 5.5 | 13.4 | 5000 | 37.4 | 137.1 | 0.33 | 0.61 |
| Ex. (I-13) | Com. (P-16) | 5.6 | 13.5 | 5000 | 37.0 | 124.7 | 0.33 | 0.61 |
| Ex. (I-14) | Com. (P-17) | 5.6 | 13.1 | 5000 | 38.3 | 138.1 | 0.33 | 0.62 |
| Ex. (I-15) | Com. (P-18) | 5.7 | 14.0 | 5000 | 35.6 | 129.9 | 0.33 | 0.61 |
| Ex. (I-16) | Com. (P-19) | 5.5 | 12.8 | 5000 | 39.2 | 136.2 | 0.33 | 0.62 |
| Ex. (I-17) | Com. (P-20) | 5.5 | 13.7 | 5000 | 36.6 | 123.3 | 0.33 | 0.62 |
| Ex. (I-18) | Com. (P-21) | 5.7 | 14.2 | 5000 | 35.3 | 129.1 | 0.33 | 0.61 |
| Ex. (I-19) | Com. (P-22) | 5.7 | 14.1 | 5000 | 35.5 | 121.3 | 0.33 | 0.62 |
| Ex. (I-20) | Com. (P-24) | 5.7 | 14.5 | 5000 | 34.6 | 119.3 | 0.33 | 0.62 |
| Ex. (I-21) | Com. (P-27) | 5.7 | 14.2 | 5000 | 35.2 | 131.2 | 0.33 | 0.62 |
| Ex. (I-22) | Com. (P-28) | 5.6 | 14.6 | 5000 | 34.3 | 114.5 | 0.33 | 0.62 |
| Ex. (I-23) | Com. (P-30) | 5.7 | 16.1 | 5000 | 31.0 | 112.9 | 0.33 | 0.62 |
| Ex. (I-24) | Com. (P-31) | 5.7 | 15.9 | 5000 | 31.4 | 116.8 | 0.33 | 0.62 |
| Ex. (I-25) | Com. (P-32) | 5.7 | 16.4 | 5000 | 30.6 | 108.4 | 0.33 | 0.61 |
| Ex. (I-26) | Com. (P-34) | 5.7 | 16.1 | 5000 | 31.1 | 108.5 | 0.33 | 0.61 |
| Ex. (I-27) | Com. (P-35) | 5.6 | 16.1 | 5000 | 31.0 | 114.4 | 0.33 | 0.61 |
| Ex. (I-28) | Com. (P-36) | 5.7 | 16.2 | 5000 | 30.9 | 106.8 | 0.33 | 0.61 |
| Ex. (I-29) | Com. (P-37) | 5.7 | 16.3 | 5000 | 30.7 | 108.2 | 0.33 | 0.61 |
| Ex. (I-30) | Com. (P-38) | 5.7 | 16.1 | 5000 | 31.0 | 114.9 | 0.33 | 0.61 |
| Ex. (I-31) | Com. (P-40) | 5.7 | 16.1 | 5000 | 31.0 | 115.3 | 0.33 | 0.62 |
| Ex. (I-32) | Com. (P-41) | 5.7 | 14.7 | 5000 | 34.1 | 121.2 | 0.33 | 0.61 |
| Ex. (I-33) | Com. (P-42) | 5.7 | 15.1 | 5000 | 33.2 | 110.6 | 0.33 | 0.61 |
| Ex. (I-34) | Com. (P-44) | 5.7 | 15.3 | 5000 | 32.7 | 113.6 | 0.33 | 0.61 |
| Ex. (I-35) | Com. (P-45) | 5.7 | 14.9 | 5000 | 33.6 | 114.3 | 0.33 | 0.61 |
| Ex. (I-36) | Com. (P-46) | 5.6 | 15.1 | 5000 | 33.2 | 119.7 | 0.33 | 0.61 |
| Ex. (I-37) | Com. (P-47) | 5.6 | 15.5 | 5000 | 32.2 | 112.8 | 0.33 | 0.62 |
| Ex. (I-38) | Com. (P-51) | 5.6 | 15.6 | 5000 | 32.1 | 120.9 | 0.33 | 0.62 |
| Ex. (I-39) | Com. (P-53) | 5.6 | 15.7 | 5000 | 31.8 | 114.1 | 0.33 | 0.61 |
| Ex. (I-40) | Com. (P-56) | 5.7 | 16.3 | 5000 | 30.7 | 114.2 | 0.33 | 0.61 |
| Ex. (I-41) | Com. (P-60) | 5.7 | 16.3 | 5000 | 30.6 | 115.5 | 0.33 | 0.62 |
| Ex. (I-42) | Com. (P-62) | 5.6 | 16.1 | 5000 | 31.0 | 116.8 | 0.33 | 0.61 |
| Ex. (I-43) | Com. (P-63) | 5.6 | 16.3 | 5000 | 30.6 | 110.4 | 0.33 | 0.61 |
| Ex. (I-44) | Com. (P-69) | 5.7 | 14.9 | 5000 | 33.4 | 116.7 | 0.33 | 0.62 |
| Ex. (I-45) | Com. (P-71) | 5.6 | 13.5 | 5000 | 37.1 | 130.7 | 0.33 | 0.61 |
| Ex. (I-46) | Com. (P-72) | 5.5 | 13.2 | 5000 | 37.9 | 133.0 | 0.33 | 0.62 |
| Ex. (I-47) | Com. (P-73) | 5.6 | 12.9 | 5000 | 38.6 | 138.1 | 0.33 | 0.61 |
| Ex. (I-48) | Com. (P-74) | 5.5 | 13.1 | 5000 | 38.1 | 134.5 | 0.33 | 0.62 |
| Ex. (I-49) | Com. (P-75) | 5.5 | 13.6 | 5000 | 36.8 | 125.7 | 0.33 | 0.62 |
| Ex. (I-50) | Com. (P-82) | 5.5 | 13.8 | 5000 | 36.1 | 126.3 | 0.33 | 0.62 |
| Ex. (I-51) | Com. (P-83) | 5.5 | 13.2 | 5000 | 37.8 | 134.0 | 0.33 | 0.61 |
| Ex. (I-52) | Com. (P-84) | 5.6 | 13.3 | 5000 | 37.7 | 130.6 | 0.33 | 0.62 |
| Ex. (I-53) | Com. (P-85) | 5.6 | 14.5 | 5000 | 34.4 | 114.2 | 0.33 | 0.62 |
| Ex. (I-54) | Com. (P-89) | 5.5 | 13.0 | 5000 | 38.5 | 142.9 | 0.33 | 0.62 |
| Ex. (I-55) | Com. (P-90) | 5.6 | 13.7 | 5000 | 36.5 | 130.2 | 0.33 | 0.62 |
| Ex. (I-56) | Com. (P-94) | 5.7 | 14.3 | 5000 | 35.1 | 130.5 | 0.33 | 0.62 |
| Ex. (I-57) | Com. (P-95) | 5.5 | 13.2 | 5000 | 37.8 | 136.1 | 0.33 | 0.62 |
| Ex. (I-58) | Com. (P-96) | 5.6 | 14.3 | 5000 | 35.1 | 130.1 | 0.33 | 0.62 |

From the results of the above table 4, it is confirmed that luminous efficiency and lifetime of OLED are improved when the compound of the present invention is used as material of a hole transport layer.

Particularly, luminous efficiency is improved when Comparative compounds 2 to 5 are used as material of a hole transport layer, wherein these compounds have a structure in which one amine group through a linking group (including a direct bond) is bonded to a dibenzofuran or a dibenzothiophene core, compared with Comparative compound 1, wherein Comparative compound 1 is NPB, which is generally used as material of a hole transport layer. Luminous efficiency and lifetime are improved when the compounds of the present invention are used as material of a hole transport layer, wherein the present compounds have a structure in which two amine groups through a linking group are bonded to a dibenzofuran or a dibenzothiophene core, compared with Comparative compounds 1 to 5.

Compound of the present invention has a higher packing density than Comparative compounds 2 to 5 when material of OLED is deposited, wherein the compound of the present invention has a structure in which two amine groups through a linking group are bonded to a heterocyclic ring (dibenzofuran or a dibenzothiophene core), and Comparative compounds 2 to 5 have a structure in which one amine group through a linking group (including a direct bond) is bonded to a dibenzofuran or a dibenzothiophene core. Therefore, it is inferred that compound of the present invention has thermal stability because Joule heating is generated little. Further, it is confirmed that color purity is increased because the excessive electrons are prevented from transferring from the light emitting layer to the hole transport layer due to relatively high T1 value, and the lifetime is increased because thermal damage caused by the emission at the interface of a hole transport layer is reduced.

Also, even though similar core is used, it will be very difficult for those skilled in the art to infer the properties showing in a transport layer formed by the inventive compound because it is necessary to grasp interrelation between hole transport layer and a light emitting layer (host).

[Example II-1] Green OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine (hereinafter, "NPB") was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 90:10.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example II-2] to [Example II-62] Green OLED (an Emission-Auxiliary Layer)

The OLEDs were fabricated in the same manner as described in Example II-1 except that the compounds P-2 to P-96 of the present invention described in Table 5, instead of the compound P-1 of the present invention, were used as an emission-auxiliary layer material.

[Comparative Example II-1] to [Comparative Example II-6]

In case of Comparative Example II-1, the OLED was fabricated in the same manner as described in Example II-1 except that an emission-auxiliary layer was not formed. In case of Comparative Examples II-2 to II-6, the OLEDs were fabricated in the same manner as described in Example II-1 except that the Comparative compounds 4 and 5 above, and the Comparative compounds 6, 7 and 8 below described in Table 5 instead of the compound P-1 of the present invention were used as an emission-auxiliary layer material.

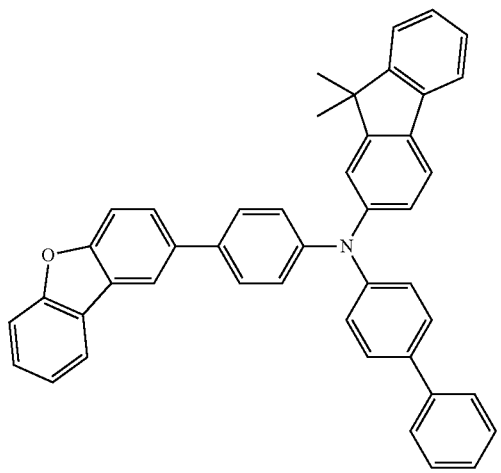

<Comp. compound 6>

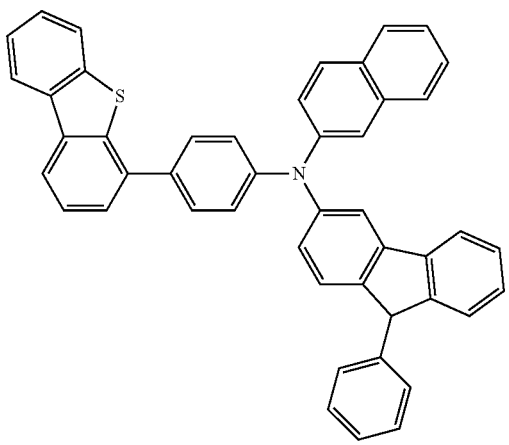

<Comp. compound7>

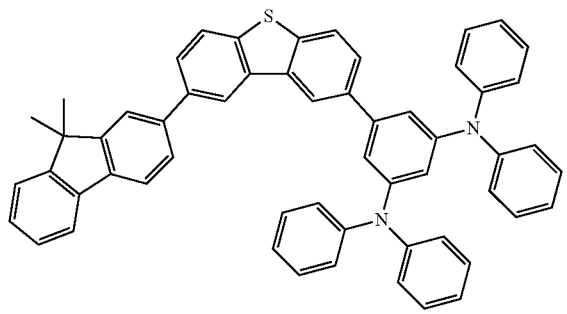

<Comp. compound 8>

Electroluminescence (EL) characteristics were measured with a PR-650 (Photoresearch) by applying a forward bias DC voltage to the OLEDs prepared in Examples II-1 to II-62 of the present invention and Comparative Examples II-1 to II-6. And, the T95 life span was measured using a life time measuring apparatus manufactured by Macscience Inc. at reference brightness of 5000 cd/m$^2$. The measurement results are shown in Table 5 below.

TABLE 5

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex (II-1) | — | 6.0 | 21.5 | 5000 | 23.3 | 57.2 | 0.32 | 0.61 |
| comp. Ex (II-2) | comp. Com 4 | 6.4 | 13.6 | 5000 | 36.6 | 101.4 | 0.33 | 0.61 |
| comp. Ex (II-3) | comp. Com 5 | 6.5 | 13.5 | 5000 | 37.0 | 100.9 | 0.33 | 0.61 |
| comp. Ex (II-4) | comp. Com 6 | 6.5 | 15.4 | 5000 | 32.4 | 91.8 | 0.33 | 0.61 |
| comp. Ex (II-5) | comp. Com 7 | 6.5 | 16.7 | 5000 | 30.0 | 88.9 | 0.33 | 0.61 |
| comp. Ex (II-6) | comp. Com 8 | 6.5 | 12.5 | 5000 | 40.0 | 105.8 | 0.33 | 0.61 |
| Ex. (II-1) | Com. (P-1) | 6.4 | 10.7 | 5000 | 46.7 | 144.6 | 0.33 | 0.61 |
| Ex. (II-2) | Com. (P-2) | 6.3 | 10.5 | 5000 | 47.7 | 147.6 | 0.33 | 0.61 |
| Ex. (II-3) | Com. (P-3) | 6.3 | 10.6 | 5000 | 47.0 | 157.0 | 0.33 | 0.61 |
| Ex. (II-4) | Com. (P-6) | 6.3 | 11.0 | 5000 | 45.3 | 142.4 | 0.33 | 0.61 |
| Ex. (II-5) | Com. (P-7) | 6.4 | 10.8 | 5000 | 46.3 | 144.2 | 0.33 | 0.61 |
| Ex. (II-6) | Com. (P-8) | 6.3 | 10.7 | 5000 | 46.6 | 144.7 | 0.33 | 0.61 |
| Ex. (II-7) | Com. (P-9) | 6.4 | 11.3 | 5000 | 44.3 | 142.2 | 0.33 | 0.61 |
| Ex. (II-8) | Com. (P-12) | 6.3 | 10.9 | 5000 | 46.0 | 146.9 | 0.33 | 0.61 |
| Ex. (II-9) | Com. (P-13) | 6.3 | 10.6 | 5000 | 47.3 | 152.9 | 0.33 | 0.61 |
| Ex. (II-10) | Com. (P-14) | 6.2 | 10.3 | 5000 | 48.4 | 158.8 | 0.33 | 0.61 |
| Ex. (II-11) | Com. (P-15) | 6.3 | 10.1 | 5000 | 49.6 | 170.5 | 0.33 | 0.61 |
| Ex. (II-12) | Com. (P-16) | 6.2 | 10.2 | 5000 | 49.2 | 164.2 | 0.33 | 0.61 |
| Ex. (II-13) | Com. (P-17) | 6.2 | 10.3 | 5000 | 48.7 | 155.2 | 0.33 | 0.61 |
| Ex. (II-14) | Com. (P-18) | 6.3 | 10.4 | 5000 | 48.0 | 164.2 | 0.33 | 0.62 |
| Ex. (II-15) | Com. (P-19) | 6.4 | 10.8 | 5000 | 46.5 | 145.1 | 0.33 | 0.62 |
| Ex. (II-16) | Com. (P-20) | 6.4 | 10.8 | 5000 | 46.4 | 143.6 | 0.33 | 0.62 |
| Ex. (II-17) | Com. (P-21) | 6.4 | 10.8 | 5000 | 46.1 | 144.9 | 0.33 | 0.62 |
| Ex. (II-18) | Com. (P-22) | 6.3 | 10.5 | 5000 | 47.8 | 154.8 | 0.33 | 0.62 |
| Ex. (II-19) | Com. (P-24) | 6.4 | 10.4 | 5000 | 48.2 | 150.9 | 0.33 | 0.62 |
| Ex. (II-20) | Com. (P-25) | 6.4 | 10.7 | 5000 | 46.8 | 157.3 | 0.33 | 0.61 |
| Ex. (II-21) | Com. (P-26) | 6.4 | 10.7 | 5000 | 46.7 | 140.5 | 0.33 | 0.61 |
| Ex. (II-22) | Com. (P-27) | 6.3 | 10.7 | 5000 | 46.6 | 147.3 | 0.33 | 0.61 |
| Ex. (II-23) | Com. (P-29) | 6.4 | 10.9 | 5000 | 45.9 | 141.4 | 0.33 | 0.61 |
| Ex. (II-24) | Com. (P-30) | 6.3 | 10.7 | 5000 | 46.9 | 148.5 | 0.33 | 0.62 |
| Ex. (II-25) | Com. (P-34) | 6.3 | 10.7 | 5000 | 46.7 | 152.8 | 0.33 | 0.62 |
| Ex. (II-26) | Com. (P-35) | 6.4 | 10.9 | 5000 | 45.7 | 145.4 | 0.33 | 0.62 |
| Ex. (II-27) | Com. (P-37) | 6.4 | 10.7 | 5000 | 46.6 | 151.8 | 0.33 | 0.61 |
| Ex. (II-28) | Com. (P-38) | 6.3 | 10.9 | 5000 | 45.9 | 143.7 | 0.33 | 0.62 |
| Ex. (II-29) | Com. (P-41) | 6.4 | 10.8 | 5000 | 46.5 | 154.5 | 0.33 | 0.61 |
| Ex. (II-30) | Com. (P-42) | 6.3 | 10.4 | 5000 | 48.1 | 153.1 | 0.33 | 0.61 |
| Ex. (II-31) | Com. (P-44) | 6.4 | 10.9 | 5000 | 46.0 | 140.8 | 0.33 | 0.61 |
| Ex. (II-32) | Com. (P-45) | 6.3 | 10.5 | 5000 | 47.8 | 157.2 | 0.33 | 0.62 |
| Ex. (II-33) | Com. (P-46) | 6.2 | 10.6 | 5000 | 47.1 | 153.9 | 0.33 | 0.62 |
| Ex. (II-34) | Com. (P-49) | 6.3 | 10.8 | 5000 | 46.5 | 157.2 | 0.33 | 0.61 |
| Ex. (II-35) | Com. (P-62) | 6.4 | 11.0 | 5000 | 45.6 | 146.3 | 0.33 | 0.61 |
| Ex. (II-36) | Com. (P-69) | 6.3 | 10.5 | 5000 | 47.4 | 148.0 | 0.33 | 0.62 |
| Ex. (II-37) | Com. (P-71) | 6.3 | 10.2 | 5000 | 49.1 | 155.8 | 0.33 | 0.62 |
| Ex. (II-38) | Com. (P-72) | 6.2 | 10.2 | 5000 | 48.8 | 161.4 | 0.33 | 0.62 |
| Ex. (II-39) | Com. (P-73) | 6.2 | 10.0 | 5000 | 50.1 | 171.6 | 0.33 | 0.61 |
| Ex. (II-40) | Com. (P-74) | 6.2 | 10.0 | 5000 | 50.0 | 170.5 | 0.33 | 0.62 |
| Ex. (II-41) | Com. (P-75) | 6.2 | 9.9 | 5000 | 50.6 | 173.3 | 0.33 | 0.62 |
| Ex. (II-42) | Com. (P-76) | 6.3 | 9.8 | 5000 | 51.0 | 173.3 | 0.33 | 0.61 |
| Ex. (II-43) | Com. (P-77) | 6.3 | 9.8 | 5000 | 51.0 | 174.1 | 0.33 | 0.62 |
| Ex. (II-44) | Com. (P-78) | 6.3 | 10.2 | 5000 | 49.2 | 157.6 | 0.33 | 0.62 |
| Ex. (II-45) | Com. (P-79) | 6.2 | 10.0 | 5000 | 49.9 | 167.2 | 0.33 | 0.61 |
| Ex. (II-46) | Com. (P-80) | 6.3 | 10.0 | 5000 | 50.1 | 168.1 | 0.33 | 0.61 |
| Ex. (II-47) | Com. (P-81) | 6.2 | 10.2 | 5000 | 49.2 | 171.3 | 0.33 | 0.62 |
| Ex. (II-48) | Com. (P-82) | 6.2 | 10.3 | 5000 | 48.7 | 157.8 | 0.33 | 0.62 |
| Ex. (II-49) | Com. (P-83) | 6.3 | 10.0 | 5000 | 50.0 | 170.0 | 0.33 | 0.61 |
| Ex. (II-50) | Com. (P-84) | 6.3 | 10.0 | 5000 | 49.9 | 170.9 | 0.33 | 0.62 |
| Ex. (II-51) | Com. (P-85) | 6.3 | 10.4 | 5000 | 48.0 | 151.9 | 0.33 | 0.62 |
| Ex. (II-52) | Com. (P-86) | 6.3 | 10.4 | 5000 | 47.9 | 156.9 | 0.33 | 0.62 |
| Ex. (II-53) | Com. (P-87) | 6.2 | 10.3 | 5000 | 48.4 | 159.5 | 0.33 | 0.61 |
| Ex. (II-54) | Com. (P-88) | 6.2 | 10.2 | 5000 | 49.1 | 156.5 | 0.33 | 0.62 |
| Ex. (II-55) | Com. (P-89) | 6.3 | 10.3 | 5000 | 48.4 | 162.6 | 0.33 | 0.61 |
| Ex. (II-56) | Com. (P-90) | 6.2 | 10.2 | 5000 | 48.9 | 167.0 | 0.33 | 0.62 |
| Ex. (II-57) | Com. (P-91) | 6.2 | 10.6 | 5000 | 47.2 | 152.4 | 0.33 | 0.61 |
| Ex. (II-58) | Com. (P-92) | 6.3 | 10.6 | 5000 | 47.2 | 155.2 | 0.33 | 0.61 |
| Ex. (II-59) | Com. (P-93) | 6.3 | 10.3 | 5000 | 48.6 | 164.1 | 0.33 | 0.62 |
| Ex. (II-60) | Com. (P-94) | 6.3 | 10.4 | 5000 | 48.2 | 164.8 | 0.33 | 0.62 |
| Ex. (II-61) | Com. (P-95) | 6.3 | 10.5 | 5000 | 47.5 | 157.4 | 0.33 | 0.62 |
| Ex. (II-62) | Com. (P-96) | 6.3 | 10.6 | 5000 | 47.2 | 153.7 | 0.33 | 0.62 |

[Example III-1] Red OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm.

A light emitting layer with a thickness of 30 nm was deposited on the emission-auxiliary layer by using the CBP as a host material and bis-(1-phenylisoquinolyl)iridium(□) acetylacetonate ("(piq)$_2$Ir(acac)") as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example III-2] to [Example III-48] Red OLED (an Emission-Auxiliary Layer)

The OLEDs were fabricated in the same manner as described in Example III-1 except that the compounds P-2 to P-96 of the present invention described in Table 6, instead of the compound P-1 of the present invention, were used as an emission-auxiliary layer material.

[Comparative Example III-1] to [Comparative Example III-6]

In case of Comparative Example III-1, the OLED was fabricated in the same manner as described in Example III-1 except that an emission-auxiliary layer was not formed. In case of Comparative Examples III-2 to III-6, the OLEDs were fabricated in the same manner as described in Example III-1 except that the Comparative compounds 4, 5, 6, 7 and 8 above described in Table 6 instead of the compound P-1 of the present invention were used as an emission-auxiliary layer material.

Electroluminescence (EL) characteristics were measured with a PR-650 (Photoresearch) by applying a forward bias DC voltage to the OLEDs prepared in Examples III-1 to III-48 of the present invention and Comparative Examples III-1 to III-6. And, the T95 life time was measured using a life time measuring apparatus manufactured by Macscience Inc. at reference brightness of 2500 cd/m$^2$. The measurement results are shown in Table 6 below.

TABLE 6

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex (III-1) | — | 6.5 | 33.8 | 2500 | 7.4 | 63.8 | 0.66 | 0.32 |
| comp. Ex (III-2) | comp. Com 4 | 6.9 | 25.4 | 2500 | 9.8 | 95.5 | 0.66 | 0.33 |
| comp. Ex (III-3) | comp. Com 5 | 6.8 | 25.3 | 2500 | 9.9 | 96.7 | 0.66 | 0.33 |
| comp. Ex (III-4) | comp. Com 6 | 6.9 | 26.6 | 2500 | 9.4 | 91.0 | 0.66 | 0.32 |
| comp. Ex (III-5) | comp. Com 7 | 6.9 | 27.7 | 2500 | 9.0 | 88.5 | 0.66 | 0.33 |
| comp. Ex (III-6) | comp. Com 8 | 6.8 | 23.0 | 2500 | 10.9 | 95.7 | 0.66 | 0.33 |
| Ex. (III-1) | Com. (P-1) | 6.7 | 20.7 | 2500 | 12.1 | 133.0 | 0.66 | 0.33 |
| Ex. (III-2) | Com. (P-2) | 6.7 | 19.9 | 2500 | 12.6 | 136.5 | 0.66 | 0.33 |
| Ex. (III-3) | Com. (P-3) | 6.7 | 18.4 | 2500 | 13.6 | 136.1 | 0.66 | 0.33 |
| Ex. (III-4) | Com. (P-6) | 6.8 | 20.8 | 2500 | 12.0 | 128.2 | 0.66 | 0.32 |
| Ex. (III-5) | Com. (P-14) | 6.8 | 18.4 | 2500 | 13.6 | 145.0 | 0.66 | 0.32 |
| Ex. (III-6) | Com. (P-15) | 6.7 | 15.8 | 2500 | 15.8 | 159.3 | 0.66 | 0.32 |
| Ex. (III-7) | Com. (P-16) | 6.6 | 17.0 | 2500 | 14.7 | 156.3 | 0.66 | 0.32 |
| Ex. (III-8) | Com. (P-17) | 6.6 | 17.3 | 2500 | 14.4 | 152.8 | 0.66 | 0.32 |
| Ex. (III-9) | Com. (P-18) | 6.7 | 16.8 | 2500 | 14.9 | 154.9 | 0.66 | 0.32 |
| Ex. (III-10) | Com. (P-19) | 6.7 | 20.2 | 2500 | 12.4 | 126.7 | 0.66 | 0.32 |
| Ex. (III-11) | Com. (P-20) | 6.7 | 20.4 | 2500 | 12.3 | 134.0 | 0.66 | 0.32 |
| Ex. (III-12) | Com. (P-21) | 6.8 | 20.4 | 2500 | 12.2 | 127.0 | 0.66 | 0.33 |
| Ex. (III-13) | Com. (P-22) | 6.8 | 19.1 | 2500 | 13.1 | 140.0 | 0.66 | 0.32 |
| Ex. (III-14) | Com. (P-24) | 6.8 | 17.7 | 2500 | 14.1 | 147.8 | 0.66 | 0.33 |
| Ex. (III-15) | Com. (P-30) | 6.8 | 19.6 | 2500 | 12.8 | 137.5 | 0.66 | 0.32 |
| Ex. (III-16) | Com. (P-31) | 6.8 | 21.2 | 2500 | 11.8 | 128.2 | 0.66 | 0.33 |
| Ex. (III-17) | Com. (P-34) | 6.7 | 19.9 | 2500 | 12.6 | 137.0 | 0.66 | 0.32 |
| Ex. (III-18) | Com. (P-45) | 6.7 | 17.4 | 2500 | 14.4 | 147.1 | 0.66 | 0.33 |
| Ex. (III-19) | Com. (P-46) | 6.8 | 18.6 | 2500 | 13.5 | 138.7 | 0.66 | 0.32 |
| Ex. (III-20) | Com. (P-49) | 6.7 | 18.3 | 2500 | 13.6 | 138.2 | 0.66 | 0.32 |
| Ex. (III-21) | Com. (P-69) | 6.8 | 18.0 | 2500 | 13.9 | 139.2 | 0.66 | 0.32 |
| Ex. (III-22) | Com. (P-70) | 6.7 | 19.2 | 2500 | 13.0 | 142.4 | 0.66 | 0.32 |
| Ex. (III-23) | Com. (P-71) | 6.6 | 17.3 | 2500 | 14.4 | 151.6 | 0.66 | 0.33 |
| Ex. (III-24) | Com. (P-72) | 6.6 | 17.2 | 2500 | 14.5 | 152.2 | 0.66 | 0.32 |
| Ex. (III-25) | Com. (P-73) | 6.7 | 17.1 | 2500 | 14.6 | 150.5 | 0.66 | 0.33 |
| Ex. (III-26) | Com. (P-74) | 6.6 | 17.1 | 2500 | 14.6 | 155.2 | 0.66 | 0.32 |
| Ex. (III-27) | Com. (P-75) | 6.6 | 15.5 | 2500 | 16.1 | 165.4 | 0.66 | 0.32 |
| Ex. (III-28) | Com. (P-76) | 6.6 | 14.8 | 2500 | 16.9 | 169.7 | 0.66 | 0.32 |
| Ex. (III-29) | Com. (P-77) | 6.6 | 15.2 | 2500 | 16.5 | 168.8 | 0.66 | 0.32 |
| Ex. (III-30) | Com. (P-78) | 6.6 | 16.6 | 2500 | 15.1 | 156.9 | 0.66 | 0.32 |
| Ex. (III-31) | Com. (P-79) | 6.6 | 15.8 | 2500 | 15.8 | 157.0 | 0.66 | 0.32 |

TABLE 6-continued

| compound | | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (III-32) | Com. (P-80) | 6.6 | 15.9 | 2500 | 15.7 | 163.1 | 0.66 | 0.33 |
| Ex. (III-33) | Com. (P-81) | 6.7 | 15.8 | 2500 | 15.8 | 160.6 | 0.66 | 0.32 |
| Ex. (III-34) | Com. (P-82) | 6.6 | 16.4 | 2500 | 15.2 | 151.2 | 0.66 | 0.32 |
| Ex. (III-35) | Com. (P-83) | 6.7 | 15.9 | 2500 | 15.7 | 161.8 | 0.66 | 0.33 |
| Ex. (III-36) | Com. (P-84) | 6.7 | 16.1 | 2500 | 15.5 | 159.0 | 0.66 | 0.32 |
| Ex. (III-37) | Com. (P-85) | 6.8 | 17.7 | 2500 | 14.1 | 148.9 | 0.66 | 0.33 |
| Ex. (III-38) | Com. (P-86) | 6.8 | 17.4 | 2500 | 14.3 | 144.0 | 0.66 | 0.32 |
| Ex. (III-39) | Com. (P-87) | 6.7 | 16.9 | 2500 | 14.8 | 152.3 | 0.66 | 0.33 |
| Ex. (III-40) | Com. (P-88) | 6.6 | 16.8 | 2500 | 14.9 | 149.3 | 0.66 | 0.33 |
| Ex. (III-41) | Com. (P-89) | 6.7 | 18.0 | 2500 | 13.9 | 146.1 | 0.66 | 0.33 |
| Ex. (III-42) | Com. (P-90) | 6.6 | 16.5 | 2500 | 15.2 | 151.8 | 0.66 | 0.32 |
| Ex. (III-43) | Com. (P-91) | 6.8 | 17.6 | 2500 | 14.2 | 144.3 | 0.66 | 0.32 |
| Ex. (III-44) | Com. (P-92) | 6.8 | 17.5 | 2500 | 14.3 | 145.5 | 0.66 | 0.32 |
| Ex. (III-45) | Com. (P-93) | 6.6 | 17.1 | 2500 | 14.6 | 151.2 | 0.66 | 0.33 |
| Ex. (III-46) | Com. (P-94) | 6.6 | 16.7 | 2500 | 15.0 | 150.5 | 0.66 | 0.32 |
| Ex. (III-47) | Com. (P-95) | 6.7 | 18.1 | 2500 | 13.8 | 142.2 | 0.66 | 0.33 |
| Ex. (III-48) | Com. (P-96) | 6.8 | 17.8 | 2500 | 14.0 | 147.5 | 0.66 | 0.33 |

From the results shown in Tables 5 and 6, it can be seen that, the luminous efficiency and lifetime of the organic electroluminescent device are remarkably improved when compounds of the present invention were used as an emission-auxiliary layer material, compared with that of Comparative Example II-1 to Comparative Example III-5.

From these results, it is confirmed that luminescent efficiency and lifetime of device are improved when Comparative Compounds 4 to 8 and the compound of the present invention are used as an emission-auxiliary layer material, among them, particularly the compound of the present invention, compared with device not having an emission-auxiliary layer. This is because when material having a structure in which a hetero ring (dibenzofuran or dibenzothiophene) core and two amine groups are bonded to each other through a linker is used not only as a electron transport layer material but also an emission-auxiliary layer material, the structure serves as a major factor in improving the performance of a device, as a result, the charge can be balanced and electrons can be blocked.

When Compound of the present invention having a deep HOMO energy level are used as an emission-auxiliary layer material, a hole can be smoothly transferred to a light emitting layer, resulting in preventing positive polaron from accumulating at the interface of the light emitting layer, thereby reducing the interface deterioration and increasing the charge balance in the light emitting layer. As a result, it is confirmed that the luminous efficiency and lifetime are improved.

Taken together, the previously described properties of high thermal stability, high T1 values, and deep HOMO energy levels, it can be seen that the band gap, the electrical characteristics, the interface characteristics, and the like may be largely changed depending on heterocyclic core and the number of amino groups bonded to a linker, and it can be confirmed that this is a major factor in improving the performance of the device.

In addition, in the evaluation results of the device fabrication described above, even though the characteristics of devise have been described when the compound of the present invention is used as material of only one layer of the hole transport layer and an emission-auxiliary layer, the compound of the present invention can be used as material of both the hole transport layer and an emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1 below:

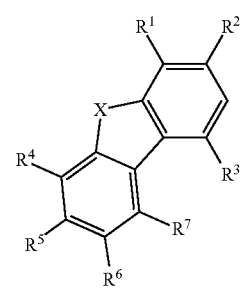

[Formula 1]

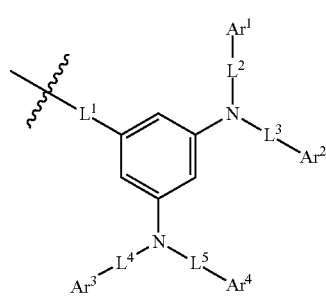

[Formula 2]

wherein,

X is O or S,

R$^1$ to R$^3$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and the above formula 2, and with the proviso that at least one of $R^1$ to $R^3$ is the above formula 2, $R^4$ to $R^7$ are each independently selected from the group consisting of hydrogen, deuterium, tritium, halogen, a cyano group, a nitro group, a $C_6$-$C_{60}$ aryl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and with the proviso that dibenzofuryl group and dibenzothienyl group are excluded from $R^4$ to $R^7$; neighboring $R^4$ to $R^7$ may be optionally linked each other to form a ring;

in the Formula 2, $Ar^1$ to $Ar^4$ are each independently selected from the group consisting of a $C_6$-$C_{60}$ aryl group, a $C_2$-$C_{60}$ heterocyclic group containing at least one heteroatom selected from the group consisting of O, N, S, Si, and P, a fluorenyl group, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, $L^1$ is selected from the group consisting of a single bond, a $C_6$-$C_{60}$ arylene group and a $C_2$-$C_{60}$ heterocyclic group containing at least one heteroatom selected from O, N, S, Si, and P, $L^2$ to $L^5$ are each independently selected from the group consisting of a single bond, a $C_6$-$C_{60}$ arylene group, a $C_2$-$C_{60}$ heterocyclic group containing at least one heteroatom selected from O, N, S, Si, and P, a fluorenylene group, a fused ring group of a $C_3$-$C_{60}$ aliphatic ring and a $C_6$-$C_{60}$ aromatic ring, and an $C_1$-$C_{60}$ aliphatic hydrocarbon group, each of $L^1$ to $L^5$, except for a single bond, may be optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, when $R^1$ to $R^3$, and $Ar^1$ to $Ar^4$ are each the aryl group, fluorenyl group, heterocyclic group, fused ring group, alkyl group, alkenyl group, alkynyl group, alkoxyl group, or aryloxy group, each of these may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when those substituents are adjacent, they are linked each other to form a ring, and when $R^4$ to $R^7$ are each the aryl group, heterocyclic group, fused ring group, alkyl group, alkenyl group, alkynyl group, alkoxyl group, or aryloxy group, each of these may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group except dibenzofuryl group and dibenzothienyl group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, wherein Formula 1 above is represented by any one of Formulas 3 to 5 below:

[Formula 3]

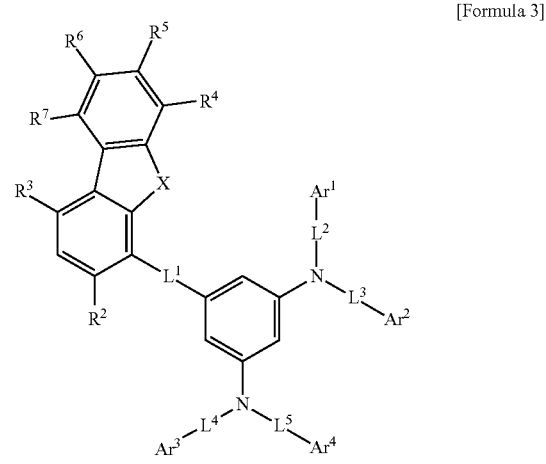

[Formula 4]

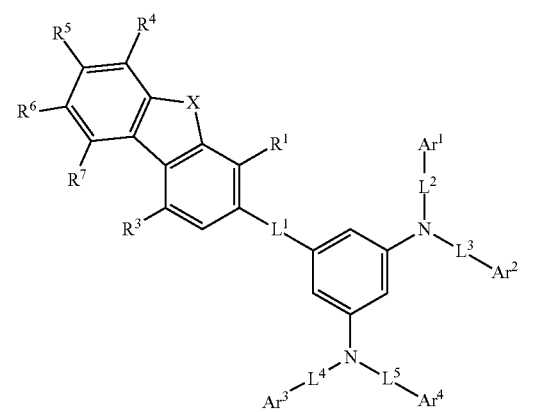

-continued

[Formula 5]

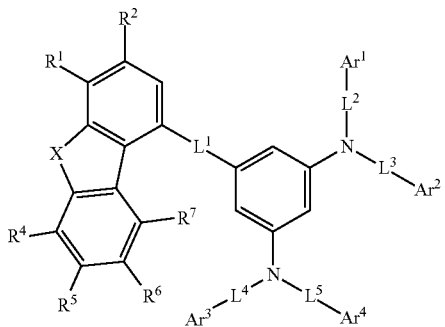

in Formulas 3 to 5, X, $R^1$ to $R^7$, $Ar^1$ to $Ar^4$, and $L^1$ to $L^5$ are the same as defined in claim 1.

3. The compound of claim 1, wherein Formula 1 above is represented by any one of Formulas 6 to 9 below when at least one pair of $R^4$ and $R^5$, $R^5$ and $R^6$, and $R^6$ and $R^7$ are linked each other to form a ring:

[Formula 6]

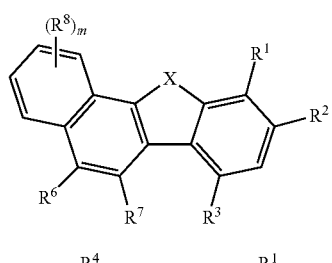

[Formula 7]

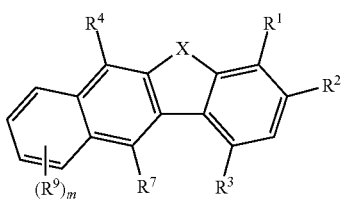

[Formula 8]

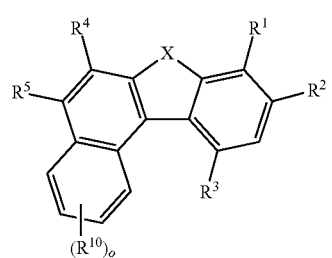

[Formula 9]

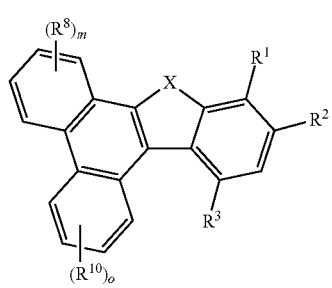

in Formulas 6 to 9, X, $R^1$ to $R^7$ are the same as defined in claim 1, and $R^8$ to $R^{10}$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, m, n and o are each an integer of 0 to 4, and $R^8$s to $R^{10}$s are each the same or different from each other when m, n and o are each an integer of 2 or more.

4. The compound of claim 1, wherein Formula 2 above is represented by any one of Formulas 10 to 14 below:

[Formula 10]

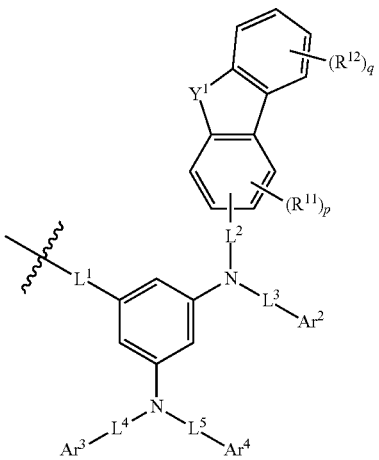

[Formula 11]

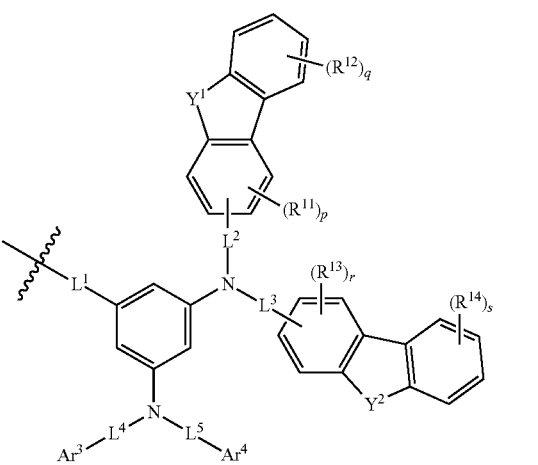

[Formula 12]

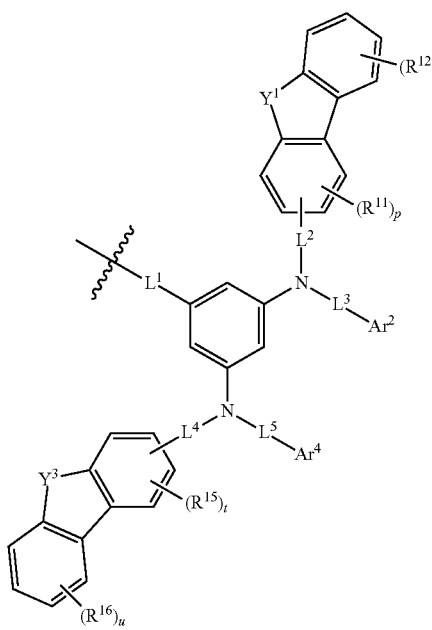

[Formula 13]

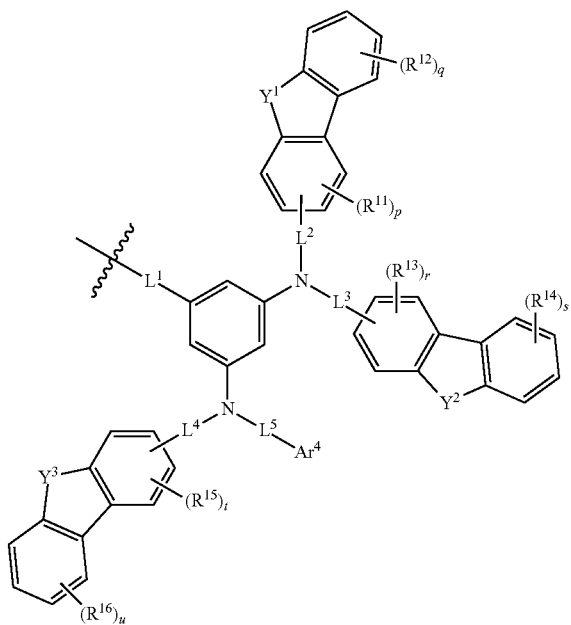

[Formula 14]

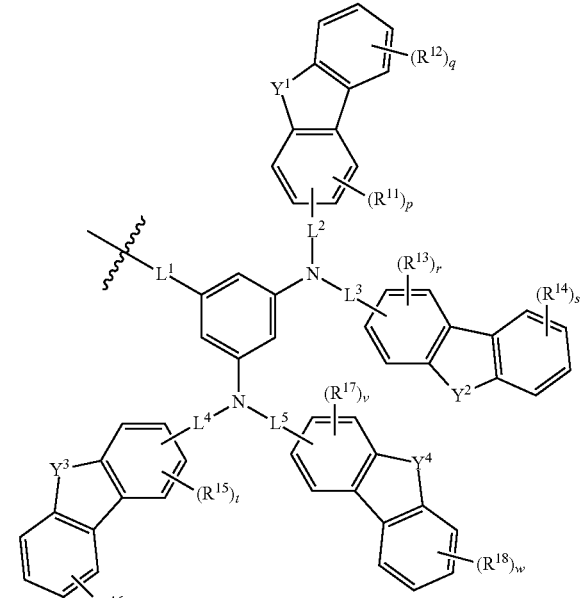

in Formulas 10 to 14, $Ar^2$ to $Ar^4$, and $L^1$ to $L^5$ are each the same as defined in claim 1, $Y^1$ to $Y^4$ are each independently S, O, $C(R^a)(R^b)$ or $N(R^c)$, wherein $R^a$ to $R^c$ are each independently a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, wherein $R^a$ and $R^b$ may be optionally linked each other to form a spiro compound together with C bonded to them, $R^{11}$ to $R^{18}$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group; when a plurality of $R^{11}$s to $R^{18}$s are present, at least one pair of neighboring groups of $R^{11}$, $R^{12}$, $R^{13}$, $R^{14}$, $R^{15}$, $R^{16}$, $R^{17}$ and $R^{18}$ may be linked each other to form a ring, p, r, t and v are each an integer of 0 to 3, $R^{11}$, $R^{13}$, $R^{15}$ and $R^{17}$ are each the same or different from each other when p, r, t and v are each an integer of 2 or more, and q, s, u and w are each an integer of 0 to 4, $R^{12}$, $R^{14}$, $R^{16}$ and $R^{18}$ are each the same or different from each other when q, s, u and w each an integer of 2 or more.

5. The compound of claim 1, wherein Formula 1 is any one of the compounds below:

P-1
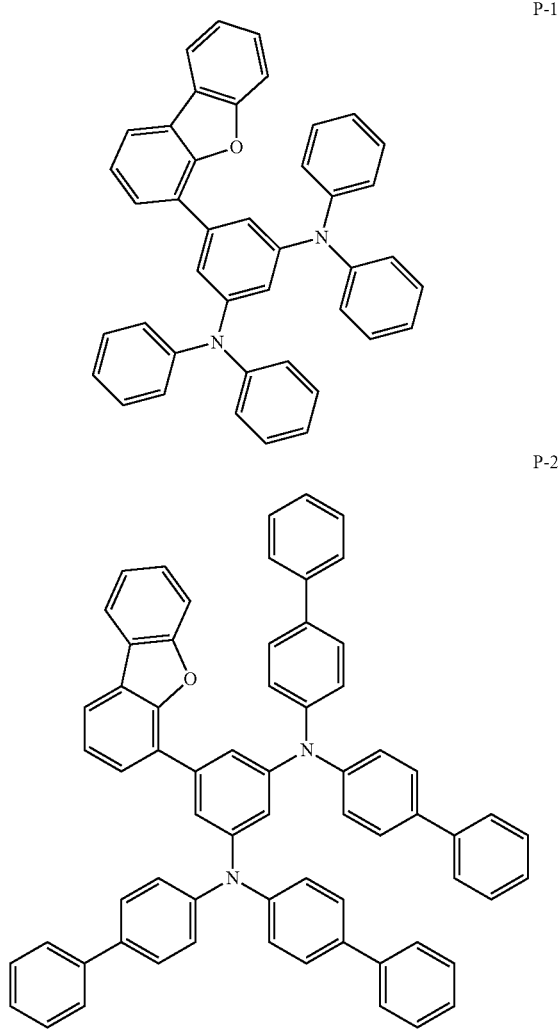
P-2
P-3
P-4
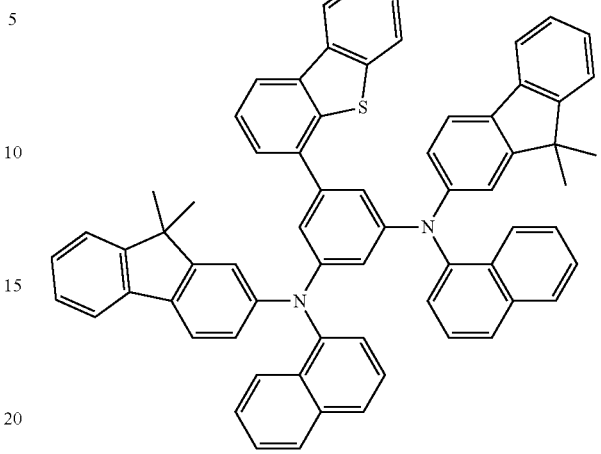
P-5
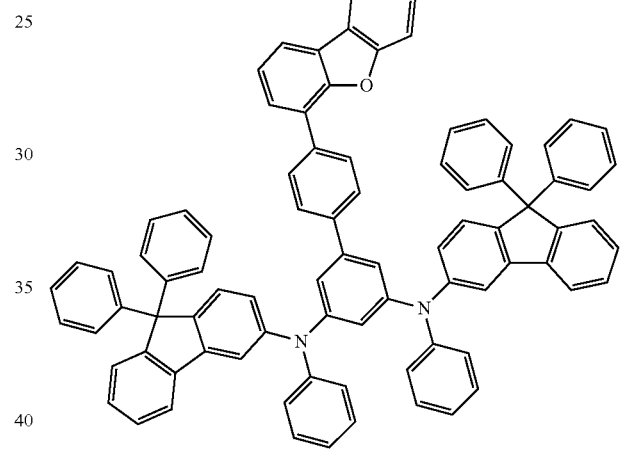
P-6
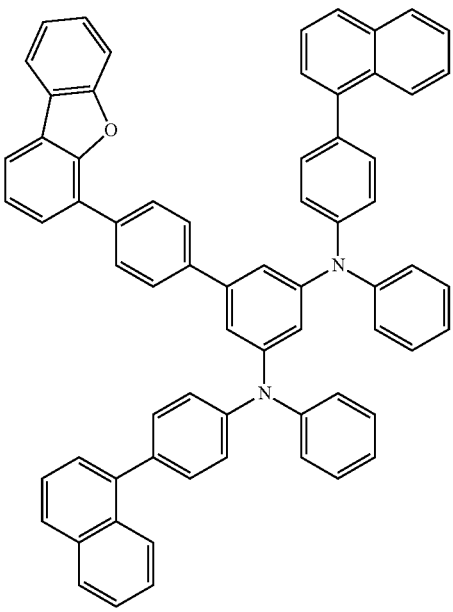

P-7
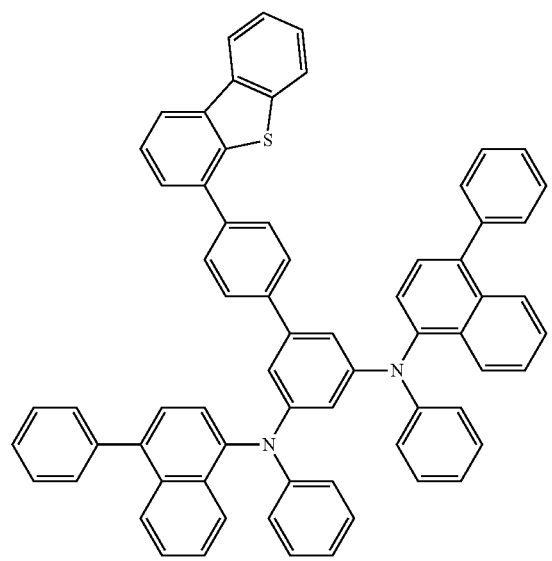
P-8
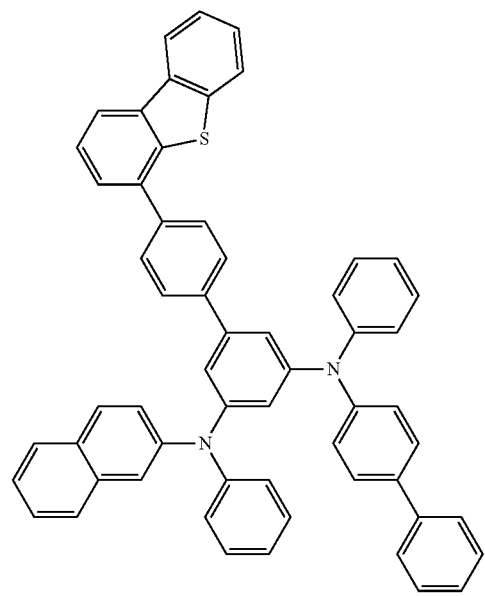
P-9
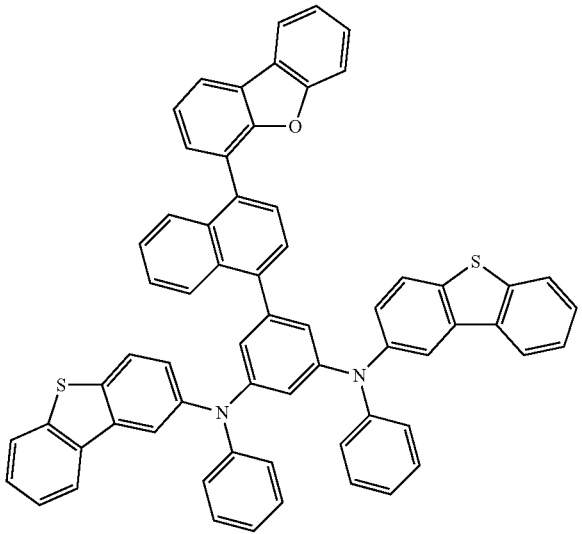
P-10
P-11
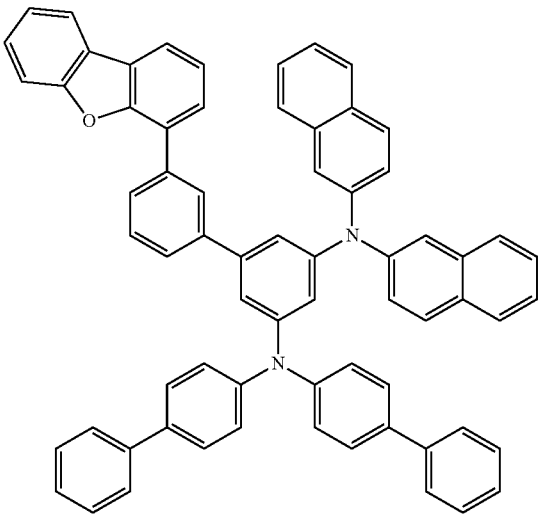

P-12
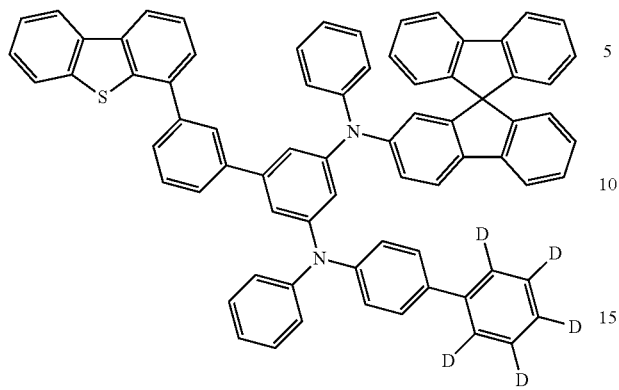
P-13
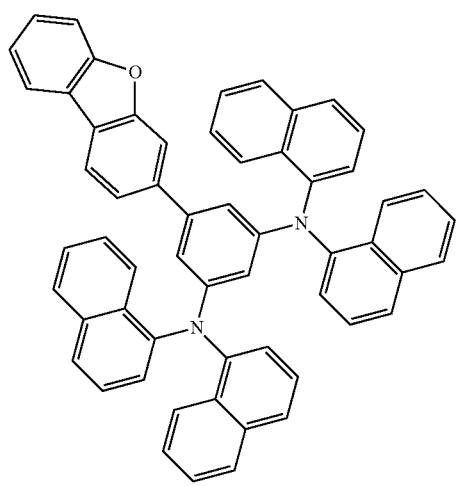
P-14
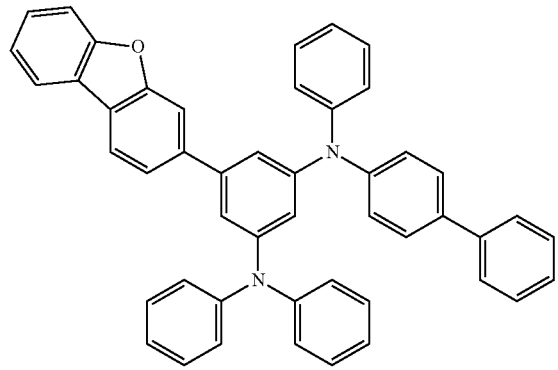
P-15
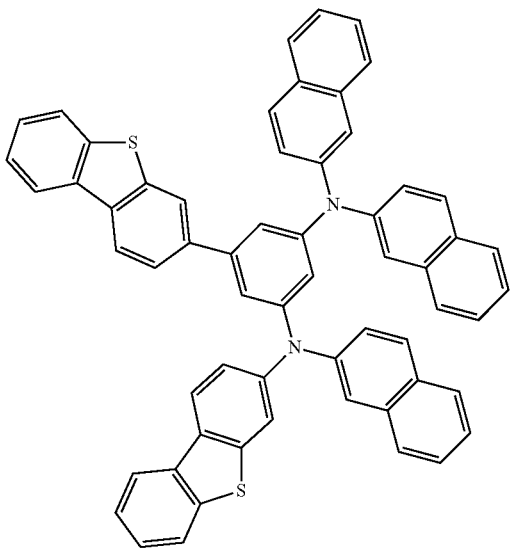
P-16
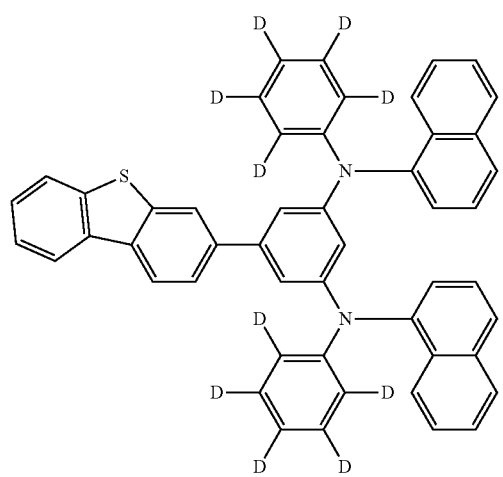
P-17
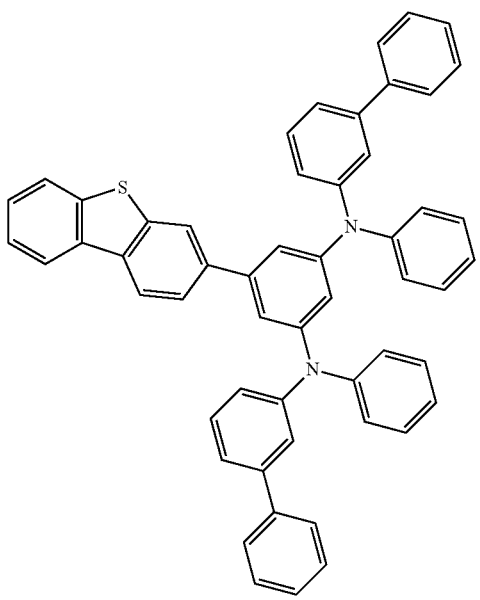

P-18
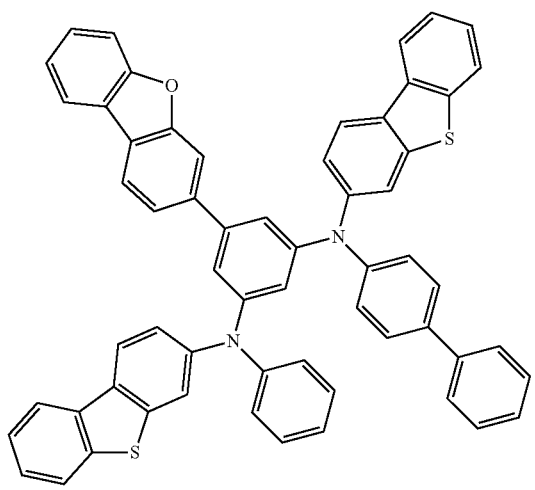
P-19
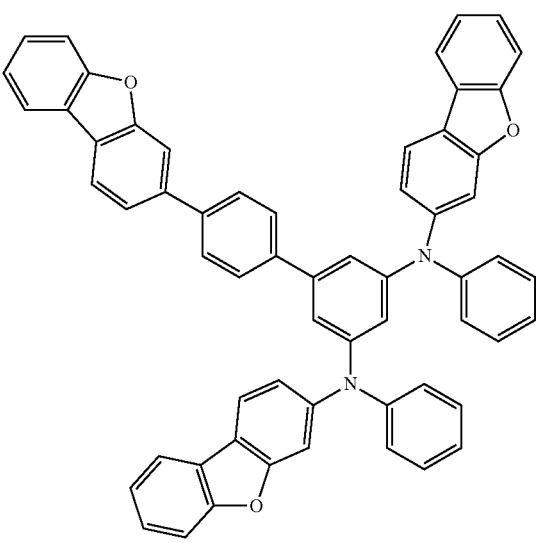
P-20
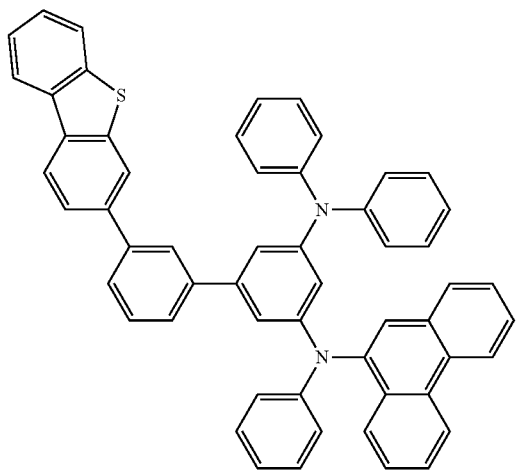
P-21
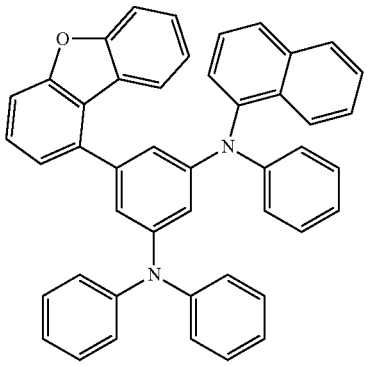
P-22
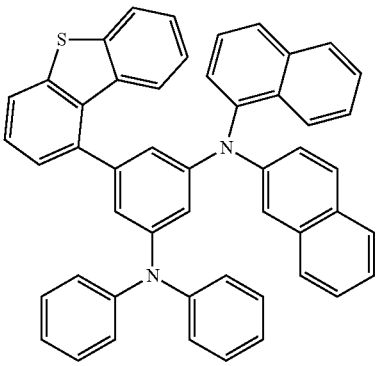
P-23
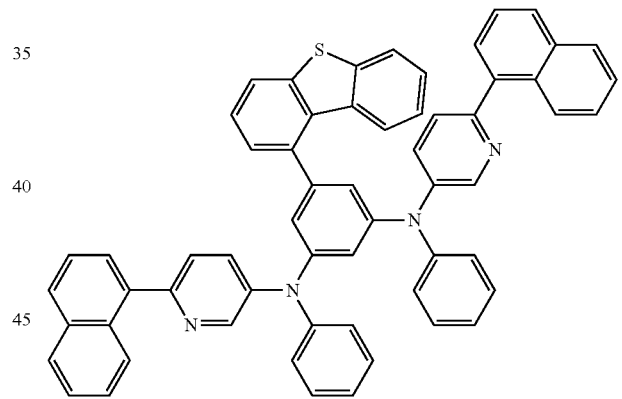
P-24
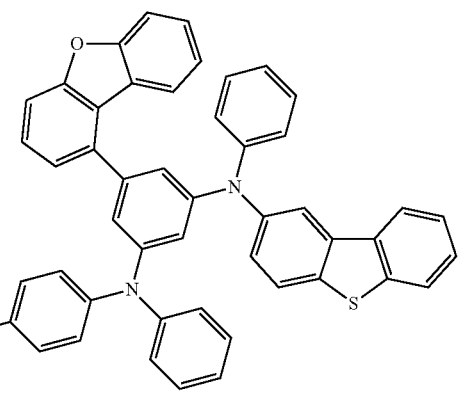

P-25
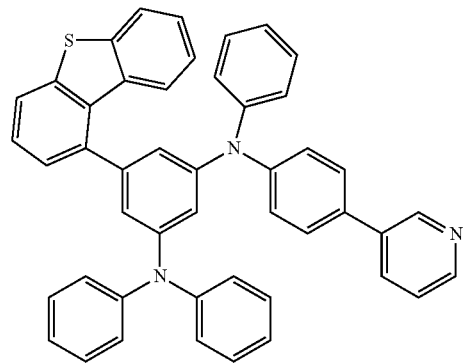
P-26
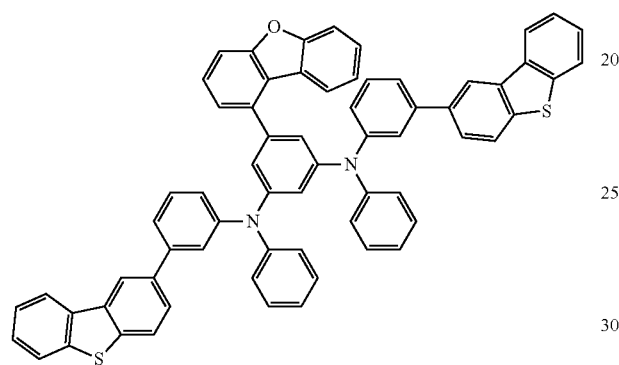
P-27
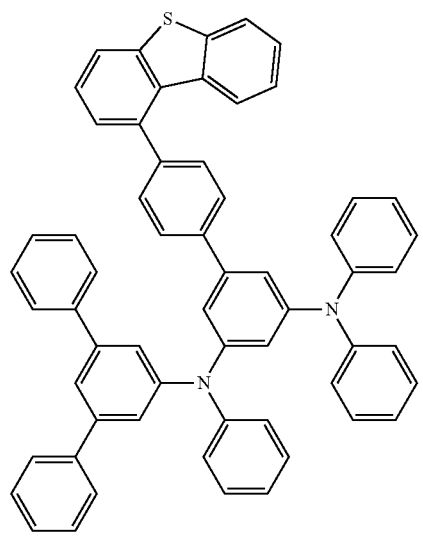
P-28
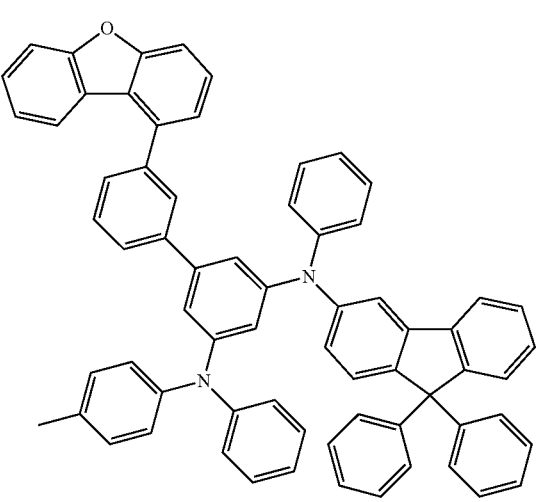
P-29
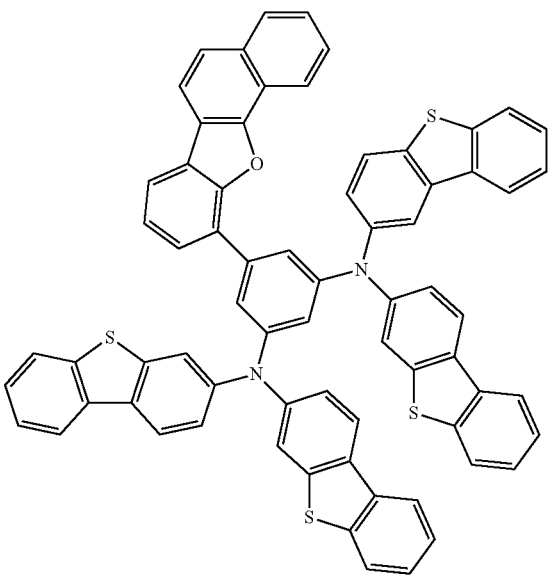
P-30
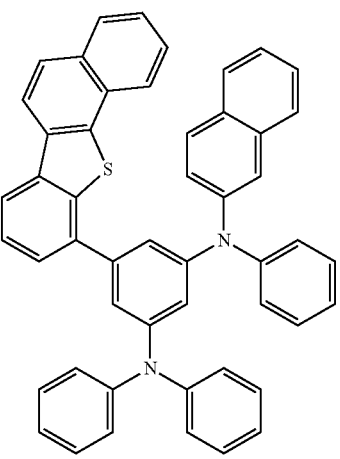

P-31
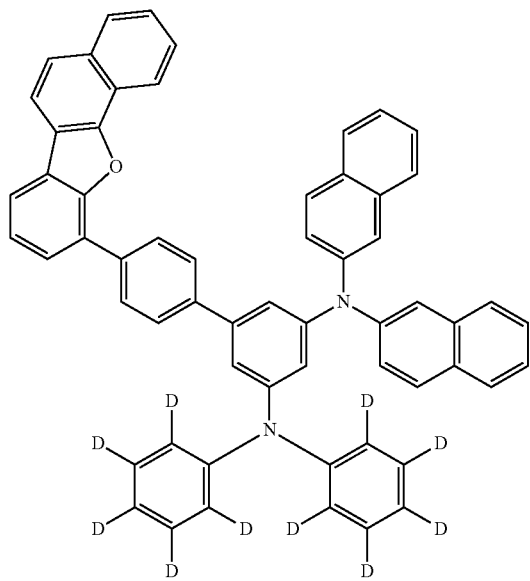
P-32
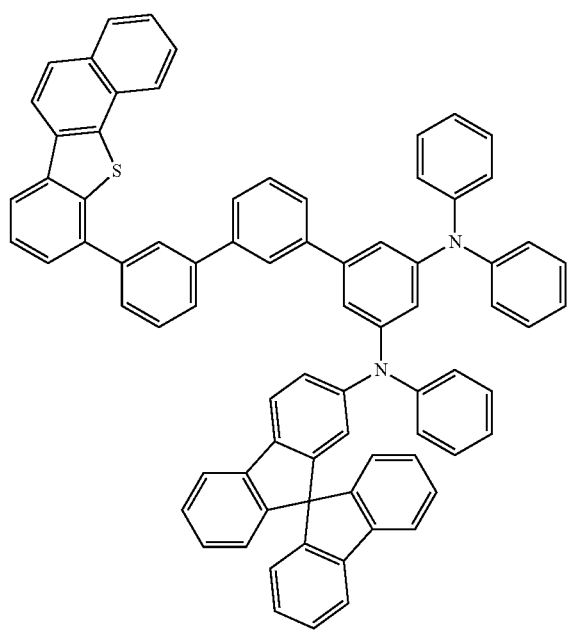
P-33
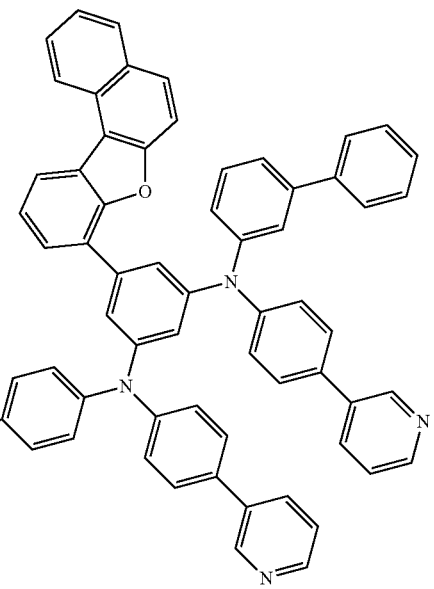
P-34
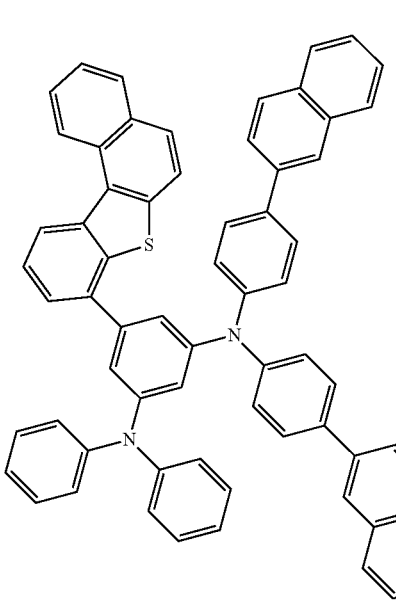

P-35
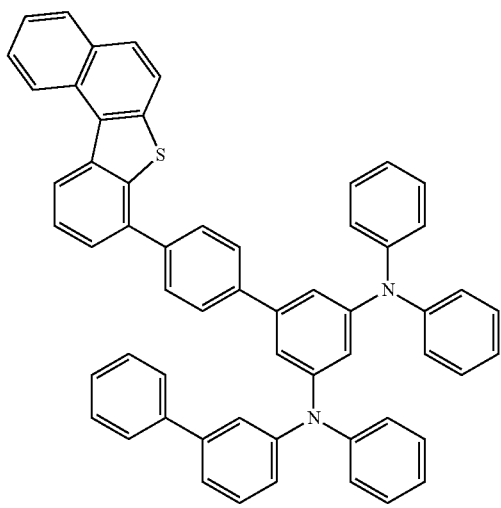
P-36
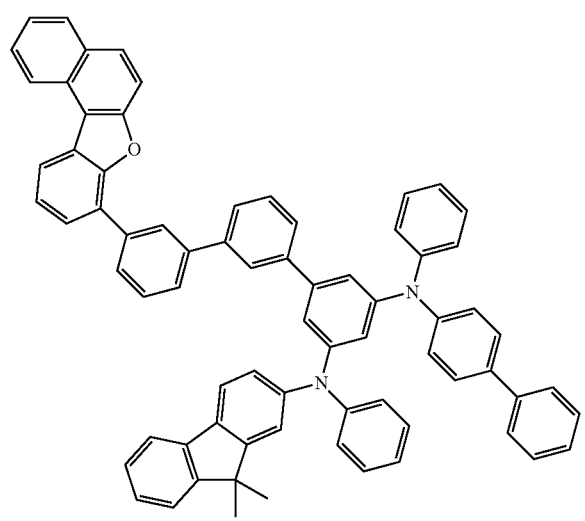
P-37
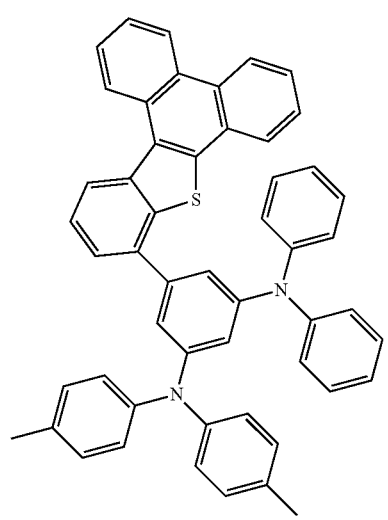
P-38
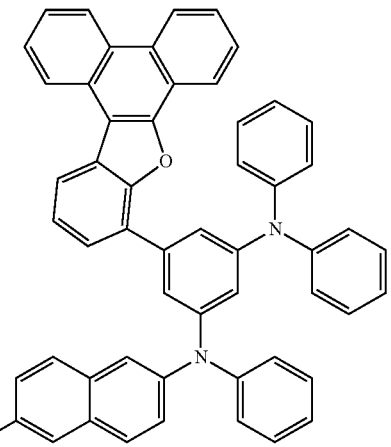
P-39
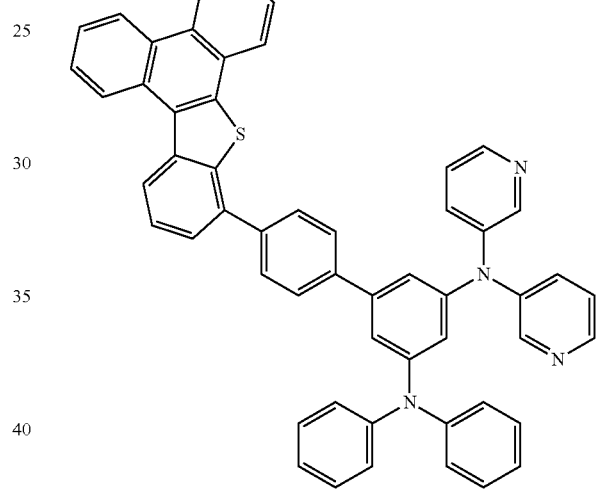
P-40
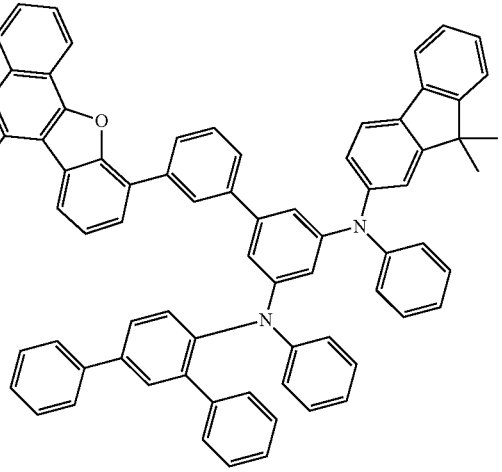

P-41
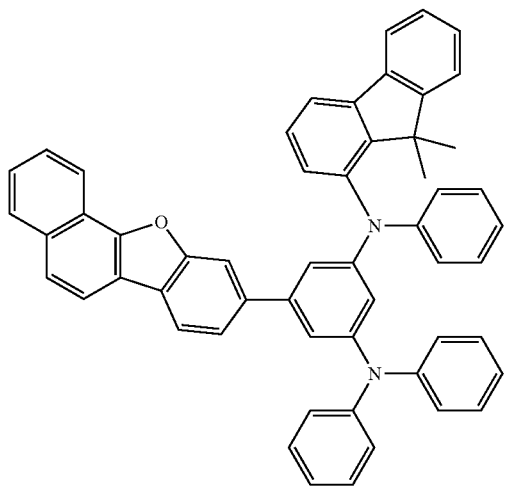
P-42
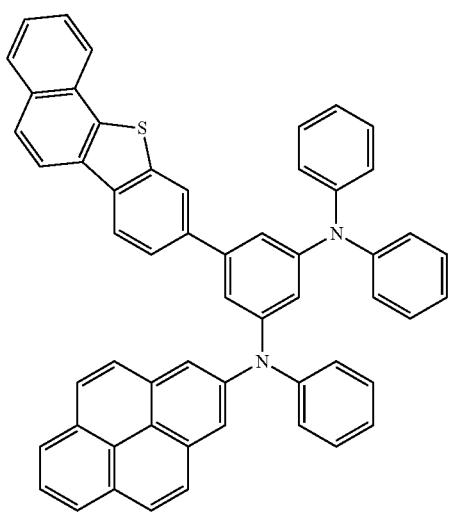
P-43
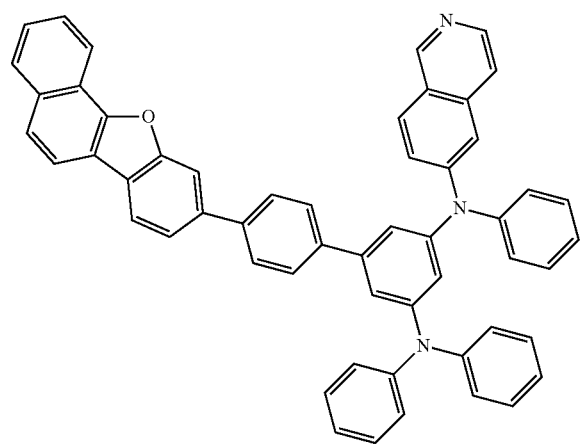
P-44
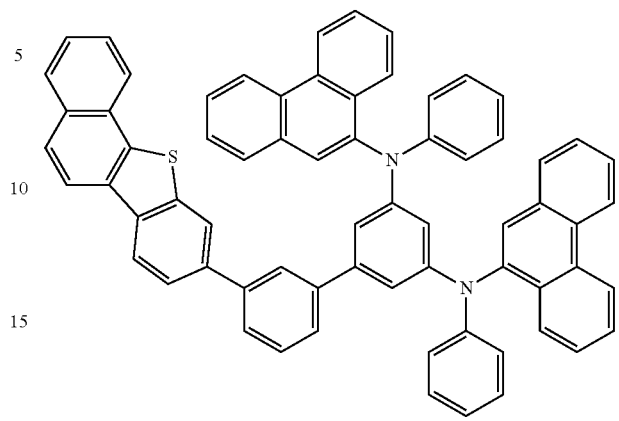
P-45
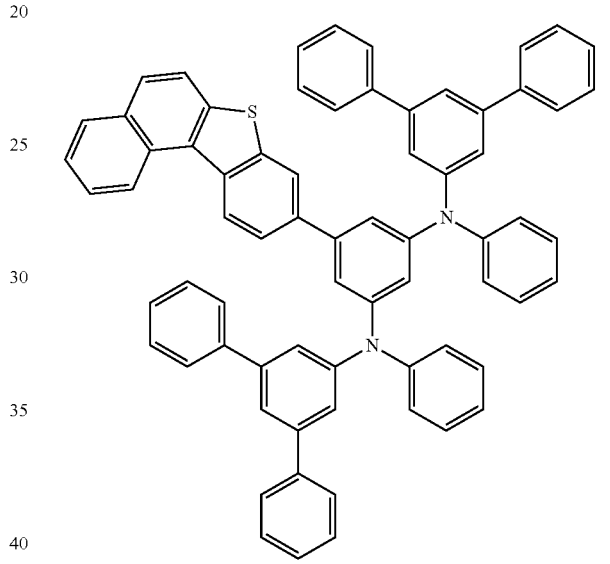
P-46
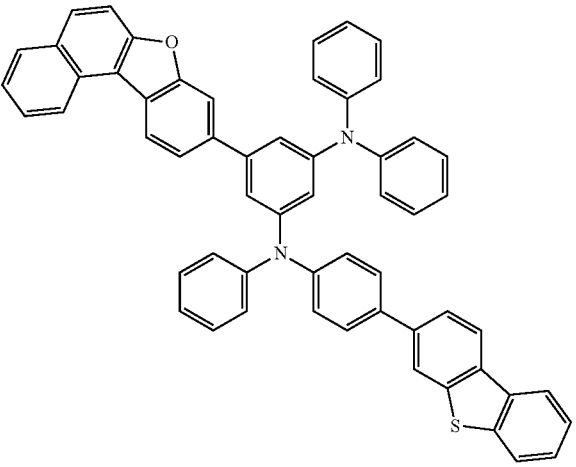

-continued
P-47
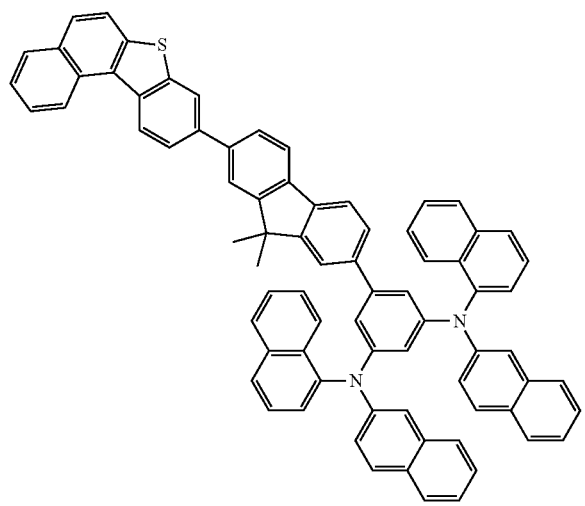
P-48
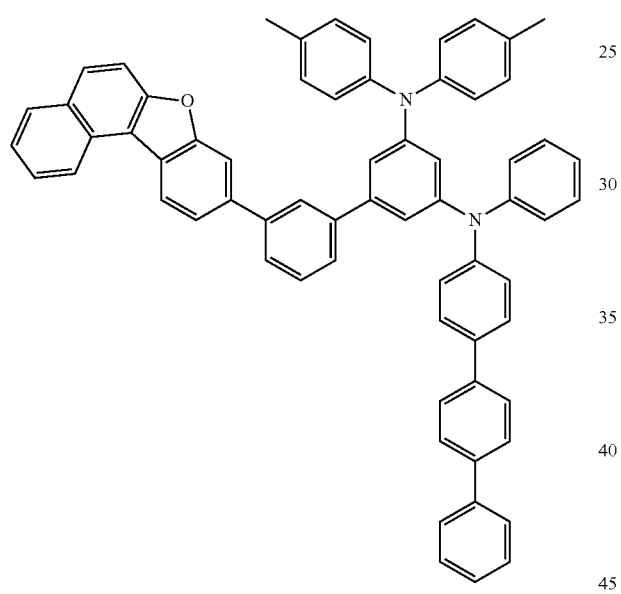
P-49
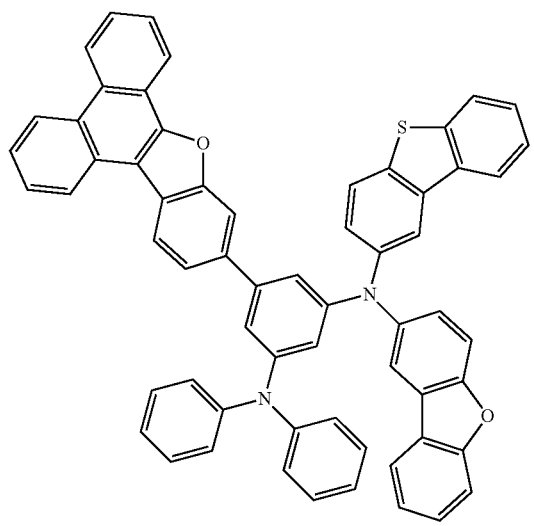
-continued
P-50
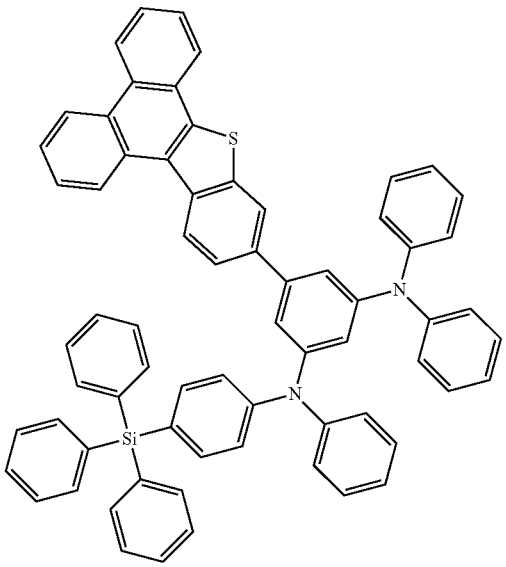
P-51
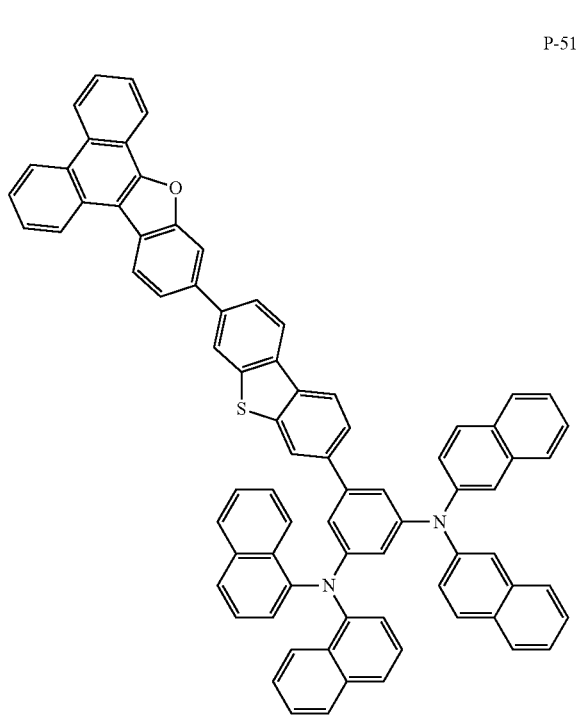

-continued
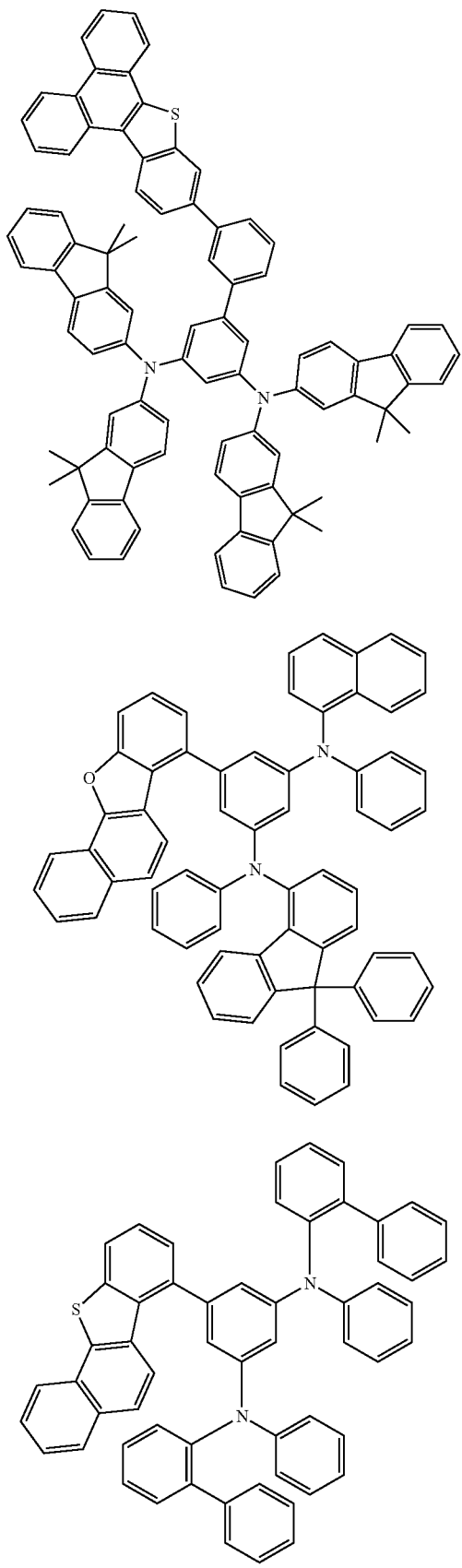
P-52
P-53
P-54
-continued
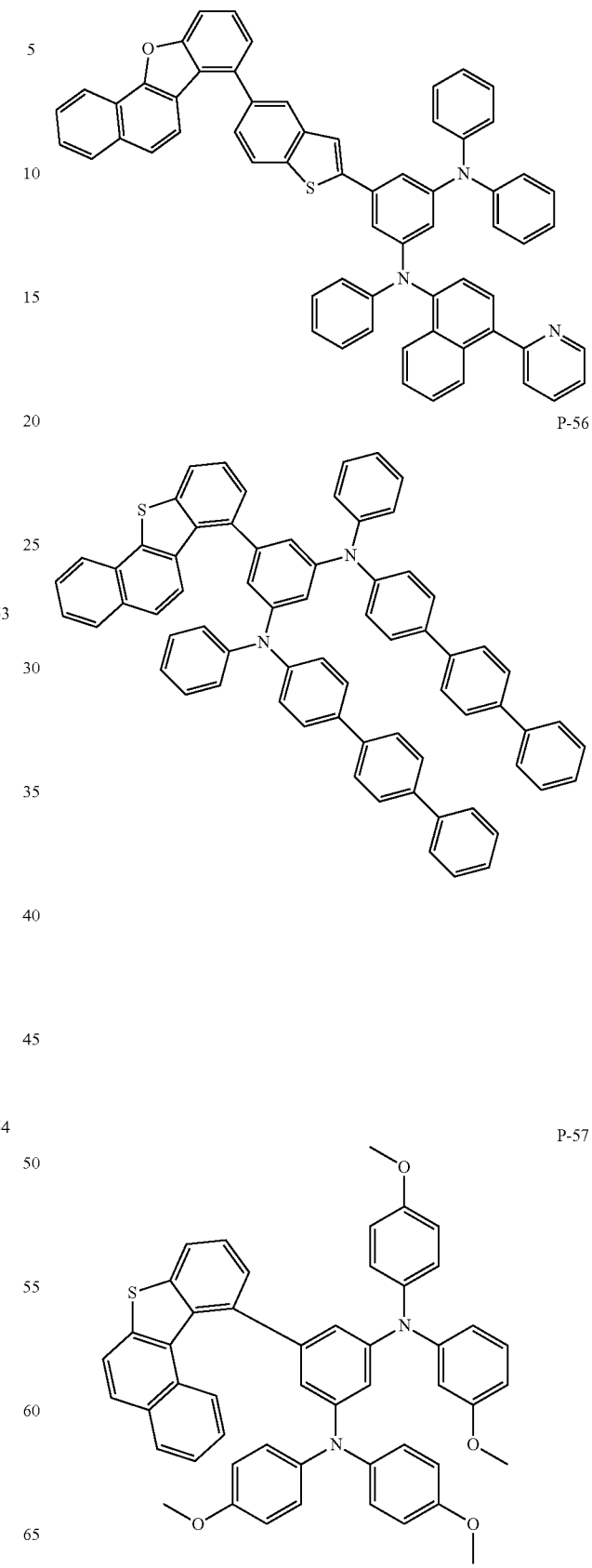
P-55
P-56
P-57

-continued
P-58
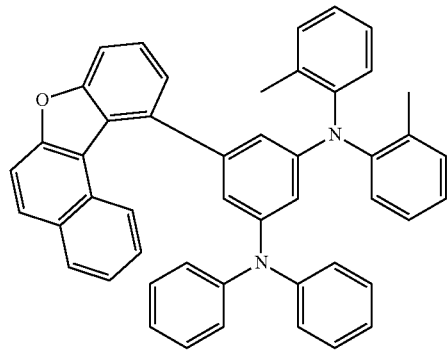
P-59
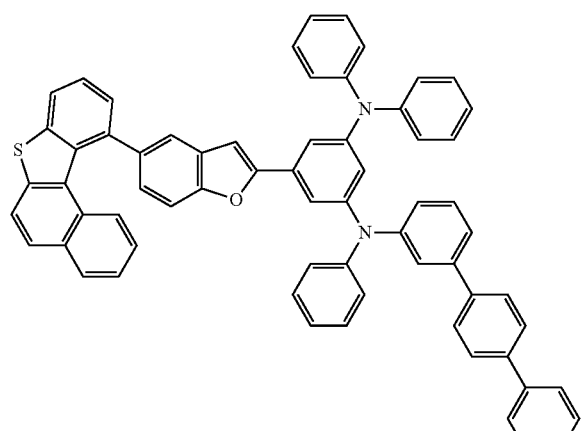
P-60
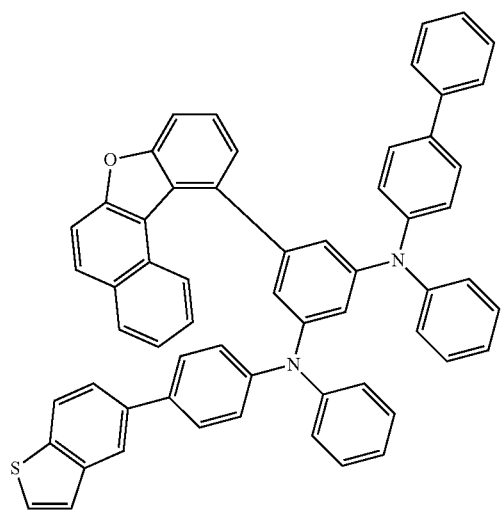
-continued
P-61
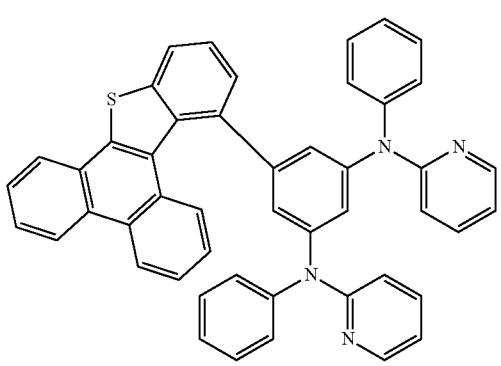
P-62
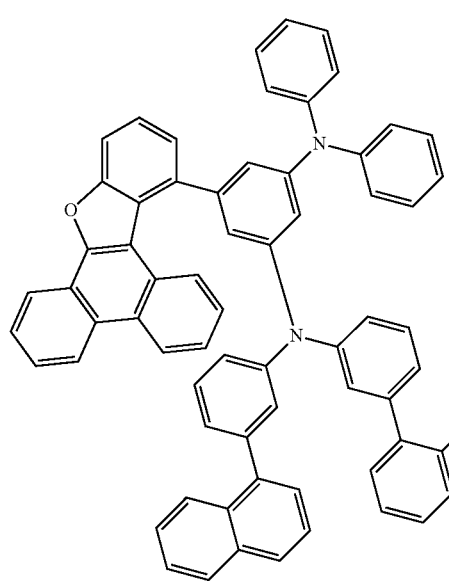
P-63
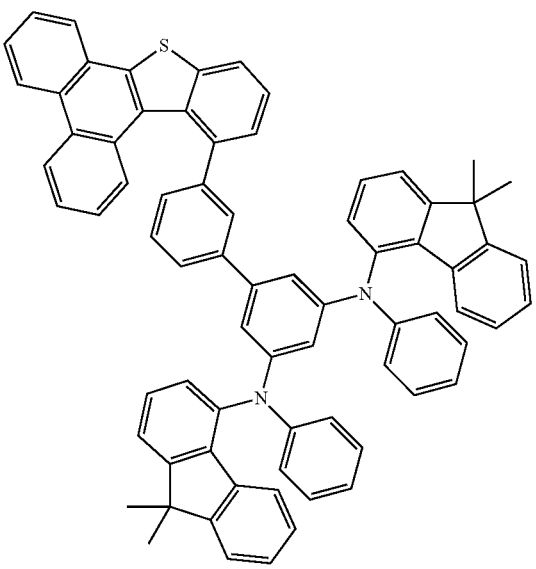

P-64
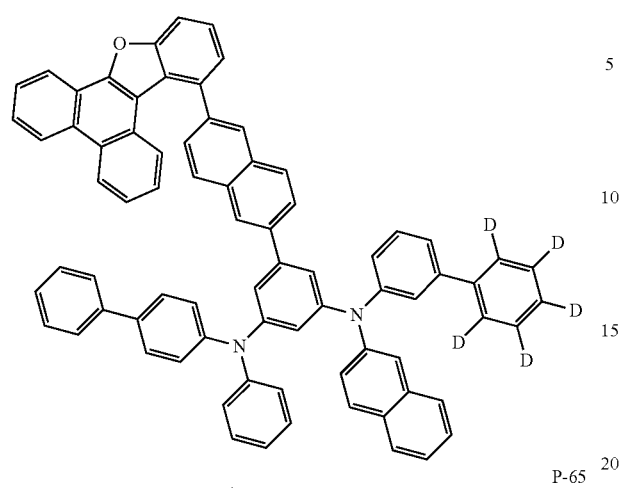
P-65
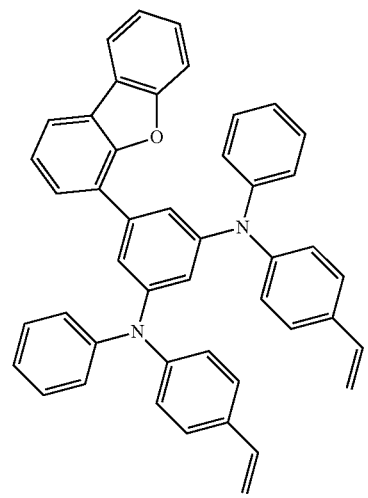
P-66
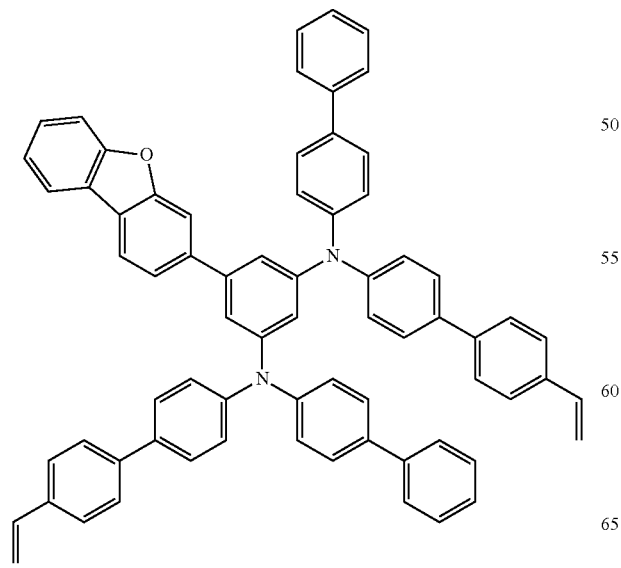
P-67
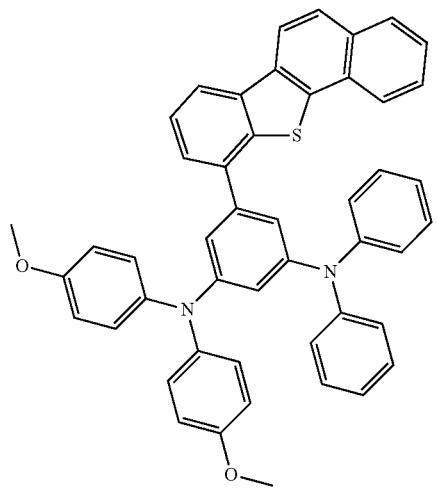
P-68
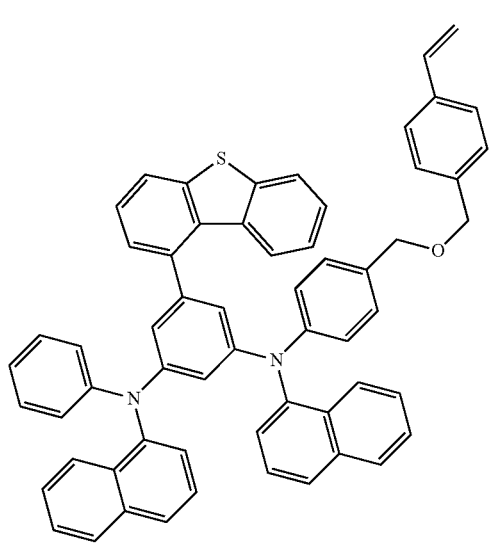
P-69
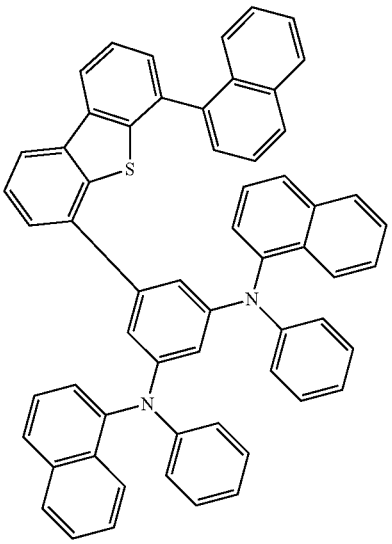

P-70
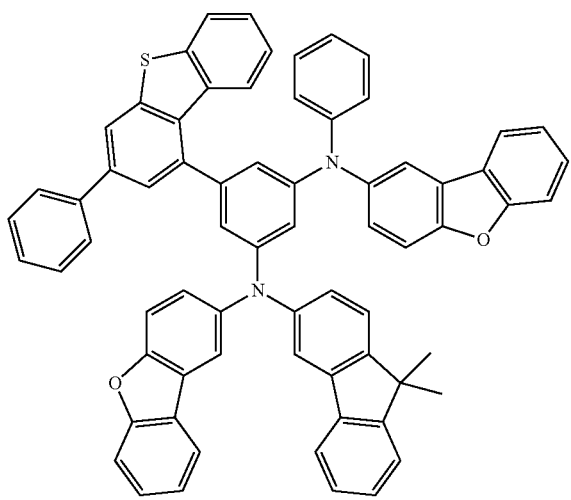
P-73
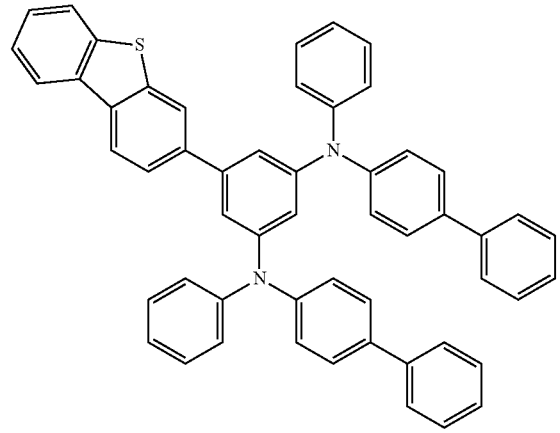
P-71
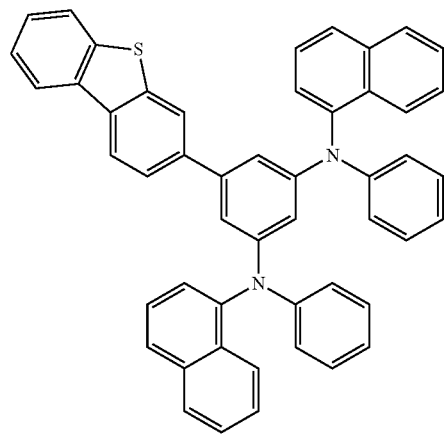
P-74
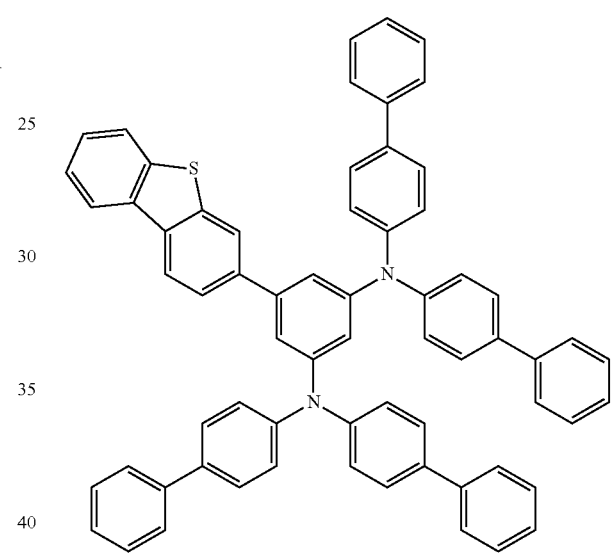
P-72
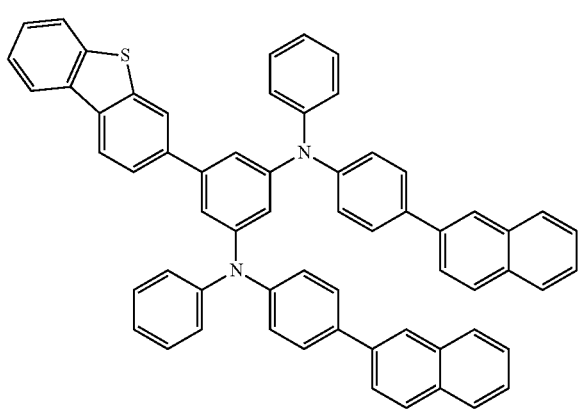
P-75
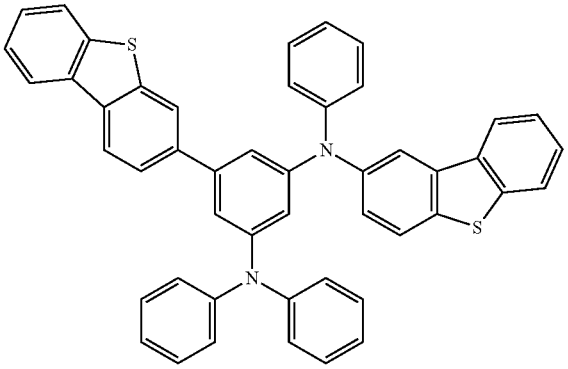

P-76
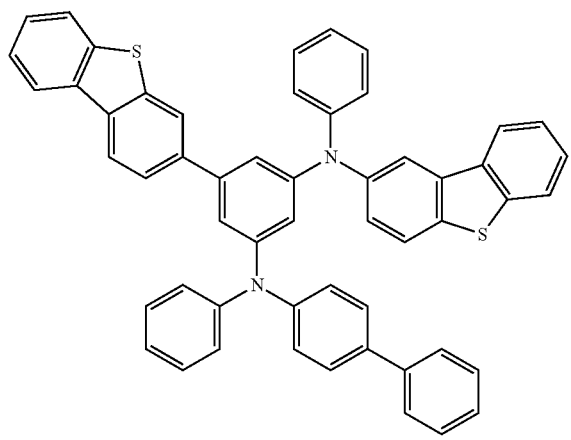
P-77
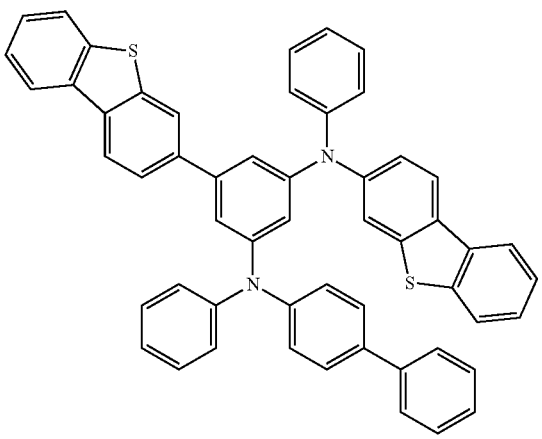
P-78
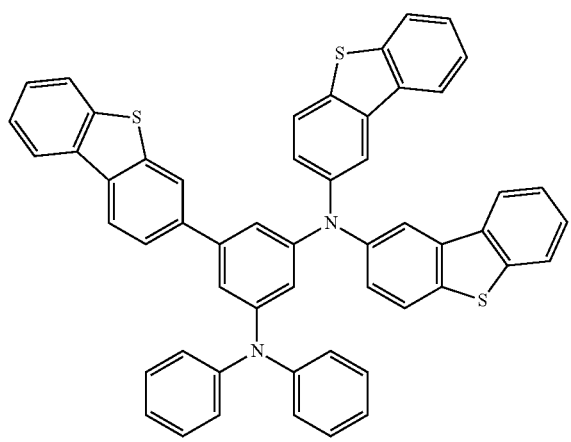
P-79
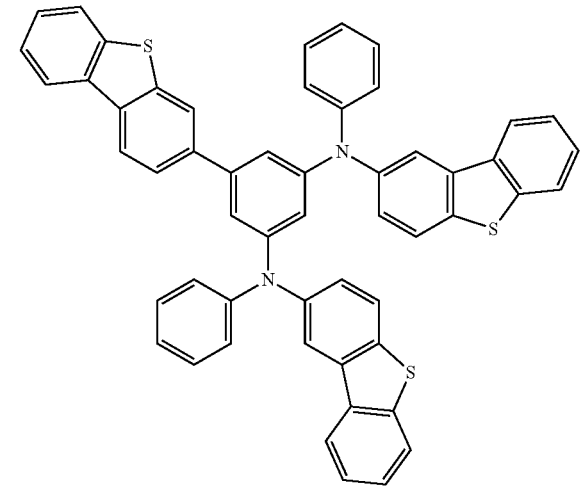
P-80
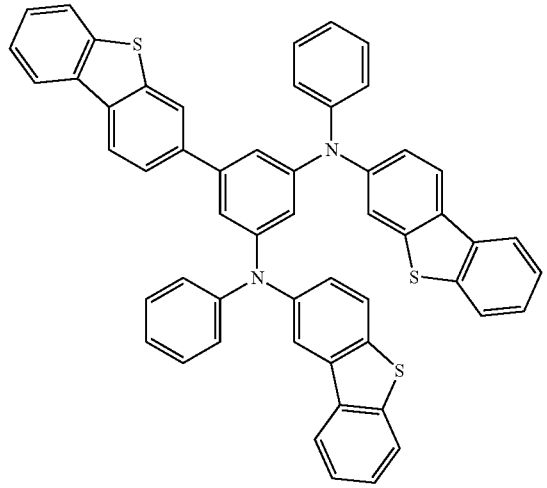
P-81
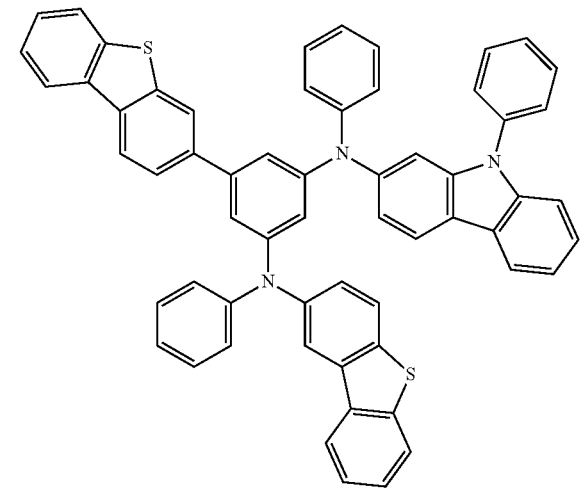

P-82
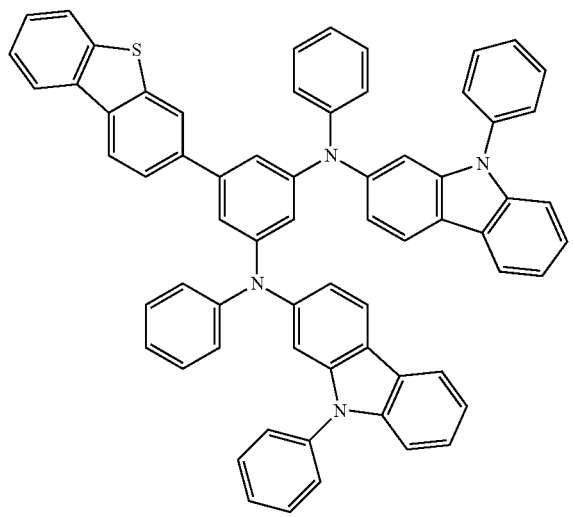
P-83
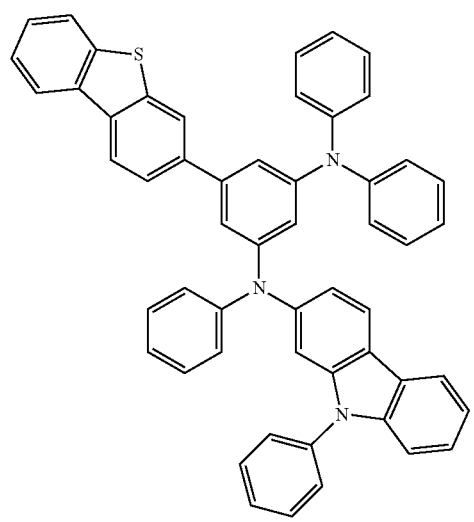
P-84
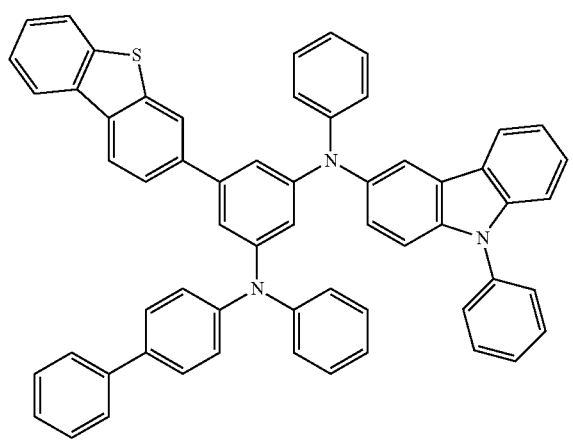
P-85
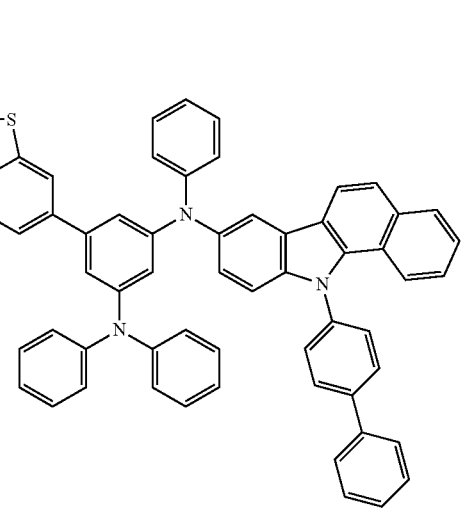
P-86
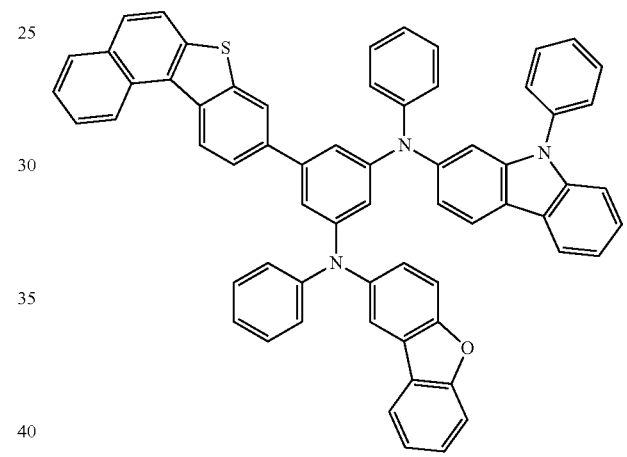
P-87
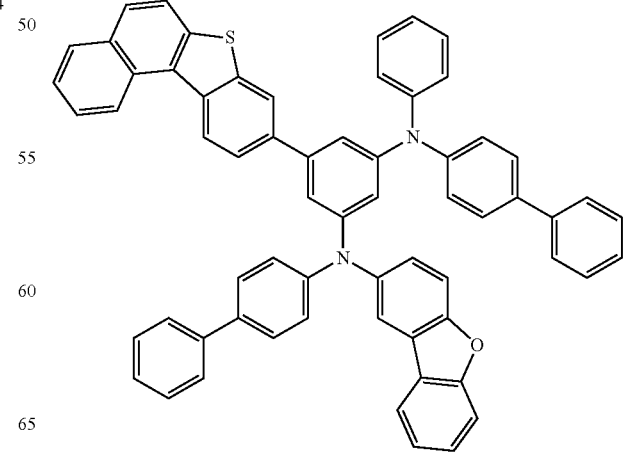

P-88
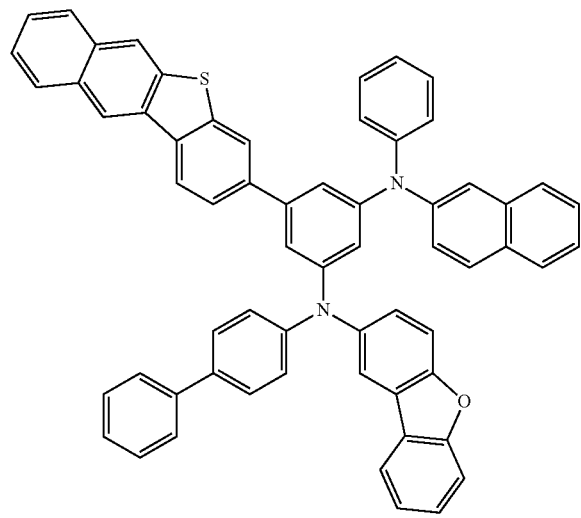
P-89
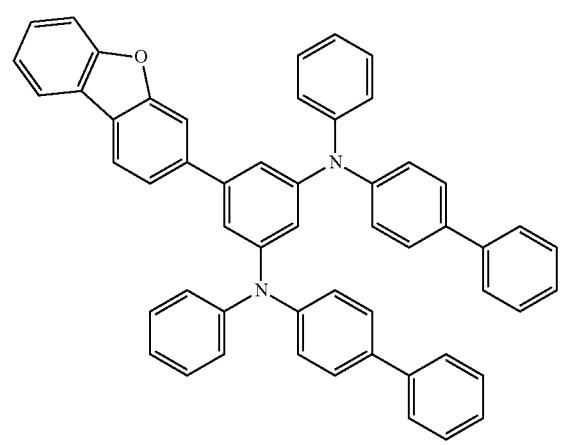
P-90
P-91
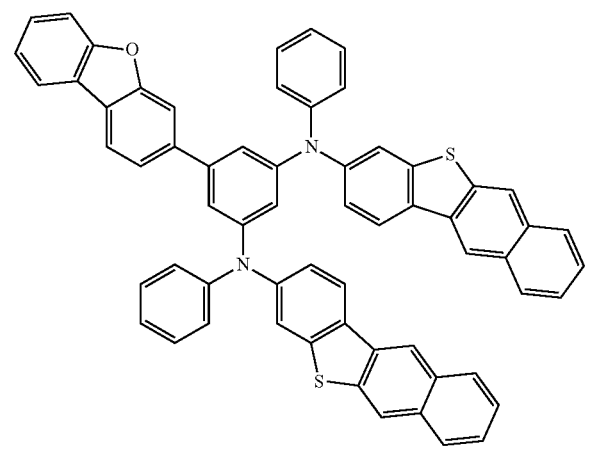
P-92
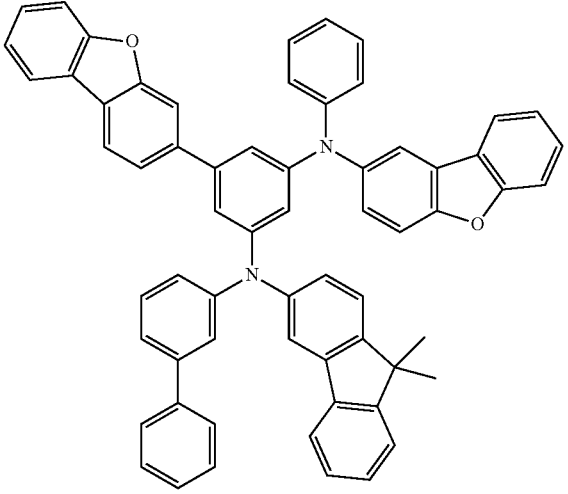
P-93

P-94
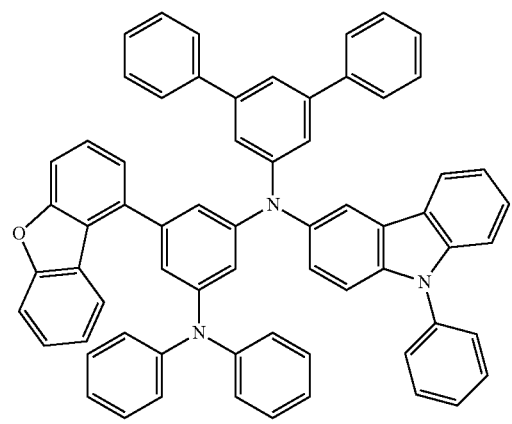
P-97
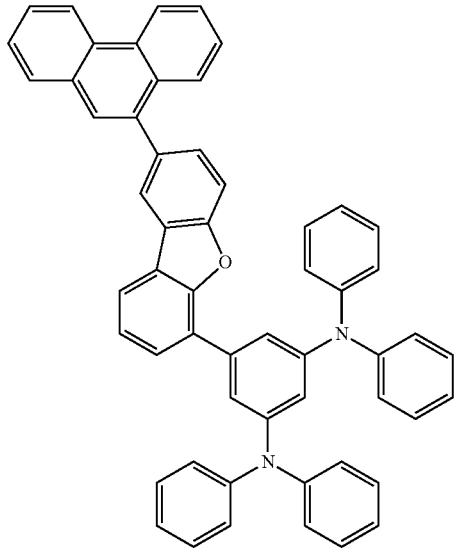
P-95
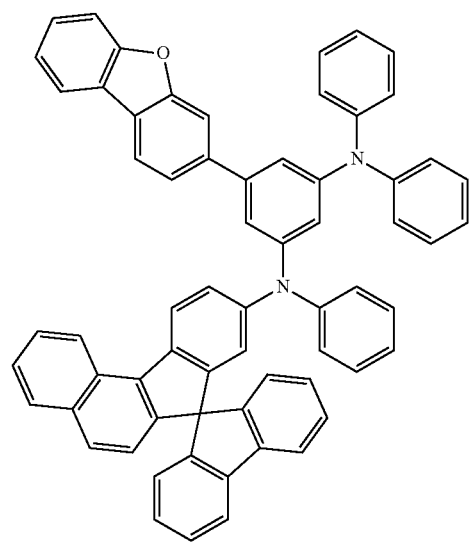
P-98
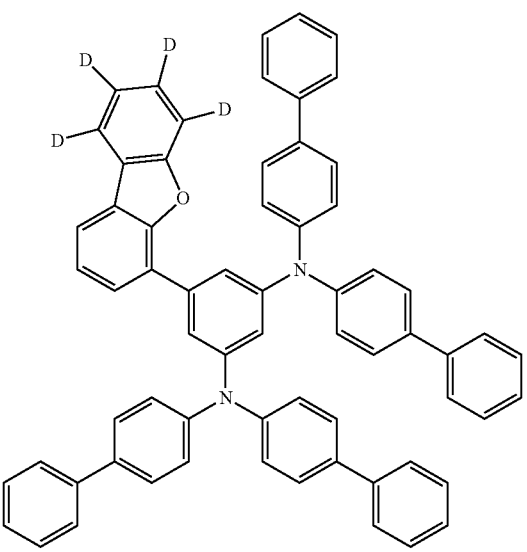
P-96
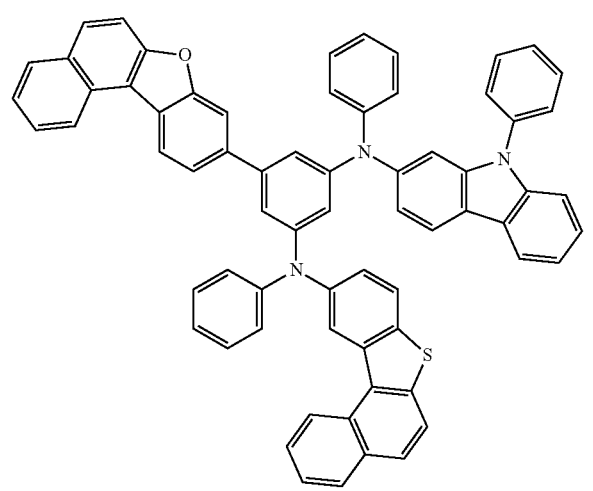
P-99
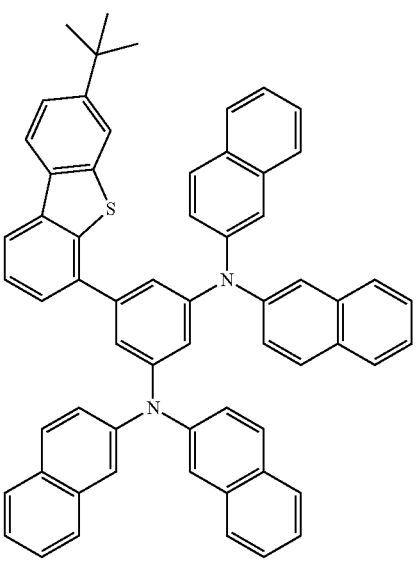

P-100
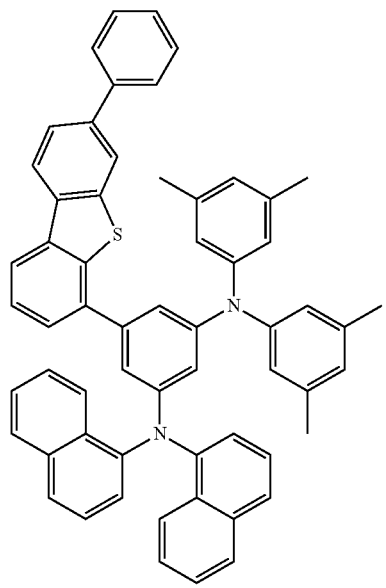
P-102
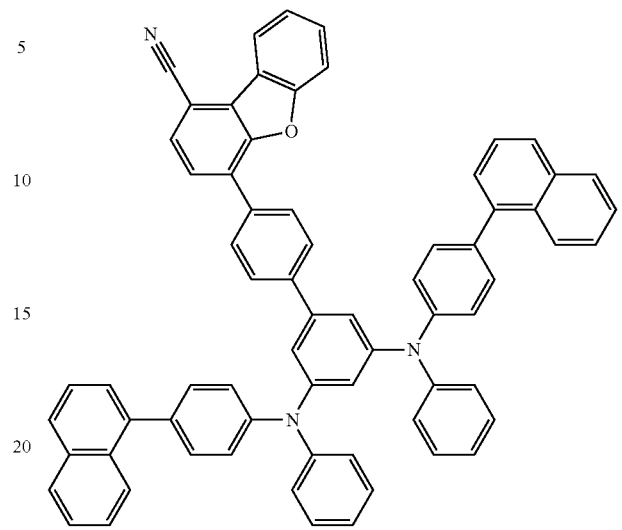
P-101
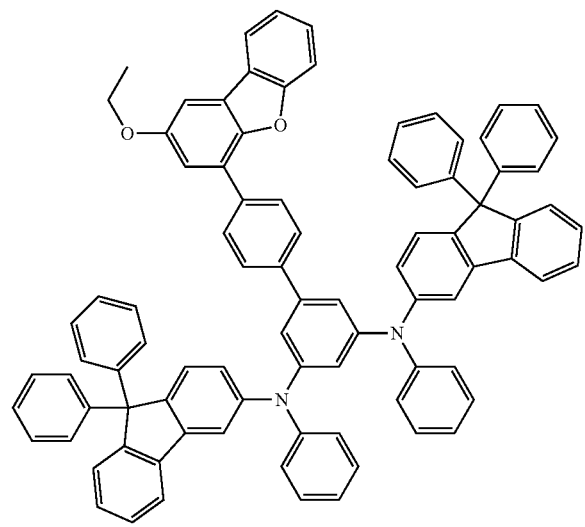
P-103
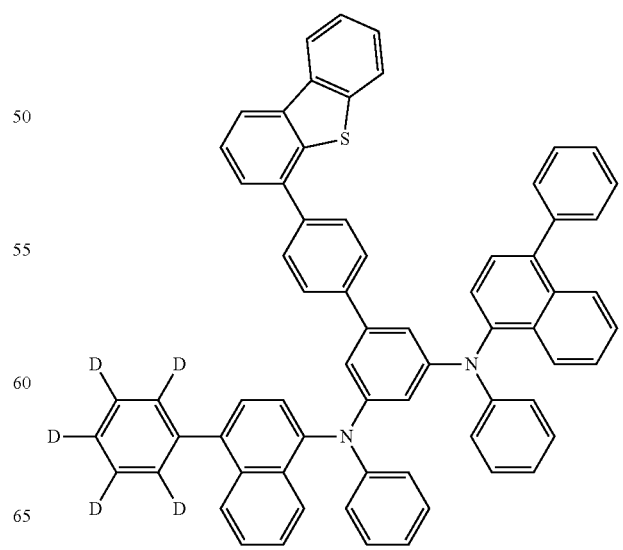

P-104
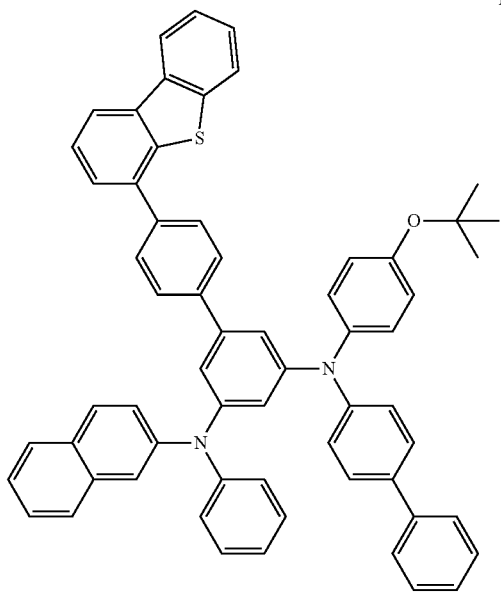
P-107
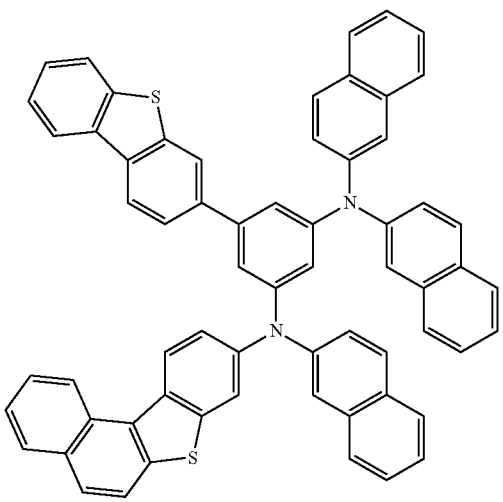
P-105
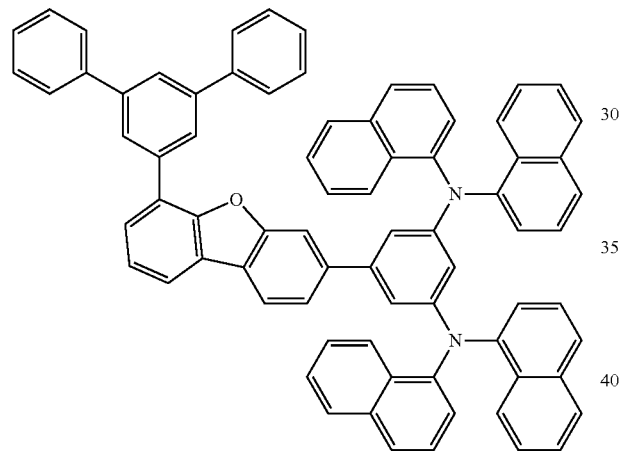
P-108
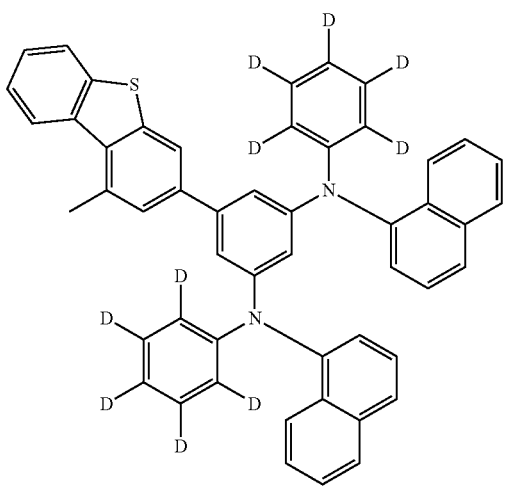
P-106
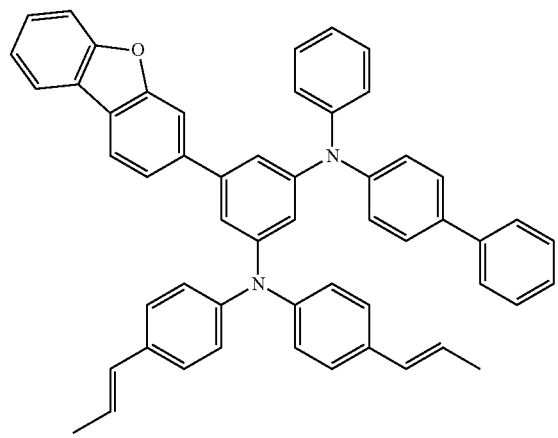
P-109
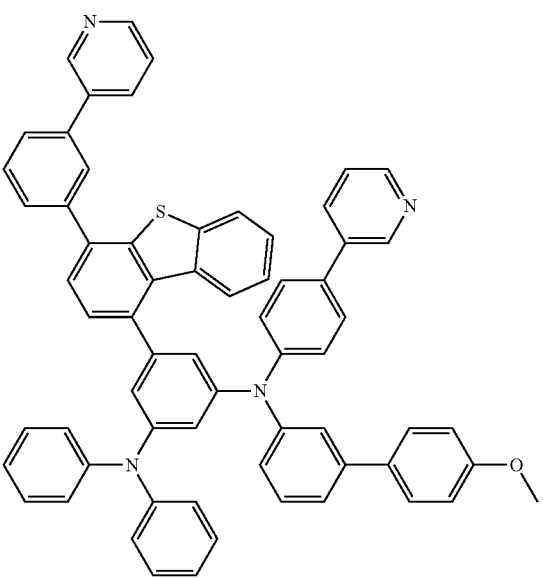

P-110
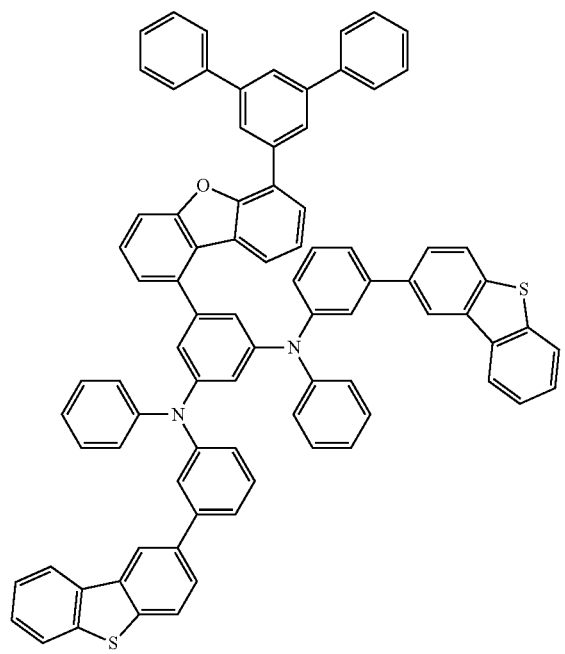
P-111
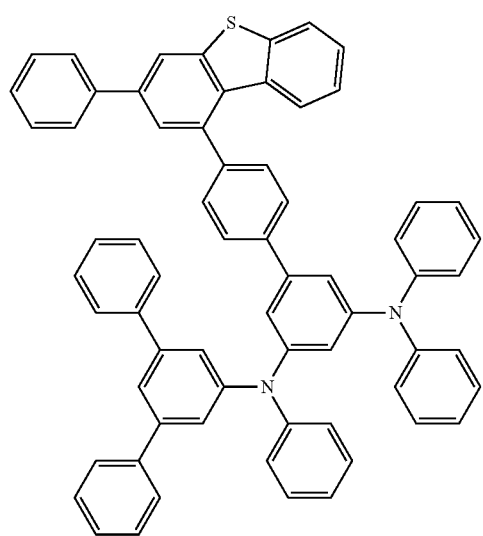
P-112
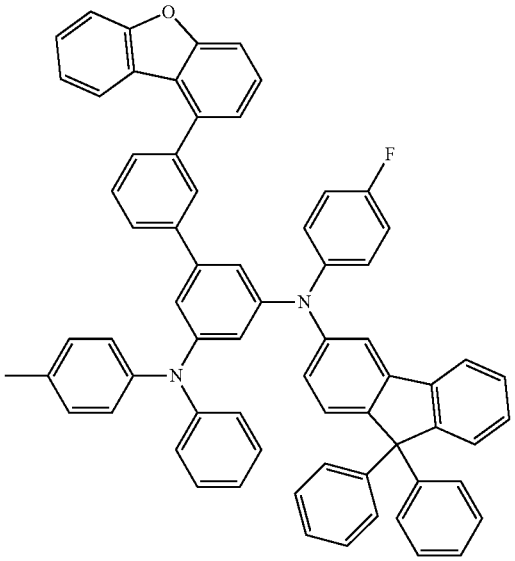
P-113
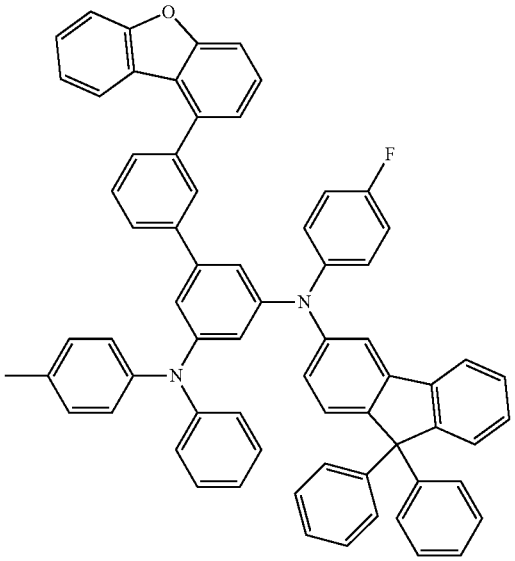
P-114
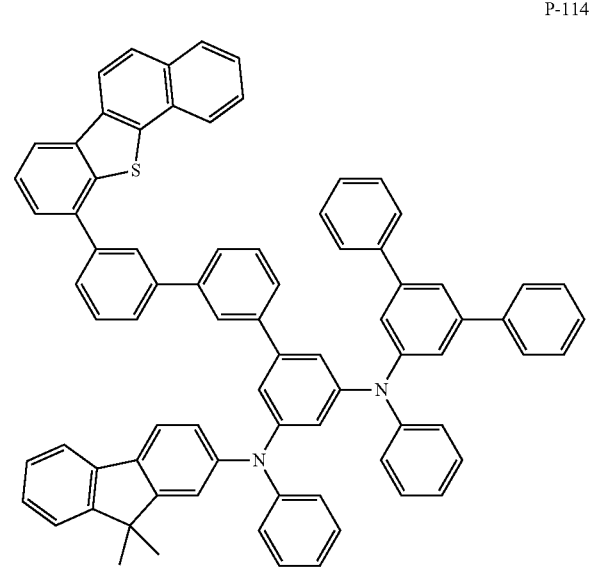

P-115
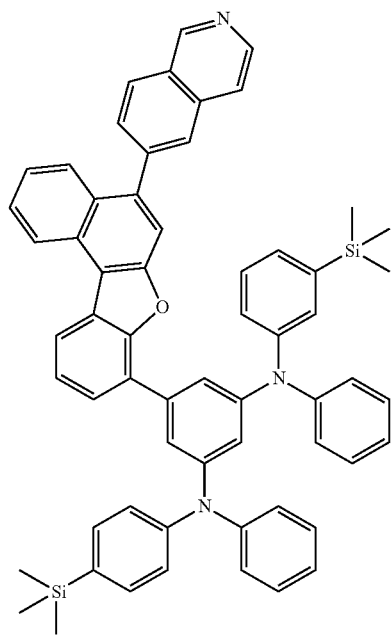
P-116
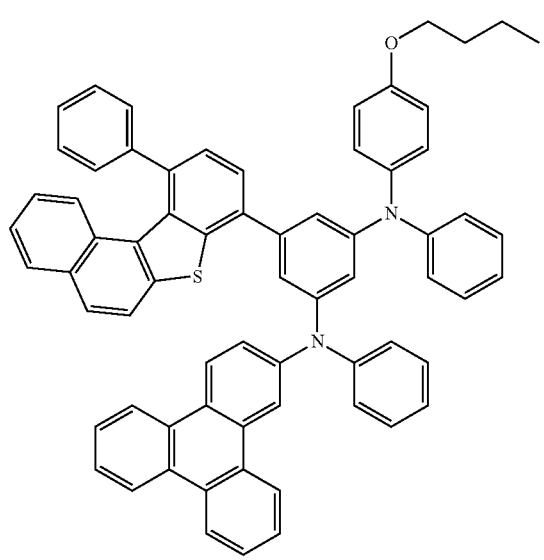
P-117
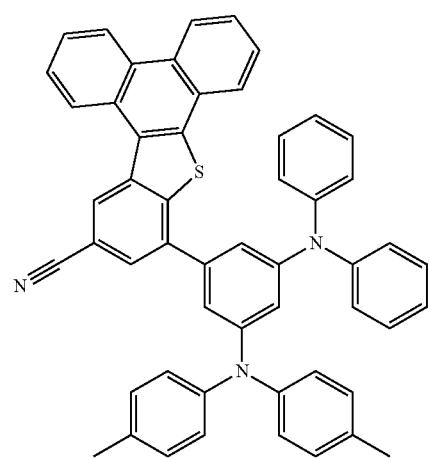
P-118
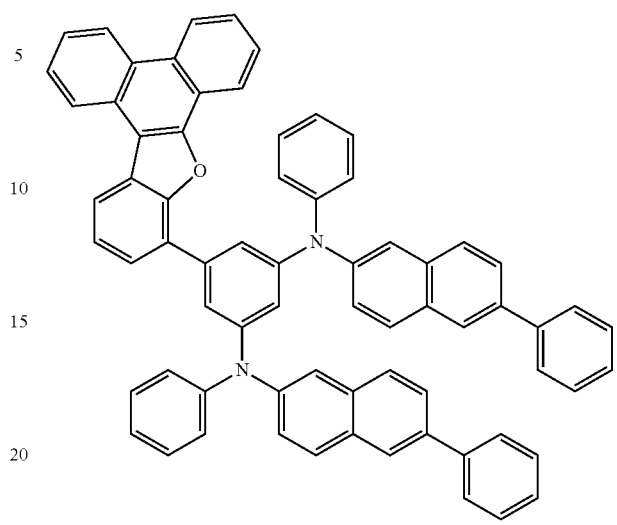
P-119
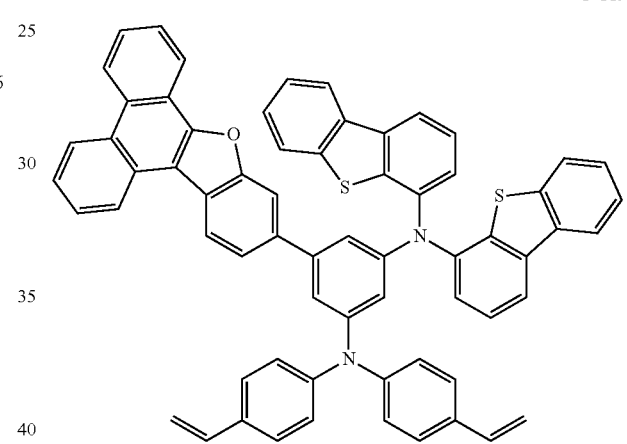
P-120
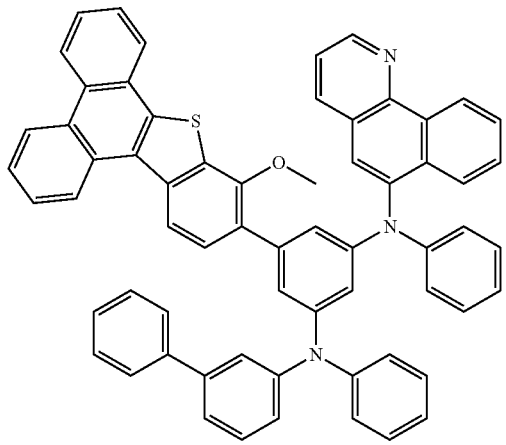

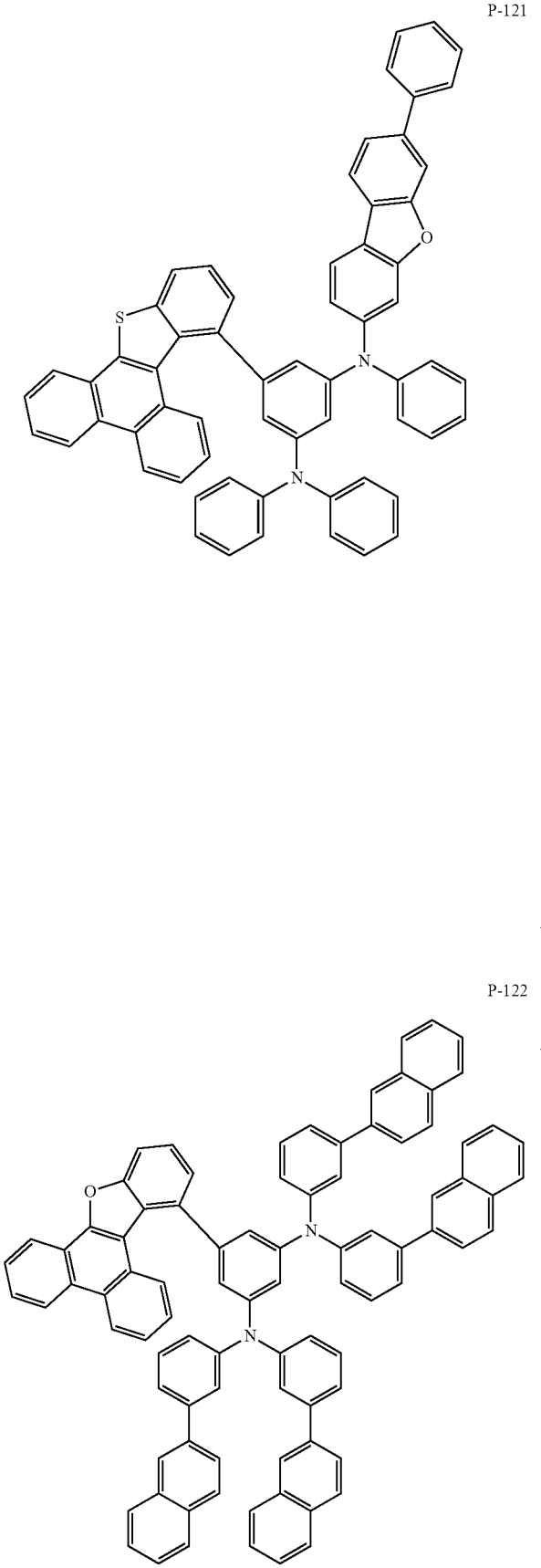

6. An organic electric element comprising a first electrode, a second electrode, and an organic material layer formed between the first electrode and the second electrode, wherein the organic material layer comprises the compound of claim 1.

7. The organic electric element of claim 6, wherein the compound is comprised in at least one of a hole injection layer, a hole transport layer, an emission-auxiliary layer, an light emitting layer, an electron transport-auxiliary layer, an electron transport layer and an electron injection layer, and the compound is a single compound or a mixture of two or more different kinds.

8. The organic electric element of claim 6, wherein the organic material layer is formed by any one of the processes of spin coating, nozzle printing, inkjet printing, slot coating, dip coating or roll-to-roll.

9. An electronic device comprising a display device and a control unit for driving the display device, wherein the display device comprises the organic electric element of claim 6.

10. The electronic device of claim 9, wherein the organic electric element is at least one of an organic light emitting diode, an organic solar cell, an organic photo conductor, an organic transistor, and an element for monochromatic or white illumination.

* * * * *